US012226562B2

(12) United States Patent
Vecten et al.

(10) Patent No.: US 12,226,562 B2
(45) Date of Patent: Feb. 18, 2025

(54) AUTOMATED EXTRACORPOREAL BLOOD TREATMENT APPARATUS

(71) Applicant: NextKidney SA, Lausanne (CH)

(72) Inventors: Didier Vecten, Lausanne (CH); Ricardo Allendes, Lausanne (CH); Paul Vescovo, Lausanne (CH)

(73) Assignee: NEXTKIDNEY SA, Lausanne (CH)

( * ) Notice: Subject to any disclaimer, the term of this patent is extended or adjusted under 35 U.S.C. 154(b) by 78 days.

(21) Appl. No.: 16/766,761

(22) PCT Filed: Oct. 31, 2018

(86) PCT No.: PCT/IB2018/058547
§ 371 (c)(1),
(2) Date: May 26, 2020

(87) PCT Pub. No.: WO2019/087103
PCT Pub. Date: May 9, 2019

(65) Prior Publication Data
US 2020/0316283 A1    Oct. 8, 2020

(30) Foreign Application Priority Data

Oct. 31, 2017 (EP) .................................... 17199362
Oct. 31, 2017 (EP) .................................... 17199363
(Continued)

(51) Int. Cl.
A61M 1/36    (2006.01)
A61M 1/14    (2006.01)
(Continued)

(52) U.S. Cl.
CPC ........ *A61M 1/3644* (2014.02); *A61M 1/1524* (2022.05); *A61M 1/154* (2022.05);
(Continued)

(58) Field of Classification Search
CPC .............. A61M 1/3644; A61M 1/1603; A61M 1/1621; A61M 1/267; A61M 1/3627;
(Continued)

(56) References Cited

U.S. PATENT DOCUMENTS 6,284,142 B1    9/2001 Muller
8,029,454 B2    10/2011 Kelly
(Continued)

FOREIGN PATENT DOCUMENTS

EP    0 755 273 B1    10/1999
EP    2368586 A2 *  9/2011 .......... A61M 1/1006
(Continued)

OTHER PUBLICATIONS

Decision to Grant a European patent pursuant to Article 97(1)EPC for EP Application n° 18811065.4 / Patent n° 3703775.
(Continued)

Primary Examiner — Magali P Slawski
Assistant Examiner — Bernadette Karen McGann
(74) Attorney, Agent, or Firm — NIXON & VANDERHYE

(57) ABSTRACT

The present invention provides an extracorporeal dialysis apparatus which allows the automation of some operations in order to make possible a safe home treatment or to facilitate the treatment process for example the priming and/or the blood return process. Thus, the object is to automatically perform a series of processes from hemodialysis preparation to treatment completion safely, reliably and speedily, and to significantly reduce the labor and supply costs.

41 Claims, 53 Drawing Sheets

(30) Foreign Application Priority Data

Dec. 20, 2017 (EP) .................................. 17209117
Dec. 20, 2017 (EP) .................................. 17209126

(51) Int. Cl.
    *A61M 1/16*       (2006.01)
    *A61M 1/26*       (2006.01)
    *A61M 39/10*     (2006.01)
    *A61M 39/22*     (2006.01)

(52) U.S. Cl.
CPC .......... *A61M 1/155* (2022.05); *A61M 1/1561* (2022.05); *A61M 1/1565* (2022.05); *A61M 1/1603* (2014.02); *A61M 1/1621* (2014.02); *A61M 1/267* (2014.02); *A61M 1/362227* (2022.05); *A61M 1/36224* (2022.05); *A61M 1/36225* (2022.05); *A61M 1/362261* (2022.05); *A61M 1/362265* (2022.05); *A61M 1/3627* (2013.01); *A61M 39/10* (2013.01); *A61M 39/22* (2013.01); *A61M 1/1566* (2022.05); *A61M 1/362266* (2022.05); *A61M 1/3646* (2014.02); *A61M 2205/3337* (2013.01); *A61M 2205/50* (2013.01)

(58) Field of Classification Search
CPC .. A61M 1/3646; A61M 1/1643; A61M 1/365; A61M 1/3424; A61M 39/10; A61M 39/22; A61M 2205/3337; A61M 2205/50; A61M 2205/502; A61M 2205/273; A61M 2209/08; A61M 2209/082; A61M 2209/084
See application file for complete search history.

(56) References Cited

U.S. PATENT DOCUMENTS

| | | | |
|---|---|---|---|
| 8,114,276 B2 | 2/2012 | Childers | |
| 8,444,587 B2 * | 5/2013 | Kelly | A61M 1/282 604/4.01 |
| 8,512,553 B2 | 8/2013 | Cicchello | |
| 8,523,799 B2 | 9/2013 | Biesel et al. | |
| 8,585,634 B2 | 11/2013 | Neftel | |
| 8,597,505 B2 | 12/2013 | Fulkerson et al. | |
| 9,526,820 B2 | 12/2016 | Beiriger | |
| 9,931,456 B2 * | 4/2018 | Rovatti | G01M 3/2846 |
| 2003/0209884 A1 | 11/2003 | Joie | |
| 2005/0055242 A1 | 3/2005 | Bello | |
| 2005/0209563 A1 | 9/2005 | Hopping et al. | |
| 2009/0012461 A1 | 1/2009 | Childers | |
| 2010/0192686 A1 | 8/2010 | Kamen et al. | |
| 2012/0267291 A1 | 10/2012 | Coates | |
| 2012/0267309 A1 * | 10/2012 | Peters | A61M 60/113 210/644 |
| 2014/0088493 A1 | 3/2014 | Pan | |
| 2014/0216250 A1 | 8/2014 | Meyer et al. | |
| 2014/0299544 A1 * | 10/2014 | Wilt | A61M 60/554 417/474 |
| 2015/0122721 A1 | 5/2015 | Childers | |
| 2015/0367062 A1 | 12/2015 | Brugger | |
| 2016/0106906 A1 | 4/2016 | Buckberry | |
| 2017/0143888 A1 | 5/2017 | Childers et al. | |
| 2020/0179224 A1 | 6/2020 | Wolf | |

FOREIGN PATENT DOCUMENTS

| | | | | |
|---|---|---|---|---|
| EP | 2609944 A1 | 7/2013 | | |
| EP | 2896417 A1 | 7/2015 | | |
| EP | 3011984 A1 | 4/2016 | | |
| EP | 3703775 B1 | 2/2022 | | |
| EP | 3703776 B1 | 2/2022 | | |
| GB | 2110564 A | 6/1983 | | |
| JP | H09-239024 A | 9/1997 | | |
| JP | 2007-500522 A | 1/2007 | | |
| JP | 2012-200275 A | 10/2012 | | |
| KR | 10-2012-0093823 A | 8/2012 | | |
| RU | 93276 U1 | 4/2010 | | |
| WO | WO 2005009511 A2 | 2/2005 | | |
| WO | WO-2009055639 A2 * | 4/2009 | ............ | A61M 1/14 |
| WO | WO 2011017215 | 2/2011 | | |
| WO | 2014155137 A1 | 10/2014 | | |
| WO | WO-2015130205 A1 * | 9/2015 | ............ | A61M 1/28 |
| WO | 2016/104720 A1 | 6/2016 | | |
| WO | WO-2016164643 A1 * | 10/2016 | ......... | A61M 1/3629 |
| WO | 2017/141747 A1 | 8/2017 | | |
| WO | 2018210926 A1 | 11/2018 | | |
| WO | WO 2018210926 | 11/2018 | | |

OTHER PUBLICATIONS

Decision to Grant a European patent pursuant to Article 97(1)EPC for EP Application n° 18811066.2 / Patent n° 3703776.
European Grant Certificate for EP Application n° 18811065.4 / Patent n° 3703775.
European Grant Certificate for EP Application n° 18811066.2 / Patent n° 3703776.
Russian Office Action mailed on Feb. 3, 2022 for Application N° RU 2020-117675.
Russian Search Report mailed on Feb. 3, 2022 for Application N° RU 2020-117675.
USPTO Office Action of Jan. 18, 2022 from a related application with the U.S. Appl. No. 16/766,757.
EPO Search Report mailed May 11, 2018 for Application EP17209117.5.
EPO Written Opinion mailed May 11, 2018 for Application EP17209117.5.
International Search Report mailed Feb. 11, 2019 for Application PCT/IB2018/058539.
International Search Report mailed Feb. 18, 2019 for Application PCT/IB2018/058547.
Written Opinion of the ISA mailed Feb. 18, 2019 for Application PCT/IB2018/058547.
Written Opinion of the ISA mailed on Feb. 11. 2019 for Application PCT/IB2018/058539.
European Opinion mailed on May 4, 2022 for Application N° EP22151016.7.
European Search Report mailed May 4, 2022 for Application N° EP22151016.7.
Office Action issued in Korean Patent Application No. 10-2020-7015410 dated Apr. 26, 2023.
Office Action issued in Chinese Patent Application No. 201880084449.7 dated Feb. 25, 2023.
Communication pursuant to Article 94(3) EPC issued in European Patent Application No. 22 151 016.7 dated May 24, 2023.
Office Action issued in Chinese Patent Application No. 201880084803.6 dated Jun. 2, 2022.
US Notice of Allowance of Sep. 26, 2022 from a related application with the U.S. Appl. No. 16/766,757.
US Office Action of Jun. 13, 2022 from a related application with the App. U.S. Appl. No. 16/766,757.
US Office Action of Jun. 27, 2023 from a related application with the U.S. Appl. No. 18/069,451.
Non-Final Rejection, issued in U.S. Appl. No. 18/621,419, dated Dec. 5, 2024.

* cited by examiner

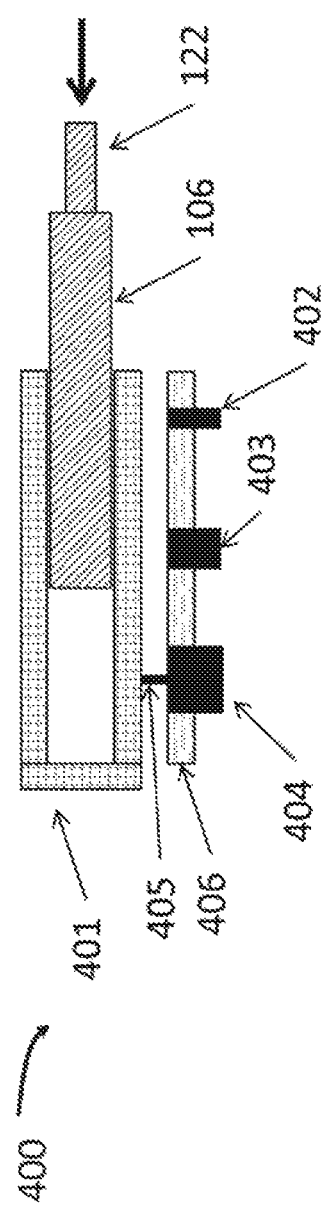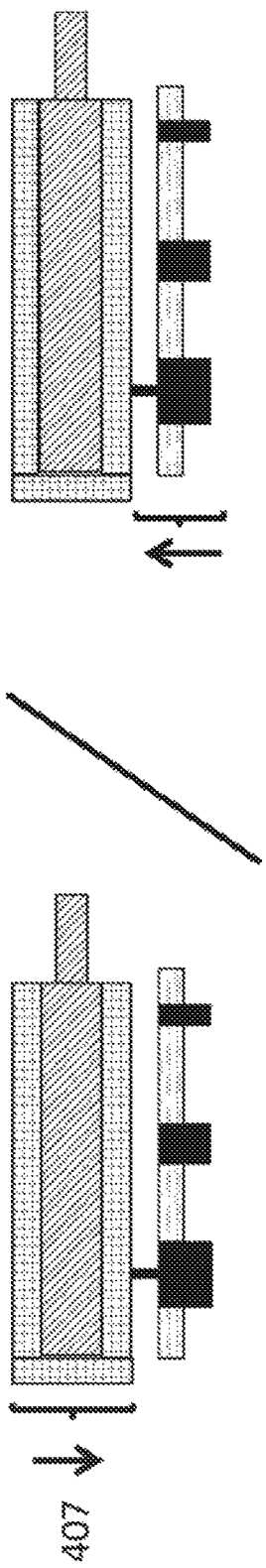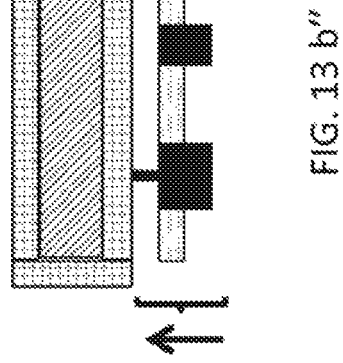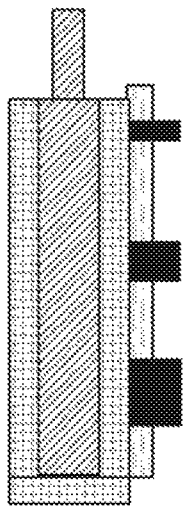
FIG. 13 a
FIG. 13 b'
FIG. 13 b"
FIG. 13 c

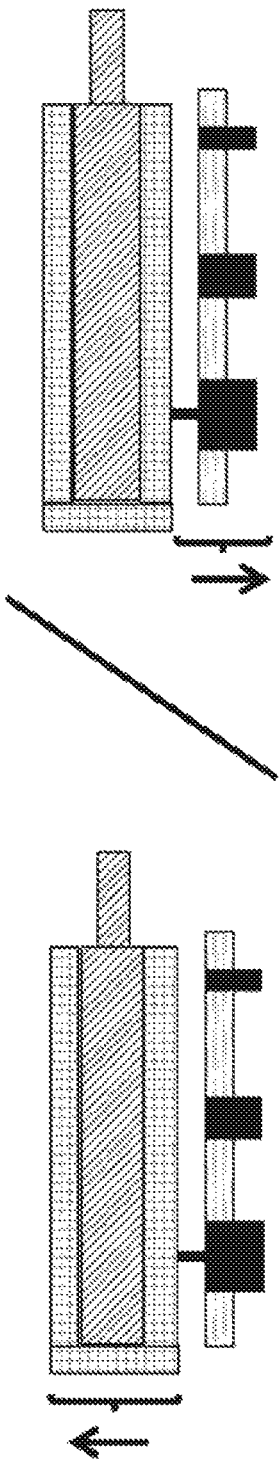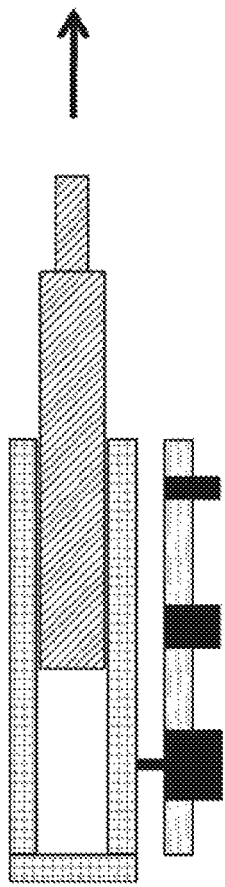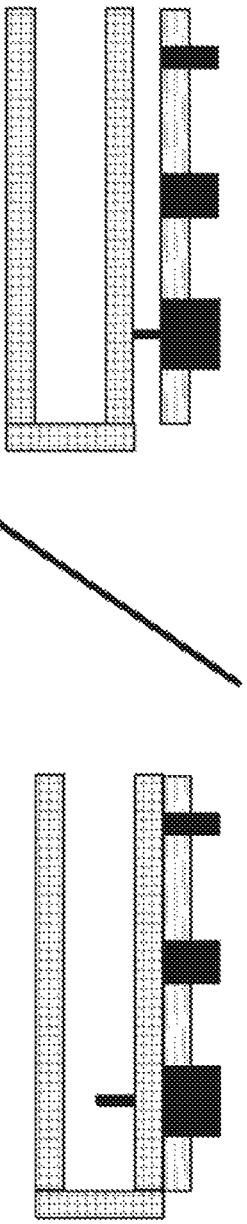

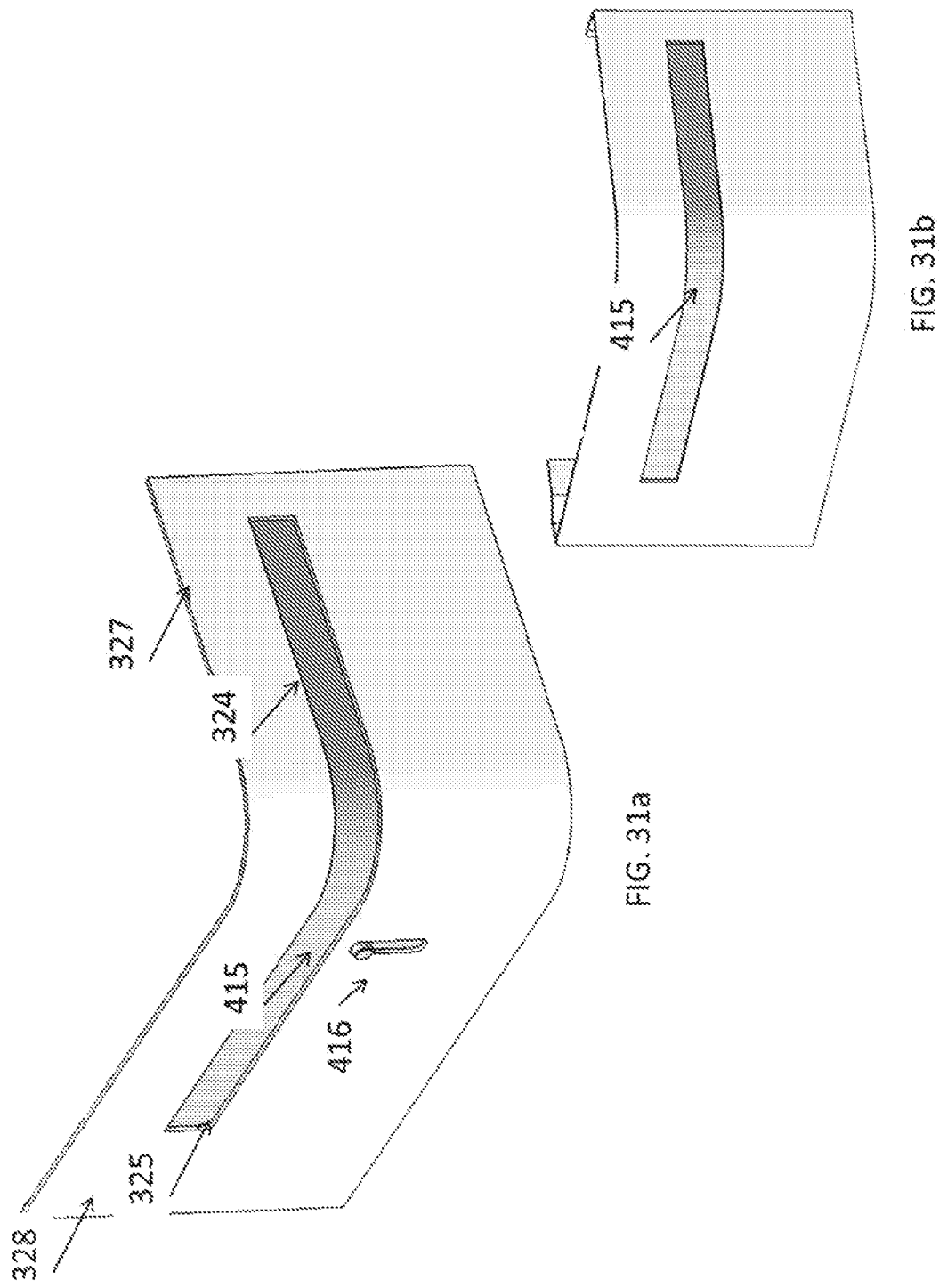

AUTOMATED EXTRACORPOREAL BLOOD TREATMENT APPARATUS

CROSS REFERENCE TO RELATED APPLICATIONS

The present application is a United States national stage application of International patent application PCT/IB2018/058547 filed on Oct. 31, 2018 that designated the United States, and claims foreign priority to four (4) European patent applications EP 17199363.7 filed on Oct. 31, 2017, EP 17199362.9 filed on Oct. 31, 2017, EP 17209117.5 filed on Dec. 20, 2017, and EP 17209126.6 filed in Dec. 20, 2017, the contents of all five (5) documents being herewith incorporated by reference in their entirety.

FIELD OF INVENTION

The present invention relates to an extracorporeal blood treatment apparatus or method such as priming or blood return process.

STATE OF THE ART

Extracorporeal blood treatment is typically used to extract undesirable matter or molecules from the patient's blood and/or add desirable matter or molecules to the blood. Such treatment is used with patients unable to effectively remove matter from their blood, such as when a patient has suffered temporary or permanent kidney failure.

This treatment is typically accomplished by removing the blood from the patient, introducing the blood into a filtration unit (for example a dialyzer) where the blood is allowed to flow past a semipermeable membrane. The semipermeable membrane selectively allows matter in the blood to cross the membrane from a primary chamber into a secondary chamber and also selectively allows matter in the secondary chamber to cross the membrane into the blood in the primary chamber, depending on the type of treatment. A number of different types of extracorporeal blood treatments may be performed:
   In an ultrafiltration (UF) treatment;
   In a hemofiltration (HF) treatment;
   In a hemodialysis (HD) treatment;
   In a hemodiafiltration (HDF) treatment.

Currently, the most widely used method of kidney dialysis for treatment of end stage renal disease is hemodialysis. In hemodialysis, the patient's blood is cleansed by passing it through the primary chamber and a dialysate solution through the secondary chamber. During dialysis, arterial and venous parts of blood line convey a patients blood to and from the filtration means (for example a dialyzer). Impurities and toxins are removed from the patient's blood by diffusion or convection across a membrane in the filtration means. Hemodialysis is commonly required three times a week with each dialysis requiring up to four to five hours in a dialysis center or at home where treatment may be more frequent (up to daily) and shorter (down to two hours). During the treatment, the patient is connected to a hemodialysis machine and the patient's blood is pumped through the machine. Catheters are inserted into the patient's veins and arteries so that blood can flow to and from the hemodialysis machine. A large amount of a dialysis solution, for example about 120 liters, is consumed to dialyze the blood during a single hemodialysis therapy.

The dialysis treatment is widely carried up in medical centers, where caregivers operate the dialysis systems and ensure a safe treatment. But in the future, more and more treatments will be performed at home and the patient will not be always accompanied by a caregiver. Thus, it is essential to simplify or to facilitate handling of the dialysis system in order to limit the risks of wrong preparation or actions or the risk of contaminations of sterile elements from the system.

Nevertheless currently, for example, priming methods for home hemodialysis treatments are based on standard manipulations done in-center. The patient or health care professional has to:
   connect/disconnect a saline bag,
   connect/disconnect the patient's catheter,
   connect saline return bag,
   orientate the dialyzer to ensure a fluid circulation from bottom to top when priming the dialysate compartment and the blood compartment of the dialyzer.

Furthermore, the more connections done by the patient/healthcare professional, the higher are the risks of contamination of the inside sterile content.

And manipulation of the dialyzer represents a risk of less efficient priming if not well oriented during its specific priming phase. If the dialyzer is oriented in the wrong direction, larger amount of air bubble may remain stuck in the dialyzer, representing a risk of air/blood interfaces (i.e. risk of local coagulation and fibers clogging), less efficient dialysis due to diminution of contact area between the blood and dialysate through the fibers, and risk of injecting air into the patient.

In conclusion, reducing the complexity of the manipulations to set-up the overall treatment and/or end of treatment, is a key advantage to facilitate the introduction of hemodialysis device at home or to facilitate the work of caregivers in dialysis centers.

GENERAL DESCRIPTION OF THE INVENTION

The present document discloses automation of extracorporeal dialysis treatment routines, which were labor intensive, require professional skills, and were considered to be difficult to rationalize, and also to enhancement of the safety of the treatment.

invention first aspect of the invention provides an extracorporeal dialysis apparatus which allows the automation of some operations in order to make possible a safe home treatment or to facilitate the treatment process for example the priming and/or the blood return process. Such an apparatus allow to automatically perform a series of processes from hemodialysis preparation to treatment completion safely, reliably and speedily, and to significantly reduce the labor and supply costs. For example, this document describes several embodiments and operating sequence Such as priming sequence, safety sequence, automatic blood-return sequence and other process, with the aim of simplifying the involvement of the patients or health care professionals by limiting the number and the complexity of manipulations.

A second aspect of the invention provides a dialysis system comprising at least one of:
   a dialyzer having a blood compartment,
   a blood circuit including at least one of:
      an arterial line having at least one of:
         a first arterial end including a first connector intended to be connected to a patient,
         a second arterial end connected to the blood compartment of the dialyzer, and
         an arterial valve, an venous line having at least one of:
  a first venous end including a second connector intended to be connected to the patient,
  a second venous end connected to the blood compartment of the dialyzer, and
  a venous valve, and
a blood pump configured to move a fluid through the blood circuit and to be actuated in at least one of a normal pump direction through the blood circuit and a reverse pump direction through the blood circuit, oppositely to the normal pump direction, and
a fluid system (for example configured to provide a fluid to, to provide a fluidic connection to, and/or to receive fluid from the blood circuit) having at least one of:
  a first storing compartment intended to store at least one of a priming solution, a rinsing solution and a solution compatible with blood,
  a first line in fluid communication with the first storing compartment, having a first valve, and connected to the blood circuit for example between the arterial connector and the blood pump,
  a second line in fluid communication with the first storing compartment, having a second valve, and connected to the blood circuit for example between the venous connector and the blood pump, and
  a third line configured to be removably connected to at least one of the first connector and the second connector.

A third aspect of the invention provides a method of priming and rinsing back of a blood processing system including a blood circuit, a dialysate circuit and a dialyzer comprising a blood compartment in fluid communication with the blood circuit, a dialysate compartment in fluid communication with the dialysate circuit and a dialysis membrane separating the blood compartment and the dialysate compartment, wherein the blood processing system further comprises a source of priming fluid in fluid communication with the blood circuit and/or the dialysate circuit, wherein the blood circuit comprises a first bag and a blood pump, the method comprising at least one of the step of:
  Moving the priming fluid from the source of priming fluid to the blood circuit
  Priming at least a part of the blood circuit with the priming fluid;
  Filling the first bag with the priming fluid;
  Priming at least a part of the blood circuit with patient blood; and
  Moving the priming fluid from the first bag through the blood circuit.

A fourth aspect of the invention provides a method of priming a blood processing system including a blood circuit, a dialysate circuit and a dialyzer comprising a blood compartment in fluid communication with the blood circuit, a dialysate compartment in fluid communication with the dialysate circuit and a dialysis membrane separating the blood compartment and the dialysate compartment, wherein the blood circuit further comprises an arterial line, a venous line and a first bag and the dialysate circuit comprises a dialysate pump and a source of priming fluid, the method comprising at least one of the steps of:
  Passing the priming fluid from the dialysate circuit to the blood circuit; and
  Filling at least partially the first bag with the priming fluid by using the dialysate pump A fifth aspect of the invention provides a dialysis system comprising at least one of:
  a dialyzer having a blood chamber, a dialysate chamber and a membrane separating the blood chamber from the dialysate chamber;
  a blood circuit including at least one of:
    an arterial line having a first end with a connector intended to be connected to a patient and a second end connected to the blood chamber of the dialyzer;
    an venous line having a first end with a connector intended to be connected to the patient and a second end connected to the blood chamber of the dialyzer;
  a blood pump adapted to move the blood circuit;
  a source of a priming fluid; and
  a first bag comprising a first port and a second port in fluid communication with blood circuit.

The first port of the first bag may be fluidly connected to the blood circuit upstream the blood pump and the second port of the first bag may be fluidly connected to the blood circuit downstream the blood pump.

LIST OF FIGURES

The present invention will be better understood at the light of the following detailed description which contains non-limiting examples illustrated by the following figures:

FIG. 1 shows a schematic view of the fluid circuits;

FIGS. 2a, b, c, d, e and f illustrate different views of embodiments of the blood circuit;

Figure 5A:
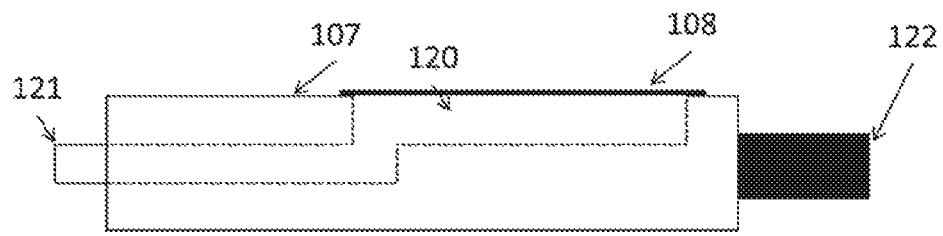
Figure 6:
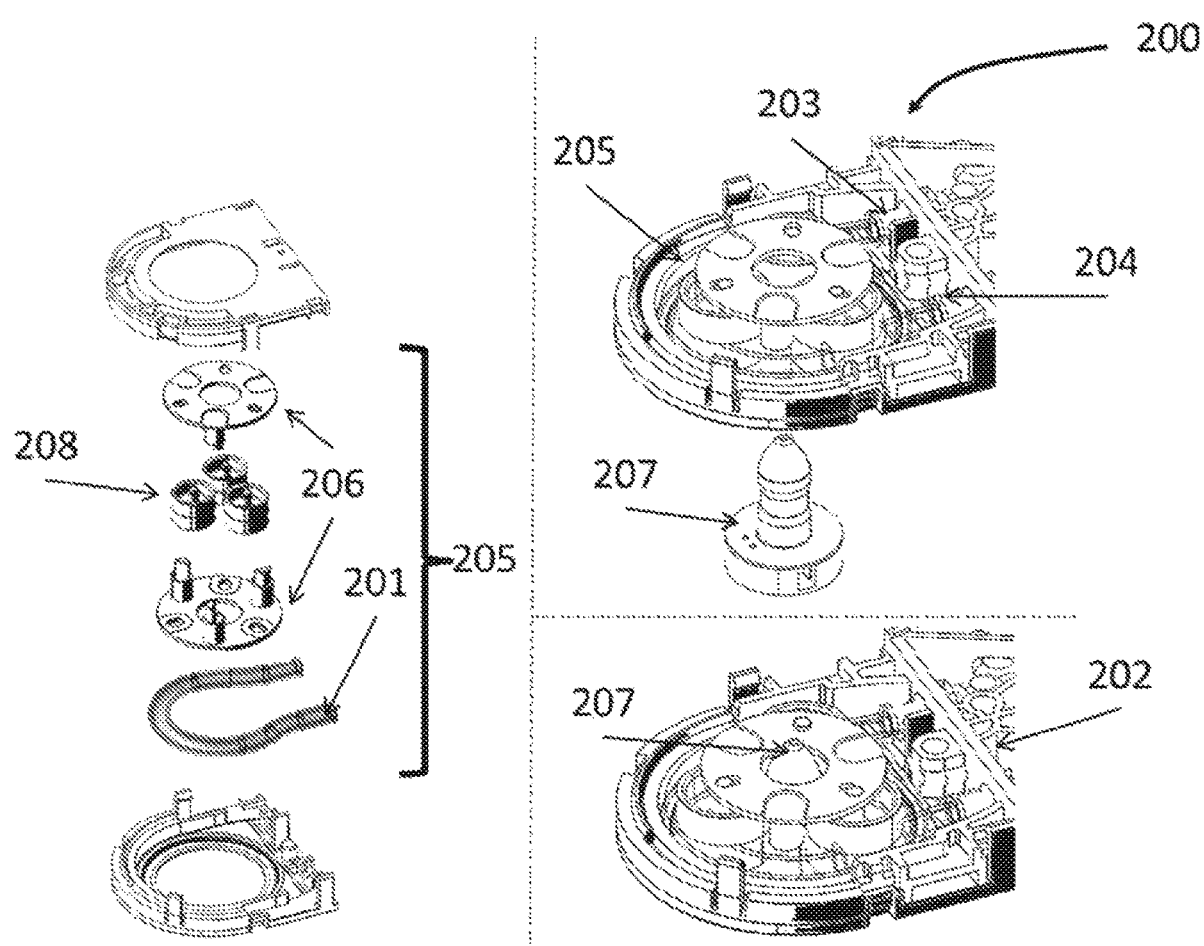
Figure 7:
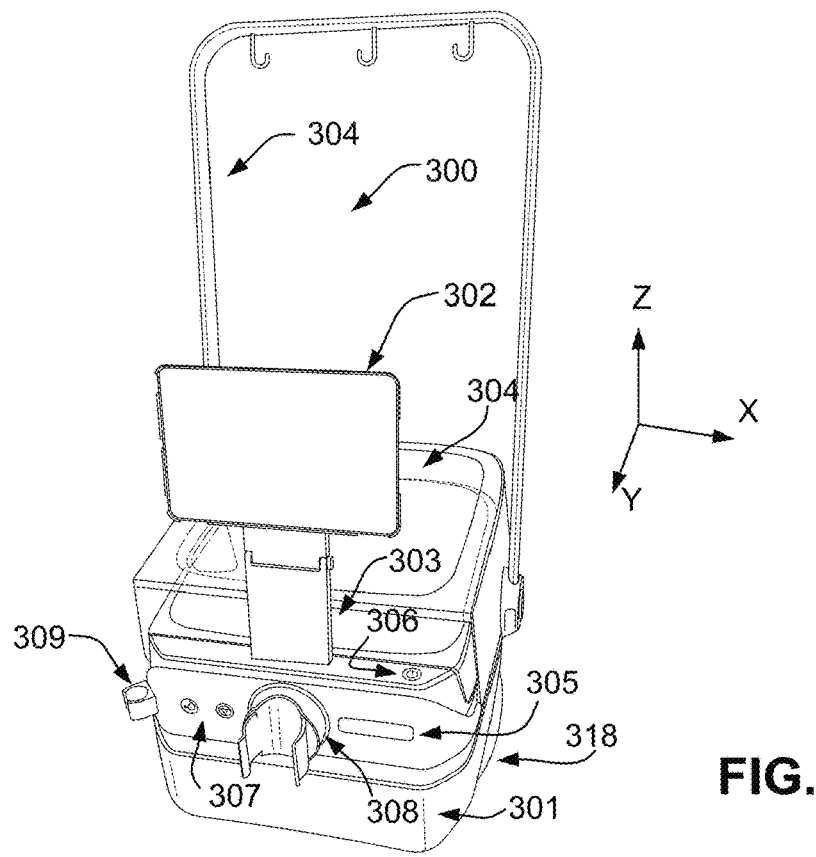
Figure 8:
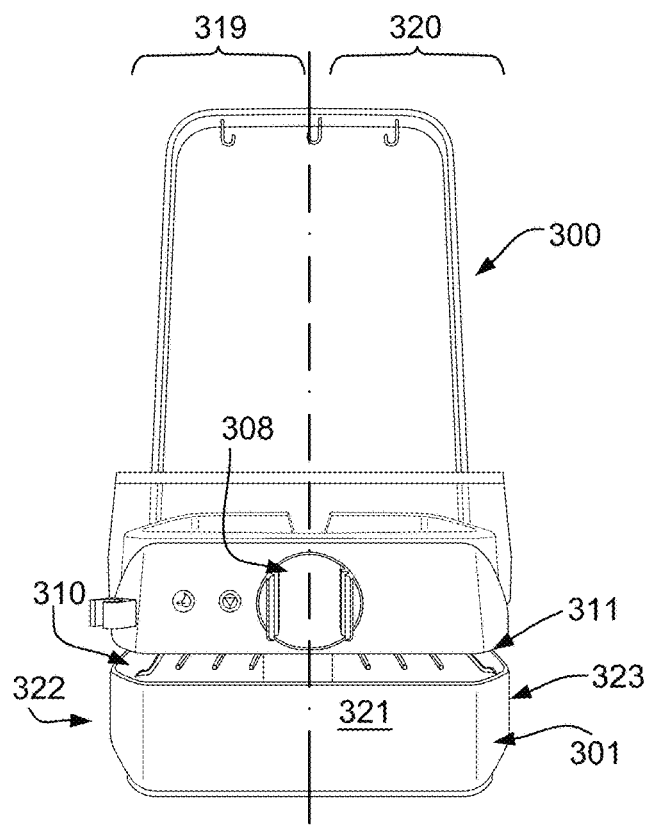
Figure 9:
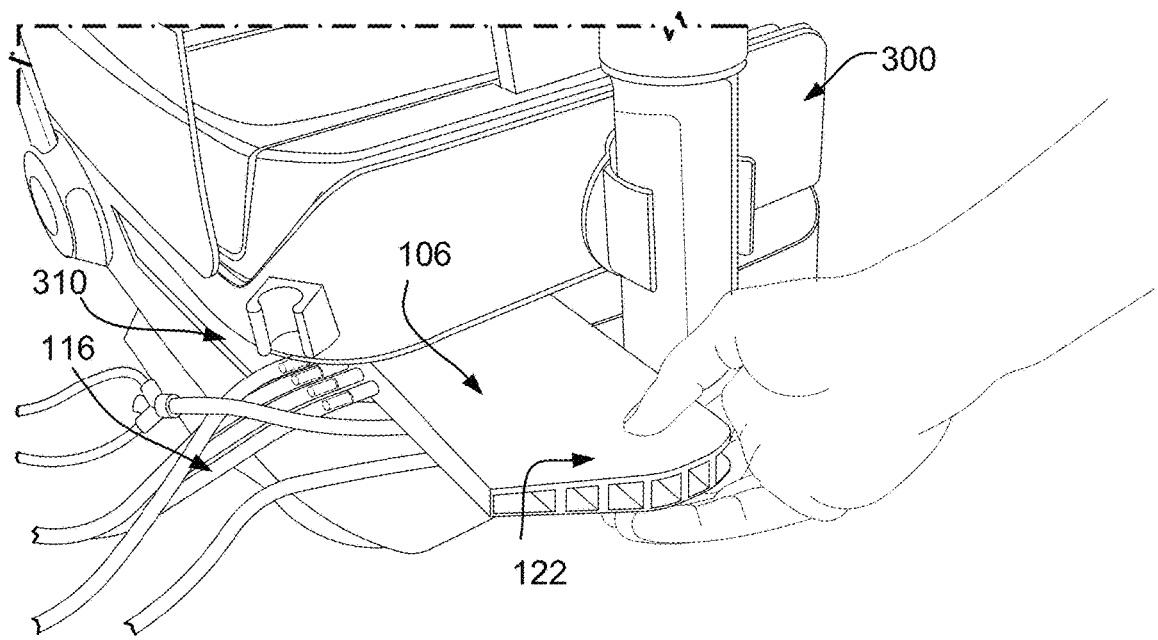
Figure 10:
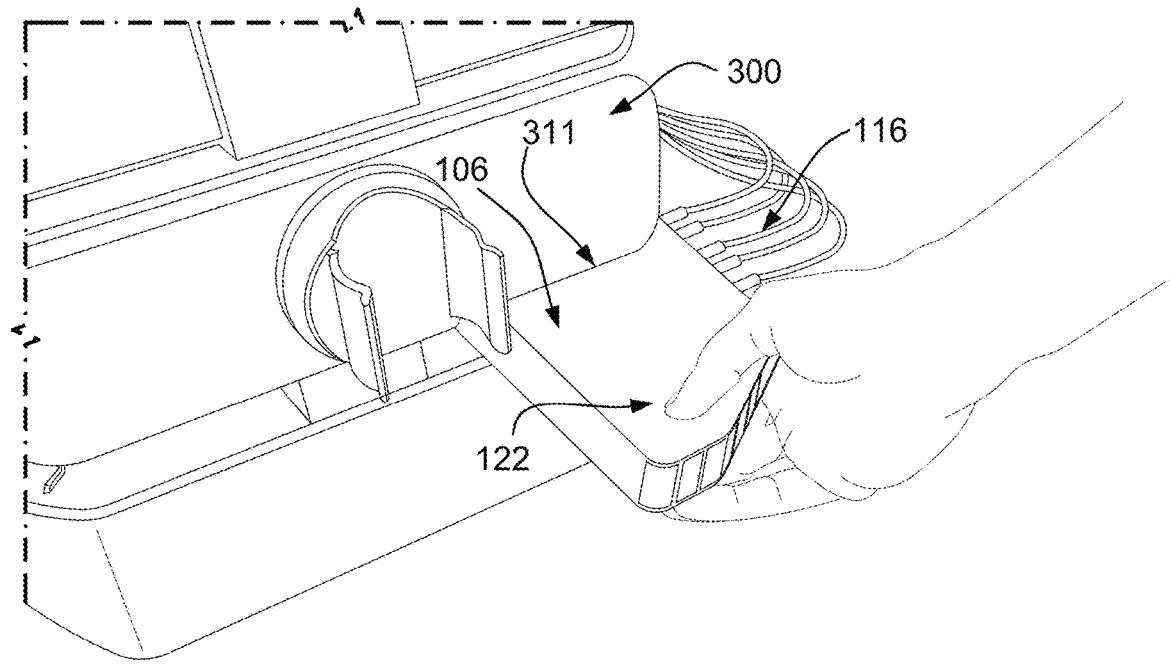
Figure 14:
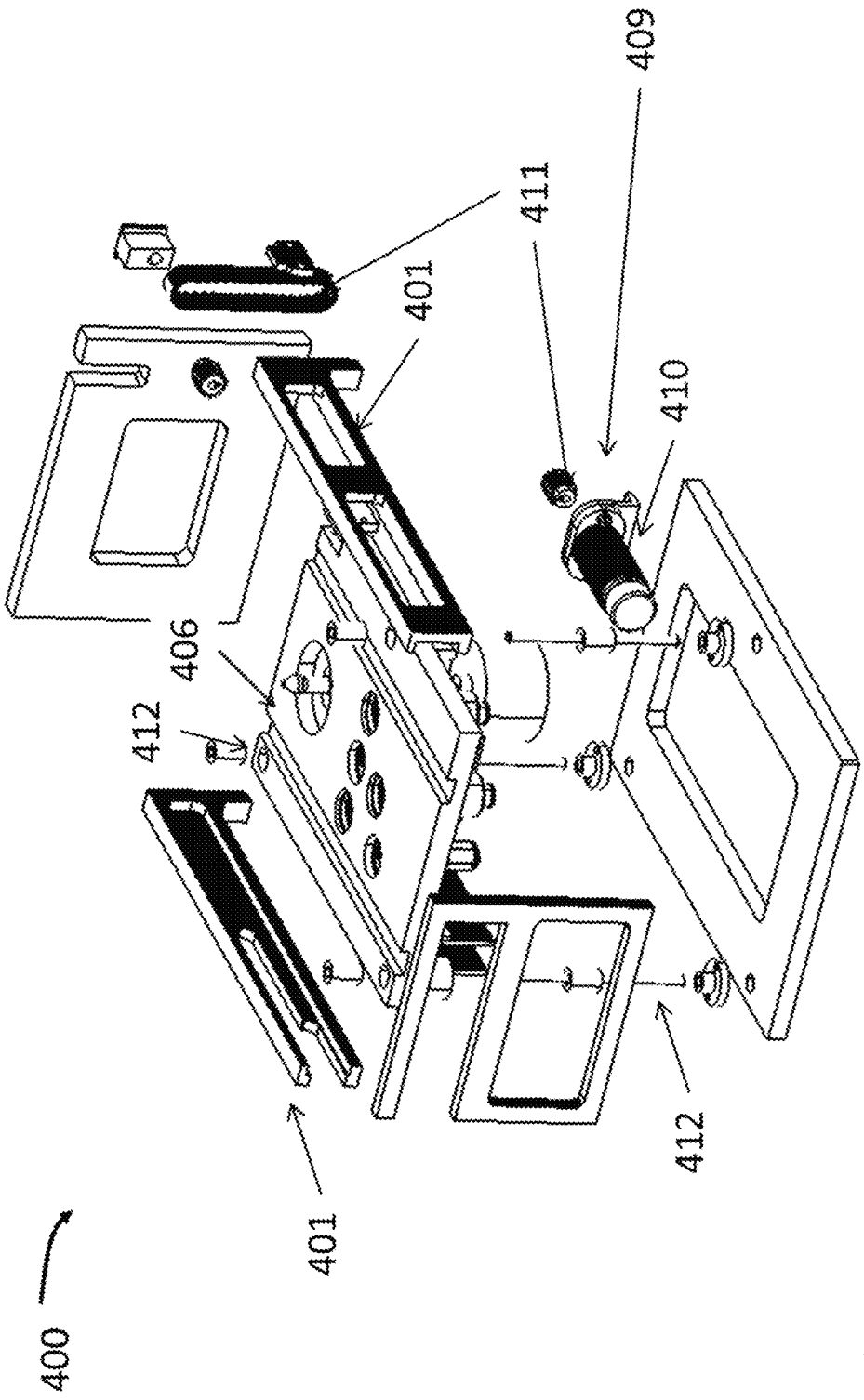
Figure 15C:
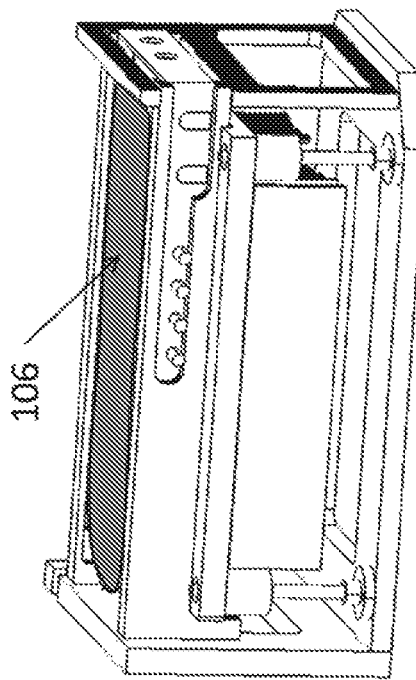
Figure 15D:
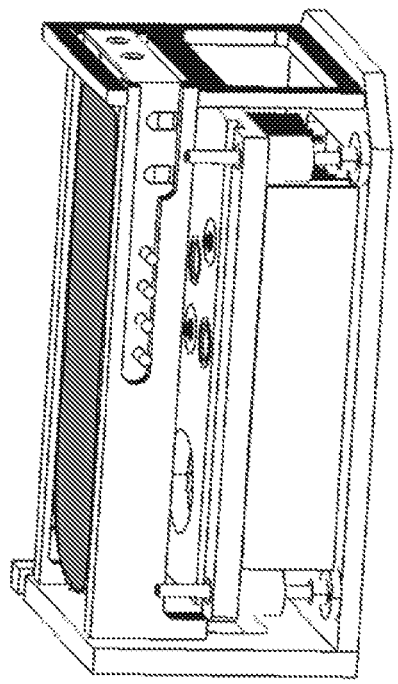
Figure 15A:
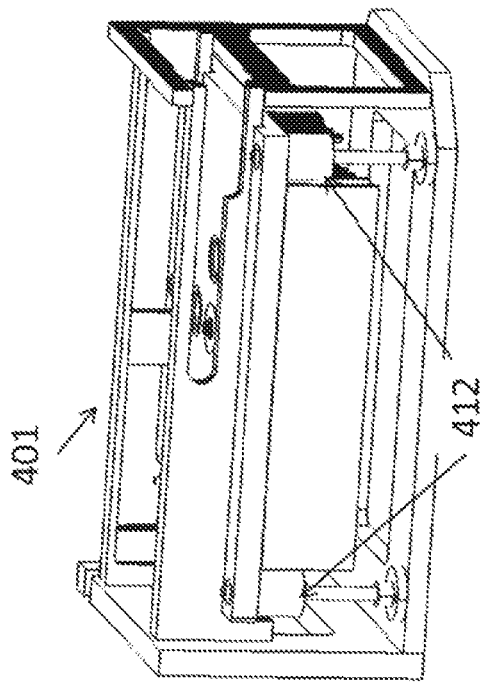
Figure 15B:
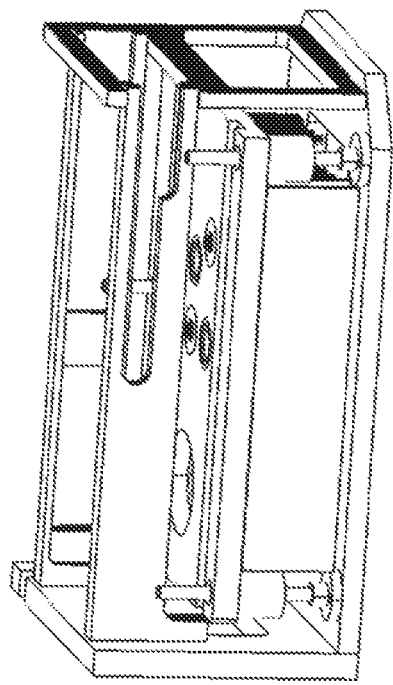
Figure 16:
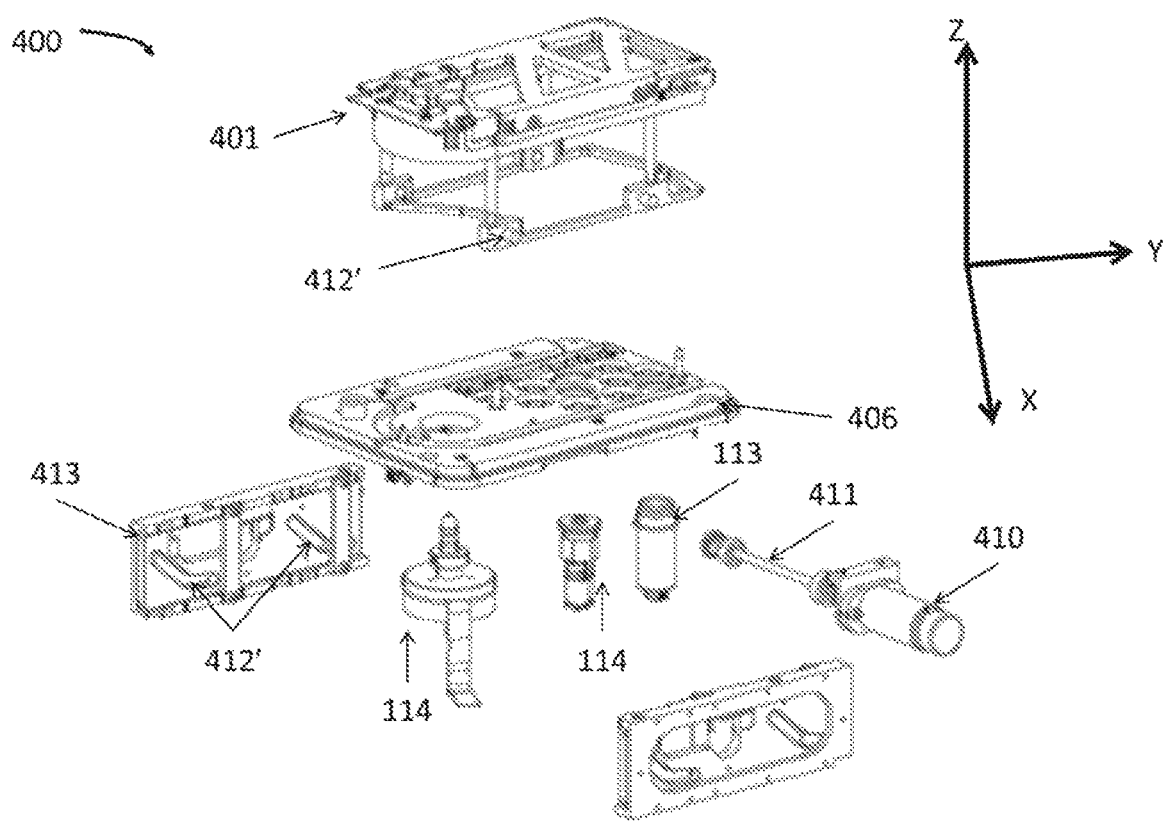
Figure 17:
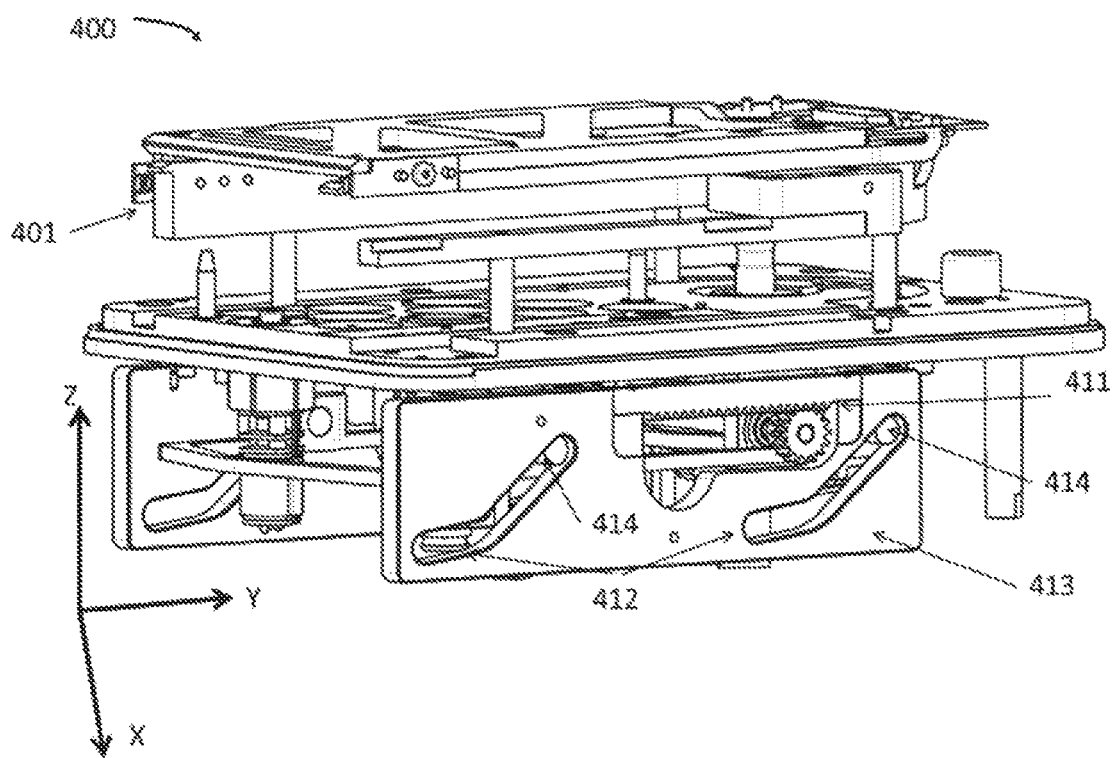
Figure 18:
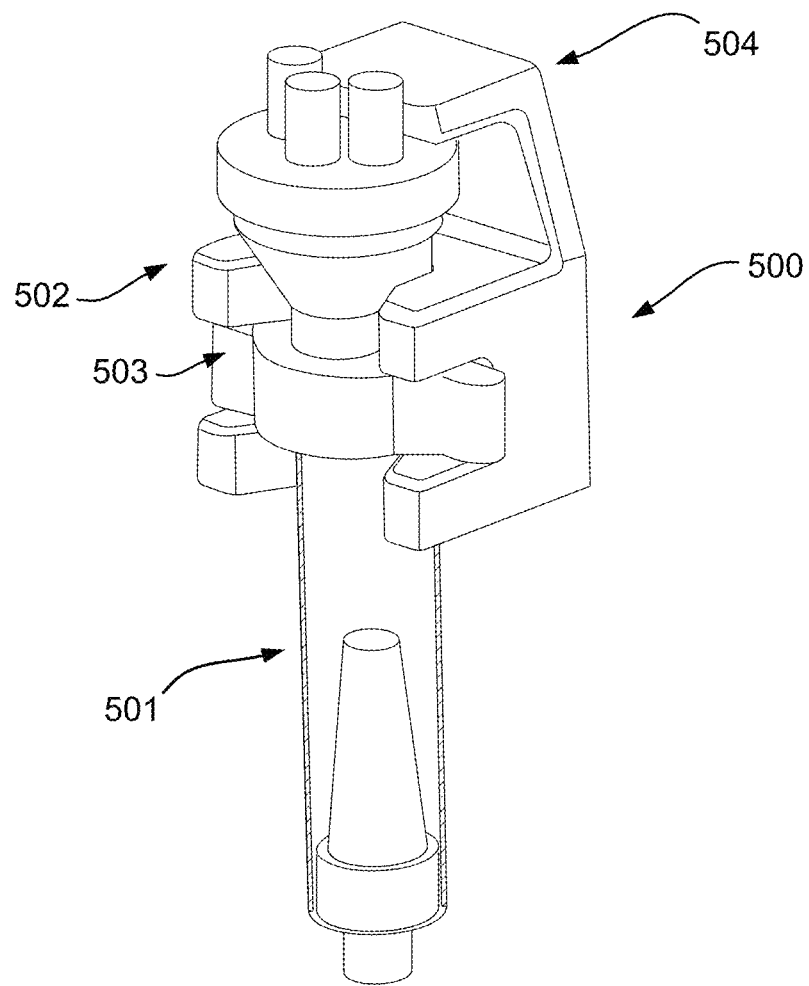
Figure 19:
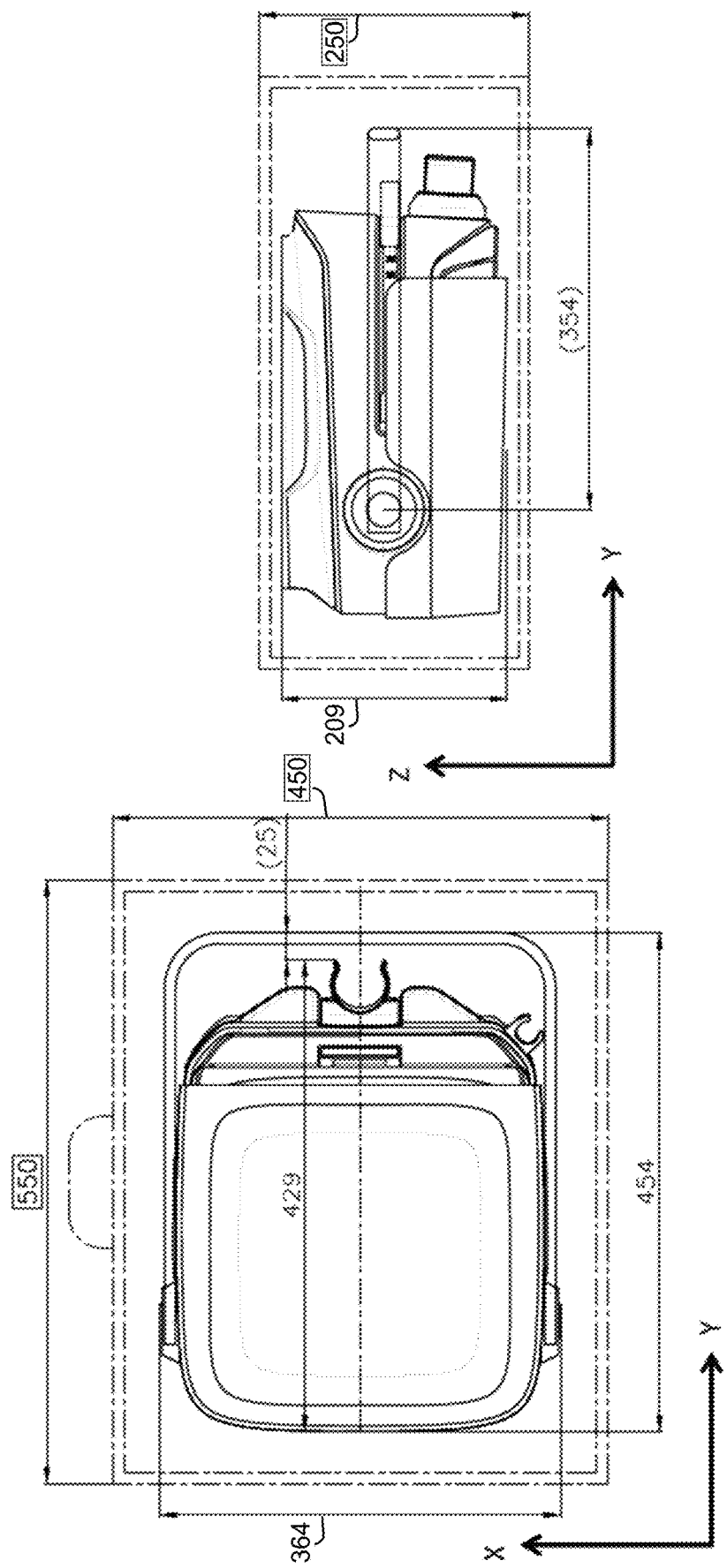
Figure 20:
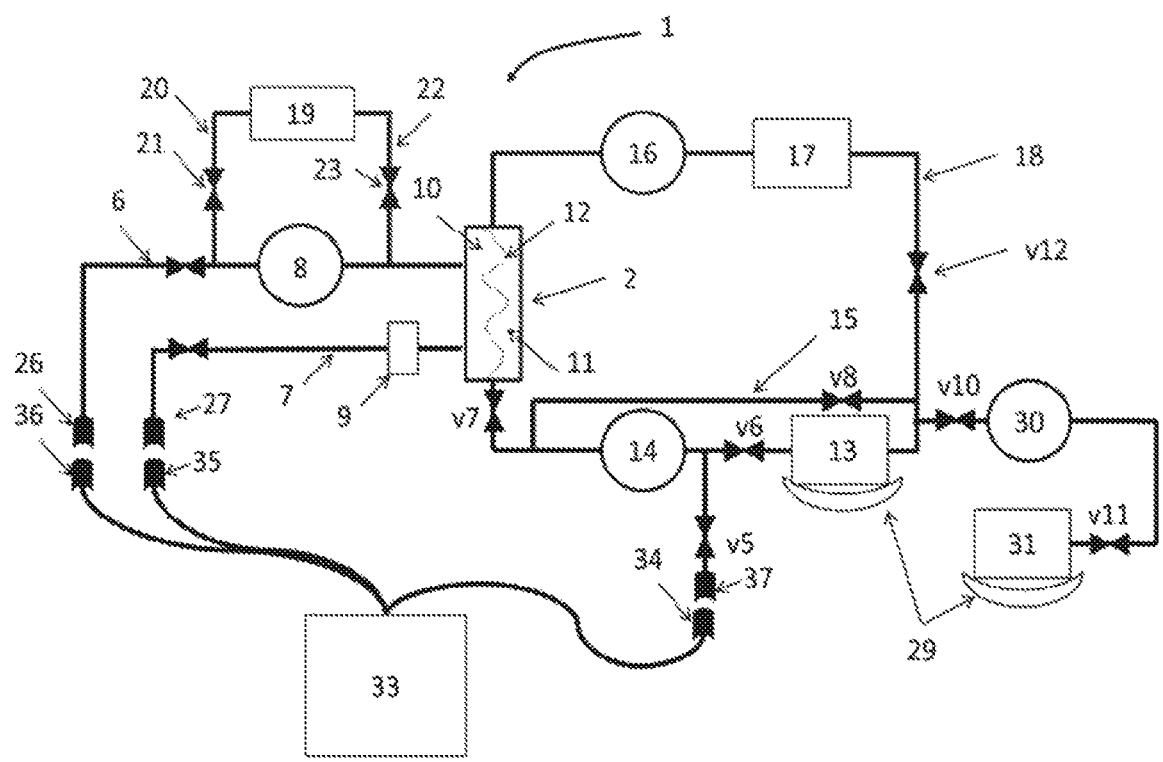
Figure 21:
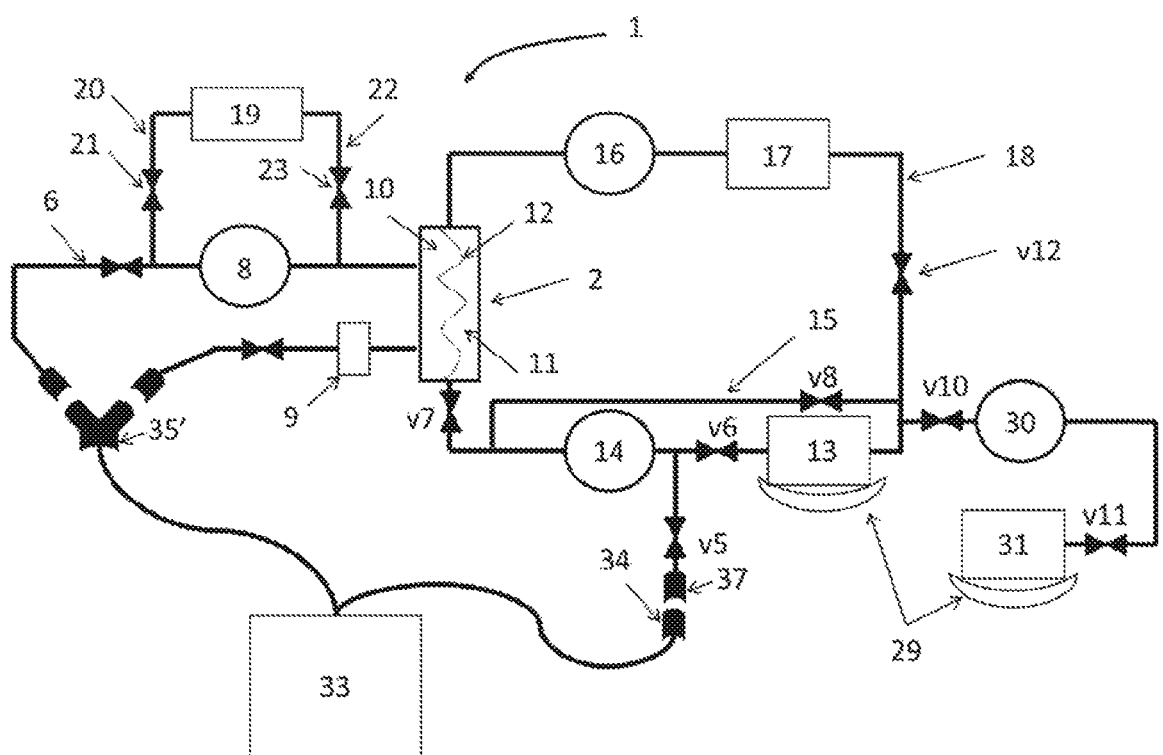

FIGS. 5a, b, b', c and c' illustrate cross-sectional views of cassette;

FIG. 6 shows the elements of the fluid pump;

FIG. 7 shows the system in operating configuration without the disposable part;

FIG. 8 shows the system in operating configuration without the disposable part;

FIG. 9 shows the insertion of a blood cassette into a dedicated opening of the system;

FIG. 10 shows the insertion of a dialysate cassette into a dedicated opening of the system;

FIGS. 11a, 11b, 12a, 12b and 12c show the apparatus in a first configuration (required for the treatment), a second configuration (enabling saving space) and a third configuration (optional 12b) (enabling the preparation of the treatment for example to access the container receiver);

FIG. 13 illustrate different views of the loading process of the cassette;

FIG. 14 shows an exploded view of one embodiment of the loading system;

FIG. 15 shows different positions of the loading system with or without cassette;

FIG. 16 shows an exploded view of one embodiment of the loading system;

FIG. 17 shows a 3d view of one embodiment of the loading system;

FIG. 18 shows a drip chamber and its support;

FIG. 19 shows a dialysis system stored in a hand luggage;

FIGS. 20 and 21 show an illustration of the system using a priming container.

FIGS. 22, 23, 24, 25 and 26 show several embodiments of openings and cassettes according to the invention.

Figure 27:
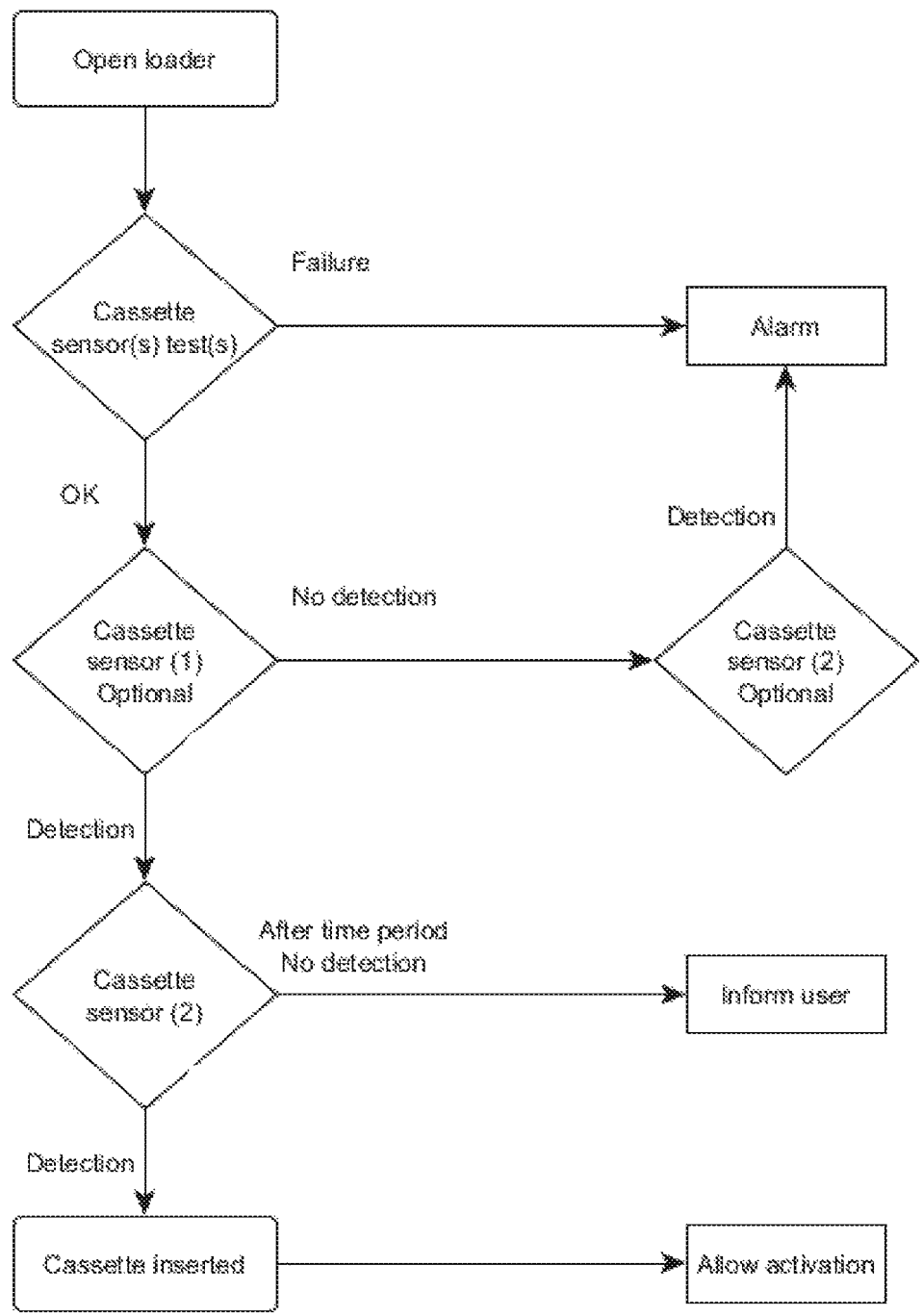

FIG. 27 shows a flowchart of cassette detection process.

Figure 28:
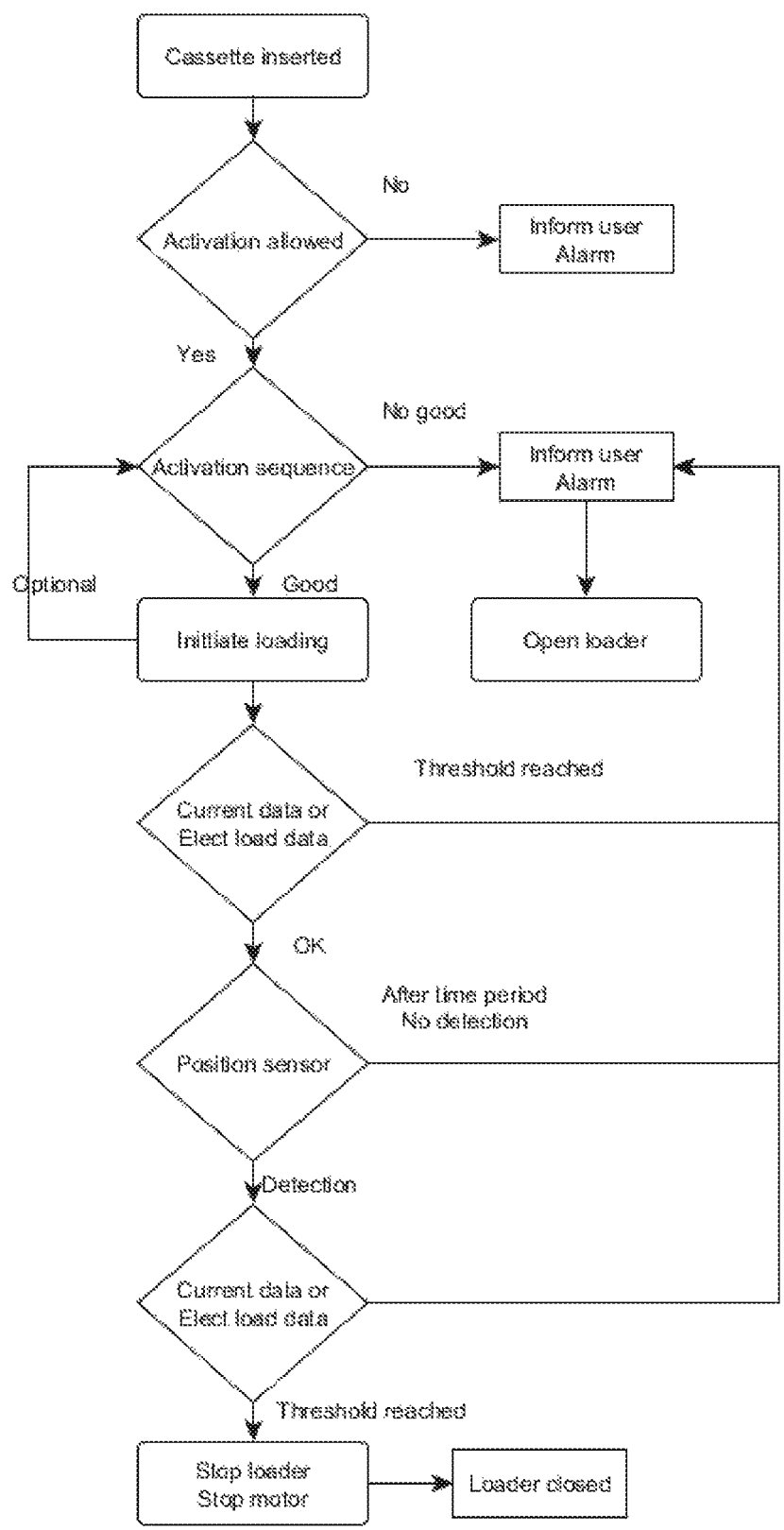

FIG. 28 shows a flowchart of loader position detection process.

Figure 29:
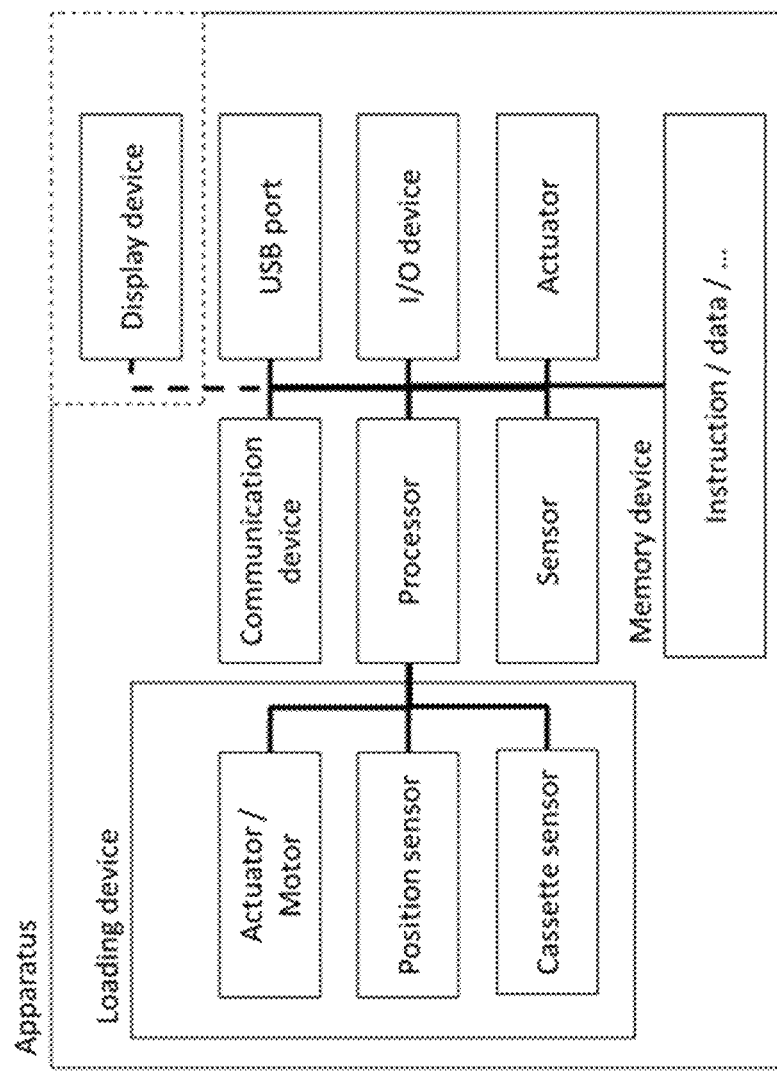

FIG. 29 shows a schematic view of an electronic device of the apparatus.

FIGS. 30a to 30h illustrate several positions of the door device.

FIGS. 31a and 31b show two embodiments of the door device.

Figure 32:
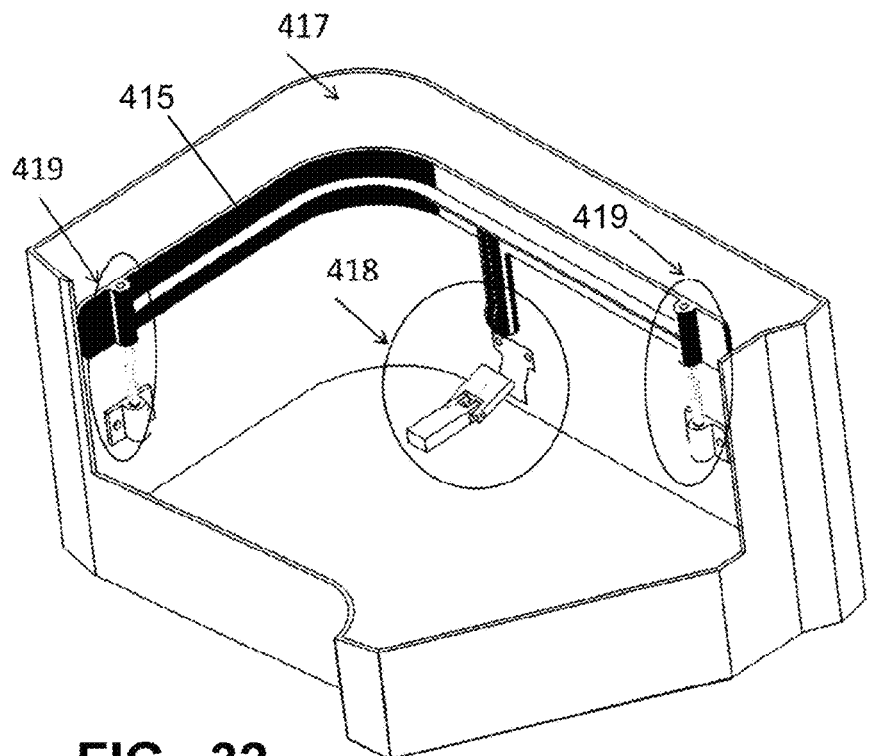

FIG. 32 is an interior view of the FIG. 31a or of the FIG. 31b.

FIGS. 33, 34, 35 and 36 show different views of a potential embodiment 600.

Figure 37:
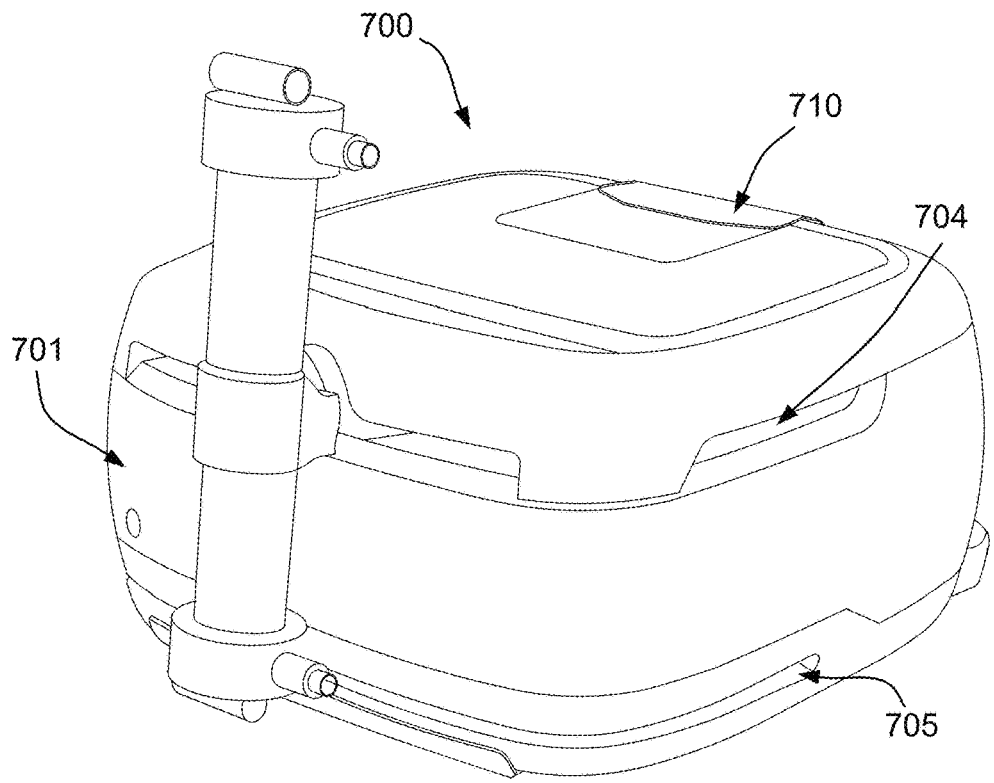
Figure 38:
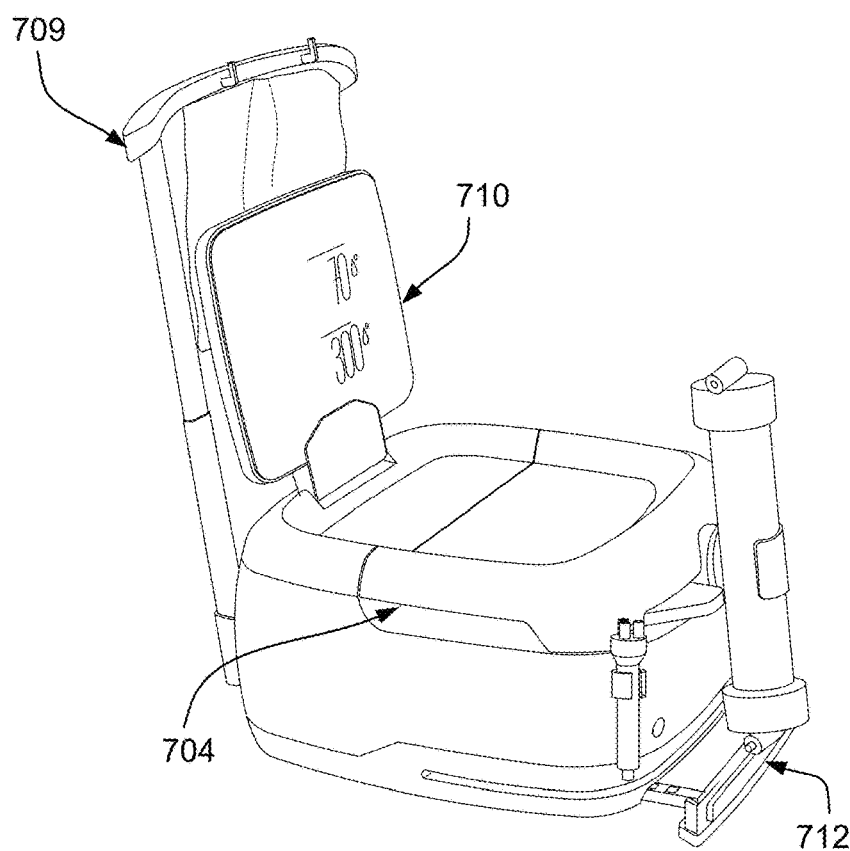
Figure 39:
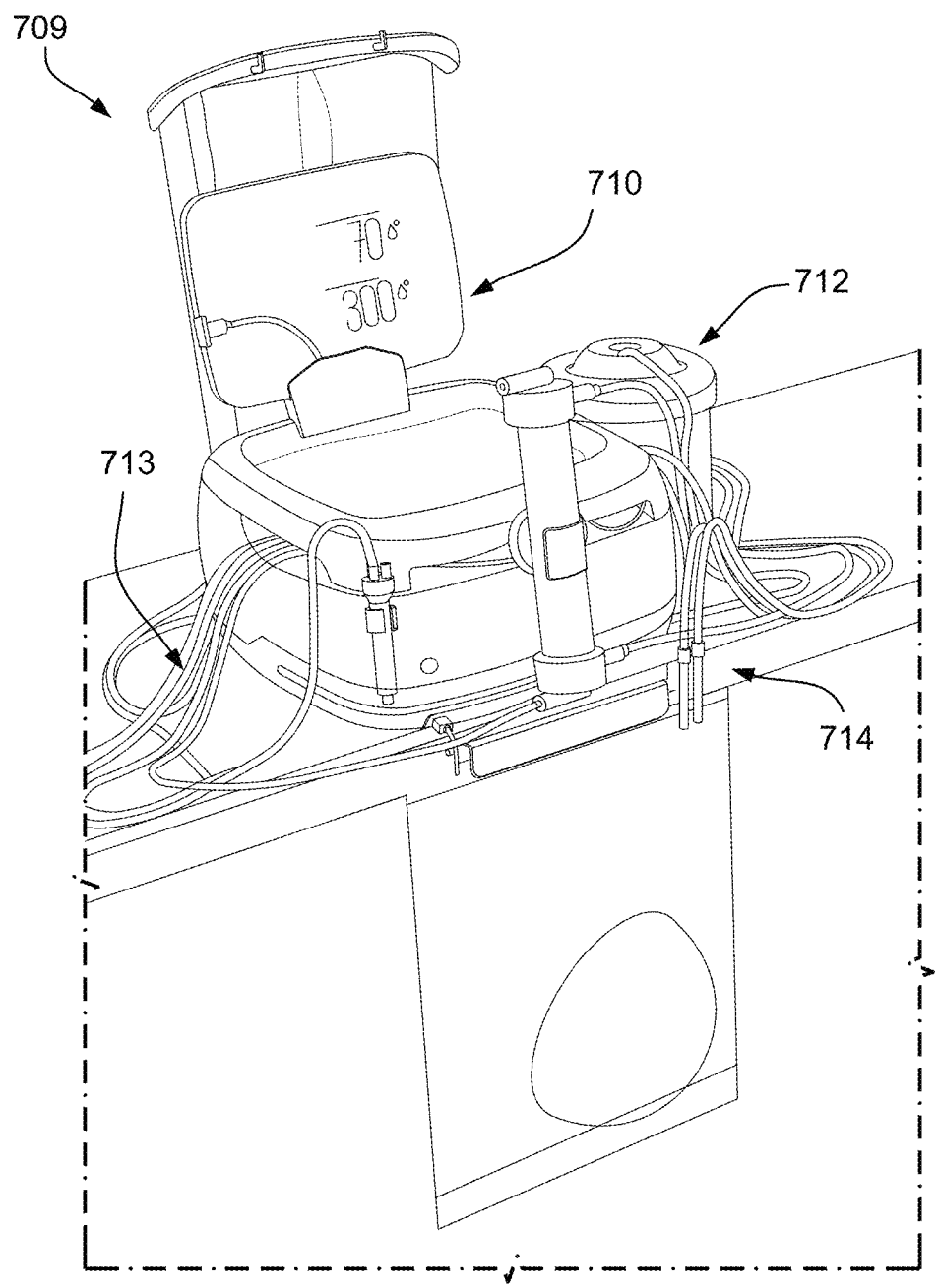

FIGS. 37, 38 and 39 show different views of a potential embodiment 700.

Figure 40:
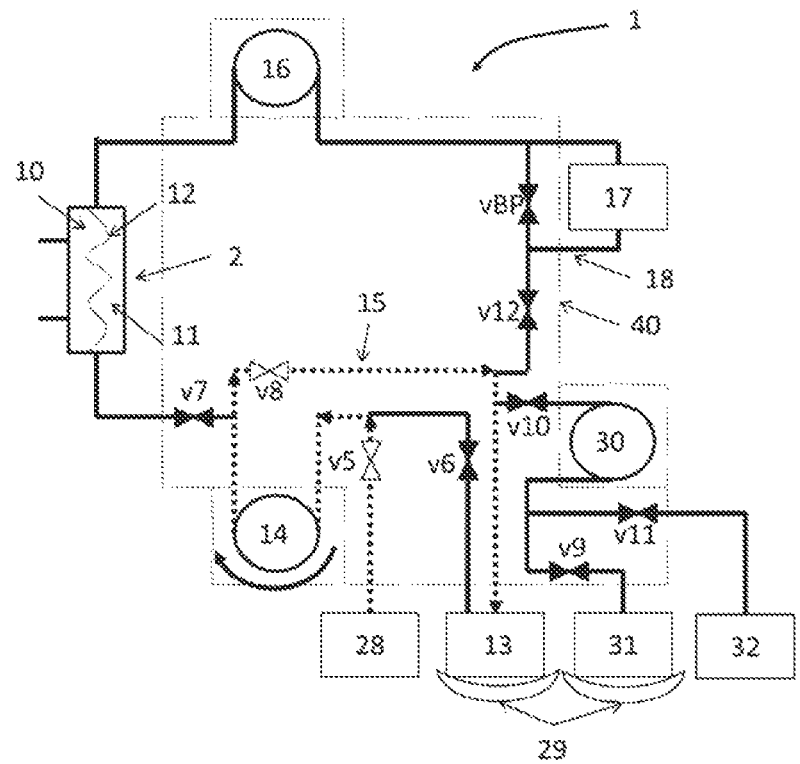

FIG. 40 illustrates a priming process of the container 13.

Figure 41:
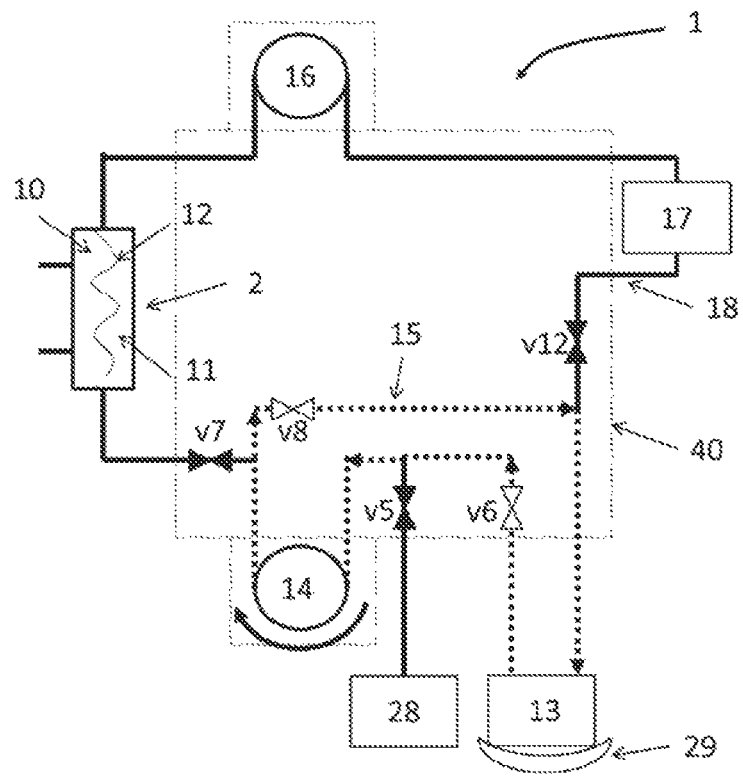

FIG. 41 illustrates a priming process of lines connected to the container 13.

Figure 42:
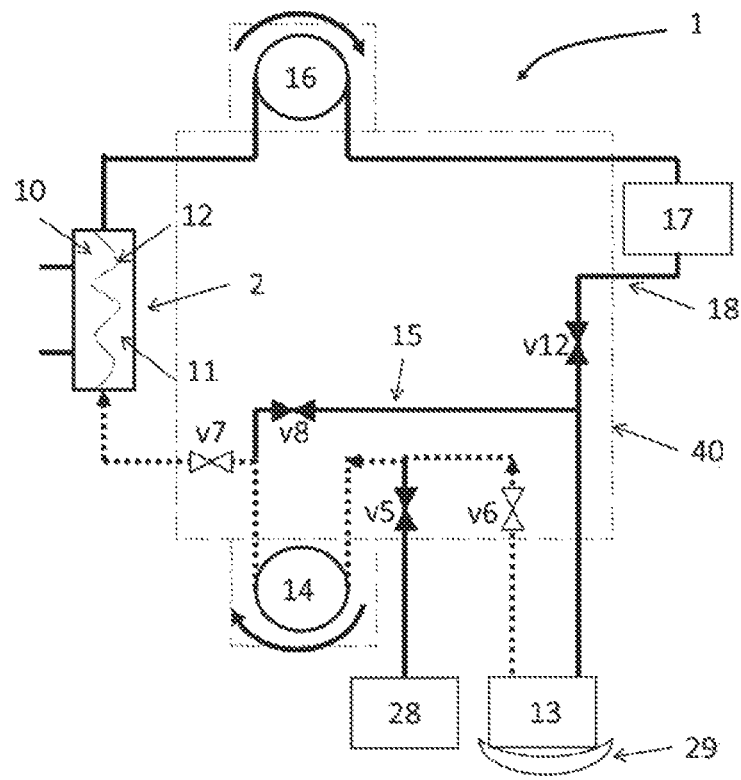

FIG. 42 illustrates a priming process of the line arranged upstream of the dialyzer.

Figure 43:
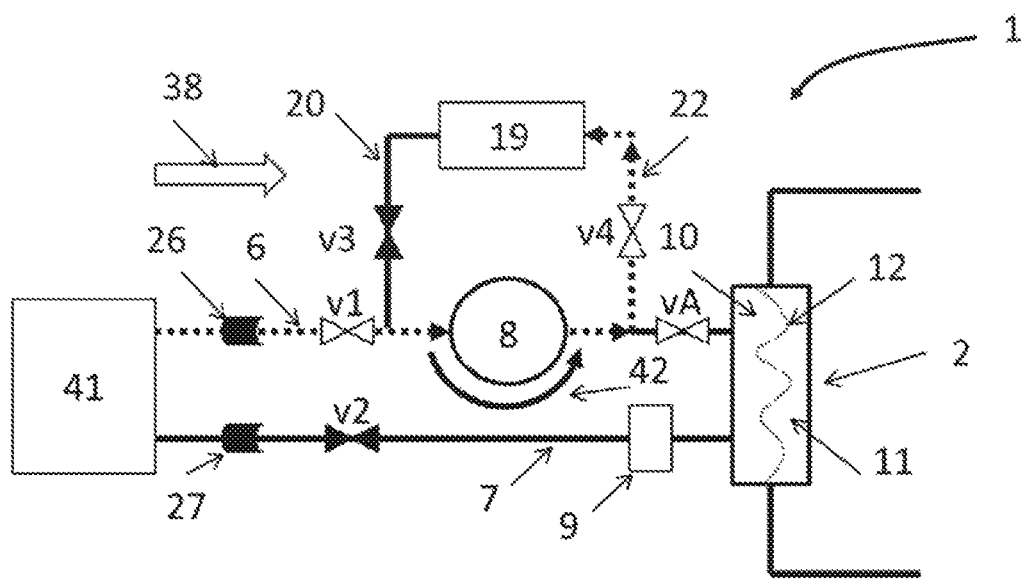

FIG. 43 illustrates a priming process of the blood return container.

Figure 44:
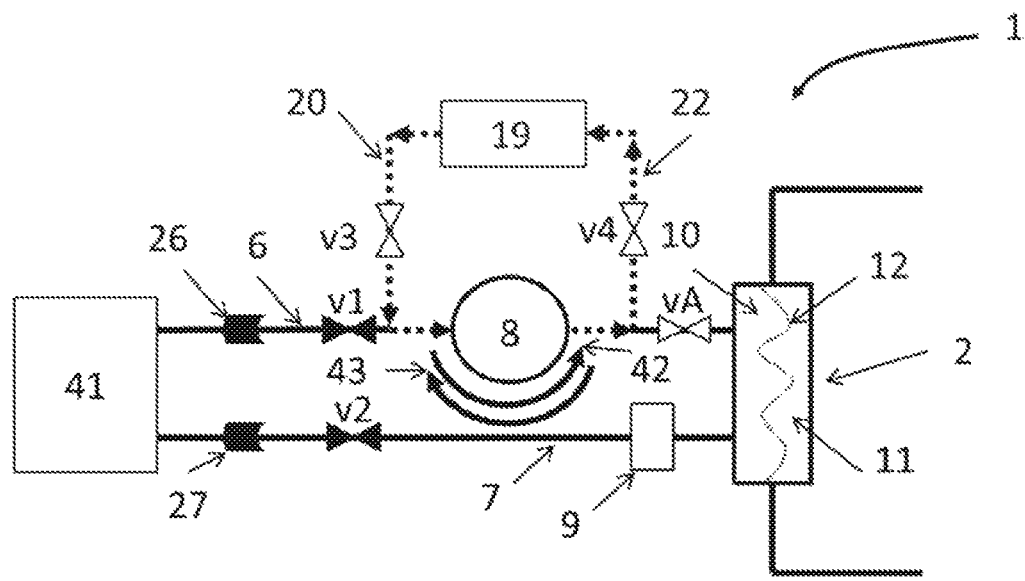

FIG. 44 illustrates a priming process of lines connected to the blood return container.

Figure 45:
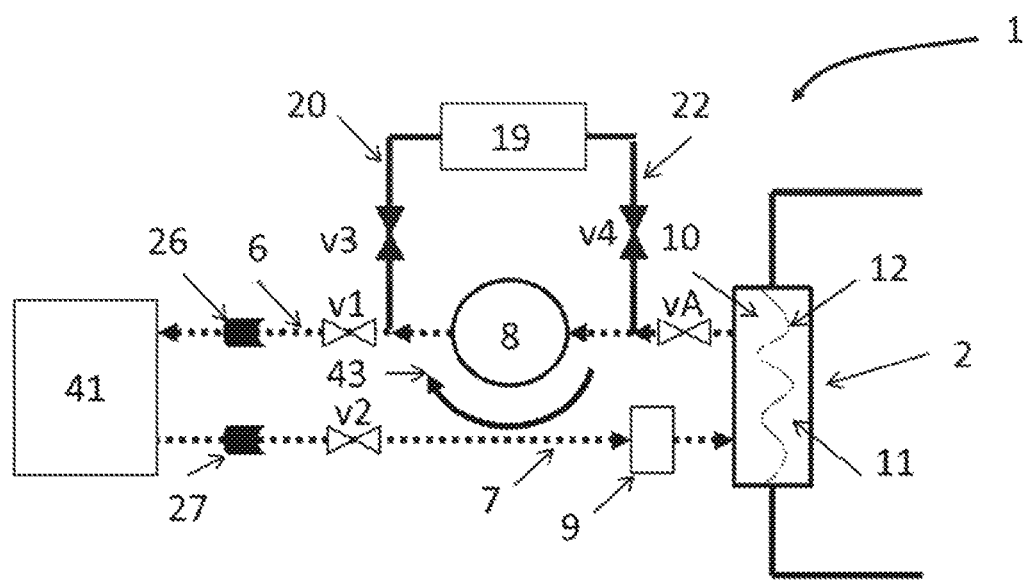

FIG. 45 illustrates a priming process of the venous line.

Figure 46:
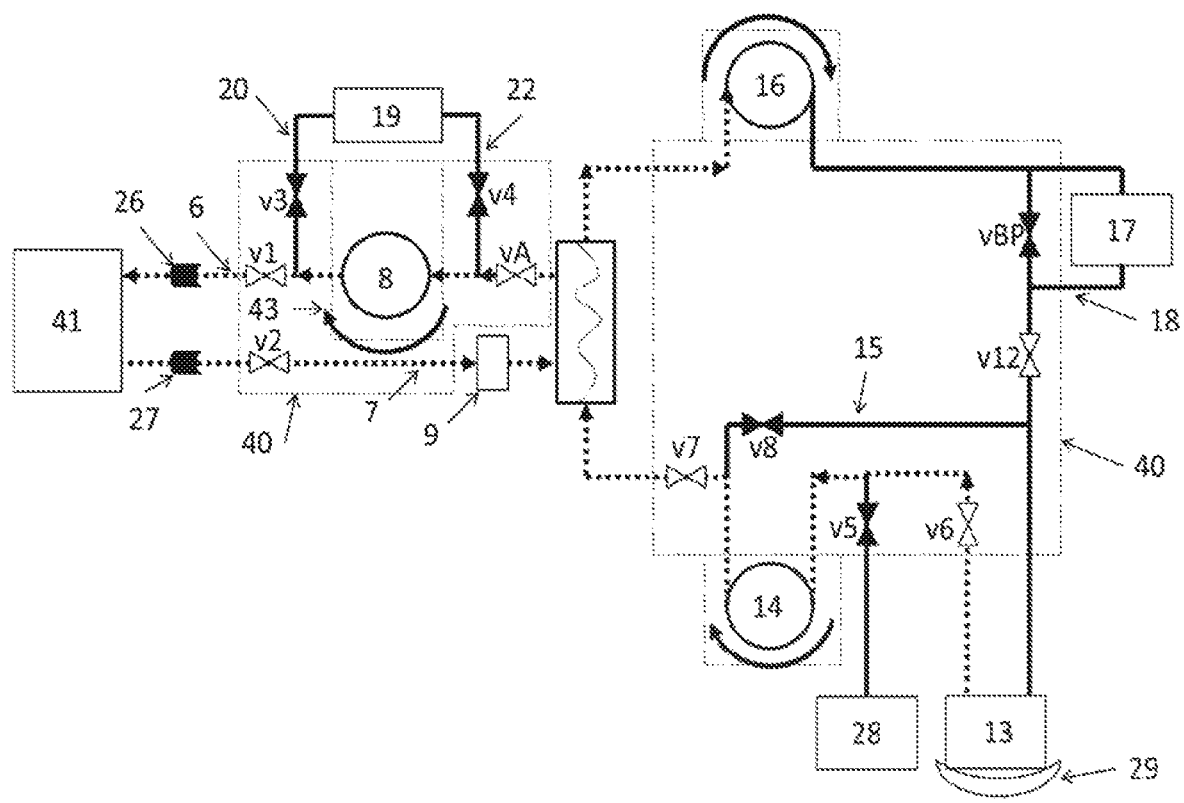

FIG. 46 illustrates a priming process of the dialyzer.

Figure 47:
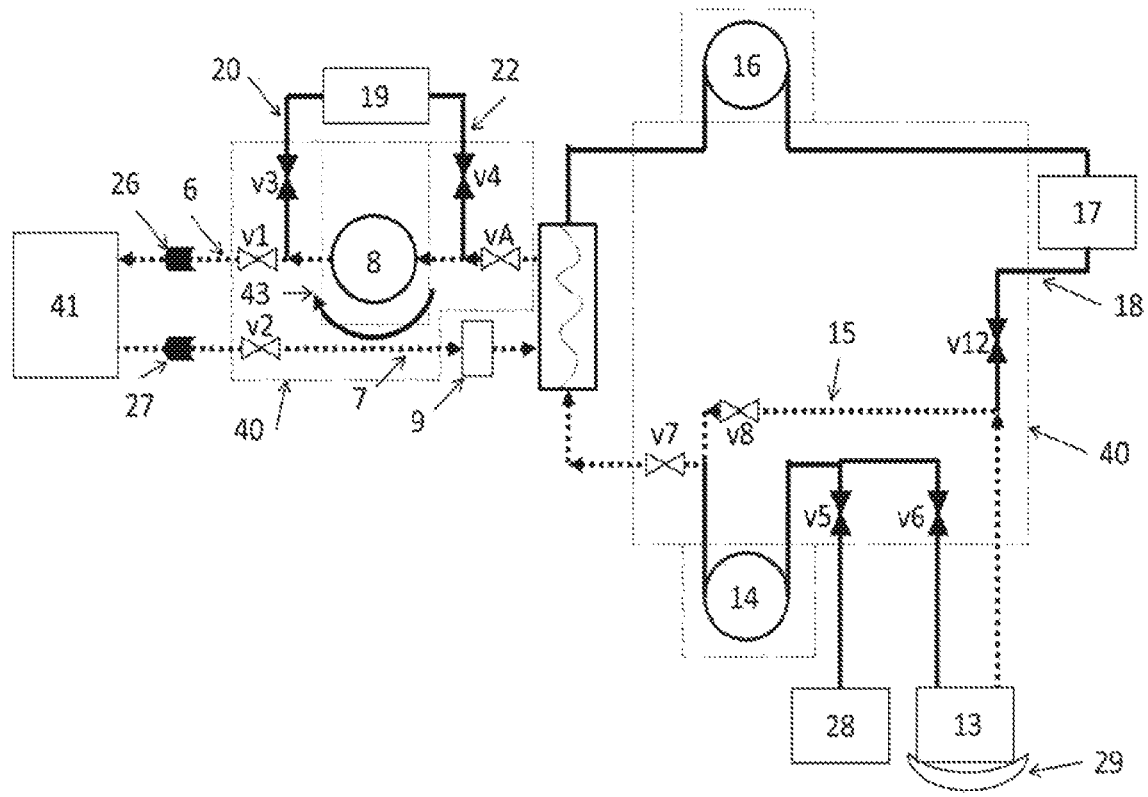

FIG. 47 illustrates a priming step of the blood circuit.

Figure 48:
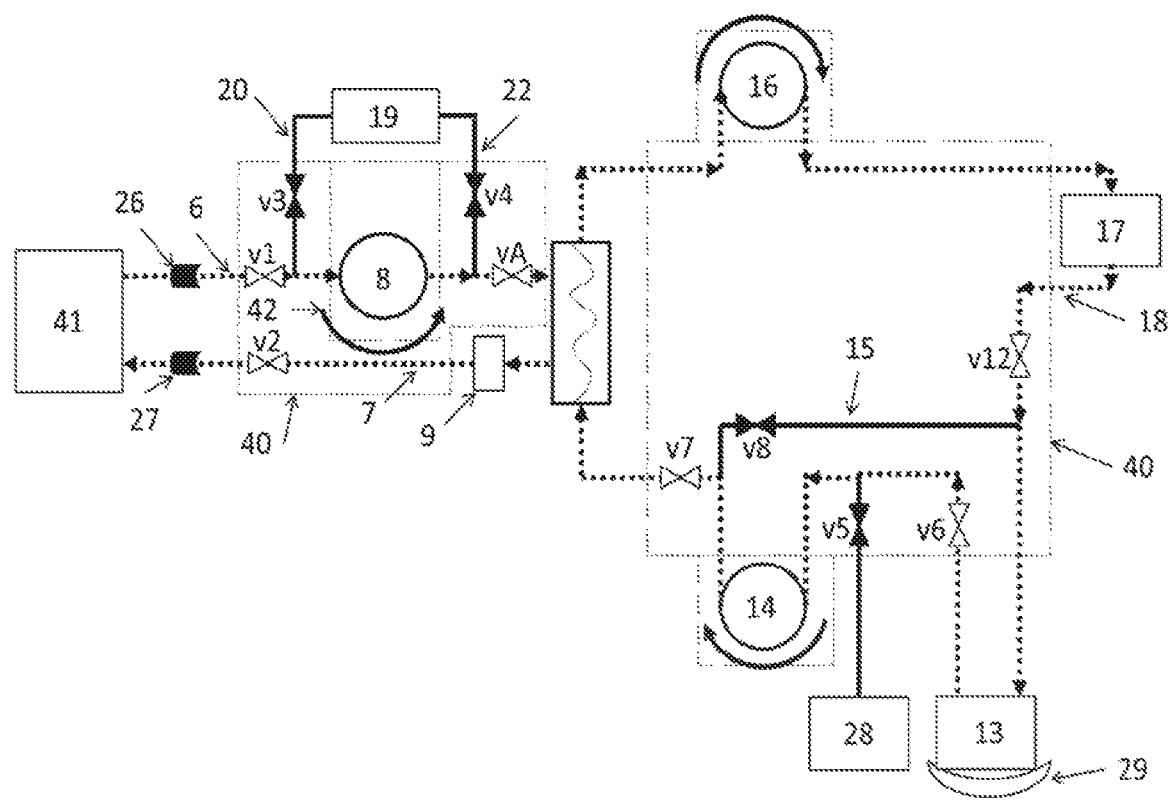

FIG. 48 illustrates a priming step of the dialysate circuit.

Figure 49:
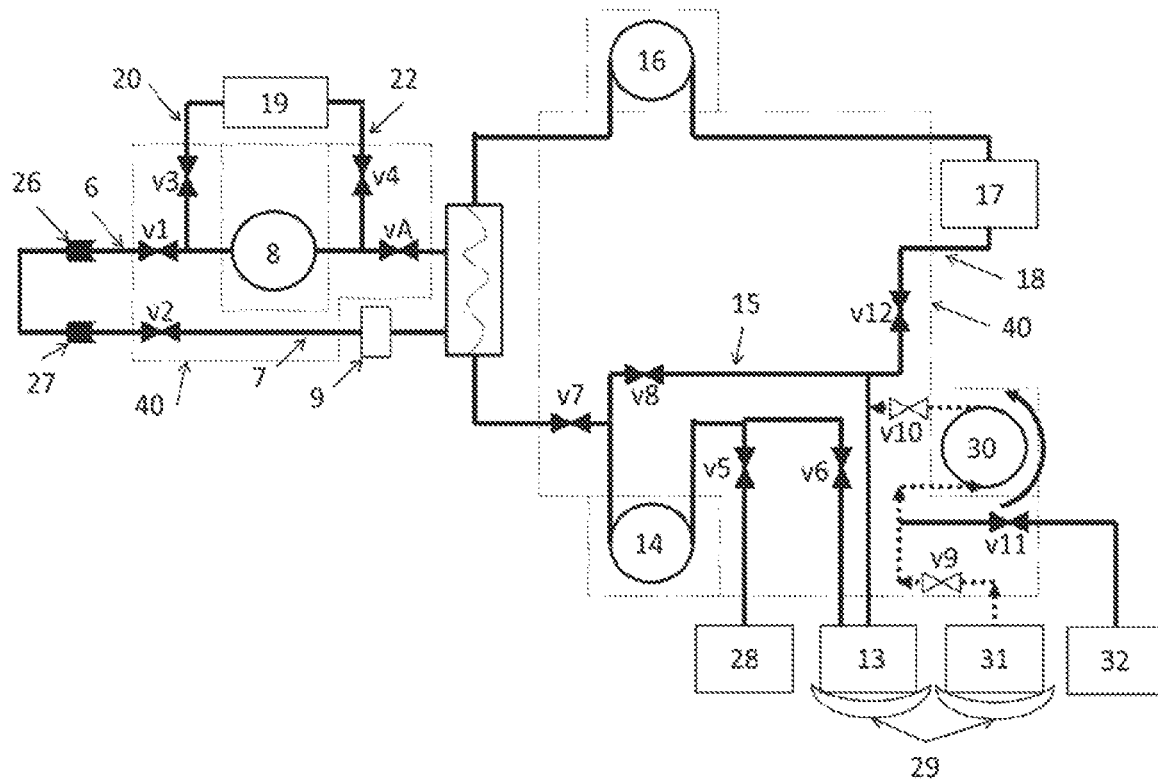

FIG. 49 illustrates a priming process of an additive line.

Figure 50:
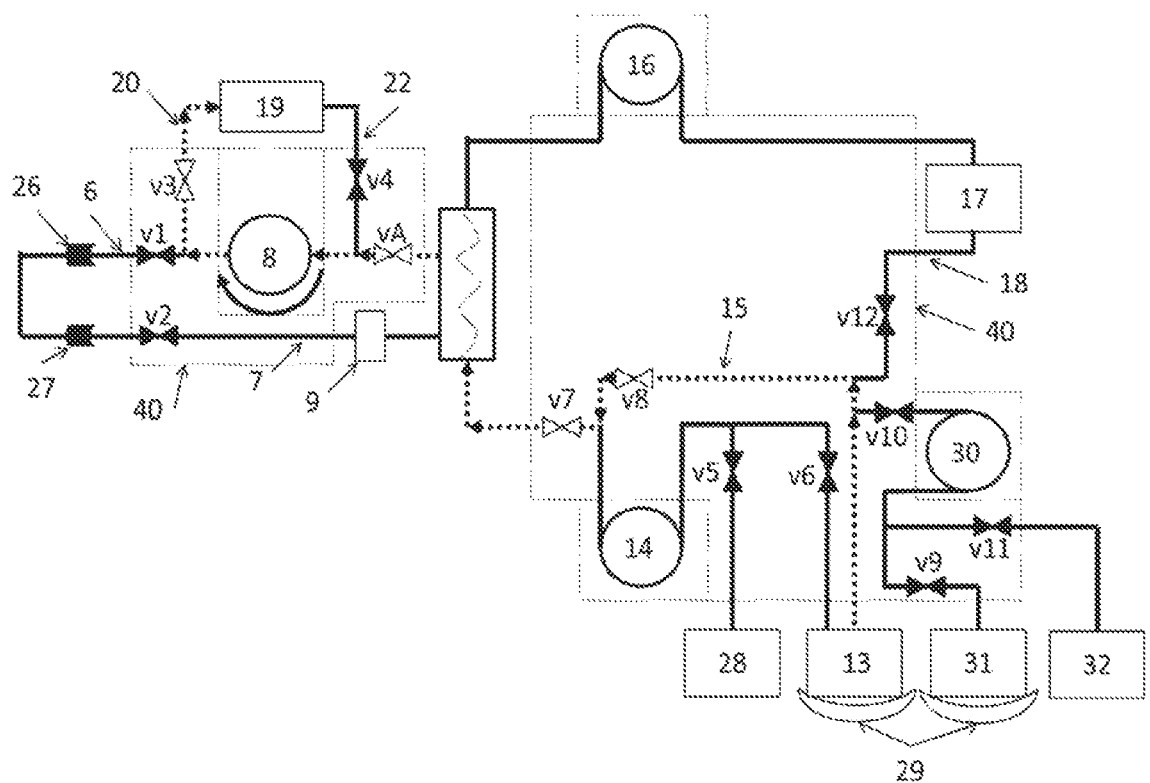

FIG. 50 illustrates a priming process of a part of the blood circuit.

Figure 51:
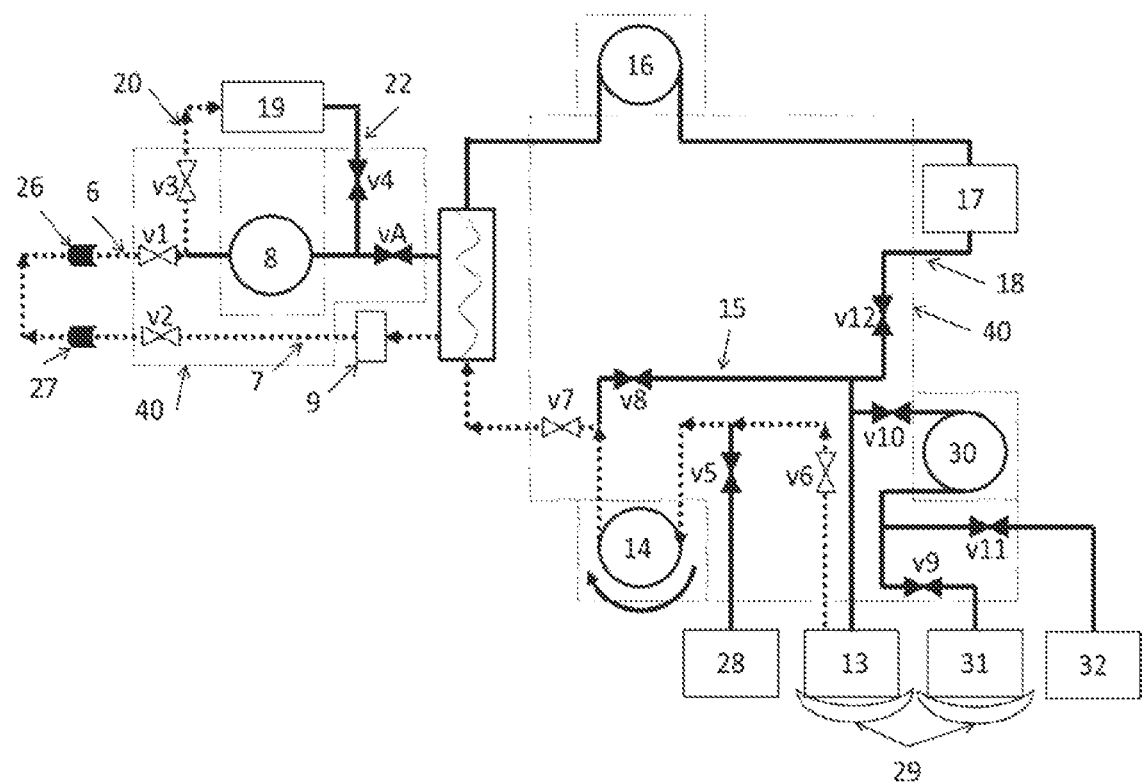

FIG. 51 illustrates a priming process of a part of the blood circuit.

Figure 52:
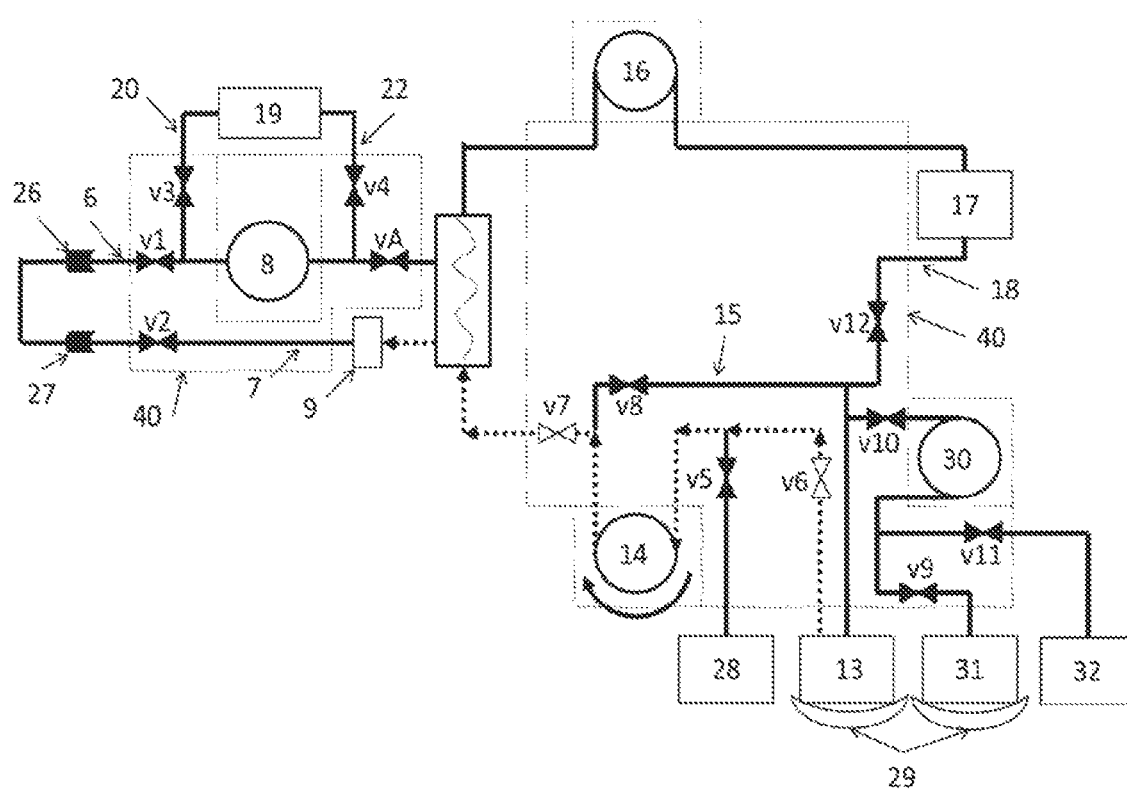

FIG. 52 illustrates a priming process of a drip chamber.

Figure 53:
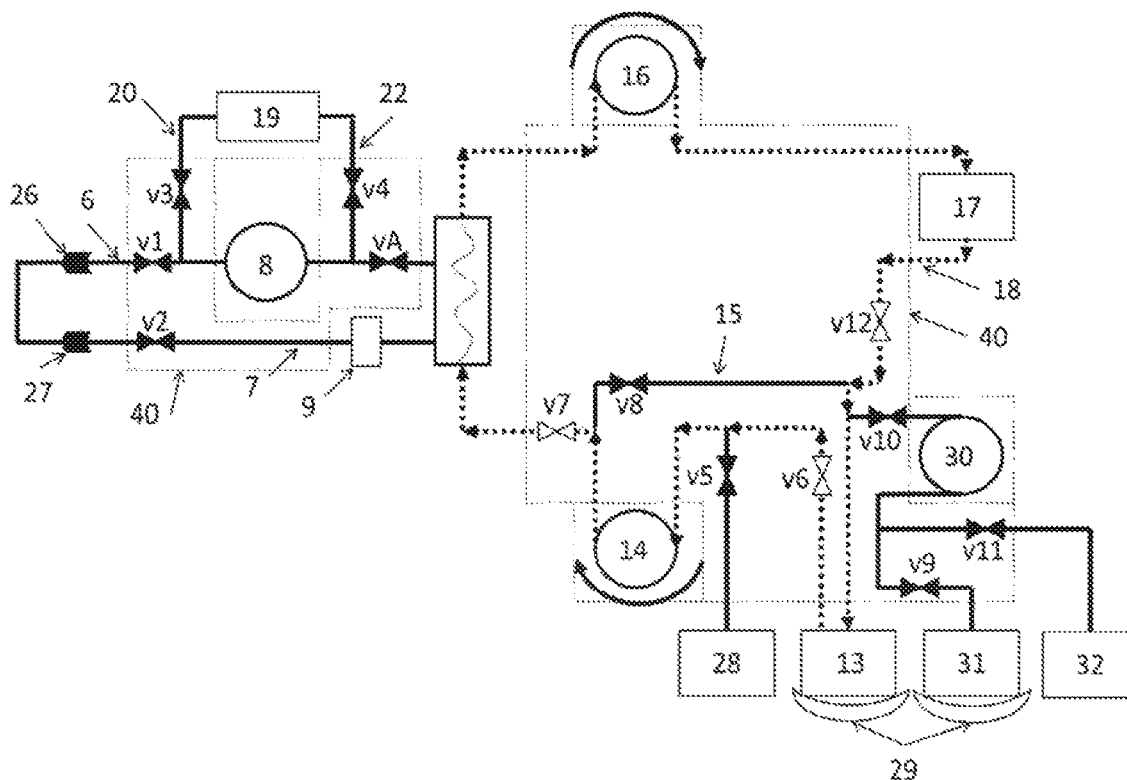

FIG. 53 illustrates a priming step of the dialysate circuit.

Figure 54:
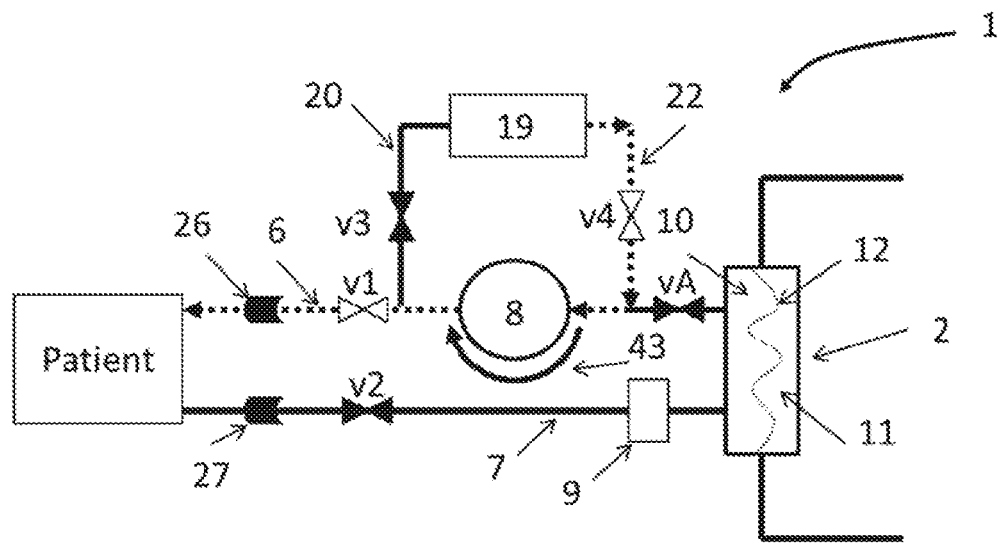

FIG. 54 illustrates a first blood return step.

Figure 55:
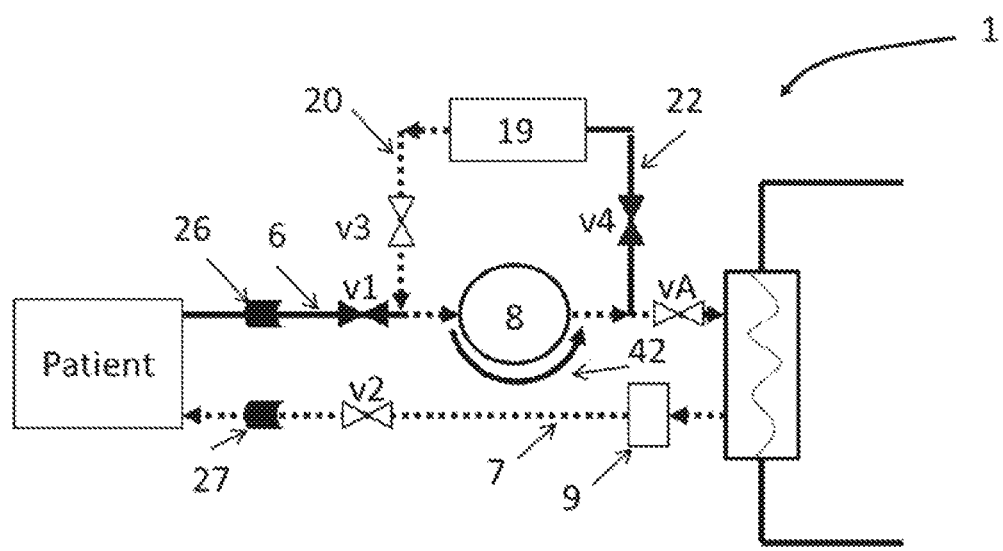

FIG. 55 illustrates a second blood return step.

FIGS. 56, 57, 58, 59, 60 and 61 illustrate several priming sequences according to an embodiment.

FIGS. 62, 63, 64, 65, 66, 67 and 68 illustrate several priming sequences according to an embodiment.

FIGS. 69, 70, 71, 72, 73, 74 and 75 illustrate several priming sequences according to an embodiment.

LIST OF ELEMENTS 1 extracorporeal blood treatment system
2 dialyzer
3 blood circuit
4 dialysate circuit
4' additional circuit/line for example (concentrate or initial supply circuit)
5 patient
6 arterial line
7 venous line
8 blood pump
9 drip chamber
10 first chamber
11 second chamber
12 membrane
13 bag/container
14 first dialysate pump
15 dialysate line
15' by pass line
16 second dialysate pump
17 element for receiving the solution from the diaylzer
18 loop line
19, 19', 19" container (blood return container) (internal or storing compartment of a container)
20 line
21 valve
22 line
23 valve
24 arterial valve
25 venous valve
26 arterial connector
27 venous connector
28 initial supply container
29 weight balance
30 pump
31 supply container (for example concentrate supply bag)
32 supply container
33 single priming container (internal or storing compartment of a container)
34 first connector
35, 35' second connector
36 third connector
37 dialysate circuit connector
38 normal flow direction (blood circuit)
39 normal flow direction (dialysate circuit)
40 potential limit of the cassette
41 supply container (internal or storing compartment of a container)
42 normal pumping direction
43 reversed pumping direction
44 sorbent connector
45 first spike
100 second spike
100 blood purification system
101 disposable part
102 reusable part/apparatus
103 dialyzer
104 sorbent
105 bag
106 cassette
107 rigid frame
108 membrane
109 handle
110 processor
111 screen (device for example tablet with a touch screen)
112 other element such as button
113 sensor
114 actuator
115 other elements connected to the processor and operatively and removably coupled to the disposable part
116 tube
120 cavity
121 port
122 handle
123 valve seat
124 fluid pathway
200 cassette with a part of a pump
201 flexible tube
202 fluid pathway of the cassette
203 inlet port of the pump
204 outlet port of the pump
205 roller assembly
206 roller support
207 shaft
208 roller
300 apparatus (reusable part)
301 housing 302 display device
303 screen support
304 container support
305 additional screen
306 power button
307 emergency button
308 dialyzer support
309 drip chamber support
310 first opening
311 second opening
312 pole
313 hook
314 rotating fixing element
315 movable container support
316 container receiver
317 fixing element
318 recess
319 first portion
320 second portion
321 front panel
322 side panel
323 side panel
324 opening of the first side
325 opening of the second side
326 insertion direction
327 first side of the housing
328 second side of the housing
400 loading system
401 cassette holder
402 dedicated active element (for example sensor)
403 dedicated active element (for example valve actuator)
404 dedicated active element (for example motor of the pump)
405 shaft of the motor
406 support of the dedicated active elements
407 movement of the cassette holder
408 movement of the dedicated active element
409 drive mechanism
410 motor
411 drive assembly
412 guiding assembly
412' guiding or sliding element
413 support of guiding element
414 pin
415 door
416 door actuator
417 housing interior
418 lock system
419 opening
420 part of housing
421 elastic element
422 coupling element
423 flexible element
500 drip chamber support
501 drip chamber
502 body
503 lock
504 mechanical coding system
600 dialysis system
601 apparatus
602 blood cassette
603 dialysate cassette
604 first door
605 second door
606 dialyzer
607 housing
608 dialyzer support
609 pole
610 display device
611 weighting scale
612 sorbent device
613 tubes
614 weighting bag
615 apparatus support
700 dialysis system
701 apparatus
702 blood cassette
703 dialysate cassette
704 door
705 heating compartment
706 dialyzer
707 housing
708 dialyzer support
709 pole
710 display device
711 weighting scale
712 sorbent device
713 tubes
714 weighting bag
715 apparatus support

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. It is to be understood that even if the document describes a haemodialysis system, some embodiments described therein may also be used for or arranged in a peritoneal dialysis system or other blood treatment purification systems such as for example continuous renal replacement therapy (CRRT). The following detailed description, therefore, is not to be taken in a limiting sense.

All scientific and technical terms used herein have meanings commonly used in the art unless otherwise specified. The definitions provided herein are here to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" and "1" are generally employed in its sense including "and/or" unless the content clearly dictates otherwise.

As used herein, "solution compatible with blood" or the like generally means "a physiologically compatible solution for contacting blood, a physiologically compatible solution for infusion to a subject or a solution for blood rinse back to a subject".

As used herein, "at least one of A, B, and C", "at least one of A, B or C", "selected from the group consisting of A, B, C, and combinations thereof" or the like are used in their open ended sense including" only A, or only B, or only C, or any combination of A, B and C" unless the content clearly dictates otherwise.

The texts or terms written in brackets have to be understood as an optional feature, a synonym, the similar terms or an example.

Fluid Circuit(S)

Figure 1:
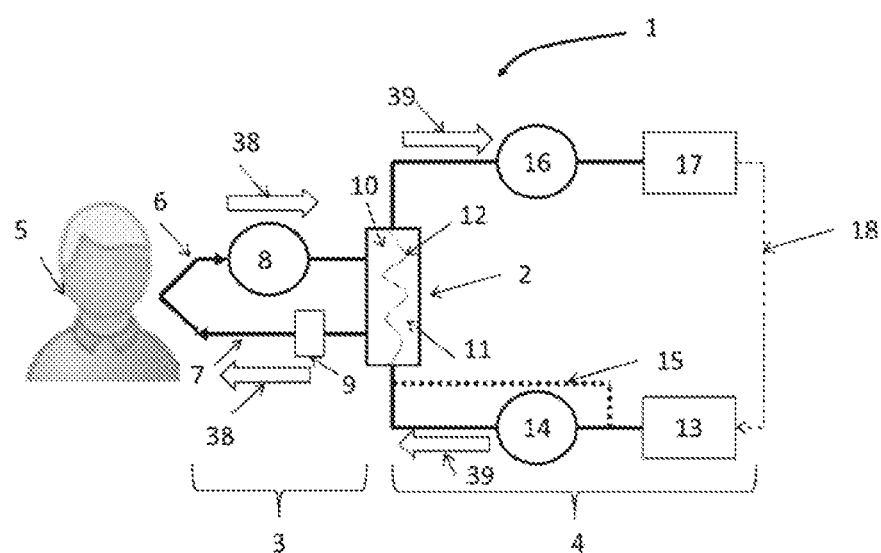

Referring to the FIG. 1, the extracorporeal blood treatment system 1 may comprise a dialyzer 2, a blood circuit 3 and a dialysate circuit 4.

The blood circuit 3 (also called extracorporeal circuit) connects the patient 5 to the dialyzer 2. More specifically, the blood circuit 3 comprises an arterial (blood) line 6 and a venous (blood) line 7 which connect the patient 5 to the dialyzer 2. The arterial line 6 may comprise a removable arterial connector 26 intended to be connected to a patient and the venous line 7 may comprise a removable venous connector 37 intended to be connected to a patient The blood circuit 3 comprises at least one pump 8 for pumping fluid through the blood circuit, for example blood to or from the dialyzer 2. The blood pump 8 may be, for example, a peristaltic pump, a pumping chamber, . . . . Further, a clamp may be arranged and located in the blood circuit 3, for example a valve. Still further, an air sensor may be located within the extracorporeal circuit. The air sensor may, for example, detect the presence of air within the extracorporeal circuit. A drip chamber may be arranged and located within the extracorporeal circuit, for example in the venous line 7. The drip chamber may, for example, remove the air bubbles present in the blood circuit. An air sensor may be arranged downstream a drip chamber and/or upstream at least one of a valve and the removable venous connector 27. Air (or other fluid or gas) may be present in the blood circuit 3 prior to the treatment. As a result, the patient or other health professional may need to prime the extracorporeal circuit 3 by removing it, as described thereafter.

The dialyzer 2 has a first chamber/compartment 10 in which the blood is moved through, an arterial (blood) port by which the blood is entered and a venous (blood) port by which the blood is exited from. The dialyzer 2 has a second chamber/compartment 11 in which a dialysate solution is moved through, a first (dialysate) port by which the dialysate solution (more particular a fresh dialysate or regenerated dialysate) is entered and a second (dialysate) port by which the dialysate solution (more particular an used dialysate) exits the dialyzer. The used dialysate is a dialysate solution which exits from the second dialysate port and may comprise ultra-filtrate (mixed to other liquids). The ultra-filtrate is a liquid which comprises the excess water of the patient. The dialyzer 2 has a membrane 12 separating the first chamber from the second chamber. The membrane may be adapted (for example, the membrane may be semi permeable) to allow passage of fluid or components from the first chamber to the second chamber (and/or inversely from the second to the first chamber).

The dialysate circuit 4 comprises at least one pump adapted to convey a fluid through the dialysate circuit 4, for example a dialysate solution to or from the dialyzer 2. Preferentially, the dialysate circuit 4 may have a first dialysate pump 14 adapted to pump a solution (for example, a solution stored in the bag 13) to the dialyzer 2. The bag 13 may store a dialysate solution as a fresh dialysate or other solution as a priming solution. The bag 13 may be initially empty. The bag 13 may be in fluid communication with the dialyzer 2 via a fluidic line. This fluidic line may include the first dialysate pump 14 or may be a by-pass adapted to by-pass the fluidic line including the first dialysate pump 14. The fluidic line may comprise a valve in order to open or close the fluidic communication between the bag 13 and the dialyzer 2. The dialysate circuit 4 may have a second dialysate pump 16 adapted to pump the solution exiting from the dialyzer 2, such as the used dialysate and/or the ultrafiltrate. This solution may be moved up to an element 17 which is adapted to receive for example the used dialysate and/or ultratfiltrate. This element may be a bag (adapted to store the solution) or a sorbent device (adapted to clean or to regenerate the solution). The dialysate circuit may comprise a loop line 18 adapted to allow a fluid communication between the bag 13 and the element 17 (in particular when the element 17 is a sorbent). In this case the bag 13 comprises an outlet in fluidic communication with the dialyzer 2 and an inlet in fluidic communication with the element 17 (for example a sorbent device). The dialysate circuit may comprise at least one of valve and sensor such as a pressure sensor, level sensor, weight scale, flow meter, blood sensor, ammoniac sensor, . . . . The dialysate pump may be, for example, a peristaltic pump, a pumping chamber, . . . . Air (or other fluid or gas) may be present in the dialysate circuit prior to the treatment. As a result, the patient or other health professional may need to prime the dialysate circuit by removing it, as described thereafter. A by-bass may be arranged between the second dialysate pump 16 and the bag 13 in order to by pass the element 17 (for example the sorbent device when the sorbent is no longer usable).

Blood Circuit

Turning now to the FIG. 2, the blood circuit may comprise a bag 19 adapted to receive and/or to store a solution and to be in direct fluid communication with the arterial line and/or with the venous line. The term "direct fluid communication" is employed here as "physically and fluidly connected to and in fluid communication at least temporarily with" without passing by another fluid pathway, filter, dialyzer, sorbent or pump. A valve may be used in order to control (by the apparatus, automatically or not) the direct fluid connection. The bag 19 may be empty at the start of the treatment. The bag 19 may be filled with a saline solution or other solution compatible with blood. The bag 19 may be used to prime the blood circuit and/or to push the blood back to the patient, as described thereafter. Preferentially, the bag 19 may be initially substantially empty (of liquid and/or of gas) and sterilised. During the priming process of the blood circuit, the bag 19 may be filled with a priming solution (which may be a saline solution or a dialysate solution or other) and/or with the fluid (for example the gas) initially stored in the fluid pathway of the blood circuit before the treatment. The bag 19 may comprise a degassing device such as a vent with a hydrophobic membrane in order to expel the gas (for example air) which may be stored or injected into the bag (the storing compartment of the bag). The bag 19 may be sized in order to store a volume of fluid which is substantially equivalent or superior (for example more or less twice the volume defined thereafter) to a volume defined by the interior wall of the blood circuit (for example the volume defined by the interior of the tube, of the cassette, of the blood compartment of the dialyzer and/or of the drip chamber . . . ). The bag 19 may be advantageously filled with the priming solution during the priming process, then the bag stores this solution during the treatment and at the end of the treatment, this solution may be used to push the blood back to the patient.

A volume fraction of the solution stored in the bag 19 may be injected into the blood circuit in the event of blood pressure reduction of the patient during the treatment. Thus, the system limits the amount of fluid necessary for the priming and the rinsing back process, even more when the priming solution is a dialysate solution or saline solution. Thus only one liquid solution (or a limited number of distinct solutions) may be prepared or added or used for the treatment (or at least a limited number of bags). In case where the system uses a sorbent and a concentrate solution(s), only two (or less than three) types of solution may be used a dialysate solution (and/or saline solution) and one or more concentrate solutions for the overall treatment.

A solution stored in a bag connected 28 or 33 (in direct fluid communication with) (for example shown by the FIG. 20 or 21) to the dialysate circuit (and optionally to the blood circuit) may be used to prime the blood circuit and/or to fill the bag 19. This solution may be a saline solution or a dialysate solution.

Figure 2A:
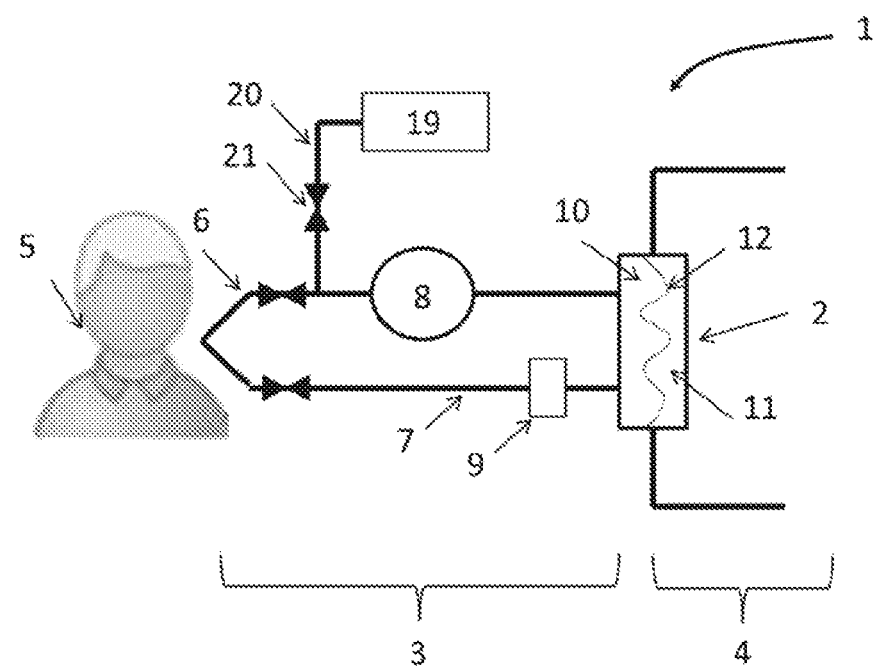

According to the FIG. 2a, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) of the pump 8 and preferentially downstream the arterial connector 26. The normal flow direction is indicated in FIG. 1 by arrow 38 for the blood circuit and arrow 39 for the dialysate circuit. The line 20 may comprise a (removable) connector and/or a valve 21 (V3) which may be controlled in order to open or to close the fluid communication by a controller device for example a processor.

Figure 2B:
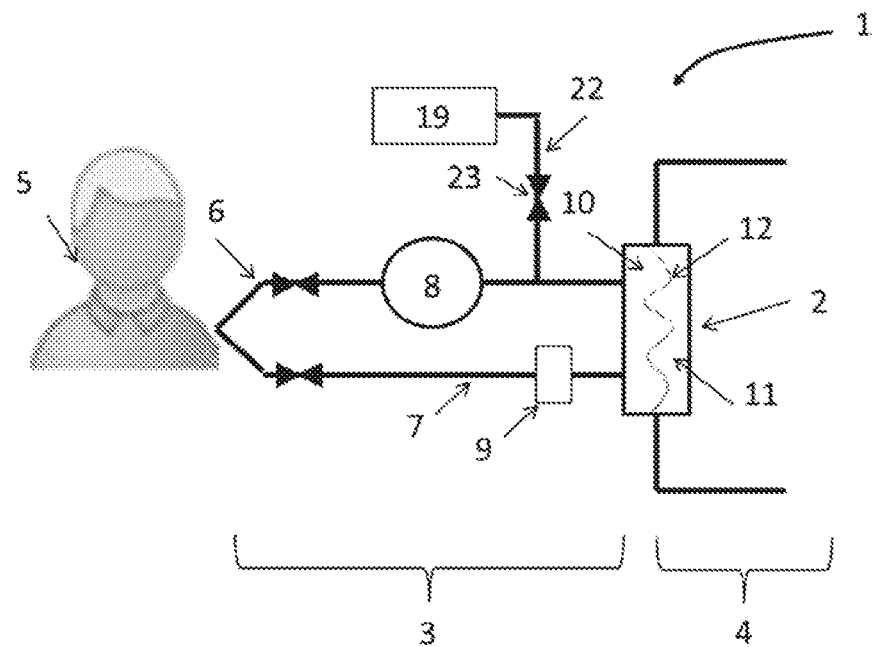
Figure 2C:
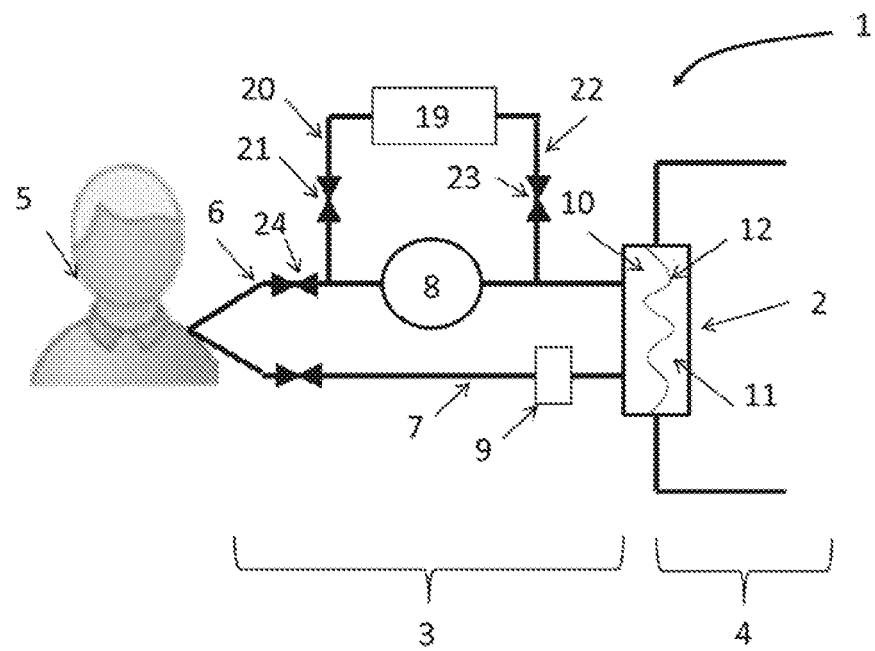

According to the FIG. 2b, the blood circuit comprises a line 22 which is in direct fluid communication with the arterial line and with the interior (for example storing compartment) of the bag 19. The connection between the line 22 and the arterial line 6 is arranged or located downstream the pump 8 ("downstream" according to the normal flow direction) and preferentially upstream to the venous connector 27 (for example upstream of at least one of the venous valve, the drip chamber and the dialyzer). The line 22 may comprise a (removable) connector and/or a valve 23 (V4) which may be controlled in order to open or to close the fluid communication by a controller device for example a processor. In another embodiment as partially described by the FIG. 2d, the blood circuit may comprise a line 22 which is in direct fluid communication with the venous line 7 and with the interior (for example storing compartment) of the bag 19. The connection between the line 22 and the venous line 7 is arranged or located downstream the pump 8, for example upstream or downstream of the dialyzer (according to the normal flow direction). The line 22 may comprise a valve 23 (V4) which may be controlled in order to open or to close the fluid communication by a controller device for example a processor According to the FIG. 2c, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) the pump 8. The line 20 may comprise a valve 21 (V3) which may be controlled in order to open or to close the fluid communication by for example a processor. The blood circuit further comprises a line 22 which is in direct fluid communication with the arterial line and with the interior (for example storing compartment) of the bag 19. The connection between the line 22 and the arterial line 6 is arranged or located downstream the pump 8 but upstream the dialyzer. The line 22 may comprise a valve 23 (v4) which may be controlled in order to open or to close the fluid communication.

Figure 2D:
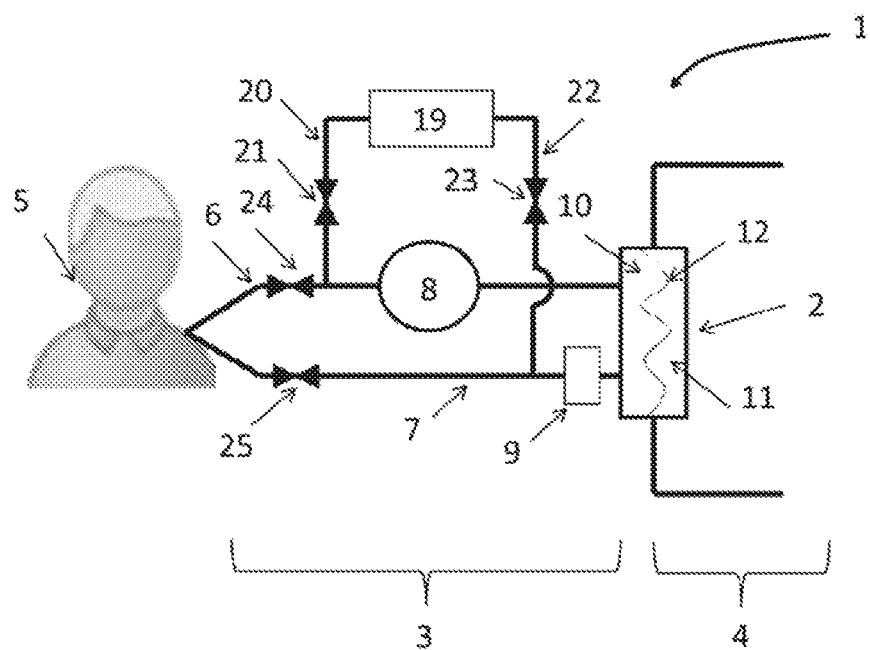

According to the FIG. 2d, the blood circuit comprises a line 20 which is in direct fluid communication with the arterial line and with the interior (for example storing compartment) of the bag 19. The connection between the line 20 and the arterial line 6 is arranged or located upstream ("upstream" according to the normal flow direction) the pump 8. The line 20 may comprise a valve 21 (V3) which may be controlled in order to open or to close the fluid communication by for example a processor. The blood circuit further comprises a line 22 which is in direct fluid communication with the venous line 7 and with the interior (for example storing compartment) of the bag 19. The connection between the line 22 and the venous line 7 is arranged or located downstream the pump 8 (and/or the dialyzer and/or the drip chamber). The line 22 may comprise a valve 23 (v4) which may be controlled in order to open or to close the fluid communication.

The blood circuit may comprise an arterial valve 24 (V1) arranged and located in the arterial line 6. The arterial valve 24 may be controlled in order to open or close the arterial line. The arterial valve may be arranged/located upstream the pump 8 and/or upstream the line 20 and/or the line 22. The blood circuit may comprise a venous valve 25 arranged and located in the venous line 7. The venous valve 25 may be controlled in order to open or close the venous line 7. The venous valve may be arranged/located downstream the pump 8 and/or downstream the line 20 and/or the line 22 and/or downstream the drip chamber 9. The arterial valve 24 and/or the venous valve 25 may be arranged into the blood cassette and may comprise flexible tube which may be pinched by a pinch valve.

Figure 2E:
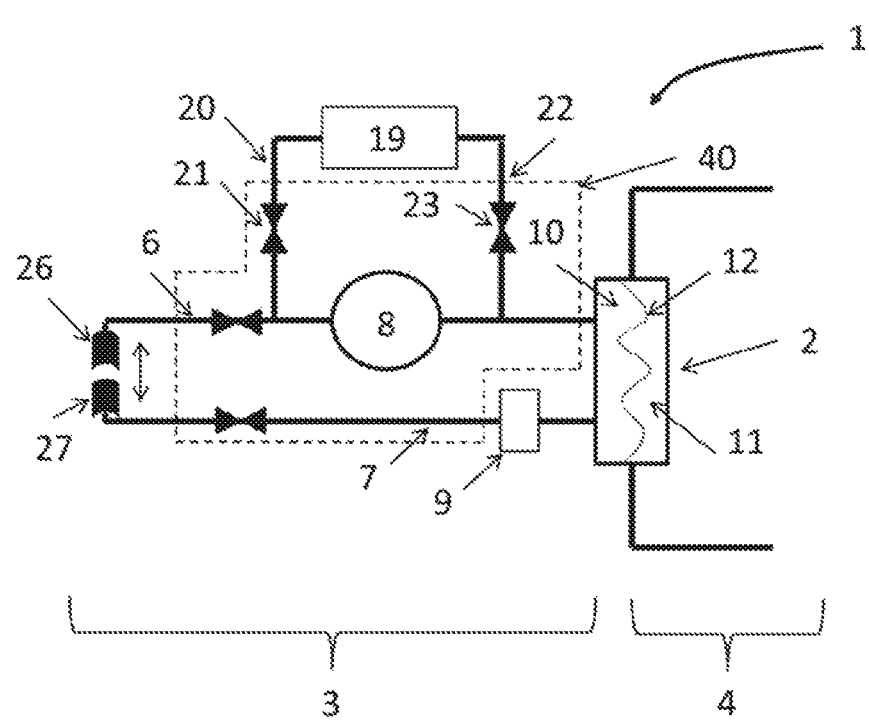

According to the FIG. 2e, the blood circuit comprises an arterial connector 26 arranged/located at an end of the arterial line 6. The arterial connector 26 is adapted and intended to be connected to a catheter of the patient. And the blood circuit comprises a venous connector 27 arranged/located at an end of the venous line 7. The venous connector 27 is adapted and intended to be connected to a catheter of the patient.

The arterial connector 26 and the venous connector 27 may be adapted to be connected together in order to allow a fluid communication between the arterial line 6 and the venous line 7 (without requiring to pass through the dialyzer) and to create a (closed) loop of the blood circuit. If the arterial connector 26 and the venous connector 27 cannot be directly connected together, the system may comprise an interconnector device comprising a first end adapted and intended to be connected to the arterial line 6 and a second end adapted and intended to be connected to the venous line 7. The interconnector device allows a fluid communication between the arterial line 6 and the venous line 7 and creates a (closed) loop of the blood circuit.

Figure 2F:
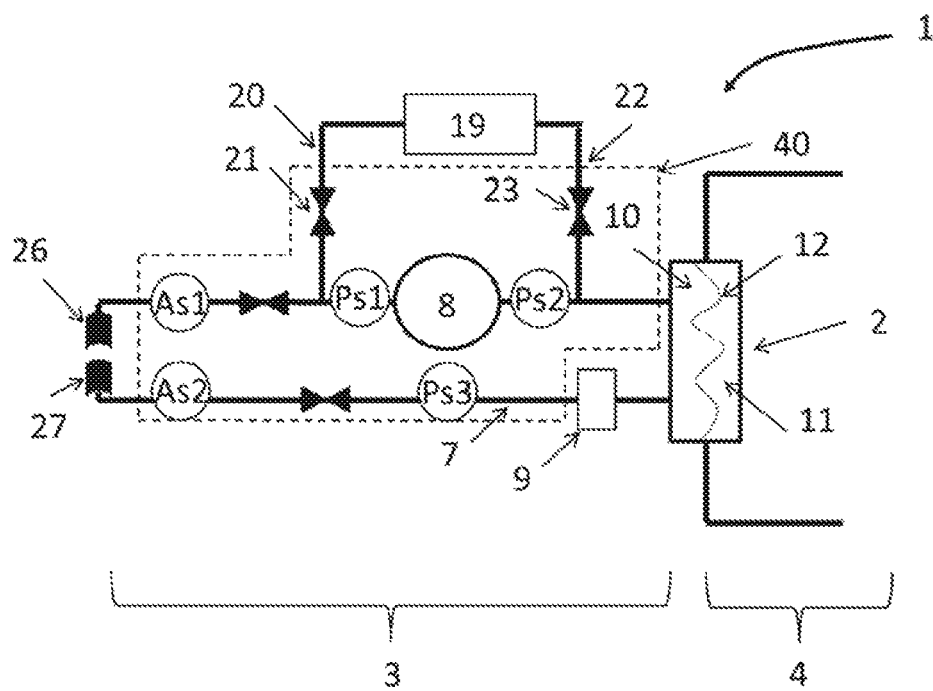

According to the FIG. 2f, the blood circuit may further comprise at least one of an air sensor (As1, As2) and a pressure sensor (Ps1, Ps2, Ps3). Preferentially, a first air sensor may be configured to cooperate with the arterial line 6 and a second air sensor may be configured to cooperate with the venous line 7. The air sensor may be configured to cooperate with the fluid pathway of the blood cassette. The first air sensor may be arranged downstream the arterial connector but preferentially upstream the arterial valve. The second air sensor may be arranged upstream the venous connector but preferentially downstream the venous valve. Preferentially, a first pressure sensor and a second pressure sensor may be configured to cooperate with the arterial line 6 and a third pressure sensor may be configured to cooperate with the venous line 7. The pressure sensor may be configured to cooperate with the fluid pathway of the blood cassette. The first pressure sensor may be arranged upstream the blood pump 8 but preferentially downstream the connection with the line 20. The second pressure sensor may be arranged downstream the blood pump 8 but preferentially upstream the connection with the line 22. The third pressure sensor may be arranged upstream the venous valve but preferentially downstream the drip chamber.

Dialysate Circuit

Figure 3:
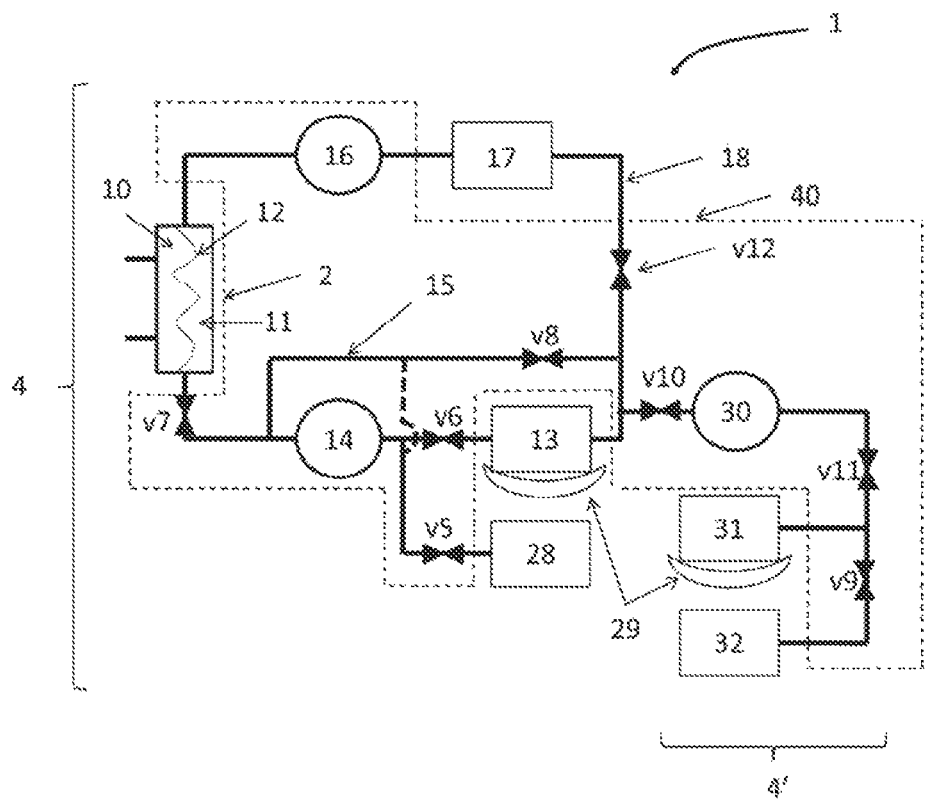
FIG. 3 illustrates a dialysate circuit according to one embodiment.

Referring now to the FIG. 3, the dialysate circuit may have a bag 28 which may store a solution for example a dialysate solution (such as an initial supply of dialysate) or a priming solution (which may be dialysate solution, a saline solution or other). This bag 28 may be used to add liquid solution into the loop circuit of dialysate or to initially fill the bag 13 (if the bag is initially empty for example before starting the treatment) or to prime at least a part of the circuit(s). The bag 28 may be in direct fluid communication with the first dialysate pump 14 via a line which may comprise a valve v5. The bag 28 may be in direct fluid communication with the by-pass line 15 via a line which may comprise a valve v5, in this case, the bag 28 may be used so as to remove a volume fraction of the solution from the dialysate loop circuit, for example from the bag 13 (close V8 and V7, open V6 and V5 and actuate the first dialysate pump). The by-pass line 15' may comprise a valve v8. The loop line 18 may comprise a valve v12. The bag 13 may be in direct fluid communication with the first pump via a line comprising a valve v6.

The dialysate circuit may have a supply circuit/line 4' (also called an additive circuit or concentrate circuit). This supply circuit 4' may comprise at least one supply pump (for example a concentrate pump 30) in fluid communication with the loop circuit of dialysate for example to the loop line 18 or to the bag 13 in order to add a solution (for example concentrate or saline or dialysate or other fluid different from dialysate) into the loop circuit of the dialysate upstream of the bag 13 or directly into the bag 13. This supply circuit may have a flow meter or a balance chamber in order to control or to monitor the concentrate adds to the loop circuit of the dialysate. The supply pump may be adapted to control and/or to monitor the amount of concentrate added to the loop circuit of dialysate. The supply circuit may comprise a valve v10 located downstream the supply pump 30 and/or upstream to the connection with the loop circuit of the dialysate. The supply circuit 4' may comprise one or more bag (31, 32) which may store a solution such as a concentrate solution (also called diluted solution or additive solution), a saline solution and/or a dialysate solution for example an initial supply of dialysate or other solution different from dialysate. This supply circuit may be also used so as to remove a volume fraction of the solution from the dialysate loop circuit. In this case the supply pump 30 is accurate in reverse mode the bag 32 may receive the removed solution. The bag 32 may be weight in order to monitor the volume of removed solution.

In one embodiment, the supply bag 32 stores a saline solution or pure water and the system does not comprise any initial supply bag of dialysate. Thus the dialysate is prepared from the saline solution or pure water and concentrate solution before starting the treatment into the bag 13 which may be initially empty. The processor may take into account the fact that the prepared dialysate solution will be regenerated/recycled through the sorbent device multiple times during the treatment and thus prepare a predetermined initial volume of dialysate solution before starting the treatment. In particular, the volume of dialysate solution initially prepared may be smaller than the volume of dialysate solution used at the end of the treatment due to the UF and/or the volume of added concentrate accumulated during the treatment.

The dialysate circuit 4 may be adapted to allow flowing, pumping, circulating a fluid in two opposite directions for example through the by-pass line 15. The dialysate pump may be adapted to pump in two directions for example in a first direction from the bag 13 to the dialyzer and a second direction which is a direction opposite to the first direction.

The bag 28 may be used to fill the bag 13 by actuating the dialysate pump in the first direction (if the bag 28 is connected to the line of the pump), in this case the solution initially stored in the bag 28 passed through the pump 14, then through the line 15 and reach the bag 13. V6 and V7 are closed and V5 and V8 are opened. If the bag 28 is connected to the line 15 (via the dash line), the bag 28 may be used to fill the bag 13 by actuating the dialysate pump in the second direction, the solution initially stored in the bag 28 is passed through the line 15, then through the pump 14 and reach the bag 13. V7 and V8 are closed and V5 and V6 are opened.

The system may comprise one or more balance (weight scale) and/or a heater 29 adapted to weigh or heat the solution store in at least one of the bag 13 13, 28, 31 and 32.

Preferentially, the dialysate circuit comprises a sorbent device adapted to clean the used dialysate, in order to use the dialysate solution several times. In this case, the concentrate solution may be added into the dialysate circuit over the course of treatment. Thus, a treatment may be performed with less than 10 liters of initial dialysate, preferentially less than 5 liters of initial dialysate, and more preferentially less than 4 liters of initial dialysate.

Figure 3A:
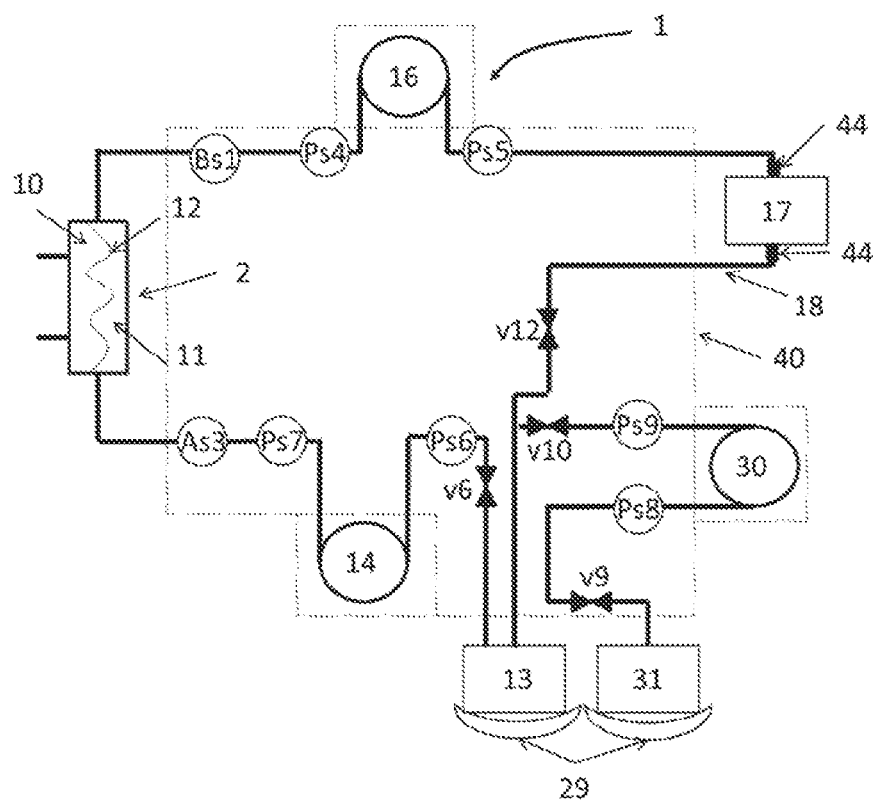
FIG. 3a illustrates a dialysate circuit with sensors according to one embodiment.

According to the FIG. 3a, the dialysate circuit may further comprise at least one of an air sensor (As3), a pressure sensor (Ps4, Ps5, Ps6, Ps7, Ps8, Ps9) and a blood sensor (Bs1). Preferentially, a third air sensor (As3) may be configured to cooperate with the dialysate line. The air sensor may be configured to cooperate with the fluid pathway of the dialysate cassette. The third air sensor may be arranged upstream the dialyzer 2 but preferentially downstream the bag 13.

Preferentially, at least one pressure sensor of the dialysate circuit may be configured to cooperate with the fluid pathway of the dialysate cassette and more particularly with at least pumping device of the dialysate circuit (or connected line). Thus, each pumping device may comprise a pressure sensor located upstream the pumping device and another pressure sensor located downstream the pumping device.

Preferentially, a blood sensor (Bs1) may be configured to cooperate with the dialysate line. The blood sensor may be configured to cooperate with the fluid pathway of the dialysate cassette. The blood sensor may be arranged downstream the dialyzer 2 but preferentially upstream the pump 16.

Single Priming Container

The system may comprise a (single) priming container 33 (for example shown by the FIGS. 20 and 21) in fluid communication with at least one of the blood circuit and the dialysate circuit during the priming process in order to prime at least a part of both circuits. As the other bag of the system, the single priming container 33 may be a bag having one or more flexible wall sealed to a rigid wall another flexible wall.

The system may comprise a dialysate circuit having a dialysate connector 37, a blood circuit having an arterial connector 26 and a venous connector 27 and a priming container having a storage compartment. The system may be adapted to provide a fluid connection (only during the priming process of the system before starting the treatment) between the storage compartment of the priming container 33 and the connectors (dialysate connector, arterial connector and venous connector).

The system may further comprise at least one of a first pump dedicated to the blood circuit, a second pump dedicated to the dialysate circuit, a memory having computer-executable instructions dedicated to the priming process, a processor connected to the memory and the pumps. Both pumps may be adapted to move the priming solution (initially stored in the priming container) through the fluid circuits. The processor is adapted to control the pumps (successively or simultaneously) according to the computer-executable instructions in order to automatically perform all or a part of the priming process.

The single priming container may store a saline solution, a dialysate solution or other compatible solution (compatible with blood and/or dialysate).

If the single priming container stores a saline solution or other compatible solution to prepared dialysate solution (for example pure water, . . . ), at least a part of the dialysate solution (used for the treatment) may be automatically prepared from this stored solution. In this case, a volume fraction of the solution initially stored in the single priming container is added to the bag 13 in order to prepare a dialysate solution before starting the treatment and a concentrate solution may be also added to the bag 13. In this case, the processor may be programmed in order to automatically move a predetermined volume fraction of the solution (initially stored in the container 33) to the bag 13 and a predetermined volume fraction of concentrate solution (initially stored in the container 31) to the bag 13. The processor may take into account the fact that the prepared dialysate solution will be regenerated/recycled through the sorbent device multiple times during the treatment and thus prepare a predetermined initial volume of dialysate solution before starting the treatment. In particular, the volume of dialysate solution initially prepared may be smaller than the volume of dialysate solution used at the end of the treatment due to the UF and/or the volume of added concentrate accumulated during the treatment. Furthermore, the priming solution may be also added to the bag 19 (of the blood circuit) and used at the end of the treatment as described above.

If the single priming container stores a dialysate solution or other compatible solution with the blood, a volume fraction of the solution initially stored in the single priming container may be added to the bag 13 (for example if the bag 13 is empty at the beginning of the treatment). Furthermore, the priming solution may be also added to the bag 19 and used at the end of the treatment as described above.

Thus, a (the single) priming container may be used to supply a solution to the bag 19 and/or to the bag 13 and/or to prime the blood circuit 3 and/or the dialysate circuit 4. In other terms, the volume of the storage compartment of the single priming container may take into account a required volume for the bag 13, a required volume for the bag 19 and/or a required volume for priming the fluid pathway of both circuits (for example the pathway, the dialyzer, the sorbent, . . . ).

The single priming container may comprise one, two or three outlets.

Referring now to the FIG. 20, the single priming container 33 comprises three outlets, for example three tubes and/or three connectors. Each outlet is in fluid communication with the solution stored in the container and may comprise a dedicated connector. A first connector 34 may be adapted or intended to be connected to a dialysate circuit connector 37. This dialysate circuit connector may be connected to a tube which may extend up to the dialysate cassette. A clamp or a valve V5 may be used to clamp or to close this fluid pathway. In the cassette, this fluid pathway may be in fluid connection with the dialysate circuit for example to the fluid pathway between the bag 13 and the pump 14 (as the bag 28 which is used in an other embodiment). A second connector 35 may be adapted or intended to be connected to the venous connector 27 and a third connector 36 may be adapted or intended to be connected to the arterial connector 26.

Referring now to the FIG. 21, the single priming container comprises two outlets, for example two tubes and/or two connectors. Each outlet is in fluid communication with the solution stored in the container and may comprise a dedicated connector. A first connector 34 may be the same of the connector 34 described above via the FIG. 20. A second connector may have one or two ports. If the second connector 35 has only one port, the system needs to have an adapter so as to connect the second connector to the arterial connector 26 and to the venous connector 27. If the second connector 35 has two ports, a first port may be is adapted or intended to be connected to the venous connector 27 and a second outlet port may be adapted or intended to be connected to the arterial connector 26.

If the single priming container comprises only one outlet for example one tube and/or one connector, this connector may have three ports (one for the dialysate circuit and two for the blood circuit as described above) or the system may use an adapter having one inlet port and three outlet ports as the concept described above.

Overall System

The overall system may have a reusable part and a disposable part. The disposable part comprises the elements which have to be discarded after a predetermined number of uses, for example, after a single use. The working life of the disposable part may directly depend on the number of treatment. These elements may be the elements which have been wetted by the dialysate or by the blood, for example, at least part of the blood circuit and/or at least a part of the dialysate circuit and/or the dialyzer.

The disposable part of the blood circuit may comprise at least one of a tube, a connector, a port, a cassette, a valve, . . . . The disposable part of the dialysate circuit may comprise at least one of a tube, a connector, a port, a cassette, a valve, . . . .

Preferentially, the reusable part comprises the expensive elements for example the sensor, the electronic part, the screen, the actuator of the valve or of the pump, the processor, the memory. The reusable part is successively used with several disposable parts. The reusable part may comprise components which may be replaced when the components are too worn, become broken or after a predetermined period of time, but much longer than a single treatment. The change of the reusable part may depend on the component wear.

Figure 4:
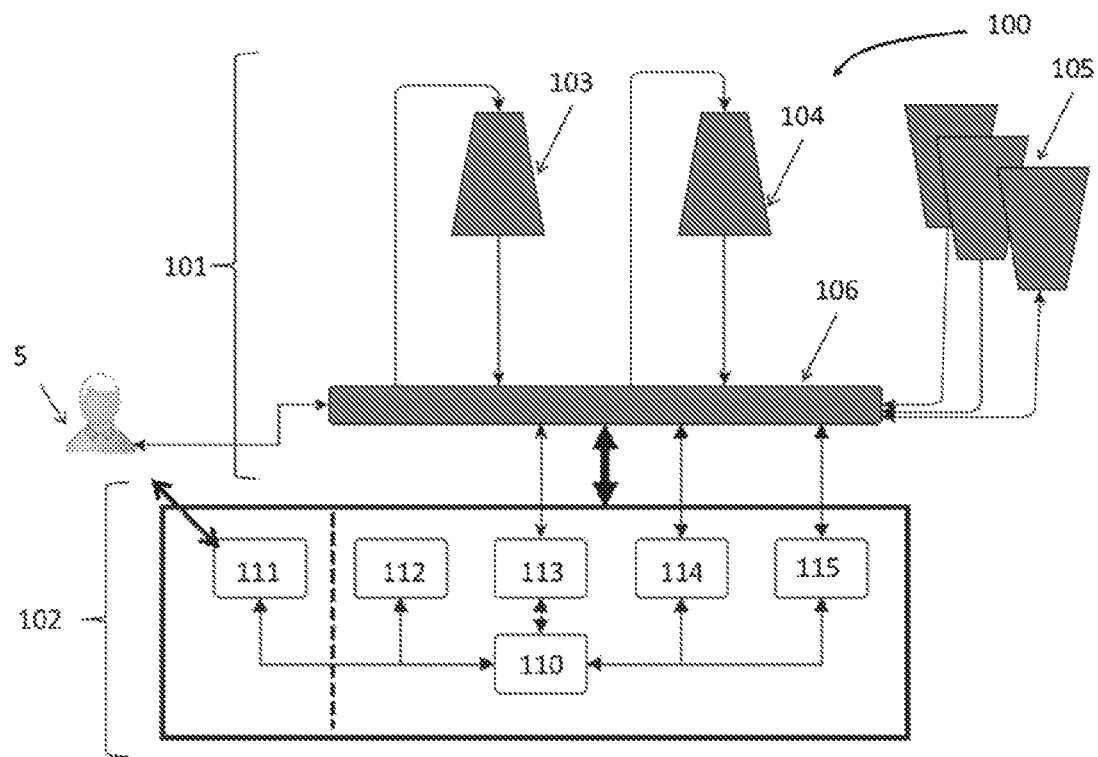
FIG. 4 shows the interaction between the disposable part and the reusable part.

According to the FIG. 4, the overall system 100 may comprise a disposable part 101 and a reusable part 102 (also called apparatus). The disposable part 101 may comprise at least one of a dialyzer 103, a sorbent 104, a bag 105 and a cassette 106. The reusable part 102 may comprise at least one of one or more processors 110, one or more screens 111, other elements 112 connected to the processor such as one or more buttons, one or more sensors 113, one or more actuators 114 and other elements 115 connected to the processor 110 and operatively and removably coupled to the disposable part. The elements (111, 112, 113, 114, 115, 110) may be arranged into the housing of the reusable part. The screen 111 may be touch screen and may be removably coupled to the housing comprising the other elements of the reusable part 102. All or a part of the elements may be connected or coupled to the processor in order to control or monitor the treatment. The processor 110 may execute computer-executable instructions stored in a memory of the system. The sensor 113 may be adapted and intended to be operatively coupled to the disposable part 101.

The active part of the sensor 113 (for example the part which senses) may be located in the reusable part. In this case, the disposable may comprise a coupling element adapted to removably couple the sensor with the disposable part 101. The active part of the sensor (such as probe) may be located/arranged in the disposable part, in this case, the sensor part located into the reusable part may be the connection element allowing the communication between the processor 110 and the active part of the sensor located in the disposable part.

The actuator 114 may be operatively coupled with the disposable part in such a manner that the actuator may act on the disposable part, for example open/close a valve, actuate the pump, . . . .

The element 115 may be a weight scale or a heater controlled by the processor.

Cassette(s)

The system may comprise one or more cassettes which define at least a part of the fluidic pathway of the blood circuit and/or of the dialysate circuit. A cassette is preferentially a part of the disposable part 106 (as shown in the FIG. 4). The system may comprise a single cassette comprising a part of the blood circuit and a part of the dialysate circuit. Preferentially, the system comprises two distinct cassettes: a first cassette dedicated to the blood circuit, adapted and intended to receive blood (and optionally a priming solution, saline solution, pure water solution, dialysate solution or other blood compatible solution) and a second cassette dedicated to the dialysate circuit, adapted and intended to receive a dialysate solution or other compatible solution for the treatment. The FIGS. 2e and 3 show a potential limit 40 of the cassette (blood cassette and dialysate cassette). The pumping device(s) may be a part of the cassette or may be arranged outside of the cassette.

The (blood and/or dialysate) cassette 106 comprises at least one valve adapted and intended to be operatively coupled with an actuator 114 of the reusable part. The (blood and/or dialysate) cassette 106 may comprise at least a part of a pump adapted and intended to be operatively coupled with an actuator 114 of the reusable part.

The cassette 106 comprises a rigid frame 107 adapted to receive a part of the fluid pathway of the circuit (blood or dialysate). As shown by the FIG. 5, the cassette includes a fluid cavity 120 (arranged into the rigid frame for example), one or more port 121 and/or one or more flexible membrane 108 adapted to cover the fluid cavity 120.

The flexible membrane may comprise a coupling area adapted to be operatively coupled with a valve actuator and/or a measurement area adapted to be operatively coupled with a sensor of the reusable part of the system.

The cassette (the blood and/or dialysate cassette) may further comprise a handle 122 adapted to be gripped by the fingers of a user hand.

The membrane may comprise a valve portion adapted to close and open the fluid pathway of the cassette. In this cassette, a lug/head of the valve actuator of the reusable part of the system may push the valve portion against the rigid part (for example the internal wall of the cavity of the rigid frame) in order to close the fluid pathway. The membrane may be formed/molded/structured so as to have a determined shape at the contact portion 124 with the valve seat 123 in order to improve the tightness of the valve. The membrane (in particular the coupling area) may be formed/molded/structured so as to have a determined shape such as a clip element adapted to be removably coupled to a head of a valve actuator (not show).

Figure 5B:
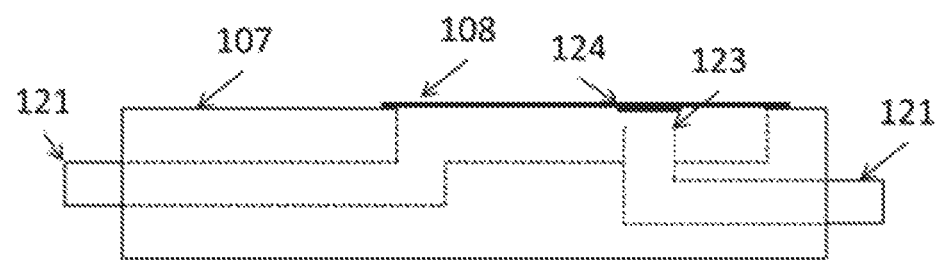
Figure 5B:
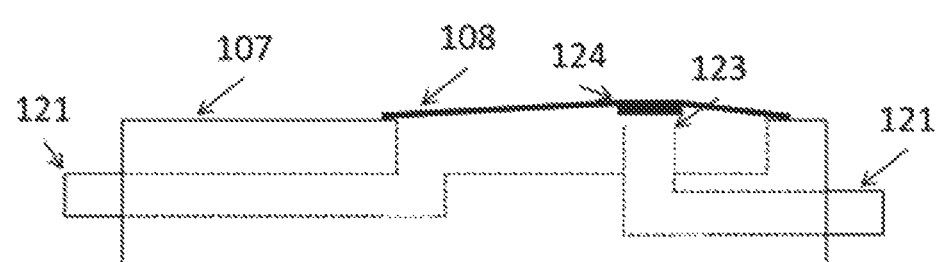

The FIGS. 5b and 5b' show a schematic view (cross section) of the cassette 106 wherein the valve is in an open position. The membrane (in particular the contact 124) is spaced apart from the valve seat 123. In the FIG. 5b, the membrane and the valve seat of the rigid frame are designed in order to have a rest position of the valve which is an open position. In the FIG. 5b', the membrane and the valve seat of the rigid frame are designed in order to have an open position when the membrane is pulled (for example by the valve actuator).

Figure 5C:
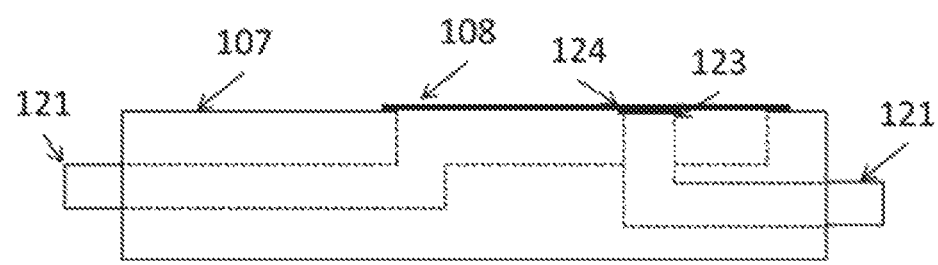
Figure 5C:
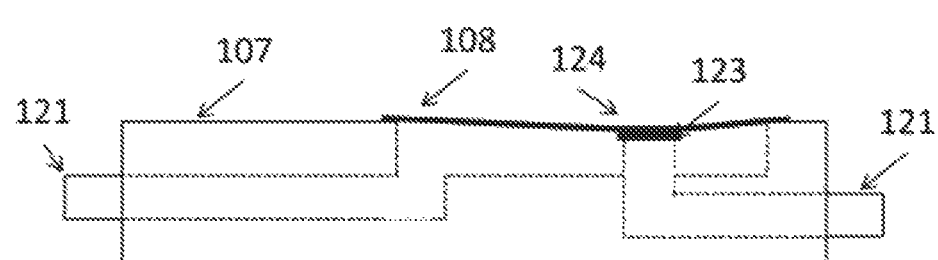

The FIGS. 5c and 5c' show a schematic view (cross section) of the cassette 106 wherein the valve is in a closed position. The membrane is in contact with the valve seat 123. In the FIG. 5c, the membrane and the valve seat of the rigid frame are designed in order to have a rest position of the valve which is a closed position. In the FIG. 5c', the membrane and the valve seat of the rigid frame are designed in order to have a closed position when the membrane is pushed (for example by the valve actuator) against the valve seat 123.

In one embodiment, the cassette may comprise one or more flexible tube secured in the cassette by a frame. In order to limit the haemolysis, the valve actuator may be a pinch valve actuator comprising a lug configured to pinch the flexible tube through the blood cassette.

The (blood and/or dialysate) cassette may comprise a part of the pump. In one embodiment, the pump is a peristaltic pump. In this case, the cassette comprises a flexible tube in fluid communication with a first fluid pathway and a second fluid pathway of the cassette via dedicated ports. The flexible tube is intended to be pressed by at least two roller of the pump against a rigid wall for example a part of the rigid frame of the cassette. The cassette may further comprise a roller assembly including at least two rollers, a roller support device, a coupling device intended to be operatively coupled with a pump actuator of the reusable part of the system.

Referring to the FIG. 6, the cassette comprises a flexible tube 201 which is connected to the fluid pathway 202 of the cassette 200, for example via an inlet port 203 and an outlet port 204. A roller assembly 205 is movably (by rotation) disposed into a cavity of the rigid frame of the cassette. The roller assembly 205 comprises at least two rollers 208 maintained by at least one support 206. The FIG. 6 further shows a shaft 207 which is a part of the pump actuator of the reusable part. The shaft 207 is intended to actuate the roller assembly 205. In this embodiment, the roller support 206 comprises a through hole in which the shaft 207 of the pump actuator is intended to be inserted when the cassette is loaded. The roller 208 may be drive by friction and/or may comprise a coupling device (coupled with the roller support 206) such as lug and hole or toothed gear. When the cassette is fully loaded the pump part of the cassette is operatively coupled to the pump actuator of the reusable part.

The roller 208 may be movable relative to its support, for example when the shaft of the pump actuator is inserted into the roller support 206, the external wall of the shaft pushes the roller 208, urging the roller in direction of the peripheral end of the support.

The cassette may be adapted to be inserted into an opening of the reusable part (apparatus) as described thereafter. In order to prevent any finger pinching between the cassette and the opening of the reusable part, the cassette may be adapted to be substantially fitted to the opening (so as to at least partially or fully obstruct or block the opening when a cassette is inserted). The handle and/or the tube(s) (of the cassette) may protrude from the cassette and from the housing of the apparatus when the cassette is fully inserted into the opening. Preferentially, the opening and the cassette are designed in such a manner as to never present any opening having any dimensions larger than 25 mm preferentially larger than 10 mm more preferentially larger than 8 mm or 5.6 mm when the cassette is fully inserted into the opening. For example, the cassette may comprise an edge which substantially obstructs the opening when the cassette is fully inserted into the opening (as described thereafter with the FIGS. 22 and 23). One goal of such design is to avoid the penetration of any patient's finger or object of a similar size into the lodging of the cassette when a cassette is present.

The blood circuit comprises at least two tubes (arteria line and venous line) but preferentially the blood circuit comprises a dedicated cassette and five or six tubes (or more) which extend from the (blood) cassette. A first tube connected to the patient (arterial line), a second tube connected to the patient (venous line), a third tube connected to the blood return bag 19, a fourth (optional) tube connected to the blood return bag 19, a fifth tube connected to the dialyzer 2 (arterial line) and a sixth tube connected to the dialyzer 2 (or drip chamber 9) (venous line).

The dialysate circuit comprises at least two tubes (downstream and upstream of the dialyzer) but preferentially the dialysate circuit comprises a dedicated cassette and at least seven tubes which extend from the (dialysate) cassette: a first tube to the dialyzer 2, a second tube from the dialyzer 2, a third tube to the sorbent device 17, a fourth tube from the sorbent device 17, a fifth tube from the concentrate container 31, a sixth tube to the weighting container 13 and a seventh tube from the weighting container 13. Optional tubes and connection may be: from an initial supply container 28 or priming container 33, from additional supply container 32, from an (in line) heating system . . . .

Other fluid pathway may be arranged into the cassette and at least a part of the fluid pathway comprising a valve may be arranged into the cassette. The FIG. 3 shows the potential limit 40 of the dialysate cassette. The FIG. 2e shows the potential limit 40 of the blood cassette. The shape and/or the size of these limits are just an illustration and are not to be taken in a limiting sense.

Apparatus (Reusable Part)

The apparatus (also called dialysis unit) is a reusable part of the system. The apparatus is designed to be portable by a user; nevertheless this apparatus is not designed to be fixed to the patient. As used in this specification and the appended claims, the term "portable" is generally employed in its sense including "light and small enough to be easily carried or moved" or "possible to take with you if you move to a different place" or "easily carried or conveyed by hand".

The FIGS. 7 to 12 show a first potential embodiment of the dialysis system, the FIGS. 33 to 36 show a second potential embodiment of the dialysis system and the FIGS. 37 to 39 show a third potential embodiment of the dialysis system. Even if each embodiment has a specific shape, these embodiments may comprise the same or substantially the same assemblies or sub-assemblies (such as pole, container support, scale, sensor, loading system, door device, cassette, support, fluid circuit, container receiver, functional element, electronic device, handle, display device, . . . ) described in this document.

Referring now to the FIG. 7, the apparatus 300 comprises a housing 301 in which are arranged components for controlling a dialysis treatment. For example: a processor, a valve actuator, a sensor, at last a part of a blood pump adapted to cooperate with the blood line in order to move blood through blood line when the blood line is in fluid communication with a blood source (the patient) and at last a part of a dialysate pump adapted to cooperate with the dialysate pump in order to move dialysate through the dialysate line when the dialysate line is in fluid communication with a dialysate source. The housing 301 have a front panel and side panels.

The housing may have at least one recess 318 (see FIG. 11a) designed to be grasped by the hand of a user, the at least one recess may have a gripping element (for example a shape or a structure which is easy to be grasped by the hand). Preferentially, the apparatus comprises two recesses with gripping element arranged on two opposite side panels of the housing. The recesses may be located at a lower portion of the housing.

Preferentially, the apparatus comprises a display device 302 which may be a movable screen (such as a tablet) removably fixed to the apparatus via a screen support 303. The display device may comprise several screens showing a current status of the treatment, a setting screen, a text and video instruction, patient data, treatment data, . . . . The display device may comprise a processor connected to a memory which comprises a text and video instruction, patient data, treatment data, sound files, video files, . . . . The display device 302 may be removably attached to at least one of a container support 304 (for example a pole 312 (not shown)), the housing 301 and the pole 312. The display device may comprise a display communication unit with a receiver and emitter wirelessly coupled to an apparatus communication unit arranged into the housing 301. Thus, the electronic part arranged into the housing 301 of the apparatus may wirelessly communicate with the display device. A link wire may provide the communication between the apparatus and the display device or use to recharge a battery of the display device. This link wire may comprise an USB connector or other standard connector (for example Apple standard connector). The use of a USB connector or standard connector allows using a standard tablet (I-Pad, Android tablet, . . . ) as display device. Thus, in case of failure of the original display device, the user can change with a standard tablet.

The display device 302 may be used as an electronic health booklet for the treatment. The patient brings to the doctor his display device and the doctor may monitor the treatment history and other health data of the patient. The doctor may change the treatment parameters via the display device. Furthermore the doctor may download the treatment parameters or other data from his computer (PC or other computing device of the doctor) to the display device wirelessly or via a wire connection (for example an USB connection). Furthermore, the display device may comprise an application or computer-executable instructions adapted to download data from and/or upload data to the doctor's computer and an internal memory configured to record the treatment history, the patient data (weight, blood pressure, alarm, UF, executed treatment, . . . ), the new treatment parameter, . . . .

The apparatus may comprise a standard connection port (for example USB port) connected to the electrical supply management device of the apparatus and/or connected to a processor of the apparatus, and the display device may comprise a standard connection port (for example USB port) connected to the electrical supply management device of the display device (connected to the battery of the display device) and/or connected to a processor of the display device.

The apparatus may further comprise an additional screen 305, a power button 306 or an emergency button 307. The additional screen 305 is designed to bring information to the user in a concise manner.

The display device provides more detail (videos, instructions, advises, . . . ) than the additional screen (alarms, failures, current treatment, progress bar, . . . ). The power button 306 may be designed to turn on or off the apparatus or to turn off all or a part of apparatus lights. The emergency button 307 may be designed to be activated during the treatment for example to command a premature end of treatment (for example to launch the blood return process before the end of the treatment). These buttons and screen are preferentially connected (via a wire connection) to the processor of the apparatus. In one embodiment, similar buttons may be arranged on and may be enable via the display device (via the touch screen for example).

The apparatus may comprise a dialyzer support 308 (configured and intended to removably secure the dialyzer) and a drip chamber support 309 (configured and intended to removably secure the drip chamber) which may be arranged on the front panel of the housing 301, on a lateral panel of the housing 301 or on a container support 304 (for example fixed to the pole).

Figure 33:
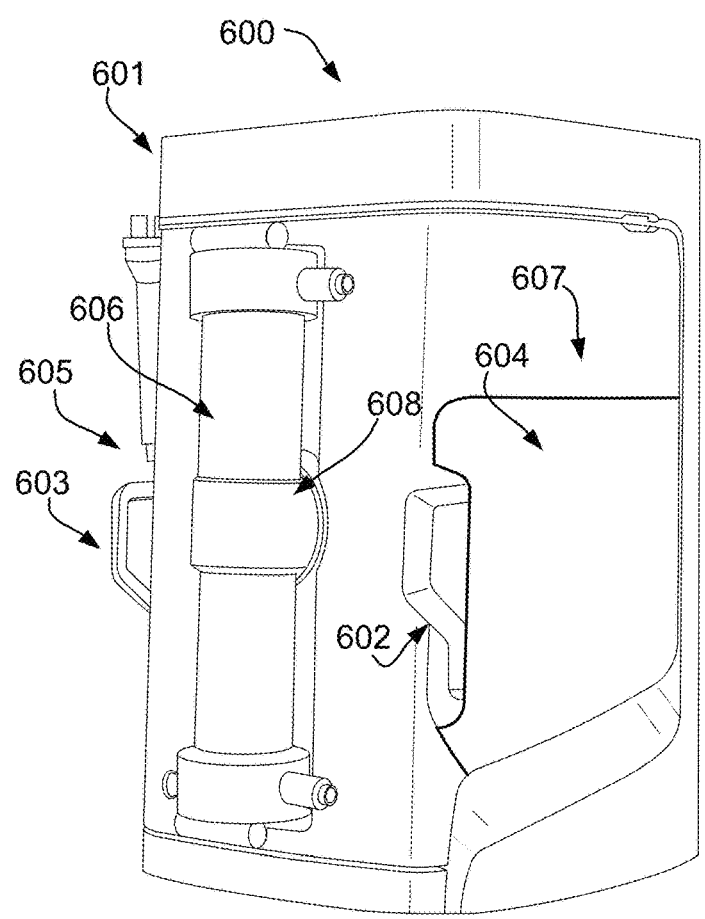

Preferentially the housing comprises at least one opening (slot or groove) adapted to allow inserting one or two cassettes of the disposable part into the apparatus. The FIG. 7 shows a single opening and the FIG. 8 shows two distinct openings. The opening may be substantially horizontally (or vertically or inclined) extended on the front panel and/or a lateral panel of the housing 301. The FIG. 33 shows two vertical (and preferentially lateral) openings closed by vertical doors (such sliding door, retractable door, revolving door or swing door). The FIG. 37 shows horizontal opening(s) closed by door(s) (a single door or two doors) (such sliding door, retractable door, revolving door or swing door) which may be adapted or configured to be used as a container receiver.

In case where the disposable part comprises two distinct cassettes, a single opening may be adapted for both cassettes or two openings may be arranged through the housing. In case where the apparatus comprises two distinct openings for inserting the cassettes through the housing, a first opening may be arranged in a first portion of the housing and the second opening may be arranged in a second portion (which may be opposite to the first portion).

For example, the FIG. 8 shows a housing 301 with a first opening 310 and a second opening 311. The first opening is horizontally extended through a first portion 319 of the housing 301. For example, the first opening 310 is horizontally extended from a part of the front panel 321 to a part of the side panel 322 of the first portion 319. The second opening 311 is horizontally extended through the second portion 320 of the housing 301. For example, the second opening 311 is horizontally extended from a part of the front panel 321 to a part of the side panel 323 of the second portion 320.

Between the both openings, the apparatus may comprise a rigid structure adapted to support the weight of the elements arranged above the openings so as not to deform the general structure of the apparatus.

The first opening 310 may be dedicated to the blood cassette and the second opening may be dedicated to the dialysate cassette. The FIG. 8 shows a first opening smaller than the second opening. The apparatus and/or the cassette may further comprise a mechanical coding in order to prevent the insertion of a cassette in a non-dedicated opening. Thus, the user cannot insert a blood cassette in the second opening and/or a dialysate cassette in the first opening. Preferentially the dialyzer support 308 is arranged between both openings and the drip chamber support at the first portion 319. The dialyzer support is configured in order not to obstruct any opening when the dialyzer is secured on its support, such that the cassette may be loaded to or unloaded from the apparatus.

The first portion may be called the blood side of the apparatus because this side receives the opening dedicated the blood cassette. The second portion may be called the dialysate side of the apparatus because this side receives the opening dedicated the dialysate cassette.

Referring now to the FIG. 9, the user inserts a blood cassette through the first opening. In this embodiment, the blood cassette comprises a handle 122 by which the user grasps the blood cassette. The blood cassette is engaged and slid into the apparatus according to an axe defined by the apparatus 300 (Y or X axes). The cassette 106 further comprises at least one tube 116 which extends from a side of the cassette (preferentially a side which is perpendicular to the side comprising the handle or other side than the side of the handle or same side than the handle). At least one opening is adapted to allow the passage of the tube outside the apparatus through the opening of the side panel of the first portion (for example). To insert the blood cassette, the user manipulates the blood cassette by the handle, enters the cassette through the opening (for example of the front panel or of the side panel) and slides the cassette until the end of the path. At the end of the path, a sensor is adapted to detect the presence of the inserted cassette. This sensor sends (to the processor) data in order to inform the processor that the cassette is inserted.

Referring now to the FIG. 10, the user inserts a dialysate cassette through the second opening. In this embodiment, the dialysate cassette comprises a handle 122 by which the user grasps the dialysate cassette. The dialysate cassette is engaged and slid into the apparatus 300 according to an axe defined by the apparatus (Y or X axes). Said insertion axe of the dialysate may be the same of or opposite to the insertion axe of the blood cassette. The cassette 106 further comprises at least one tube 116 which extends from a side of the cassette (preferentially a side which is perpendicular to the side comprising the handle or other side than the side of the handle or same side than the handle). At least one opening is adapted to allow passage of the tube outside the apparatus 300 through the opening of the side panel of the second portion (for example). To insert the dialysate cassette, the user manipulates the dialysate cassette by the handle, enters the cassette 106 through the opening (for example of the front panel or of the side panel) and slides the cassette until the end of the path. At the end of the path, a sensor is arranged adapted to detect the presence of the cassette 106. This sensor sends to the processor the data in order to inform the processor that the cassette is inserted.

When the cassette is inserted a loading system may be automatically activated/launched. During the treatment, the opening may be closed by a door and/or a lock mechanism may bloc the cassette in an operating position. One or both may be activated by the loading system or at the start of the treatment. The lock mechanism may be a rod inserted through a hole arranged into the cassette during the loading process (for example by the loading system).

Figure 22:
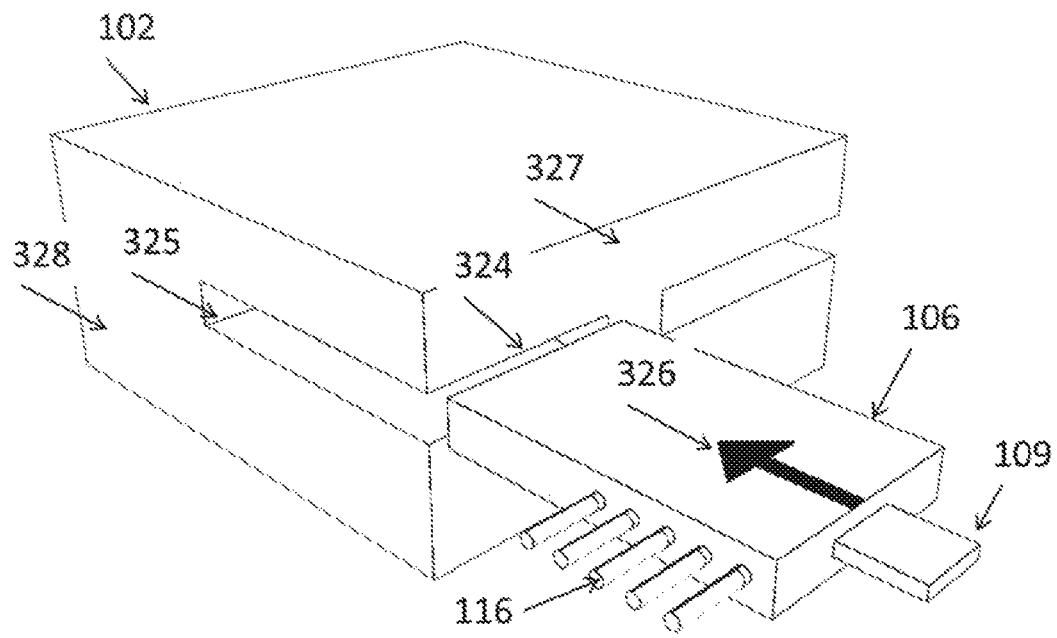
Figure 23A:
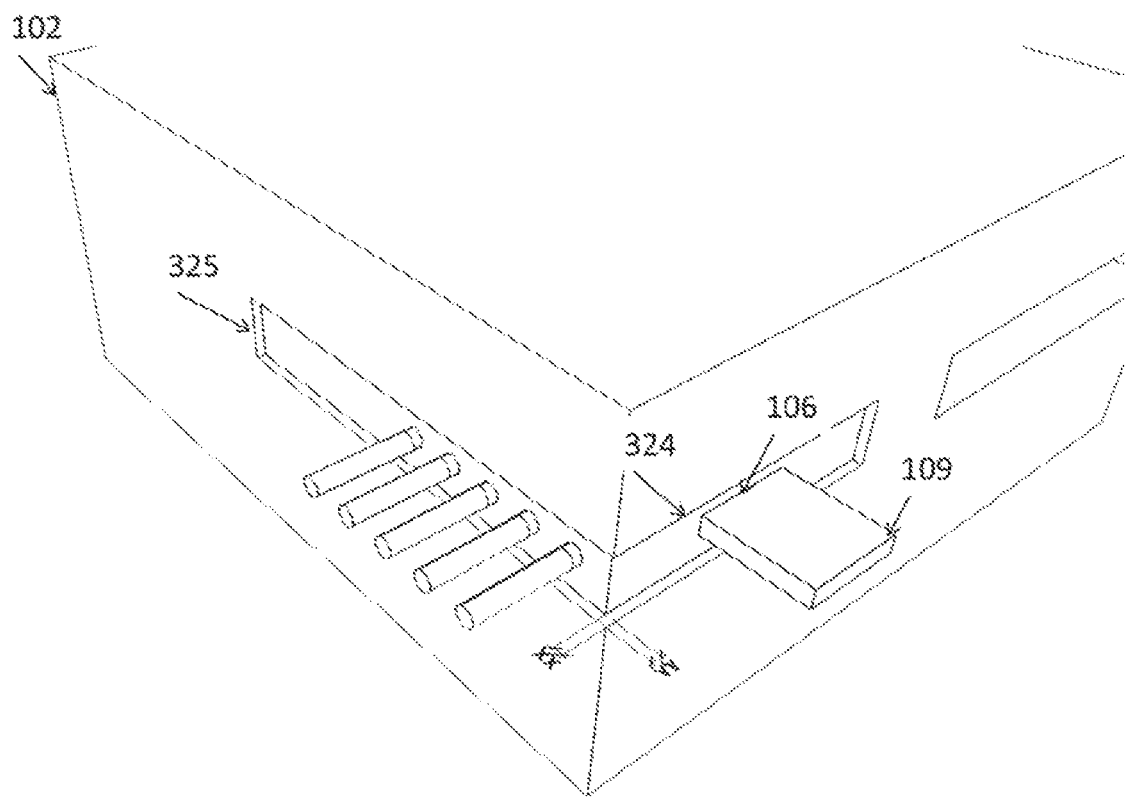
Figure 23B:
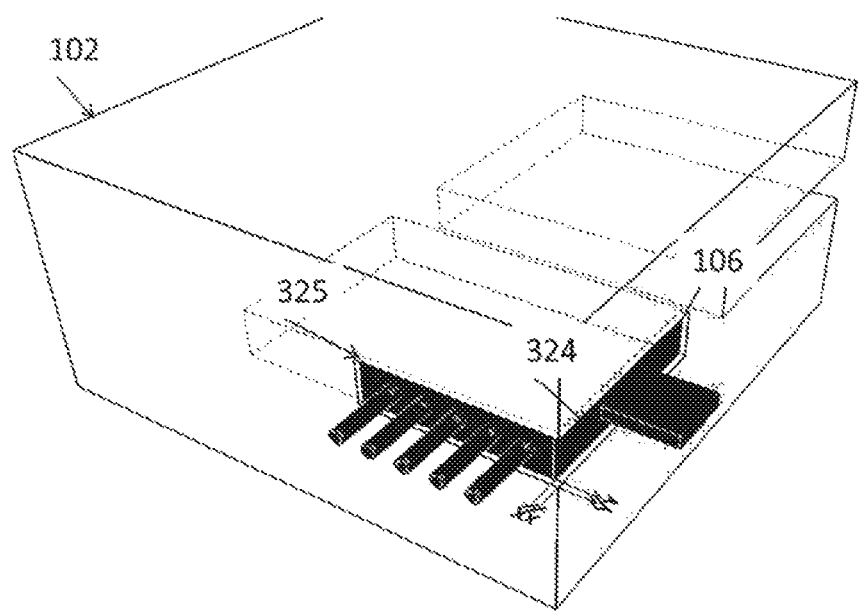
Figure 23C:
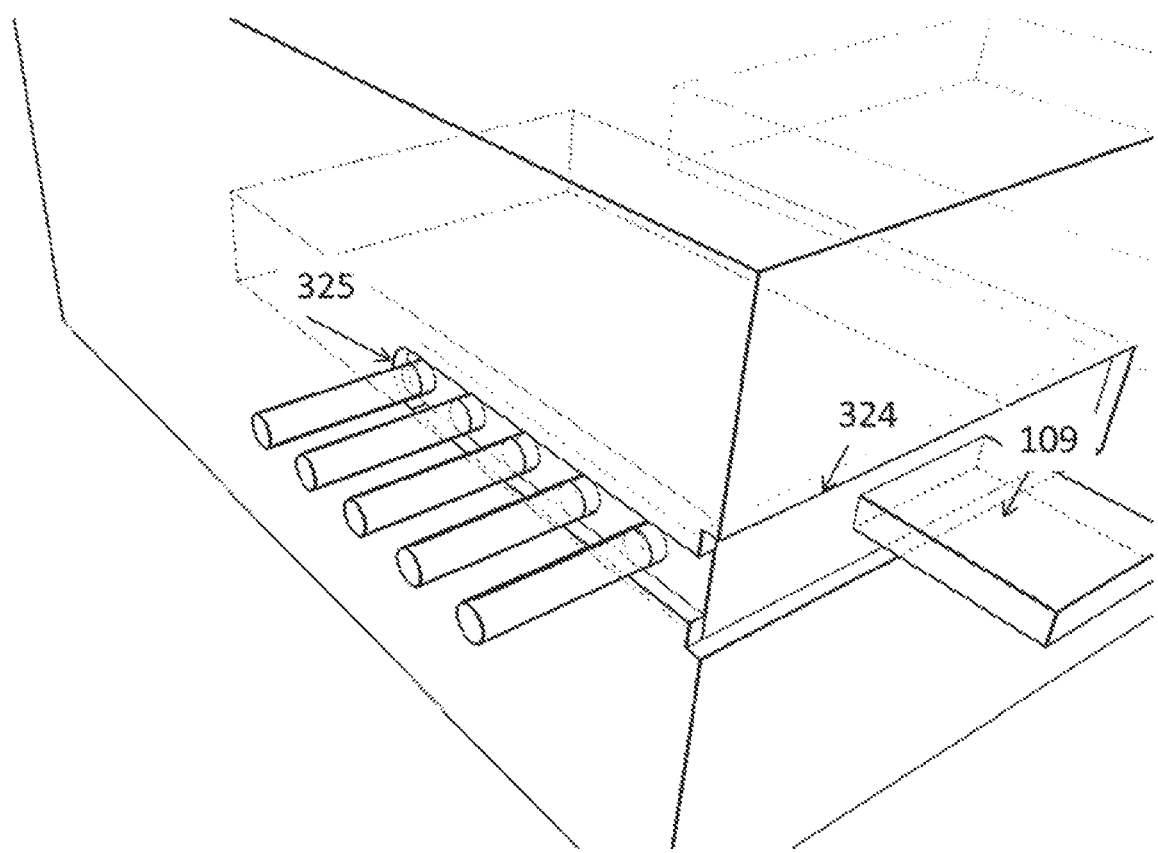

Referring now to the FIGS. 22 and 23, a cassette 106 comprises tubes 116 and an optional handle 109. The apparatus 102 comprises an opening 324 arranged on a first side 327 of the housing and an additional opening arranged on a second side 328 of the housing. Preferentially, the first side 327 is substantially perpendicular to the second side 328. The opening 324 and the additional opening 325 provide an access to a cassette holder (at least for inserting or removing the cassette). The opening 324 and the additional opening 325 provide a continuous aperture so that a part of the apparatus is cantilevered above the cassette compartment. The opening 324 and the additional opening 325 define a horizontal, inclined or vertical plan (in respect of the apparatus) in which the cassette will be inserted during at least a part of the loading process or during the treatment.

The opening 324 is adapted to allow inserting and removing the cassette, thus the opening 324 may be larger than at least the side of cassette by which the cassette is inserted. At least during the insertion phase or withdrawn phase (of the cassette), guiding elements (of the cassette holder, for example tracks) are aligned with the opening(s) and arranged along with the plan defined by the openings.

The additional opening 325 is adapted to allow at least one element to protrude from the housing, for example the tubes, handle, . . . . The additional opening 325 may be smaller than the side of the cassette by which the elements protrude. For example, the opening 324 (shown at the FIGS. 23*a*, *b* and *c*) has substantially the same size than the side of the cassette which comprises the handling element 109 while the additional opening (the side opening) 325 (as shown in the FIG. 23*c*) is shorter than the corresponding side of the cassette. The dashed line shows the limits of the cassette in the apparatus.

The FIGS. 23*a* and *b* show the references "XX" and "YY", these references illustrate the recess formed by the cassette and the housing of the apparatus when the cassette is fully inserted. The size of XX and/or YY may be as small as possible (for example depending on the manufacturing tolerances) in order to provide an area substantially plane of at least one side (comprising the opening) of the apparatus when the cassette is fully inserted.

Figure 24:
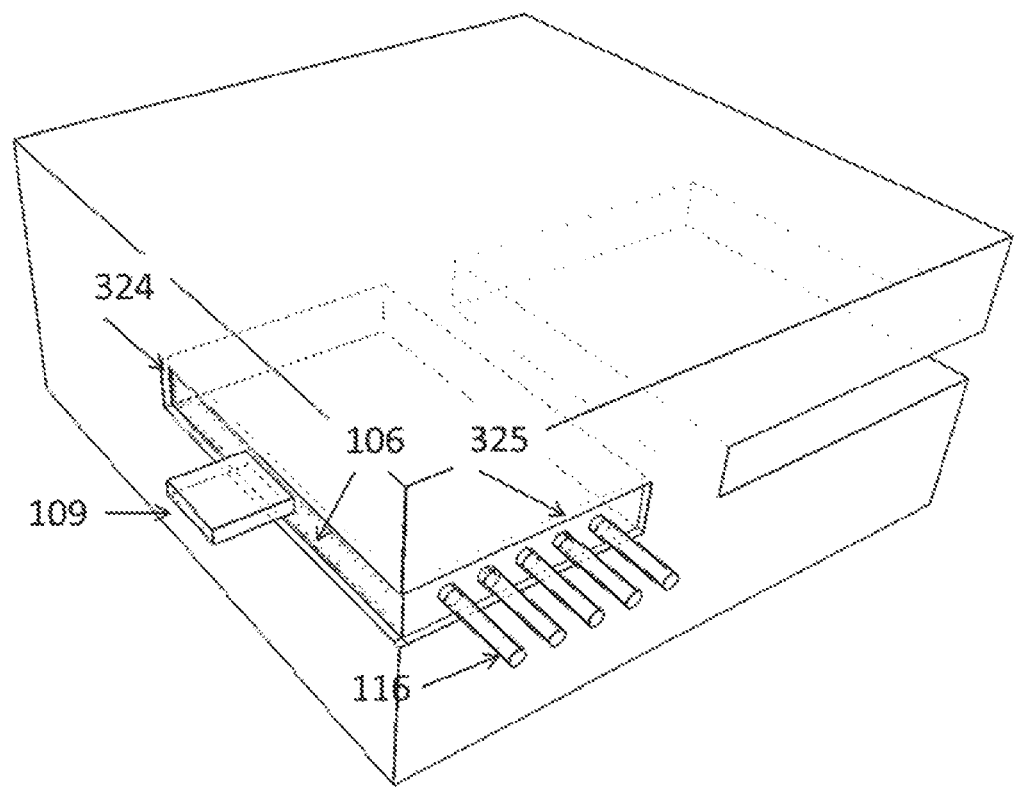
Figure 25:
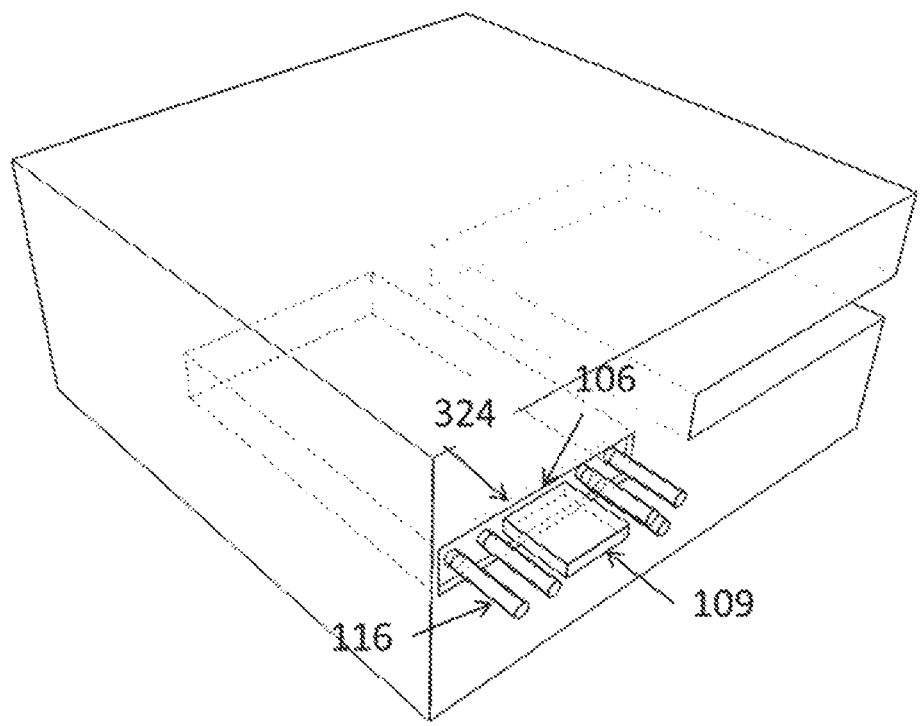
Figure 26:
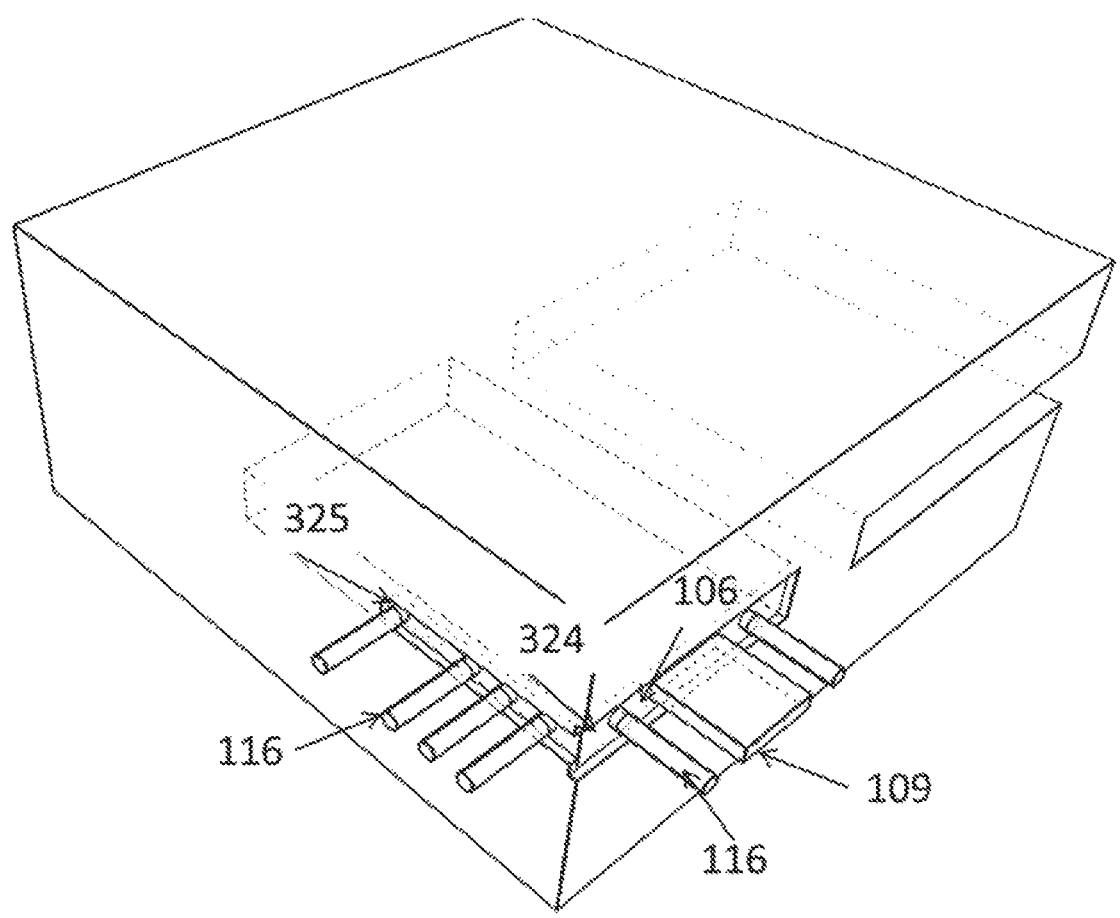

Other possible designs are shown by the FIGS. 24, 25 and 26. The FIG. 25 shows a single opening 324 (no opening 325) for the cassette and a cassette comprising tubes and optionally a handle arranged on the same side. In another embodiment, a part of the tubes are arranged on the same side of the handle and another part of the tubes are arranged on an other side of the cassette as disclosed at the FIG. 26.

All features illustrated through the FIGS. 22, 23, 24, 25 and 26 may be implemented to the blood cassette and/or the dialysate cassette and there dedicated opening(s) of the apparatus.

The apparatus may comprise container support 304 (such as a pole or a receiver) (for example as shown by the FIG. 7) intended to receive one or more container (such as bag, syringe, . . . ) during the treatment. The containers may be a part of the disposable part and the container support 304 may be a part of the reusable part. At least one container stored at least one of dialysate solution, saline solution, concentrate solution and other solution (heparin, calcium, pure water, . . . ).

As described above, the apparatus may comprise a container support 304 which is intended to receive or hold a solution bag during the treatment. The container support may be adapted to have a first position and a second position (and an optional third position). The first position is required during treatment and the second position may be required during the transport of the apparatus or when the apparatus is stored or when the apparatus does not perform any treatment. The second position allows having a compact apparatus with optimized size.

Figure 11A:
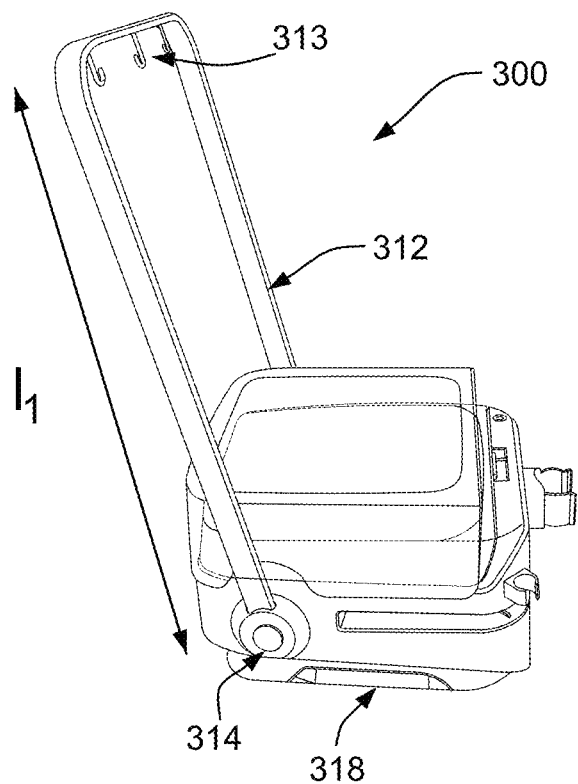
Figure 11B:
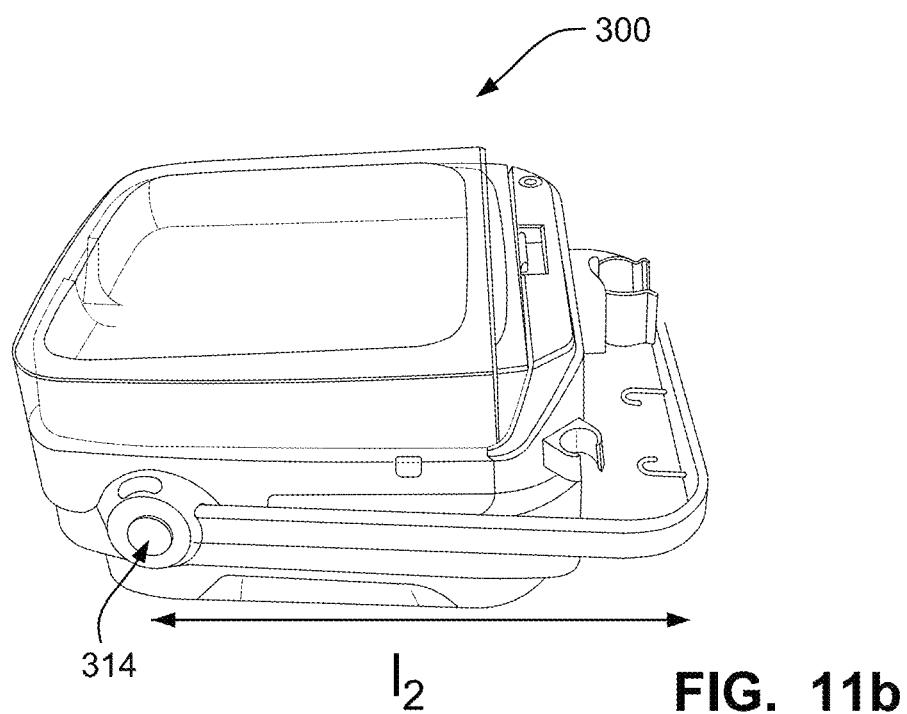

Referring to the FIGS. 11*a* and 11*b*, the apparatus 300 comprises a pole 312 adapted to hold at least one solution bag (for example: dialysate, concentrate, saline, empty bag, UF bag, drain bag, . . . ). The solution bag may be removably fixed to the pole 312 via one or more hook 313. The pole 312 comprises a first position allowing supporting the bag during treatment. The pole 312 may be telescopic in such a manner that the length (h) of the pole 312 (when is placed in the first position) may be greater than the length (12) of the pole 312 (when is placed in the second position). When the pole 312 is placed in a second position, the user may move the apparatus 300 by taking by the hand the pole 312 as a handle. The pole 312 may comprise a rotating fixing element 314 adapted to fix the pole to housing of the apparatus and to move the pole from a first position to a second position and/or vice versa. A lock device (not shown) may be adapted in order to block the pole in a predefined position. Preferentially the container 19, 28, 32 and/or 33 (for example shown by the FIG. 3, 20 or 21) is/are removably fixed to the pole 312 in preparation, priming and/or treatment configuration. The pole may comprise an electronic scale.

Figure 12A:
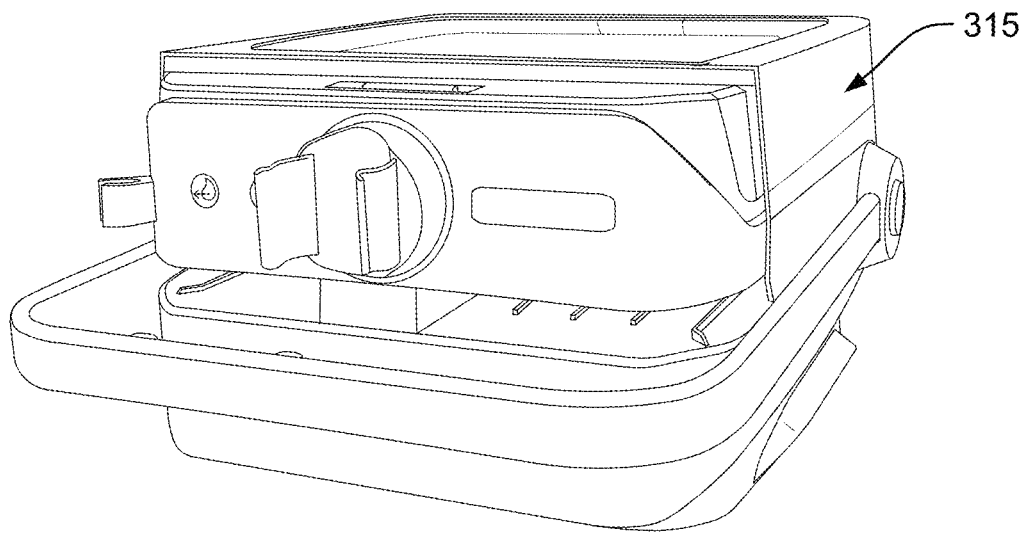

Referring to the FIGS. 12*a*, *b* and *c*, the apparatus may comprise a movable container support 315 adapted to receive a solution bag (for example: dialysate, concentrate, saline, empty bag, UF bag, drain bag, . . . ). The movable container support may comprise a receiver part having a concave shape designed to receive and to store at least one solution bag during the treatment. The apparatus 300 may comprise a fixing element 317 adapted to removably secure or to removably position or remobaly lay on the movable container support to/against the housing 301. The movable container support 315 comprises three positions, a first position required during treatment, a second position which may be required during the transport of the apparatus or when the apparatus is stored or when the apparatus does not perform any treatment and a third position providing an access to a container receiver 316 arranged below. The fixing element 317 may be a protrusion. The protrusion may comprise a protruded position allowing placing the movable container support in a first position and a retracted position allowing placing the movable container support in a second position.

The FIG. 12*a* shows the movable container support 315 in a second position. The movable container support is designed to optimize the size. The shape of the movable container support 315 and the shape of the container receiver 316 are designed in such a manner that the container receiver 316 may receive at least a part of the movable container support, for example the receiver part of the movable container support 315. Another part of the movable container support may be designed in such a manner to surround a part of the housing 301 when the movable container support is in second position.

Figure 12B:
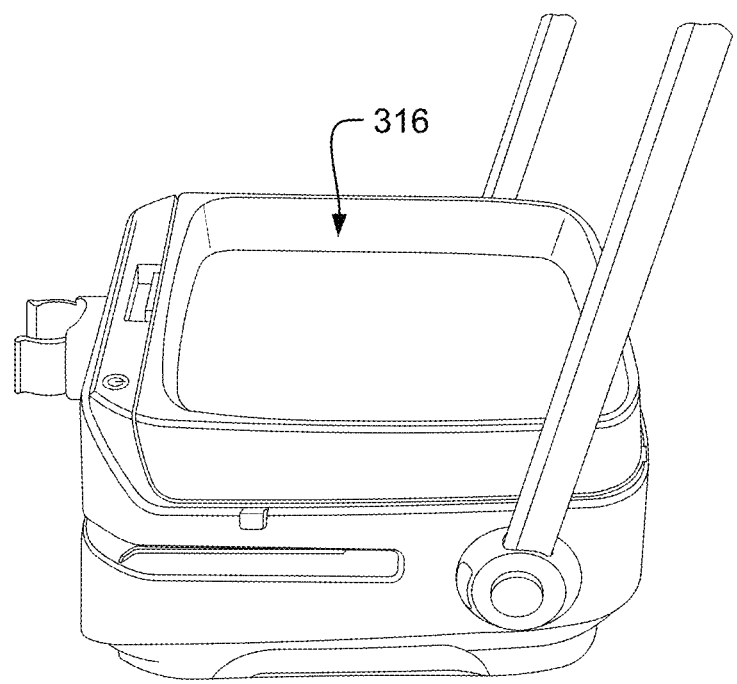

The FIG. 12b shows the movable container support in a third position so as to have an access to the container receiver 316. The movable container support may be removed from the apparatus (for example from the housing).

Figure 12C:
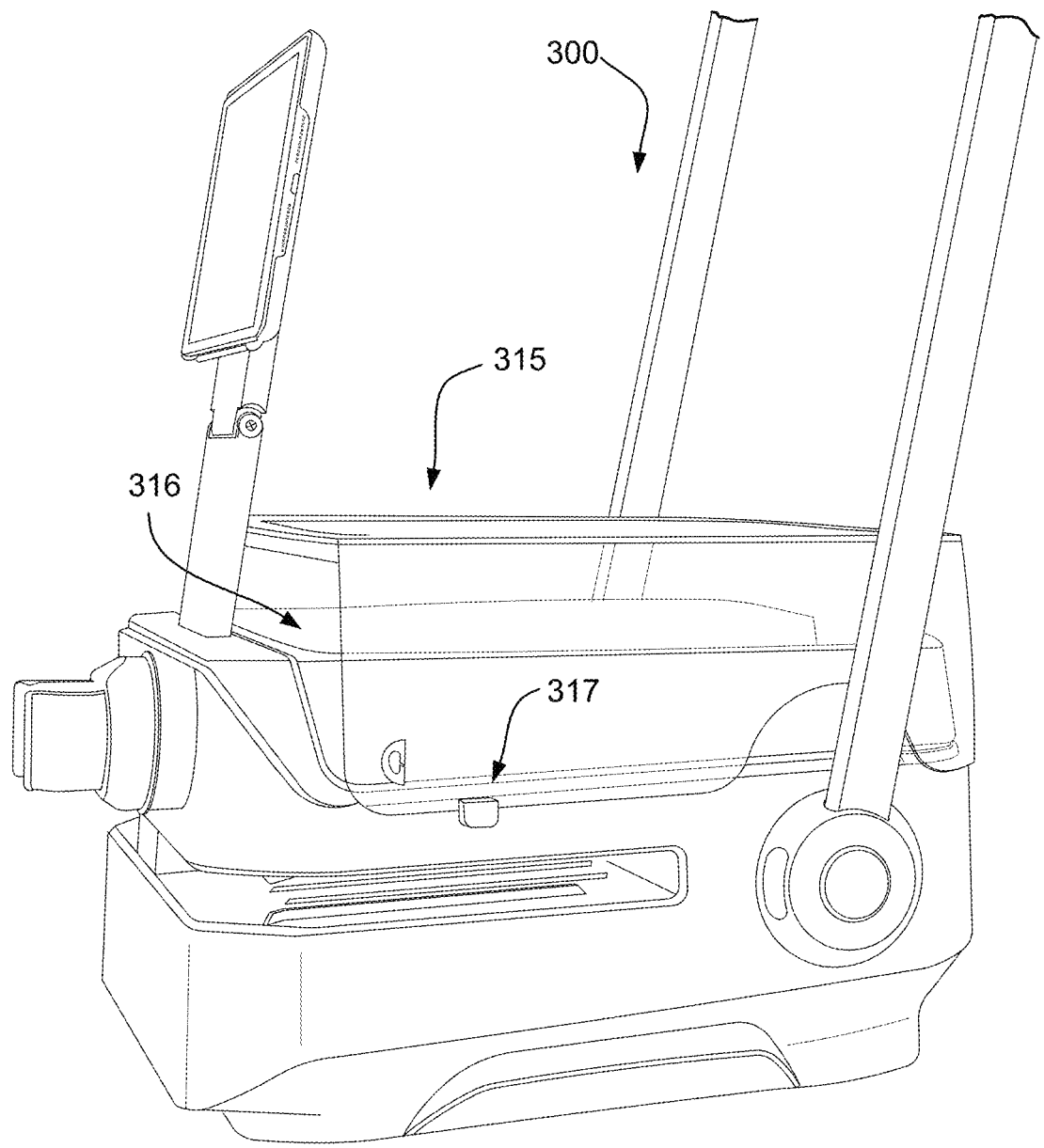

The FIG. 12c shows the movable container support 315 laid on or positioned on or secured to the fixing element 317 (for example the protrusion) when the movable container support is placed in a first position. In this position, a first solution bag may be stored in the movable container support 315 (for example a concentrate solution bag) and a second solution bag (different from the first, for example a dialysate solution bag or a saline solution bag) may be stored in the container receiver 316 (arranged below the movable container support). The container receiver 316 may comprise a heating element adapted to heat the bag stored in the container receiver. As the movable container support is placed above the heated bag, the bag stored in the movable container support can receive residual heat. The container receiver may be firmly secured to the apparatus.

This container receiver 316 may further comprise a weight scale in order to weigh the bag stored in the container receiver. The movable container support 315 may be designed in such a manner that the weigh scale is not disturbed by the movable container support or by the weight of the bag stored in the movable container support. In other terms, when the movable container support is in first position, (for example thanks to the fixing element and the shape of the container support or container receiver) the receiver part of the movable container support 316 is spaced far enough apart from the receiver part of the container receiver 316 in order to store a predetermined volume of fluid stored in the bag (received by the container receiver 316). In case where the system comprises a sorbent device and the container receiver stores the bag 13 of the FIG. 3, this volume of fluid is determined by taking into account a dialysate volume and the ultrafiltration resulting from the treatment. The dialysate volume may be a quantity commensurate with being recycled through the sorbent cartridge multiple times.

Preferentially the movable container support 315 receives a supply solution bag (for example a concentrate supply bag 31 or other) and the container receiver 316 receives a dialysate solution bag 13 (also called the weighing bag) used to mix and/or to weigh the cleaned dialysate (cleaned by the sorbent and comprising ultrafiltration) and a volume fraction of concentrate (progressively added during the treatment).

Figure 34:
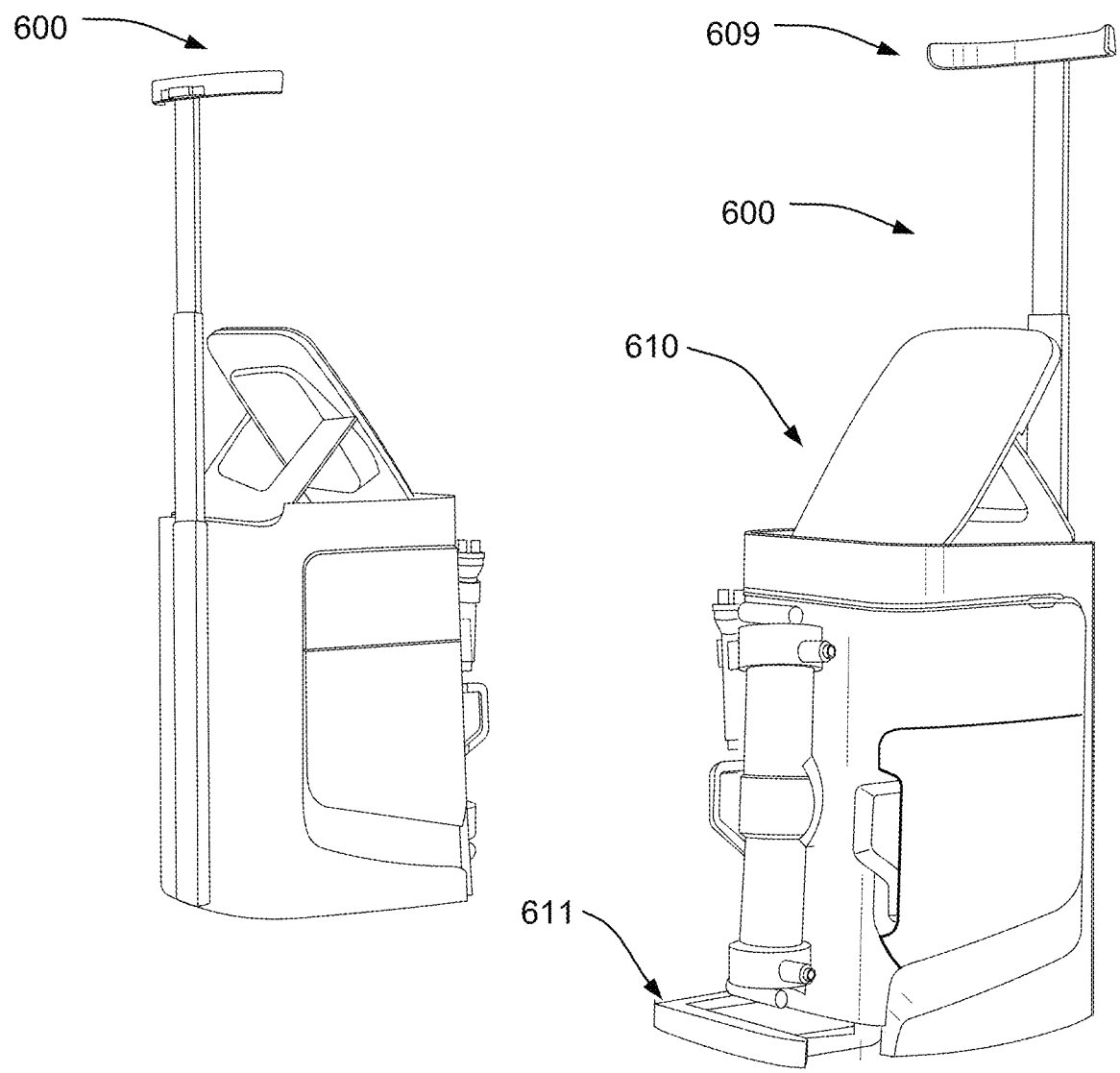
Figure 35:
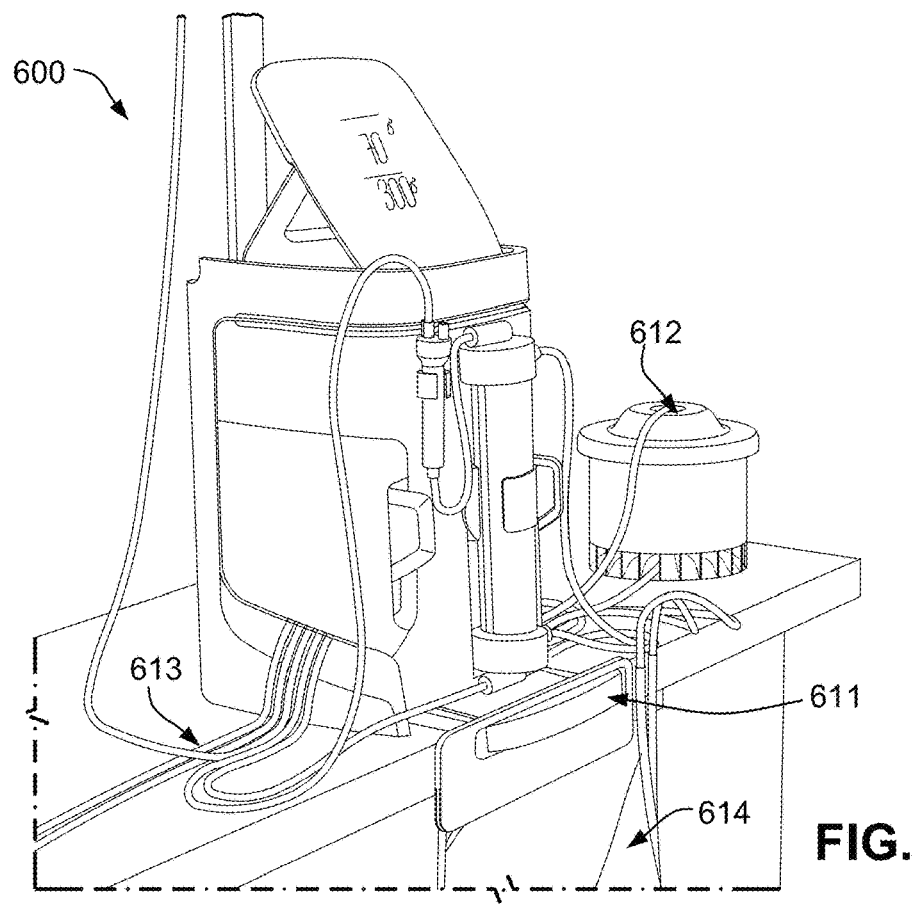

Referring now to the FIG. 33, the dialysis system 600 comprises an apparatus 601 having a housing 607, a first door 604 and a second door 605. The first door 604 is configured to allow accessing the cassette holder of the blood cassette 602 (for example). The second door 605 is configured to allow accessing the cassette holder of the dialysate cassette 603 (for example). The dialysis system 600 may comprise a loading system as described thereafter. The loading system may horizontally move the cassette holder (with or without the door) or the functional element support The FIG. 34 shows two views of the dialysis system 600 having a (extended and preferentially retractable) pole 609, a removable display device 610 and a weighting scale 611. The FIG. 35 shows the system 600 in functional condition. The system further comprises a sorbent device 612, the tubes 613 of the fluid circuits and the weighing bag 614.

Figure 36:
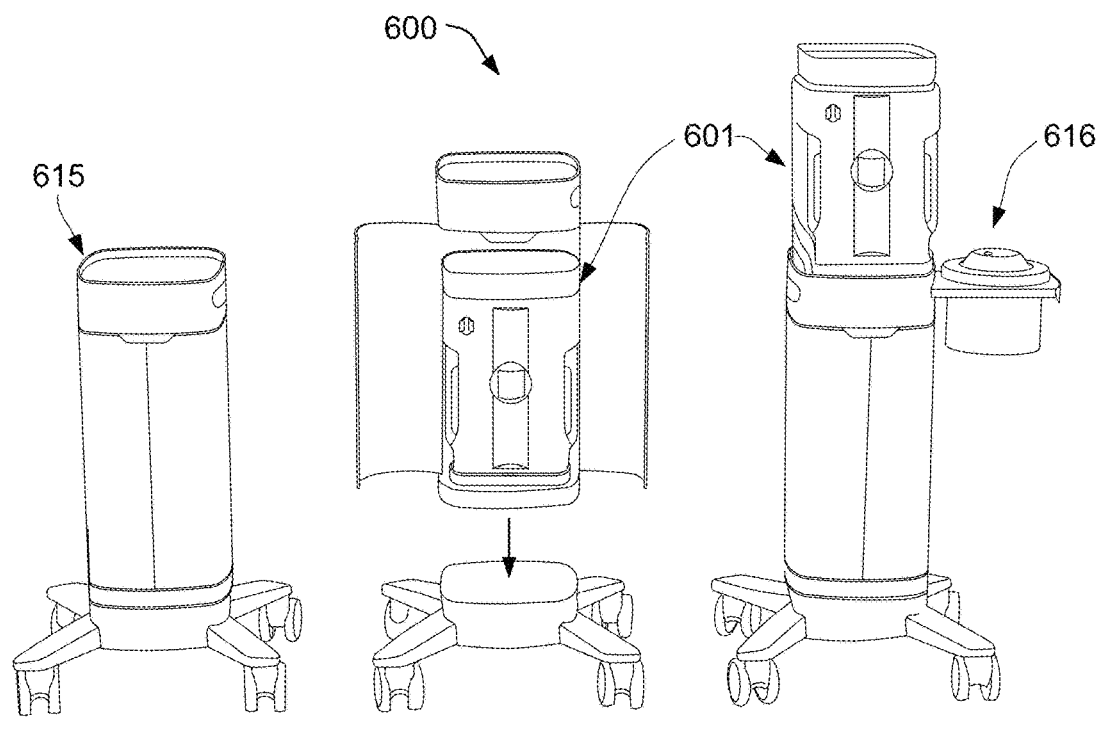

The FIG. 36 show an apparatus support 615 which may be modular and may be used as a luggage with rollers (as described thereafter). The apparatus support 615 may be configured to store the apparatus 601 into a cavity of the apparatus support 615 in transport condition. Optionally, the apparatus support 615 may be configured to support or to receive the apparatus on a surface of the apparatus support in functional condition.

The apparatus support 615 may further comprise a sorbent support 616 arranged on a side of the apparatus support and which may be retractable into the apparatus support. The apparatus support may comprise rollers, a planar surface and side doors.

The FIG. 37 shows another potential embodiment 700 having an apparatus 701, a display device 710, a door 704 allowing accessing to the cassette holder(s) and a heating compartment 705. In this embodiment, the loading system may move up and down the cassette holder with the door.

The FIG. 39 shows the system 700 in functional condition. The system further comprises a sorbent device 712, the tubes 713 of the fluid circuit and the weighing bag 714.

Loading System

Two distinct loading systems may be used for the apparatus (for example shown by the FIGS. 13 to 17). For both systems, the loading system 400 comprises at least one of a drive mechanism and a cassette holder 401 intended to removably receive a cassette. The cassette holder 401 is arranged into the housing of the apparatus. The aim of the loading system may be to enable the coupling between dedicated active elements 404 (also called components), 403, 402 of the apparatus and the cassette 106. Preferentially the dedicated active elements are the active elements which are intended to be operatively coupled to the cassette (for example to the coupling area and/or to the measurement area of the cassette) during the operating process (during the treatment, or a part of test process, for example). The dedicated active elements may be at least one of a sensor 402 (air, pressure, blood detector, . . . ), an actuator of the pump 404, a valve 403, and . . . . A part or all dedicated active element may be arranged on a support 406. Said support may be plate or a frame structured or/and intended to receive and/or to be in contact with or closer to an operative face of a cassette (in operating configuration). The operative face of the cassette is a face or a part of a face which comprises the measurement area (intended to cooperate with the pressure sensor of the apparatus) and/or the coupling area (intended to cooperate with the valve actuator, the pump mechanism or other actuator of the apparatus).

The drive mechanism is adapted to enable a first position wherein the cassette may be operatively coupled with the dedicated active elements of the apparatus and a second position wherein the cassette is not coupled with (for example spaced apart from) the dedicated active elements of the apparatus. The second position further allows charging the cassette into or removing the cassette from the cassette holder. When the loading system is in second position the opening and/or the cassette holder may be illuminated in order to inform the user that he can insert a cassette or remove the cassette. The illumination may be a specific color, for example a first color when the loading system is in a first position and a second color (different from the first) when the loading system is in a second position. Another indicator device may inform the patient about the position of the loading system, for example a sound, a voice, a movie, a text on the display device or on the additional display or a light illuminating a part of the dialyzer support.

The cassette holder 401 comprises at least one of a guiding means (for example rail or (linear) guiding element) adapted to cooperate with the cassette in order to allow a sliding (relative) movement (of the cassette relatively to at least one of the cassette holder, the components and the housing), a mechanical stop, and a sensor. The sensor may be adapted to detect an insertion of a cassette and/or a full insertion of the cassette. The sensor may be adapted to determine if the element inserted (into the opening) is a cassette or other (for example a finger, . . . ). For example the sensor may be an optical sensor connected to the processor of the apparatus. For example, a transmitter emits an (invisible infrared) light beam to a receptor. The processor detects a finger or other things when the receptor does not receive the (infrared) light beam. The cassette may be substantially transparent thus the receptor can recognize the cassette thanks to the dispersed light which is detected by a sensor. The sensor may be arranged near the opening and/or near the mechanical stop.

In one embodiment, a first sensor may be arranged close to a first end into the receiving compartment of the cassette holder (for example the opening) in order to detect the insertion of an object. A second sensor may be arranged close to another end into the receiving compartment of the cassette holder (for example an opposite end of the first end) and adapted to detect a cassette fully inserted. In this embodiment, the first sensor may be optional. When the loading system is in a second position, the display device may display a message so as to inform the user to insert the cassette. After a predetermined period of time, if the first sensor does not detect any passage then the display device may display a message so as to inform the user that no cassette has been detected and an audible alarm may be triggered. If the first sensor detects an object but the second sensor does not detect any object after a predetermined period of time, then the display device may display a message so as to inform the user that the cassette has not been fully inserted and an audible alarm may be triggered. If the first sensor and the second sensor (or at least the second sensor alone) detect the cassette then the processor may authorize the loading process (for example the passage from the second position to a first position, which also described thereafter) or may automatically initiate the drive mechanism (for example the change of position). A secure loading mechanism (as described thereafter) may check that both sensor or at least the second sensor detect the full insertion of the cassette and initiate the change of position when the user command the loading process (for example by pushing a button as described thereafter). If the user does not command the loading system, then the display device may display a message so as to prompt the patient to push the button (for example).

In brief, the method of insertion may comprise the steps of:
  Inserting the cassette through the opening of the apparatus;
  Detecting the cassette; and
  Allowing the activation of the loading system when the cassette is fully inserted.
In other terms, the processor, which operates with the loading system, is adapted to:
  Receive a signal of at least one sensor corresponding to a detection of a cassette in the cassette holder,
  Allow the activation of the loading system when the cassette is fully inserted,
The processor may be further adapted to (as similarly described thereafter)
  Receive a signal corresponding to an activation of one or more button, said activation and allowance being verified by the security loading mechanism;
  Initiate the change of position of the loading system by activating the drive mechanism.

Before starting the treatment (for example before that a fluid wets the cassette), the system may be adapted to abort the treatment if requested by the user. Thus, the system may comprise a button (for example a cancel button) arranged on the housing or displayed on the display device allowing to stop the process and to save the unused cassette. In this case, the processor may control the drive mechanism so to change the position if needed (from the first position to the second position) and the user can remove the cassette in order to use it at another time.

The cassette holder comprises one or more specific area (hole, opening, . . . ) where the dedicated active elements are intended to be coupled with the cassette.

According to a first embodiment, the drive mechanism is adapted to move the cassette holder (also called movable holder of cassette) relatively to the apparatus (for example to at least one of the housing, to the opening, and the fixed support of components). The support 406 of the dedicated active elements 406 (also called fixed support of components) may be firmly secured into the apparatus and are not moved by the drive mechanism.

According to a second embodiment, the drive mechanism is adapted to move one or more dedicated active elements (for example the support (also called movable support of components)) relatively to apparatus (for example to at least one of the housing, to the opening and the fixed holder of the cassette). The cassette holder (also called fixed holder of the cassette) may be firmly secured into the apparatus and are not moved by the drive mechanism.

According to another embodiment, the drive mechanism is adapted to move one or more dedicated active elements and the cassette holder relatively to apparatus. Thus, the drive mechanism is used to bring the dedicated active elements and the cassette holder closer or to move away.

In all cases, preferentially, the opening(s) of the housing does (do) not move with the drive mechanism. In other terms, the opening(s) of the housing may be fixed and/or may have a fixed perimeter. Thus, according to the first embodiment described above, the openings of the cassette holder are aligned with the opening of the housing only when the loading system is in second position. According to the second embodiment described above, the (openings of the) cassette holder are aligned with the opening of the housing when the loading system is in first position and when the loading system is in second position. Thanks to this embodiment, there are no risk of pinching fingers.

Referring to the FIG. 13*a*, the first embodiment and the second embodiment may be used here. The loading system 400 is in open position allowing inserting the cassette into the cassette holder. The dedicated active elements are spaced apart from the specific area.

According to the FIG. 13*b*', the cassette holder is moved by the drive mechanism relatively to the dedicated active element in order to put the loading system (or the cassette holder) in a first position. According to the FIG. 13*b*'', the dedicated active elements (or the support) are moved by the drive mechanism relatively to the cassette holder in order to put the loading system (or the dedicated active element or the support 406) in a first position.

The FIG. 13c shows the loading system 400 in the first position wherein the cassette may be coupled to the dedicated active elements. This position is maintained during the operating process, for example during the treatment.

According to the FIG. 13d', the cassette holder is moved by the drive mechanism relatively to the dedicated active element in order to put the loading system (or the cassette holder) in a second position. According to the FIG. 13d", the dedicated active elements (or the support) are moved by the drive mechanism relatively to the cassette holder in order to put the loading system (or the dedicated active element or the support 406) in a second position.

The FIG. 13e shows the loading system 400 in the second position. The dedicated active elements are spaced apart from the specific area. The cassette can be removed from the cassette holder.

The FIG. 13f shows the loading system 400 in a first position but without cassette. The FIG. 13g shows the loading system 400 in a second position without cassette. The FIGS. 13f and 13g show a rest position which may be required when the apparatus is not used or is moved.

In one embodiment, an active element (such as (pinch) valve actuator or pumping mechanism) may act in an opposite direction of the drive mechanism and may induce a non-intentional displacement of the loading system. For example, when the valve actuator is actuated to close a fluid pathway, the valve actuator may push on the cassette and induce a non-intentional displacement of at least one of the movable holder of the cassette and the movable support of the components. A first solution may be a lock device configured lock the position of at least one of the movable holder of the cassette and the movable support of the components. A second solution may be that the component(s) which may induce such non-intentional displacement is not arranged on the movable support of the components. Thus, an embodiment may comprise a fixed support of the components and a movable support of the components. One or more component (such as valve actuator, sensor, pumping device or other) may be arranged on (fixed to) the fixed support of the components while one or more component (such as valve actuator, sensor, pumping device or other) may be arranged on (fixed to) the movable support of the components. The movable support may be configured to be moved by the drive mechanism in order to move the component or the movable support in a determined position. The fixed support may be fixed to at least one of the cassette holder, the (frame of the) apparatus and the housing and is configured not to be moved by the drive mechanism (or not to cooperate with the drive mechanism).

For example, in order to prevent or limit the hemolysis, the valve(s) of the blood line may be a pinch valve configured to pinch a flexible tube (for example of the (blood) cassette). This type of valve may induce a non-intentional displacement thus the pinch valve may be arranged on a fixed support while at least one other component (pumping device, sensor, other actuator, . . . ) may be arranged on a movable support. In this case, the pinch valve (and other components fixed to the fixed support) may have at least one of an actuated state (for example closing the fluid pathway when the loading system is in first position), a non-actuated state (for example opening the fluid pathway and/or when the loading system is in second position) and a disengage state (for example when the loading system is in second position).

The loading system 400 may comprise a lock system which locks the inserted cassette in order to prevent a movement of the cassette during the treatment. This lock system may be at least one pin which cooperates with at least one cavity (for example a hole) of the cassette. The lock system may be activated by the drive mechanism. Thus, when the drive mechanism puts the loading system in the first position, the pin enters into the cavity of the cassette. And when the drive mechanism puts the loading system in the second position, the pin is removed from the cavity of the cassette. The lock system may be used to perform a fine alignment of the cassette with the dedicated active element as a guiding element when the drive mechanism puts the loading system in the first position. The alignment of the cassette with the dedicated active element may be (fully or partially) insured by the shaft of the pump. The lock system may be the shaft of the pump when insert between the rollers.

The dialysate cassette holder may comprise a "dialysate" dedicated loading system and the blood cassette holder may comprise a "blood" dedicated loading system. Both dedicated loading systems may be substantially simultaneously activated or initiated. Or each dedicated loading system has to be separately activated or initiated. In case of dedicated loading system, each dedicated loading system may comprise a dedicated drive mechanism or both dedicated loading systems may be drove by a single drive mechanism.

The drive mechanism of the loading system (dedicated or not) may be automatically activated by the processor or may be enabled when the sensor of the cassette holder detects a full insertion of the cassette into the cassette holder. The drive mechanism may be activated by the user. The apparatus may comprise a secure loading mechanism which prevents a finger pinching when the user activates the drive mechanism. The secure loading mechanism may be software solution and/or a hardware solution. For example, the apparatus may comprise two distinct buttons arranged for example on the housing or on the touch screen. Both buttons may have to be substantially simultaneously activated by the user to initiate the change of position of the loading system (from the second position to the first position). Preferentially, the buttons are spaced far enough apart from each other in order to compel the user to use both hands (for example at least the average length of a child's hand). The button may be also spaced far enough apart from the opening(s), a safe distance may be equal to the length of a hand (for example at least the average length of a child's hand).

The secure loading mechanism may be adapted for preventing the patient from inadvertently initiating the change of position. For example, the secure loading mechanism may be configured to prevent the processor from initiating the change of position unless the user activates a button (arranged on the housing or spaced apart from the housing or on the touch screen) according to an activation sequence and the sensor detect a full insertion of the cassette. The activation sequence may compel the user to hold the button activated or pressed during a predetermined time period (for example until the loading system has reached the first position). Thus, if the user no longer presses the button, the secure loading mechanism may send a signal to the processor in order to stop the loading process and go back to the second position the loading system. Thus the loading process may comprise the following steps:

Receive (by the processor) a signal corresponding to an activation of one or more button according to an activation sequence by the user, said activation being verified by the security loading mechanism;

Initiate the change of position of the loading system (or initiate the loading of the cassette into an operating configuration) by activating the drive mechanism; and, Stop the drive mechanism or put the loading in an initial position (for example in the second position) by the secure loading mechanism in case of failure (for example if the user no longer presses the button according to an activation sequence).

The apparatus may comprise a sensor adapted to monitor or to detect at least one of first position and second position of the loading system 400. The sensor may be an optical sensor, a hall effect sensor, . . . . A first sensor may be intended to detect the first position and a second sensor may be intended to detect the second position.

In operating configuration, if the processor detects a change in the position, the processor may activate (temporarily or continuously) the drive mechanism in order to maintain the good position. In other embodiment, the cassette is maintained in the correct position throughout a treatment by friction. The loading system applies a residual force on the cassette (by design) and the processor does not apply any additional power to the drive mechanism.

The electrical load data (of the drive mechanism) is transmitted to the processor (also called processing unit). The electrical load data may be the voltage applies to the motor of the drive mechanism. When the voltage reaches a predetermined value, the processor may stop the motor. The electrical load data may be also used to detect a jam condition. In order to determine if a change (a peak or a threshold) of the electrical load data is caused by an end of the loading process or by a jam condition, the system may use data sent by the position sensor. For example, when the loading system moves from the second position to the first position, the second position sensor sends a signal to the processor for example so as to inform that the loading system is no longer at the second position (or, conversely, from the first to the second position, the first position sensor sends a signal to the processor). The processor monitors the electrical load data and if a predetermined threshold is reached before receiving a signal of the first sensor (for example for informing that the first position is reached), then the processor determines a jam condition. The processor triggers an alarm and the loading system goes back to the second position automatically. If a predetermined threshold is reached after receiving a signal of the first sensor (for example for informing that the first position is reached), then the processor determines that the first position is reached and stops the motor of the loading mechanism. The processor allows passing to the next step of the process.

In brief, the method of loading may comprise the steps of:
Initiating a change of position of the loading system (for example from the second to the first position or vice-versa);
Sensing a change of position (optional) (for example via the position sensor);
Sensing an electrical load data increase; and
Causing the stop of the loading process in jam condition or when the loading system has been reached the wanted position In other terms, the processor, which operates with the loading system, is adapted to:
Initiate (for example if all condition is ok as described above) the loading process (for example initiate the motor of loading mechanism)
Receive the signal of at least one position sensor (for example from the second position sensor),
Receive the electrical load data of the motor
Stop automatically the loading process (for example the motor) when a predetermined threshold has been reached (for example of the electrical load data)

If the processor receives a signal from the other position sensor (for example the first position sensor) before reaching a predetermined threshold then the processor determine that the wanted position has been reached and passes to the next step.

If the processor does not receive any signal from the other sensor (for example the first position sensor) while a predetermined threshold is reached then the processor determines a jam condition and optionally initiates the motor in a reverse mode so as to go back to the initial position.

The predetermined threshold of the jam condition may be higher than or smaller than or equal to the predetermined threshold of the end of the loading process.

This method describes more particularly the loading process but the same concept may be applied to the unloading process.

The FIG. 14 is an exploded view of a loading system 400. The loading system 400 comprises cassette holder 401, a support 406 (for example a movable support) of the dedicated active elements and a drive mechanism 409. In this embodiment, the drive mechanism may comprise an electric motor 410, a drive assembly 411 (for example a toothed drive assembly) and a guiding assembly 412. The guiding assembly 412 may comprise one or more linear guiding element (such as rod) rod (preferentially 2, more preferentially 3) and one or more sliding element (for example through holes (preferentially 2, more preferentially 3)) intended to slide along the rod. The sliding element may be arranged on or secured to the support of the dedicated active element.

The FIG. 15 show 3D views of one embodiment of the loading system in which the drive mechanism is adapted to move the support of the dedicated active elements relatively to the apparatus. The FIG. 15a shows the loading system in a first position without cassette, the FIG. 15b shows the loading system in a second position without cassette, the FIG. 15c shows the loading system in a first position with a cassette and the FIG. 15d shows the loading system in a second position with a cassette. In this figures, the cassette is inserted through a first opening of the cassette support, the cassette holder further comprises a second opening to pass the tubes of the cassette laterally (which is perpendicular to the first opening).

The FIG. 16 discloses an exploded view of an example of the first embodiment of a loading system 400. The loading system 400 comprises cassette holder 401 (for example a movable holder of the cassette), a support 406 of the dedicated active elements and a drive mechanism 409. The drive mechanism may comprise an electric motor 410, a drive assembly 411 (for example a toothed drive assembly) and a guiding assembly. The guiding assembly may comprise one or more guiding element 412' (preferentially 2, more preferentially 4) and one or more sliding element 412' (such as pin (preferentially 2, more preferentially 4)) intended to slide along or against the guiding element. The sliding element may be arranged on or secured to the support of the dedicated active element. The guiding elements are arranged on a support 413 (for example a plate or a frame) which moves relatively to the apparatus. The guiding elements are intended to transform a first axial movement into a second axial movement which is different from the first axial movement (for example perpendicularly). The guiding elements may have an opened L shape, a comma shape, . . . The motor 410 is actuated in order to rotate a pinion gear which moves the guiding element support 413 in accordance with a Y axe. The loading system is designed in such a manner that the movement of guiding element support induces a movement of the cassette holder in accordance with a Z axe (which is perpendicular to the Y axe). For example, the cassette holder has a movement restrictor adapted to prevent movements other than Z axe movement. Thus, a Y axe movement of the guiding element induces a Z axe movement of the pin (relatively to the apparatus).

Door Device

In order to protect the active element(s) of the apparatus and/or to substantially obstruct the opening (with or without cassette), the system may comprise a door device comprising a door device (also called door) and/or a flexible element. For example the door may be a sliding door or a retractable door or a revolving door or swing door. For example the flexible element may be a sheet and may cover at least partially the opening. The flexible element may be adapted to be bend when the cassette is inserted into the opening or when tubes or handle protrude from the opening. An example of a flexible element 423 is shown in the FIG. 30g. In this case, the flexible element is fixed to the apparatus, for example to the apparatus body (such as the housing), or for example to a moveable part of the apparatus body (such as the housing).

The opening and/or the closing of the door device may be manual and/or automatic for example controlled by the processor. Preferentially, the door 415 is (initially) closed and may be open only in order to insert a cassette into the opening. The door may comprise two positions an open position which allows loading or unloading a cassette into/from the cassette holder and a closed position which substantially or at least partially obstructs the opening.

The FIGS. 31a and b show a part of the housing comprising a door device including a sliding door. The embodiment shown by the FIG. 31a further comprises a manual door actuator 416 configured to manually open and/or close the sliding door. The user can lower (or respectively pull up) the manual door actuator in order to slide the door so as to open or to close the door.

The door device may comprise a lock system 418 (for example as shown by the FIG. 32) and/or a constraint system 419 in order to maintain the door in a determined position, for example in an open position or in a closed position. At least a part of the lock system 418 and/or at least a part of the constraint system 419 may be rigidly fastened to a (rigid) body of the apparatus (for example a part of the housing).

The FIG. 32 is an interior view of a (rigid) body of the apparatus (for example a part of the housing), some elements are not shown in order to focus on the lock system 418 and the constraint system 419.

The door device may comprise a protrusion adapted to be removably coupled to the lock system 418 when the door is in a determined position (for example when the door is opened) such that the user can easily insert the cassette. The lock system may comprise elastic element (spring, elastic strip, . . . ) which constraints a retaining element (lug, clip, protrusion, anchor, . . . ) adapted to be coupled with the protrusion of the door. The lock system may be disabled by the user by pushing on the manual door actuator (for example). The lock system may be disabled by the processor via a dedicated (connected) actuator (not shown) or via the loading system. In the last case, the loading system may be adapted to disable the lock system when the loading system is actuated (when is moved from a first position to a second position and/or vice versa).

The door device may comprise a sliding element adapted to slide through a guiding element of the (rigid) body of the apparatus (for example a part of the housing) in order to restrict the movement of the door (or inversely, the apparatus body may comprise the sliding element and the door may comprise the guiding element). The sliding element may be a through hole or a protrusion of the door device and the guiding element may be a rod (for example steel rod) or a recess for example arranged on the (rigid) body of the apparatus (for example a part of the housing).

The constraint system 419 may exert a force against the door and against the (rigid) body of the apparatus (for example a part of the housing) so as to close the door or to force the door in a closed position. The constraint system 419 may comprise elastic element (spring, elastic strip, . . . ).

In a preferred embodiment, the door is opened thanks to the loading system and is closed by the constraint system. In this case, the door device and/or the loading system may comprise a coupling element 422 (as shown by the FIG. 30).

The coupling element 422 may be configured to mechanically cooperate with the loading system according to at least one dimension. The coupling element may comprise a protrusion arranged on at least one of the movable support 406 and the door device 415. The coupling device may further comprise an associated device (such as a contact space, a sliding element, a hole, a slot or a groove) configured to cooperate with the protrusion (for example by contact or slip). The coupling device may cooperate with the loading system when the loading system moves the movable support in at least one direction (for example from the first position to the second position and/or vice versa). Thus, for example, when the loading system is moved to the second position, the loading system pushes the door device down in order to open the door (and the constraint system may be compressed). When the loading system is moved to the first position, the constraint system may push up the door in order to close the door and the coupling device or the inserted cassette may limit the displacement of the door. When the The coupling element may be disabled by the processor (via for example an actuator) or via a button pushed by the user (as disclosed by the FIG. 31a) thus even if the loading is in second position, the door may be closed by disabling the coupling element.

In one embodiment, when the loading system moves in a second position, the loading system opens the door via the coupling element and then a lock system maintains the door in open position. The coupling element or the lock system may be disable in order to close the door (even if the loading system is in the first or second position) by the processor or the user as disclosed above.

Figure 30A:
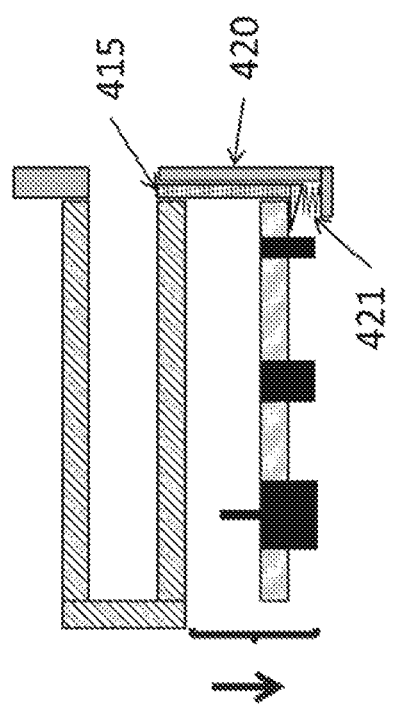
Figure 30B:
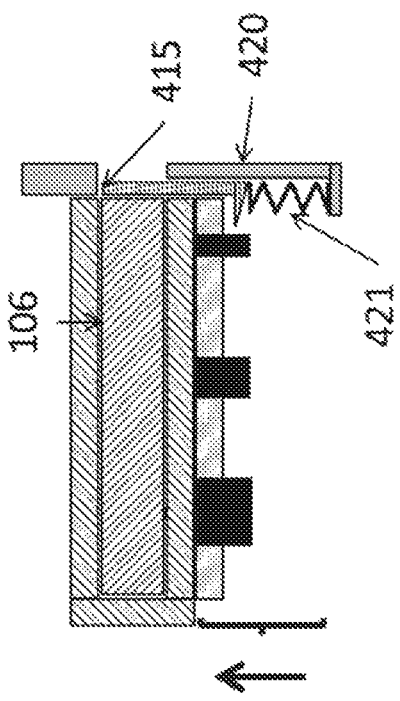
Figure 30C:
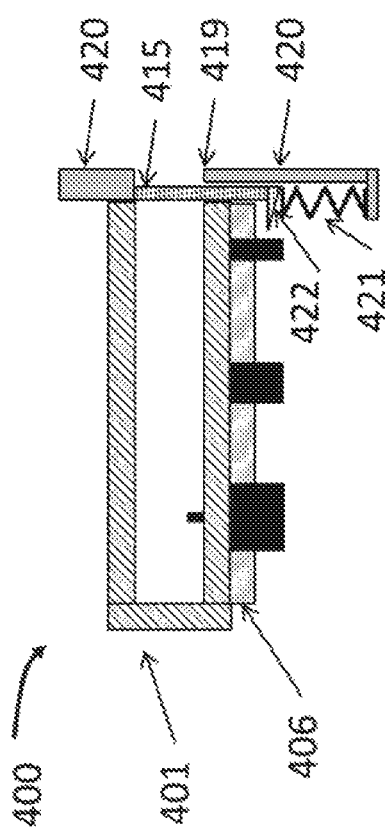
Figure 30D:
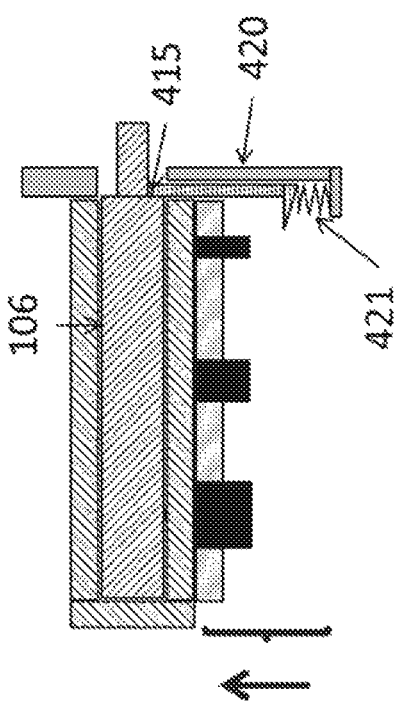
Figure 30E:
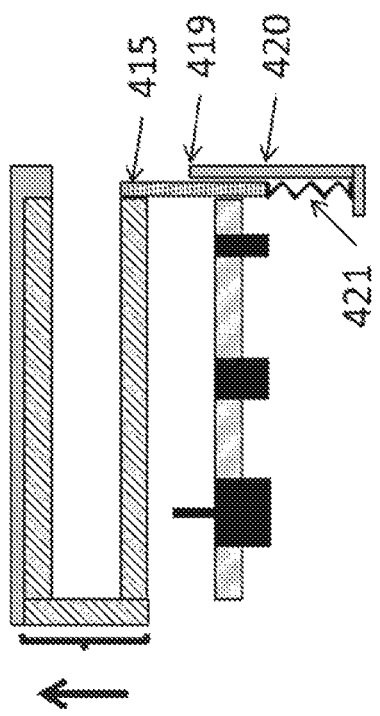

The FIG. 30a shows a door 415 in closed position and the loading system in a first position without cassette. The system comprises an elastic element 421 which may be a spring or an elastic strip or arm which constraints the door 415 in a closed position. The door and/or the loading system further comprises a coupling element 422 configured to (only) allow the loading system to move the door up to an open position (for example: from a closed position to an open position) as shown in the FIG. 30b. The FIGS. 30c and 30d show the embodiment with an inserted cassette. The cassette 106 is inserted and the loading system is in a first position. In the FIG. 30c, the door is no longer maintained in open position by the loading system but by the cassette.

The door may be used to block the cassette inserted when the loading system is in first position. In the FIG. 30d, the door is in closed position with an inserted cassette.

The door device may comprise several parts of door such that a first part of the door device may fully close the opening (for example: where the cassette does not comprise any protrusion which extends outside the apparatus (no tube no handle)) and such that a second part of the door device may maintain in a open position or in a partial closed or open position (for example: where the elements of the cassette protrudes and extends outside the apparatus (such as handle, tubes, . . . ))

Figure 30F:
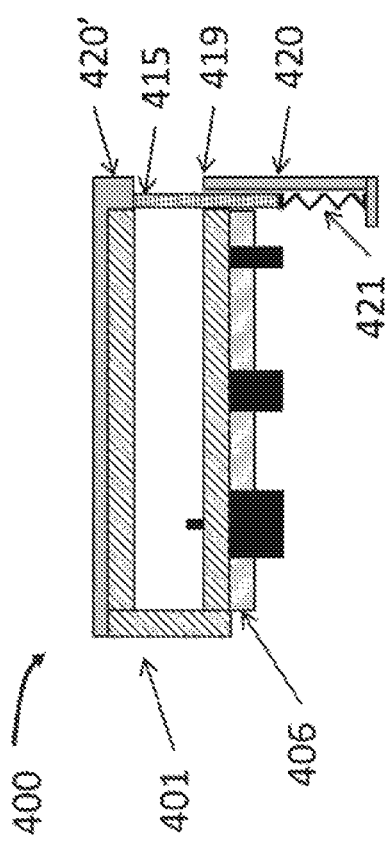
Figure 30G:
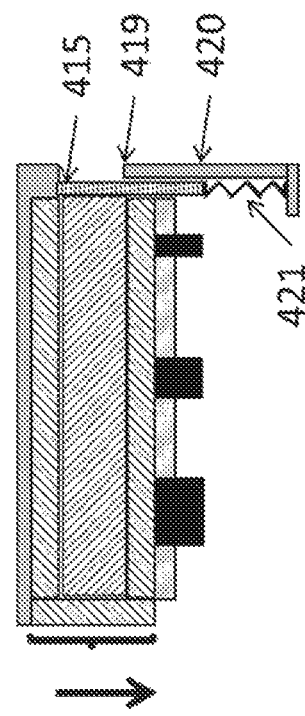
Figure 30H:
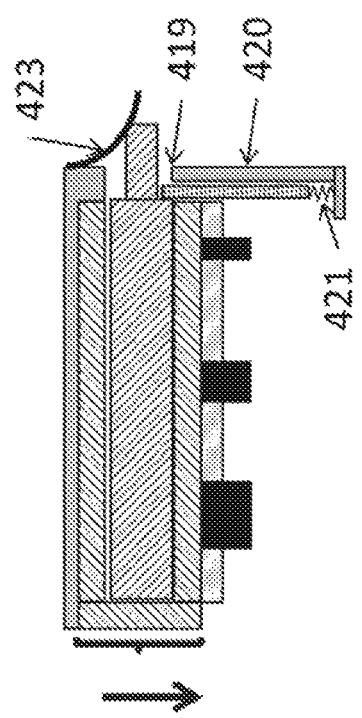

The FIGS. 30e to 30h discloses another embodiment where the loading system moves the cassette holder, for example such embodiment may be adapted for the apparatus shown in the FIG. 37. In this embodiment, the loading system may move the container receiver or the top housing up and down (and have a sliding door as described above). The FIGS. 30e to 30h show the last case. The system comprises a sliding door 415, a top housing 420', a (movable) cassette holder 401 and a (fixed) element support 406. The loading system is configured to move the cassette holder. The sliding door is maintained in a first position by an elastic element (spring or other similar element). When the loading system is in first position without cassette, the sliding door 415 is maintained in the first position by the elastic element such that the door closes the opening. In FIG. 30f, the loading system moves in the second position, the sliding door is substantially in a same previous position (a mechanical stop may maintain the sliding door in a first position) but the cassette holder is in an open position. In FIGS. 30g and h, a cassette has been inserted and the loading system is in first position. Referring to the FIG. 30g, an element of the cassette protrudes from the opening and the door is maintained by this element in the open position or in an intermediary position for example in a partial close or partial open position. Referring to the FIG. 30h, the cassette is inserted and the door is closed.

In another potential embodiment, the door device may comprise a swing door which is opened on top or laterally.

Drip Chamber Support

As shown by the FIG. 18, the drip chamber 501 is used to remove air bubble from the blood circuit. The support 500 of the drip chamber 501 is used to removably fix the drip chamber to the apparatus. The drip chamber support 500 may be arranged on a face of the apparatus housing or in the pole. The FIG. 18 shows an embodiment of the drip chamber support 500 with a drip chamber 501. The drip chamber support may comprise a body 502 secured to the apparatus and a level sensor. The level sensor may be an optical sensor, a wave sensor or a capacitive sensor. The level sensor is preferentially arranged into the body of the drip chamber support. The drip chamber support may further comprise a mechanical coding system 504 intended to maintain or insure a good/required position of the drip chamber relative to the drip chamber support or to the level sensor. The coding system 504 is designed in order to compel the position of the drip chamber relatively to the drip chamber support. For example, the drip chamber support may have a protrusion. The protrusion may be adapted to adjust the vertical position of the drip chamber in accordance with the level sensor. The drip chamber support may have a lock system 503.

Luggage

In order to improve the travel experience, the system may comprise an apparatus support (such as a bag or a luggage or a movable furniture) adapted to store the apparatus, for example a hand luggage, during the travel. The apparatus (housing with or without container support, with or without dialyzer support, . . . ) may be sized in order to be smaller than the bag (hand luggage), at least one dimension smaller than 31 cm, another dimension smaller than 51 cm and/or another dimension smaller than 61 cm.

The FIG. 19 shows an apparatus stored in hand luggage. The hand luggage is drawn in dotted line and comprises a handle. The size shown in this figure is done as an example. The bag may comprise at least two distinct housing cavities, a first housing cavity intended to receive the apparatus and a second housing cavity intended to receive the display device 302 (for example a tablet).

The hand luggage may comprise a door having an open position and a closed position. The open position of the door allows placing the apparatus into the hand luggage (for example into a dedicated housing cavity) and the closed position allows moving the hand luggage in a secure manner. The hand luggage may further comprise rigid part (for example the side wall or the upper wall or the lower wall of the hand luggage) designed to protect the apparatus.

The hand luggage may be used as an apparatus support which may comprise a platform configured to support the apparatus in operating configuration.

The hand luggage may comprise retractable handle and/or retractable rollers (or wheels).

The FIG. 36 illustrates an other embodiment of the apparatus support.

Priming Process

The following description discloses several priming steps/sequences. Each step describes a priming of a part of fluidic pathway to be carried out before starting the treatment, for example before the patient is connected to the system.

The main goal of the priming process is to remove the fluid initially present (for example air) in the blood circuit and/or in the dialysate circuit and to replace it by a priming solution (for example a liquid solution). In order to simplify the description, the document may use (in this part of the specification) the wording "air" in order to designate the fluid initially present in the circuit before the priming.

As described above, the system comprises a pump dedicated to the blood circuit, at least one pump dedicated to the dialysate circuit, a memory having computer-executable instructions including one or more operating sequence (for example for priming sequence, safety sequence, blood return sequence), a processor connected to the memory and the pumps. Both or at least one of the pumps may be adapted to move the priming solution (from a priming solution source for example from a priming supply container) through the fluid circuits. The processor is adapted to control each pump (successively or simultaneously) according to the computer-executable instructions in order to automatically perform all or a part of the priming sequence. Furthermore, the processor is configured to actuate dedicated elements of the system (such as valve opening or valve closing, pumping actuation, . . . ) depending on the computer-executable instructions.

For ease of reading, some elements may be removed from the figure.

Some valve and line may be optional for example the valve V7, line 15, . . . . The valve V12 and VA may bring some advantages but may be optional, in particular to control the flow and the air back flow through the line already primed.

Before the priming process, the user may insert the cassette(s) into the apparatus, install the dialyzer on the dialyzer support, the drip chamber on the drip chamber support, to place the additive container 31 (and optional 32), the blood return container 19 and/or the supply container (28, 33 and/or 41) for example to the pole or near the apparatus (on the table) and to place the weighing container 13 in weighing condition to the weigh scale. In one embodiment, the container 13 is placed into the container receiver 316 and the additive container is supported by the movable container support 315. In one embodiment both containers are placed into the container receiver 316 and are weighed by the same electronic scale.

Additive Line Priming

The processor may automatically trigger and perform this step for example without any user intervention.

Referring to the FIG. 49, this priming sequence may be optional (with or without shunt or container 41). The valves V9 and V10 are open and the additive pump primes the additive line. The air contained in the line goes into the weighing container 13, and is exhaust through a vent connected to the container 13. Said vent may comprise a hydrophobic filter. The step may end once the additive solution reaches the intersection with the dialysate circuit or the weighing bag. The stop trigger may be raised by pumping a volume equivalent of the portion line of the interest, or by a liquid detection sensor located arranged near the junction.

The motor rotation speed may be monitored and remain within a specific range during the step. Optionally, a pressure sensor monitors the fluid pressure upstream and/or downstream the pump (as shown by the FIG. 3a) and the processor may stop the pump after the definite volume is pumped. The monitored pressure shall correspond to the pressure generated by the "water-column" of the additive solution bag hanged to the device. This water-column will be given by the design of the device, as well as the volume solution contained in the additive bag.

At a flowrate of 15 ml/min+/−30 ml/min—corresponding to the same order of magnitude than treatment flowrate —, step duration of 40 seconds shall be considered.

Priming of the Container

The processor may automatically trigger and perform this step for example without any user intervention. This step may be triggered after one of the previous described steps, preferentially after the previous step. This step may be optional if the container 13 initially stores the initial dialysate solution.

If the weighing container 13 is initially empty (no liquid) then one of the first steps may be the priming of the container 13 and/or the purge of the line between the container 13 and the supply container 28 or 33. In this case, a supply container (for example the supply container 28 or 33) comprising an initial solution (such as dialysate solution, saline solution or pure water solution) may bring all or a part of the initial solution into the container 13 during this priming sequence.

At least one wall of the container 13, 28 or 33 may be flexible.

Focus on the FIG. 40, the system comprises a pump 14, a processor, a dialysate circuit, at least one valve, an initial supply container 28 or 33 and a container 13. The container 13 comprises an outlet port having and/or being in fluid communication with a dedicated valve V6 and an inlet port, both in fluid communication with the dialysate circuit. Furthermore, preferentially, the container 13 is a part of the dialysate loop circuit and is used as a buffer.

The initial supply container 28 or 33 comprises an outlet port having or being in fluid communication with a dedicated valve V5 and is in fluid communication with the dialysate circuit. During a part of the priming process of the system, the processor (automatically) closes the valve V6, opens the valve V5 (and preferentially V8) and actuates the pump 14 in order to move at least a part of the initial solution (also called priming solution) of the container 28 or 33 to the container 13. Preferentially, the valve V10, V7 and/or V12 are closed by the processor for example.

The system may comprise at least one weigh scale (electronic) 29 connected to the processor. During this step, the processor may monitor the volume of initial solution injected into the container 13. The weigh scale may weights the container 13 and/or the supply container 28 or 33. The system may further comprise at least one pressure sensor adapted to sense the fluid pressure in the fluidic pathway for example upstream and/or downstream of the pump 14. Furthermore, each pump may comprise two pressure sensor arranged closed to the pump, a first upstream of the pump and a second downstream of the pump.

This step may further comprise a running-in period of the pump 14 and the processor may monitor the flow rate of the pump 14. This running-in period may be particularly important if the pump 14 is a peristaltic pump (for example comprising a flexible tube compressed by roller(s) or finger(s) or other), because the flow rate of such pump may substantially shift over time in particularly at the beginning of the pumping. Thus, during this step the processor may monitor the flow rate by taking into account a volume fraction of initial solution injected into the container 13 over time, for example during one or more determined time period.

The system may further comprise a first bypass line, having a dedicated valve V8, configured in order to flow the fluid (for example the initial solution) by the pump 14 (for example) from the initial container 28 or 33 to the container 13 as disclosed by the FIG. 40 with the dashed arrow (even if the containers 28 or 33 and 13 are arranged upstream to the pump (according to the treatment operating mode)).

During the priming of the container 13, the valve V7 and the valve V12 may be closed and the valve V8 is opened (for example by the processor). The valves V7 and V12 may be optional; and during this priming step, a part of the priming solution may reach the dialyzer and/or the sorbent.

Optionally, the system may further comprise a second bypass line, having a dedicated valve VBP, configured in order to move the fluid (for example a dialysate solution or other) by the pump 16 (for example) through the filter 2 to the container 13 without passing through the sorbent device 17.

This priming step may be stopped when the supply container 28 or 33 is fully emptied or when a determined volume injected into the container 13 is reached or when a determined period of time has been elapsed since the start of the priming (for example). The end of this step may be triggered by the processor depending on the signal of a weight scale or a sensor (for example optical sensor, pressure sensor, level sensor, . . . ) of the line purged or of the container 13 or a timer or other (for example the number of rotation/revolution of the peristaltic pump).

The method of priming of the container 13 (which may be also called buffer or weighing bag or dialysate circuit container) may comprise at least one of the following steps of:

pumping a solution (for example an initial solution also called priming solution) through a fluid line of the dialysate circuit (for example having a portion in the dialysate cassette), for example from a supply (or initial) solution source (for example container 28 or 33) to the container 13, sensing a fluid parameter (such as the fluid level, the fluid pressure for example a decrease, an increase, pressure threshold or other pressure change or other fluid parameter) inside the dialysate circuit and causing the pumping to stop when a determined volume of solution is injected into the container 13 or based on a measurement data of the fluid parameter, and/or, sensing a weight of the container 13, 28 or 33 and causing the pumping to stop when a determined volume of solution is injected into the container 13 or based on a measurement data of the container weight, and/or, Monitoring the volume of fluid moved by the pump and causing the pumping to stop when a determined volume of solution is injected into the container 13; and/or, Counting the number of pump strokes and causing the pumping to stop when a determined number is reached; and/or, starting a timer and causing the pumping to stop when a determined time period is elapsed;

Optionally, pushing the air to the container 13 or to the sorbent device.

The container 13 may comprise degassing device such as a vent having a hydrophobic membrane, in order to allow purging air from the container 13 but not the liquid. If the container 13 does not comprise any vent, the volume of internal compartment of the container 13 is configured to receive a liquid volume required to perform the treatment and an air volume substantially equal to or higher than the volume of air pushed in the container 13 for example at least during this described step or during the priming process and/or the gas resulting the chemical reaction of the sorbent device.

For example, the dialysate pump may be actuated in order to move the fluid at a flow rate comprised between 1 and 600 ml/min, preferentially between 100 and 500 ml/min, more preferentially between 200 and 400 ml/min.

This step may be stopped when a volume comprised between 5000 ml and 1 ml has been injected into the container 13, preferentially between 4000 ml and 500 ml, more preferentially between 3000 ml and 1000 ml.

This step may be stopped, after a time period of less than 12 min, preferentially less than 10 min, more preferentially less than 8 min.

Priming of the Fluid Lines Connected to the Container

The processor may automatically trigger and perform this step for example without any user intervention. This step may be triggered after one of the previous described steps, preferentially after the previous step.

This step may be performed at least one time during the priming process and/or during the treatment in case where an air bubble is detected downstream the container 13 or potentially present in dialysate circuit and/or in order to (re)mix the solution (concentrate and regenerated dialysate) stored in the container 13.

The fluid lines connected to (in fluid communication with) the container 13 may be purged during a priming process, for example the fluid line connecting the outlet port to the pump 14 (to the inlet port of the pump 14). The fluid (for example air) initially present in these fluid lines may be moved to the container 13.

The valve V6 and V8 are opened and the pump 14 is actuated by the processor (for example in a normal pumping mode or in a reversed pumping mode) for example during a period of time which may depend on the length of the line and/or the flow rate of the pump 14. In this configuration, the system defines a closed loop where the fluid is moved from the container 13 to the container 13 (without the passing through the dialyzer). An air sensor arranged into the line may be also used to detect air or liquid in order to stop this step (and/or to launch this step).

The end of this step may be triggered by the processor depending on the signal of a weigh scale, a sensor (such as a level sensor, a pressure or optical sensor, . . . ) of the dialysate circuit or a timer or other (for example the number of rotation/revolution of the peristaltic pump).

This step may be performed several times during the priming sequence of the system or during the treatment as described above.

The method of purging the lines connected to the container 13 may comprise at least one of the following steps of:

Defining of a closed loop comprising the pump 14, the container 13, the container inlet fluid line and the container outlet fluid line (and for example having a portion in the dialysate cassette), pumping the solution, for example from the container 13 to the container 13, sensing a fluid parameter (fluid level, pressure and/or presence of air) inside the dialysate circuit and causing the pumping to stop when there are no longer air in the fluid lines of the closed loop or based on a measurement data of the fluid parameter, sensing a weight of the container 13 and causing the pumping to stop when the container weight is substantially stable, and/or, monitoring the volume of fluid moved by the pump and causing the pumping to stop when a determined volume of solution has been moved, counting the number of pump strokes and causing the pumping to stop when a determined number is reached, starting a timer and causing the pumping to stop when a determined time period is elapsed, or pushing the fluid (for example air) to the container 13.

For example, the dialysate pump may be actuated in order to move the fluid at a flow rate comprised between 1 and 600 ml/min, preferentially between 100 and 500 ml/min, more preferentially between 200 and 400 ml/min.

This step may be stopped when the container weight is substantially stable.

This step may be stopped, after a time period of less than 1 min, preferentially less than 45 sec, more preferentially less than 30 sec.

Priming of the Base of the Dialyzer

The processor may automatically trigger and perform this step for example without any user intervention. This step may be triggered after one of the previous described steps, preferentially after the previous step.

Focused on the FIG. 42, this step consists in filling only the base of the dialyzer (for example the dialysate compartment 11 of the dialyzer 2) in order to have the waterfront ready for dialyzer priming. This short duration step may last few seconds. During this step, air may re-enter in the fluid line connected to the container 13 (for example the fluid line connected to the inlet port of the container), in this case, the previous priming step may be repeated.

The valves V6 and V7 are opened and the pump 14 is actuated by the processor (for example) during a period of time which may depend on the length of the line and/or the flow rate of the pump 14 or until the solution has reached the dialyzer 2.

The end of this step may be triggered by the processor depending on the signal of a weigh scale, a sensor (such as a level sensor, a pressure or optical sensor, . . . ) of the purged line or a timer or other (for example the number of rotation/revolution of the peristaltic pump).

The method of Priming of the base of the dialyzer 2 may comprise at least one of the following steps of:
- pumping the priming solution through a fluid line (for example having a portion in the dialysate cassette), for example from a solution source (for example container 13 or 28 or 33) to the dialyzer 2 (the inlet port of the dialysate compartment),
- sensing a fluid parameter (fluid level, pressure and/or presence of air) inside the dialysate circuit and causing the pumping to stop when there are no longer air between the pump 14 and the dialyzer 2 or when the base of the membrane 12 or the base of the dialyzer 2 is substantially wetted by the solution or based on a measurement data of the fluid parameter,
- sensing a weight of the container (13, 28 or 33) and causing the pumping to stop when a determined volume has been moved into the fluid line or based on a measurement data of the container weight,
- starting a timer and causing the pumping to stop when a determined time period is elapsed or when the base of the membrane 12 or the base of the dialyzer 2 is substantially wetted by the solution,
- monitoring the volume of fluid moved by the pump and causing the pumping to stop when a determined volume of solution has been moved,
- counting the number of pump strokes and causing the pumping to stop when a determined number is reached,
- moving (for example by actuating the pump 16) the fluid initially stored in the fluid line not purged, for example from the dialyzer 2 to the container 13 and for example through the sorbent device 17, or
- pushing the fluid (for example air) to the container 13 or 28 or 33 or to the sorbent device.

The determined time period may be designed such that the base of the membrane 12 or the base of the dialyzer 2 is substantially wetted by the solution.

The valve V12 (and the valve VBP) may be opened in order to allow flowing the air to the container 13.

For example, the dialysate pump may be actuated in order to move the fluid at a flow rate comprised between 1 and 600 ml/min, preferentially between 100 and 500 ml/min, more preferentially between 200 and 400 ml/min.

This step may be stopped when a volume comprised between 1 ml and 500 ml has been removed from the source container, preferentially between 10 ml and 300 ml, more preferentially between 20 ml and 100 ml.

This step may be stopped, after a time period of less than 1 min, preferentially less than 45 sec, more preferentially less than 30 sec.

If the system does not comprise the valve V7, this step may be optional.

Priming of the Blood Return Container

The processor may automatically trigger and perform this step for example without any user intervention. This step may be triggered after one of the previous described steps, preferentially after the previous step.

Focused on the FIG. 43, as disclosed above, the system may comprise an arterial line 6, a venous line 7, a pump 8, a dialyzer 2 a blood return container 19 and an optional air trap 9.

Preferentially, the blood return container 19 comprises a first fluid line 20 having a dedicated valve V3 and a second fluid line 22 having a dedicated valve V4, both in fluid communication with the blood (loop) circuit, more preferentially, both are connected to the arterial line 6. Preferentially, the first fluid line 20 may be connected to the arterial line 6 upstream of the blood pump 8 (according to the normal pumping direction) and the second fluid line 22 may be connected to the arterial line 6 downstream of the blood pump 8 (according to the normal pumping direction). In this document, the arterial line 6 may extend from an arterial port of the blood circuit to an inlet port of the dialyzer and the venous line 7 may extend from an outlet port of the dialyzer to a venous port of the blood circuit.

In one embodiment, in order to prime the blood circuit, the system may comprise a supply container 41 or 33 which stores a priming solution or blood compatible solution such as saline solution, pure water solution, dialysate solution or other blood compatible solution.

Said supply container 41 or 33 may comprise a first port adapted and intended to be connected to the venous connector 27 of the venous line 7 and a second port adapted and intended to be connected to the arterial connector 26 of the arterial line 6.

At least one wall of the container 19, 41 or 33 may be flexible.

For example, this step may consist in filling the blood return container from an external solution container. As disclosed above, its duration may depend on the flow rate of the pump 8 and/or the total volume required to proceed to the blood return process (described thereafter) if during this step, the blood return container is filled of a volume at least equal to the volume required to proceed to the blood return process.

Preferentially, the pump 8 is actuated (for example by the processor) in a "normal pumping" 42 mode in order to move the priming solution from the supply container 41 or 33 to the blood return container 19. The valves V1 and V4 are opened (for example by the processor). The valve V3 is closed. The valves V2 and/or VA may be closed or here optional.

This priming step may be stopped when the supply container 41 or 33 is emptied or when a determined volume injected into the blood return container 19 is reached or when a determined period of time has been elapsed since the start of this step. The end of priming may be triggered by the processor depending on the signal of a sensor (such as a weight scale, level, pressure or optical sensor, . . . ) or a timer or other (for example the number of rotation/revolution of the peristaltic pump).

The method of priming of the blood return container 19 may comprise at least one of the following steps of:
- pumping a priming solution (also called a blood-compatible solution) through a fluid line of the blood circuit (for example having a portion in the blood cassette), for example from a supply solution source (for example container 41 or 33) to the blood return container 19,
- sensing a fluid parameter (such as the fluid pressure for example a decrease, an increase, pressure threshold or other pressure change) inside the fluid line and causing the pumping to stop when a determined volume of solution is injected into the blood return container 19 or based on a measurement data of the fluid parameter,
- sensing a weight of the supply container 41 or 33 and/or the blood return container 19 and causing the pumping to stop when a determined volume of solution is injected into the blood return container 19 or based on a measurement data of the supply container weight,
- monitoring the volume of fluid moved by the pump and causing the pumping to stop when a determined volume of solution is injected into the blood return container 19,
- counting the number of pump strokes and causing the pumping to stop when a determined number is reached, starting a timer and causing the pumping to stop when a determined time period is elapsed, or pushing the fluid (for example air) to the blood return container 19.

As described above, the volume of priming solution injected into the blood return container (during this step or during all the priming process) may be substantially equal to or higher than the volume required for the treatment. This volume required may be substantially equal to at least one of:

A volume required to perform a blood return process, for example, the volume defined by the internal wall of the blood circuit which may comprise the volume of the blood compartment of the dialyzer 2, the volume of the drip chamber 9, the tubing volume and/or the inside cavity of the cassette, or A volume of the solution which may be injected to the patient in case of low blood pressure of the patient.

The blood return container 19 may comprise degassing device such as a vent having a hydrophobic membrane, in order to allow purging air from the blood return container 19 but not the liquid.

An optional VA may be arranged upstream the input of the dialyzer and closed in order to prevent wetting a part of the dialyzer 2 (for example the top end of the dialyzer or the membrane 12 or the inlet of blood compartment) during this step.

This priming step may be performed at the end of the priming process of the blood circuit but preferentially, this priming step is performed at the beginning of the priming process of the blood circuit, for example it may be the first step of the blood circuit priming.

For example, the blood pump may be actuated in order to move the fluid at a flow rate comprised between 1 and 600 ml/min, preferentially between 100 and 500 ml/min, more preferentially between 200 and 400 ml/min.

This step may be stopped when a volume comprised between 1 ml and 600 ml has been removed from the source container, preferentially between 50 ml and 400 ml, more preferentially between 100 ml and 300 ml.

This step may be stopped, after a time period of less than 2 min, preferentially less than 1.5 min, more preferentially less than 1 min.

At the end of this step, the blood pump is stopped and the pressure sensor arranged between the pump and the line 22 measures the water column and compare to a reference data (expected pressure of the water column).

Priming of the Line Connected to the Blood Return Container

The processor may automatically trigger and perform this step for example without any user intervention. This step may be triggered after one of the previous described steps, preferentially after the previous step.

Focused on the FIG. 44, the fluid lines connected to (in fluid communication with) the blood return container 19 may be purged during a priming step. The fluid (for example air) initially present in these lines may be pushed to the blood return container 19. The valves V3 and V4 are opened and the pump 8 is actuated by the processor (for example in normal pumping mode or in reversed pumping mode) during a period of time which depends on the length of the line and/or the flow rate of the pump 8. In this configuration, the system defines a closed loop where the fluid is moved from the blood return container 19 to the blood return container 19 (without passing through the dialyzer). An air sensor arranged into the line may be also used to detect air or liquid in order to stop this step.

The end of this step may be triggered by the processor depending on the signal of a sensor (such as a pressure or optical sensor, . . . ) of the purged line or a timer or other (for example the number of rotation/revolution of the peristaltic pump).

This step may be performed several times during the priming sequence of the system.

The method of purging the lines connected to the blood return container 19 may comprise at least one of the following steps of:

defining of a closed loop comprising the pump 8, the blood return container 19 and the first fluid line and the second fluid line (and for example having a portion in the blood cassette), pumping the solution stored in the blood return container 19, for example from the blood return container 19 to the blood return container 19, in a reversed pumping mode or in a normal pumping mode or in a first pumping mode followed by a second pumping mode, sensing a fluid parameter inside the fluid lines and causing the pumping to stop when there are no longer air in the fluid lines of the closed loop or based on a measurement data of the fluid parameter, monitoring the volume of fluid moved by the pump and causing the pumping to stop when a determined volume of solution has been moved, counting the number of pump strokes and causing the pumping to stop when a determined number is reached, starting a timer and causing the pumping to stop when a determined time period is elapsed, or pushing the air to the blood return container 19.

For example, the blood pump may be actuated in order to move the fluid at a flow rate comprised between 1 and 600 ml/min, preferentially between 100 and 500 ml/min, more preferentially between 200 and 400 ml/min.

This step may be stopped when the blood return container weight is substantially stable. Otherwise, the number of pump stroke (such as pump rotation) of the blood pump may be monitored and when a threshold is reached the processor stops the blood pump.

This step may be stopped, after a time period of less than 1 min, preferentially less than 45 sec, more preferentially less than 30 sec.

At the end of this step, when the blood pump is stopped, the processor may compare the fluid pressure upstream the blood pump to the fluid pressure downstream the blood pump via at least one pressure sensor. If both are substantially equal the goal is reached if not the blood pump may be re actuated.

Priming of the Venous Line

The processor may automatically trigger and perform this step for example without any user intervention. This step may be triggered after one of the previous described steps, preferentially after the previous step.

One of the goals of this step is to fill the venous line for example at least until the base of the dialyzer's blood-side (for example the bottom end, the outlet port of the blood compartment) in order to have the waterfront ready for hollow-fibers priming. The air-trap may be also primed, up to a determined level for example until the pipe on top of the air trap (if the air trap device has such pipe).

Focused on the FIG. 45, the fluid (for example air) initially present in the venous line 7 may be pushed to the dialyzer or to the arterial line 6 or to the blood return container 19 or to the supply container 41 or 33.

The valve V2 is opened and the pump 8 is actuated by the processor in reversed pumping mode. The valve v4 is preferentially closed.

If the air and/or a part of the solution is moved to the blood return container 19, the valve v3 is opened and the valve v1 may be closed. In this case, the blood return container has to be configured to receive the volume of air pushed into the container 19. If the air is pushed to the supply container 41 or 33, the valve v1 is opened and the valve v3 may be closed. If the blood circuit comprises the valve VA, this valve is opened.

This priming step may be stopped when the supply container 41 or 33 is emptied or when a determined volume injected into the blood return container 19 is reached or when a determined period of time has been elapsed since the start of the priming or when the solution has reached the dialyzer 2. The end of this step may be triggered by the processor depending on the signal of a weight scale or a sensor (such as a pressure or optical sensor, . . . ) of the blood line or a timer or other (for example the number of rotation/revolution of the peristaltic pump).

The method of priming of the venous line 7 may comprise at least one of the following steps of:
  pumping a priming solution through a blood line (for example the venous line) of the blood circuit (for example having a portion in the blood cassette), for example from the supply solution source (for example container 41 or 33) to the dialyzer 2 (for example to the outlet port of the blood compartment), for example in a reversed pumping mode,
  sensing a fluid parameter (pressure and/or presence of air) inside the blood lines and causing the pumping to stop when the blood-compatible solution has reached the dialyzer or when the base of the membrane 12 or the base of the dialyzer 2 is substantially wetted by the solution or based on a measurement data of the fluid parameter,
  sensing a weight of the supply container 41 or 33 and causing the pumping to stop when a determined volume of blood-compatible solution is injected into the blood circuit or based on a measurement data of the supply container weight,
  monitoring the volume of fluid moved by the pump and causing the pumping to stop when a determined volume of blood-compatible solution has been moved,
  counting the number of pump strokes and causing the pumping to stop when a determined number is reached,
  starting a timer and causing the pumping to stop when a determined time period is elapsed,
  pushing the fluid (for example air) to the blood return container 19 or to the dialyzer or to the supply container 41 or 33, or
  injecting a part of the blood compatible solution into the blood return container 19.

For example, the blood pump may be actuated in order to move the fluid at a flow rate comprised between 1 and 500 ml/min, preferentially between 50 and 400 ml/min, more preferentially between 100 and 300 ml/min. The flowrate may remain relatively low (in compare to the "normal" flow rate during the blood treatment) in order to exhaust more efficiently the air contained in the hollow fibers.

A level sensor may be arranged in the drip chamber and/or the processor may monitor the signal of the level sensor in order to determine when the step may be stop.

The processor may monitor the number of pump strokes (such as pump rotations) in order to determine when the step may be stop.

This step may be stopped, after a time period of less than 1 min, preferentially less than 45 sec, more preferentially less than 30 sec.

Priming of the Dialyzer

The processor may automatically trigger and perform this step. This step may be triggered after one of the previous described steps, preferentially after the previous step. Preferentially, this step is launched without stopping the blood pump of the previous step. Optionally, this step may be launched only if the venous line and the fluidic lines of the dialysate circuit (upstream the dialyzer) have been primed.

Preferentially the blood and dialysate compartment of the dialyzer should be simultaneously primed with priming solution(s). Furthermore, optimally, the step is designed to have a simultaneous progression of the priming solutions in both compartments to optimize the priming of the dialyzer. According to an other embodiment, the blood compartment may be primed before the dialysate compartment or vice-versa.

The blood compartment may be primed with a dialysate solution or a solution different from the dialysate solution (such as a saline solution, pure water, . . . ) and the dialysate compartment may be primed with a dialysate solution or a solution different from the dialysate solution (such as a saline solution, pure water, . . . ). The priming solution of the blood circuit may be different from the priming solution of the dialysate circuit, for example a saline solution for the blood circuit and a dialysate solution for the dialysate circuit.

During this step, the blood pump is actuated in reversed pumping mode and the dialysate pump (s) in normal pumping mode. Since the blood pump is actuated in reversed pumping mode, the pressure in the blood fibers may be slightly negative, whereas the pressure in the dialysate side of the dialyzer may be in positive pressure, thus fluid motion between both compartments may occur.

During this step, the user may hold the dialyzer and/or may tap it gently until dialysate goes out of the dialyzer and reaches the output of the used dialysate pump (also called second dialysate pump). No need to orientate in one way or the other but the priming solution has to convey from the lower part of the dialyzer to the upper part.

With the prior art system, it would require a more intense rinsing and shaking of the dialyzer to exhaust the air and it would require to rotate the dialyzer several times during the priming process, which is more time consuming and complicates the overall priming sequence.

Referring now to the FIG. 46, the blood pump moves a first priming solution through the blood circuit to the dialyzer. Preferentially, the blood pump is actuated by the processor in reversed pumping mode. The first dialysate pump and the second dialysate pump move a second priming solution through the dialysate circuit. Preferentially, the first dialysate pump is actuated by the processor in normal pumping mode and the second dialysate pump is actuated by the processor in normal pumping mode, both dialysate pumps are substantially actuated at a same flow rate. If the first dialysate pump 14 is not actuated then the valve V8 is opened and the valve V6 may be closed in order to move the solution by the second dialysate pump 16.

The valves V1 and V2 are open and preferentially the valves V3 a V4 are closed. The valve V7 is open. Preferentially the valve V5 is closed (if no solution is removed and used for this step).

Depending on the actuation of the pump 14, the valve V6 is open (resp. closed) and the valve V8 is closed (resp. open). If V12 is closed then VBP is closed and in this case the sorbent device should comprise a vent with a hydrophobic filter. As already described above, the container 13 may comprise a vent with a hydrophobic filter in order to escape the air injected into the container 13.

This step may be stopped after that both compartments are substantially primed for example when a determined volume injected into the blood compartment and/or when a determined volume injected into the dialysate compartment is reached or when a determined period of time has been elapsed since the start of this step.

The end of this step may be triggered by the processor depending on the signal of a weight scale or a sensor of the blood circuit and/or of the dialysate or other. For example the dialysate circuit may comprise a sensor (for example a pressure sensor or optical sensor or other, . . . ) arranged upstream and/or downstream of the second dialysate pump. Or the processor may monitor the volume theoretically moved by the pump and/or may compute the number of pump strokes (for example the number of rotation/revolution of the peristaltic pump).

The method of priming of the dialyzer may comprise at least one of the following steps of:
- pumping a first priming solution (for example a blood compatible solution) through the dialyzer (for example through the blood compartment), for example from a priming solution source (such as the container 41 or 33) through the outlet port of the blood compartment to the inlet port of the blood compartment, for example in a reversed pumping mode, preferentially the dialyzer is arranged in such a manner that the outlet port of the blood compartment is placed lower than the inlet port of the blood compartment,
- pumping a second priming solution through the dialyzer (for example through the dialysate compartment), for example a dialysate solution from a priming solution source (such as the container 13, 28 or 33) through the inlet port of the dialysate compartment to the outlet port of the dialysate compartment, for example in a normal pumping mode, preferentially the dialyzer is arranged in such a manner that the inlet port of the dialysate compartment is placed lower than the outlet port of the dialysate compartment,
- sensing a fluid parameter inside at least one of the blood circuit and the dialysate circuit and causing the pumping to stop when dialyzer is primed (both compartments) or based on a measurement data of the fluid parameter,
- sensing a weight of at least one priming solution source (container 41, 13, 28 and/or 33) and causing the pumping to stop when a determined volume of priming solution is injected into at least one of the blood compartment and the dialysate compartment such that dialyzer is primed (both compartments) or based on a measurement data of the priming solution source weight,
- starting a timer and causing the pumping to stop when a determined time period is elapsed,
- monitoring the volume of fluid moved by the pumps and causing the pumping to stop when a determined volume of priming solution is injected into at least one of the blood compartment and the dialysate compartment such that dialyzer is at least primed (both compartments),
- counting the number of pump strokes and causing the pumping to stop when a determined number is reached,
- pushing the initial fluid (for example air) to the priming solution source or to the sorbent device, or
- controlling the pump of the blood circuit and the pump(s) of the dialysate circuit by the processor in order to substantially simultaneously move the first priming solution and the second priming solution through the dialysate compartment such that both compartments are simultaneously primed.

The volume of each compartment may be different and thus the flow rate may be different but the aim is to finish the priming of both compartments at the same time.

For example, the blood pump may be actuated in order to move the fluid at a flow rate comprised between 1 and 300 ml/min, preferentially between 25 and 200 ml/min, more preferentially between 50 and 100 ml/min. The dialysate pump(s) may be actuated in order to move the fluid at a flow rate comprised between 1 and 400 ml/min, preferentially between 50 and 300 ml/min, more preferentially between 100 and 200 ml/min.

The volume moved by the blood pump may be monitored and this step may be stopped when a volume comprised between 1 ml and 400 ml has been moved by the blood pump, preferentially between 50 ml and 300 ml, more preferentially between 100 ml and 200 ml. The volume moved by the dialysate pump(s) may be monitored and this step may be stopped when a volume comprised between 1 ml and 600 ml has been moved by the blood pump, preferentially between 100 ml and 500 ml, more preferentially between 200 ml and 400 ml.

Furthermore, the processor may monitor the number of pump strokes (such as number of revolution) of the pumps in order to determine when the step may be stop.

This step may be stopped, after a time period of less than than 2 min, preferentially less than 75 sec, more preferentially less than 60 sec.

Rinsing Dialyzer Blood Side

The processor may automatically trigger and perform this step for example without any user intervention. This step may be triggered after one of the previous described steps, preferentially after the previous step. If the user judges that the blood side of the dialyzer is not well enough primed, he can launch an additional dialyzer blood side rinsing.

This step allows a continuous rinsing of the dialyzer if it is judged to be not well enough primed. Referring to the FIG. 47, the blood pump is actuated in reversed pumping mode and the valve V8 is set in open position, allowing a slight back-filtration to occur and avoid sucking any remaining air in the fibers. This step should be monitored with the weighing bag weight measurement for example so as to ensure that enough volume remains in the weighing bag for the priming of the remaining components in the dialysate circuit and to ensure proper functioning of the sorbent device.

The valves V1 and V2 are open and preferentially the valves V3 a V4 are closed. The valves V7 and V8 are open. Preferentially, the dialysate pumps are not actuated, the valves V5 and V6 are closed and the valve V12 may be closed.

The method may comprise at least one of the following steps of:
- actuating the blood pump, for example in a reversed pumping mode,
- opening the valves V1, V2 and V8 (and optionally the valve VA),
- performing a (slight) back filtration through the dialyzer, for example in order to pass a volume fraction of solution of the dialysate circuit to the blood circuit,
- sensing a fluid parameter (for example the fluid pressure inside of a fluid line of at least one of the blood circuit and the dialysate circuit and causing the pumping to stop based on a measurement data of the fluid parameter, sensing a weight of the supply container 41 or 33 and causing the pumping to stop based on a measurement data of the supply container weight, monitoring the volume of fluid moved by the pump and causing the pumping to stop when a determined volume of solution has been moved;

counting the number of pump strokes and causing the pumping to stop when a determined number is reached, or starting a timer and causing the pumping to stop when a determined time period is elapsed.

This step may be repeated several times. For example, a volume to flow through the hollow fibers of the dialyzer during the priming may be 500 ml and an additional volume of 100 ml may be recirculated every time this step is performed. At a flowrate of 100 ml/min+/−100 ml/min, 1 minute+/−1 min may be expected.

Sorbent Cartridge Priming

The processor may automatically trigger and perform this step for example without any user intervention (or launched by the user). This step may be triggered after one of the previous described steps, preferentially after the previous step.

Referring to the FIG. 48, the blood pump pumps the priming solution (such as a saline solution) in forward direction (Treatment direction also called normal pumping mode). Both pumps from dialysate side move the solution at the same flow rate, until the sorbent cartridge is primed; the sorbent cartridge is considered as primed once dialysate gets out, even if several bubbles remain.

The pumps may be stopped as soon as the water front reaches the entrance of the weighing bag. The system is ready, and the patient needs to connect himself prior starting the treatment. It is still possible to let the blood pump run for a longer time once the sorbent cartridge is primed in order to ensure that less air persists in the dialyzer. In this case, the dialysate pumps shall remain turned-off.

The valves V1 and V2 are open and preferentially the valves V3 a V4 are closed. The valves V7 and V6 are open. Preferentially the valves V5 and V8 are closed and the optional valve V12 is open. The blood pump and the dialysate pumps are actuated in normal pumping mode. Preferentially, the blood pump moves the priming solution at a higher flow rate than the dialysate pumps.

The method may comprise at least one of the following steps of:

actuating the blood pump, for example in a normal pumping mode, actuating the dialysate pump(s), for example in a normal pumping mode, sensing the fluid (for example the fluid pressure) inside the fluid line and causing the pumping to stop based on a measurement data of the fluid parameter, sensing a weight of the supply container 41 or 33 and causing the pumping to stop based on a measurement data of the supply container weight, monitoring the volume of fluid moved by the pump(s) and causing the pumping to stop when a determined volume of solution has been moved, counting the number of pump strokes and causing the pumping to stop when a determined number is reached, or starting a timer and causing the pumping to stop when a determined time period is elapsed.

For example, the blood pump may be actuated in order to move the fluid at a flow rate comprised between 1 and 400 ml/min, preferentially between 50 and 300 ml/min, more preferentially between 100 and 200 ml/min. The dialysate pumps may be actuated in order to move the fluid at a flow rate comprised between 1 and 400 ml/min, preferentially between 50 and 300 ml/min, more preferentially between 100 and 200 ml/min.

This step may be stopped when the remaining volume of the container 13 is substantially equal to the volume required for the treatment, for example between 500 ml and 3500 ml, preferentially between 1000 ml and 3000 ml, more preferentially 1500 ml and 2500 ml.

The volume moved by the dialysate pumps may be monitored and this step may be stopped when a volume comprised between 1 ml and 1500 ml has been moved by the blood pump, preferentially between 300 ml and 1250 ml, more preferentially between 500 ml and 1000 ml.

This step may be stopped, after a time period of less than 15 min, preferentially less than 10 min, more preferentially less than 7 min.

Fully Automatic Priming Process

The following description discloses several priming steps which may be used to perform an automatic priming of the blood circuit and the dialysate circuit. Each step describes a priming of a part of fluidic pathway. Some sequence may be changed without problems.

Preferentially in this process, the arterial connector 26 is connected to the venous connector 27 or both are at least in fluid communication via a connector (a shunt).

Additive Line Priming

The processor may automatically trigger and perform a priming of the additive line as described above for example without any user intervention.

Priming of the Container

The processor may automatically trigger and perform a priming of the container 13 as described above for example without any user intervention. This step may be triggered after one of the previous described steps, preferentially after the previous step.

Priming of the Line Connected to the Container

The processor may automatically trigger and perform a priming of the line connected to the container 13 as described above for example without any user intervention. This step may be triggered after one of the previous described steps, preferentially after the previous step.

Priming of the Blood Return Container

The processor may automatically trigger and perform this step for example without any user intervention. This step may be triggered after one of the previous described steps, preferentially after the previous step.

The priming solution used for priming the dialysate circuit may be the same for the blood circuit. Furthermore the priming solution source of the dialysate circuit may be the same source for priming the blood circuit. This priming solution source may be a container arranged in the dialysate side (connected to the dialysate circuit).

During this step, the arterial connector 26 may be connected to the venous connector 27 directly or via an adapter also called shunt in order to create a fluid line between both connector. The blood set may comprise the removable shunt initially connected to the connector 26 ad 27 or the connector may be initially and removeably connected.

Referring now to the FIG. 50, one aim of the step is to prime the dialyzers blood fibers with solution pumped from the dialysate circuit side, for example through the semipermeable membrane of the dialyzer. The orientation of the dialyzer doesn't have to be changed; this step involves priming the dialysate blood fibers from bottom to top to exhaust the air more efficiently reducing the risk of negative effects as described above.

The valves V3, V7 and V8 are opened, and the dialysate is pumped with the blood pump 8 (preferentially in reversed direction) from the container 13 and injected into the blood return container 19, priming in the meantime the blood fibers of the dialyzer.

Preferentially, the blood pump 8 runs in reverse mode. Using a single pump is a preferred solution than using simultaneously the first dialysate pump and the blood pump; because in the last case, it requires a pressure control mode of the pump motor revolution speed to avoid creating over/under-pressures areas due to unequal pump flow-rates. The blood pump is used instead of dialysate pumps to drive the dialysate in the blood fibers more efficiently. As described above, the blood return container may be initially empty and may be fill during at least one priming step. This container may be initially connected to the blood set and may be removeably (or not) connected to the blood set.

The volume capacity of the disposable components of the system (dialyzer, tubing etc) is relatively well known. Based on this value, the weight of the source container (for example the container 13 or 28) is monitored to know the volume added in the blood return container. As described above, the step will end as soon as the expected volume is added in the blood return bag. (The target volume to add should be enough to prime the blood fibers of the dialyzer.). The volume injected into the blood return container is already described above.

The method of priming of the blood return container 19 (and the blood compartment) may comprise at least one of the following steps of:
  actuating the blood pump, preferentially in reverse mode,
  optionally, controlling the dialysate pump(s) such that the dialysate pump(s) are not actuated,
  passing (pulling) a solution through the blood circuit, the dialysate circuit and the dialyzer, for example from a supply solution source (for example container 13 or 28) to the blood return container 19,
  priming the blood compartment of the dialyzer,
  sensing a fluid parameter (such as the fluid pressure for example a decrease, an increase, pressure threshold or other pressure change) inside at least one fluid line of the blood circuit or dialysate circuit and causing the pumping to stop when there is enough solution in the blood return container 19 or based on a measurement data of the fluid parameter,
  sensing a weight of the supply solution source container and/or the blood return container 19 and causing the pumping to stop when there is enough solution in the blood return container 19 or based on a measurement data of the supply container weight,
  monitoring the volume of fluid moved by the pump and causing the pumping to stop when a determined volume of solution is injected into the blood return container 19,
  counting the number of pump strokes and causing the pumping to stop when a determined number is reached,
  starting a timer and causing the pumping to stop when a determined time period is elapsed, or
  moving the initial fluid (for example air) to the blood return container 19.

A first volume of solution may be injected into the blood return container during this step and a second volume of solution may be injected into the blood return container during a following step. The total volume injected is equal or larger than the volume required as described above.

Priming of the Venous Line and the Shunt

The processor may automatically trigger and perform this step for example without any user intervention. This step may be triggered after one of the previous described steps, preferentially after the previous step.

The FIG. 51 illustrates the following step of blood side priming. The valves V1, V2, V3, V6 and V7 are opened and the first dialysate pump moves a solution stored in the container 28 or 13 to the blood return bag, flowing through the bottom end of the semi-permeable membrane of the dialyzer, through the drip chamber, and through the shunt. V8 is closed and the blood pump and the second dialysate pump are not actuated. It allows performing the priming without the need to connect an extra bag during the priming sequence.

In another case similar to the priming of the blood return container, the blood pump is actuated in a normal pumping mode (and the first dialysate pump may be not actuated) and the valve V3 is closed while the valve V4 is opened. If the first dialysate pump is not actuated then the valve V6 is closed and the valve V8 is opened. Nevertheless if the first dialysate pump is no actuated, such a sequence may empty the drip chamber.

During this phase, the completion of the volume contained in the blood return container may be performed and may be monitored by a weight-scale.

The method of priming of the venous line may comprise at least one of the following steps of:
  actuating the first dialysate pump, preferentially in normal pumping mode,
  passing (pushing) a solution through the blood circuit, the dialysate circuit and the dialyzer, for example from a supply solution source (for example container 13 or 28) to the blood return container 19,
  sensing a fluid parameter (such as the fluid pressure for example a decrease, an increase, pressure threshold or other pressure change) inside at least one fluid line of the blood circuit or dialysate circuit and causing the pumping to stop when there is enough solution in the blood return container 19 or based on a measurement data of the fluid parameter,
  sensing a weight of the supply solution source container and/or the blood return container 19 and causing the pumping to stop when there is enough solution in the blood return container 19 or based on a measurement data of the supply container weight,
  Monitoring the volume of fluid moved by the pump and causing the pumping to stop when a determined volume of solution is injected into the blood return container 19,
  counting the number of pump strokes and causing the pumping to stop when a determined number is reached,
  starting a timer and causing the pumping to stop when a determined time period is elapsed, or
  moving the initial fluid (for example air) to the blood return container 19.

Priming of the Drip Chamber

The processor may automatically trigger and perform this step for example without any user intervention. This step may be triggered after one of the previous described steps, preferentially after the previous step.

Referring now to the FIG. 52, Valves V6 and V7 are opened and the first dialysate pump moves a solution from a container 28 or 13 to the drip chamber flowing through the semi-permeable membrane of the dialyzer. The output of the drip chamber may be occluded by the closed-valve V2 or by another means. Thus, the pressure will increase in the system until reaching the cracking pressure of the check valve (for example a check valve) connected on top of the chamber. Thus, the liquid level increases in said chamber. Preferentially, the cracking pressure of the check valve (for example a check valve) should not be higher than the maximal transmembrane pressure given by the dialyzer specifications.

The first dialysate pump may be preferred to the blood pump (with V3 and VA open and all other valve closed); indeed, the volume contained in the blood return bag has reached its target value required for the blood return, and we do not want to lose the track of the contained volume. Thus, the first dialysate pump is thereby used to pump from the container and the added volume in the blood circuit can be tracked as well with the help of the weight scale.

The first dialysate pump will be regulated with a target output pressure, and the liquid level inside the chamber is monitored by a liquid level sensor, which indicates the end of the step.

This step may be performed just after the previous described step without stopping the first dialysate pump.

The method of priming of the drip chamber may comprise at least one of the following steps of:
- actuating the first dialysate pump, preferentially in normal pumping mode,
- passing (pushing) a solution through the blood circuit, the dialysate circuit and the dialyzer, for example from a supply solution source (for example container 13 or 28) to the drip chamber,
- reaching a determined fluid pressure into the drip chamber,
- sensing a fluid parameter (such as the fluid pressure, level sensor for example a decrease, an increase, pressure threshold or other pressure change) inside at least one fluid line of the blood circuit or dialysate circuit and causing the pumping to stop when there is enough solution in the drip chamber or based on a measurement data of the fluid parameter,
- sensing a weight of the supply solution source container and causing the pumping to stop when there is enough solution in the drip chamber or based on a measurement data of the supply container weight,
- monitoring the volume of fluid moved by the pump and causing the pumping to stop when a determined volume of solution is injected into the drip chamber,
- counting the number of pump strokes and causing the pumping to stop when a determined number is reached,
- starting a timer and causing the pumping to stop when a determined time period is elapsed, or
- exiting the air by a valve connected to the drip chamber.

Priming of the Line Connected to the Blood Return Container

The processor may automatically trigger and perform a priming of line connected to the blood return container 19 as described above for example without any user intervention. This step may be triggered after one of the previous described steps, preferentially after the previous step.

Blood Circulation State

The processor may automatically trigger and perform this step for example without any user intervention. This step may be triggered after one of the previous described steps, preferentially after the previous step.

Before proceeding to the priming of the dialysate side, a blood circulation state may be performed to let possible remaining bubbles getting out of the dialyzer. If so, the air will be trapped in the drip chamber, and the level will decrease. This step will be followed by the same step previously described to re-adjust the liquid in the chamber level. The blood pump may be actuated in normal pumping mode. The valves V3 and V4 are preferentially closed and the valve V1, V2 and VA are open.

Priming of the Dialysate Compartment of the Dialyzer

The processor may automatically trigger and perform this step for example without any user intervention. This step may be triggered after one of the previous described steps, preferentially after the previous step.

FIG. 53 illustrates the priming of the dialysate circuit side. Dialysate is pumped from the container 13 or 28 with the first dialysate pump (and preferentially the second dialysate pump) and the treatment configuration of the dialysate circuit is used with V6, V7 and V12 opened. The dialyzer get primed as well as the sorbent cartridge, and all the air contained in these components goes into the container 13 or 28, where it can be exhaust with the vent.

An important point is the following: the dialysate compartment of the dialyzer will also be primed from the bottom to the top to exhaust the air contained in the dialysate compartment more efficiently. The first dialysate pump pumps at a constant defined flow rate, and the second dialysate pump is input-pressure regulated. The input pressure of the second dialysate pump should not overcome the cracking pressure of the check valve (for example a check valve) from the drip chamber. Preferentially, the first dialysate pump and the second dialysate pump convey the solution at a same flow rate.

The stop of the pumps should be triggered by the weight removed from the container 13 or 28, knowing the filling volume of the dialysate side components. It should be stopped at the intersection with the inlet of additive solution.

The method of priming of the full dialysate circuit may comprise at least one of the following steps of:
- actuating the first dialysate pump and second dialysate pump,
- optionally, controlling the dialysate pump(s) such that input pressure of the second dialysate pump should not overcome the cracking pressure of the check valve (for example a check valve) from the drip chamber,
- passing a solution through the dialysate circuit, for example from a supply solution source (for example container 13 or 28) to the container 13,
- priming the dialysate compartment of the dialyzer,
- priming the sorbent device,
- sensing a fluid parameter (such as the fluid pressure for example a decrease, a increase, pressure threshold or other pressure change) inside the dialysate circuit and causing the pumping to stop when the dialysate circuit is primed or based on a measurement data of the fluid parameter,
- sensing a weight of the supply solution source container and causing the pumping to stop when the dialysate circuit is primed or based on a measurement data of the supply container weight,
- monitoring the volume of fluid moved by the pump and causing the pumping to stop when the dialysate circuit is primed,
- counting the number of pump strokes and causing the pumping to stop when a determined number is reached,
- starting a timer and causing the pumping to stop when a determined time period is elapsed, or
- moving the initial fluid (for example air) to the container 13.

Blood Patient Priming

This step is performed after the priming sequence with the priming solution. The user removes the shunt or the container 41 and connected the blood circuit to the patient.

During this step, the priming solution is replaced by the blood patient the dialysate contained in the blood-circuit side. The valves V1 and V2 are opened and the blood pump pumps in forward direction (normal pumping mode). The blood is pumped out from the patient through the arterial line; in the meanwhile the priming solution contained in the lines is injected into the patient through the venous line until the overall dialysate volume gets into the patient. This injected volume is relatively well known and may be added to the target fluid-volume to remove from the patient by ultrafiltration. After this step, without interrupting the blood flow, the dialysate pumps are started and the treatment begins.

In one embodiment, a part of the priming solution (stored in the blood circuit after the priming sequence) may be injected into the blood return container. In all cases the volume of priming solution (injected to the patient) during this step may be added to the target fluid-volume to be removed from the patient by ultrafiltration.

Preparing Dialysate

The processor may automatically trigger and perform this step for example without any user intervention. This step may be triggered after one of the previous described steps, preferentially before starting the treatment or before the step previously described.

If the container 13 contains a solution different from a dialysate solution, a dialysate solution has to be prepared based on the solution contained in the container 13 and by adding additive for example stored in the additive supply container. The pump 30 is actuated and the dialysate solution is prepared into the container 13. The weight scale of the container 13 or 31 may be monitored and the processor control the volumes injected.

The method of preparing or regenerating a dialysate solution may comprise at least one of the following steps of:
  providing a container 13,
  providing an additive source for example an additive container 31,
  if the container 13 is empty fill the container from a solution source 28 or 32 or other (pure water solution, saline solution or other compatible solution for preparing a dialysate solution),
  moving an additive solution from the additive source to the container 13,
  sensing a fluid parameter (such as the fluid level, the fluid concentration, the fluid pressure) inside the dialysate circuit and causing the pumping to stop when the dialysate solution is prepared or based on a measurement data of the fluid parameter,
  sensing a weight of the container 13 or 31 and causing the pumping to stop when the dialysate solution is prepared or based on a measurement data of the container weight,
  monitoring the volume of fluid moved by the pump and causing the pumping to stop when the dialysate solution is prepared,
  counting the number of pump strokes and causing the pumping to stop when a determined number is reached,
  starting a timer and causing the pumping to stop when a determined time period is elapsed, or
  performing a running-in period of an additive pump.

Other Potential Priming Sequences

The following description describes several priming steps/sequences which may be performed by the embodiments previously described or with embodiments described below. All or a part of the following priming steps/sequences may be integrated to the priming process described above and/or vice versa.

The FIGS. 56 to 75 describe a dialysate circuit which is substantially similar to the dialysate circuit described above. For all embodiments described in this document, the system may comprise sorbent connectors 44 intended to be (removably) connected to the sorbent device 17. This sorbent connector 44 may be adapted to be removably interconnected (linked together) in order to provide a fluidic connection of dialysate circuit without sorbent device, for example during a part of the priming process (for example in order to prevent that the dialysate solution flows through the sorbent). The valve v12 may be optional. The bypass of the dialysate line 15' and the dedicated valve v8 may be optional. The initial supply container 28 and the dedicated valve v5 may be optional; in this case the initial dialysate container may be the weighing bag 13. The supply container 32 and the dedicated valve v11 may be optional.

The FIGS. 56 to 75 further describe a blood circuit connected to a fluid system intended to exchange fluid with the blood circuit. In this case, the blood circuit is connected to one or more (preferentially at least two, more preferentially at least three) lines in fluid communication with a first internal compartment of the fluid system (for example an internal compartment of the container 19. At least during the priming process, the first internal compartment and the blood circuit may define a loop circuit. A first line may draw the solution from the first internal compartment and a second line may reinject the solution into the first internal compartment. In order to prevent a recirculation of the air, the second line is connected to an internal tube (extending into the internal compartment) which is longer than the internal tube which is connected to the first line.

More particularly, the FIGS. 56 to 68 describe a fluid system comprising a single container 19 storing a fluid for priming the blood circuit and for moving the blood back the patient at the end of the treatment. The single container 19 may comprise a single internal compartment in fluidic connection with the arterial line 6, the venous line 7, the line 20 and the line 22. The blood circuit may comprise other container(s) for other fluid (for example heparin, calcium, . . . ).

Focus on the FIGS. 56 to 61, the arterial line 6 and the line 22 may be connected to a first spike 45 while the venous line 7 and the line 20 may be connected to a second spike 46. Preferentially, the first spike 45 and the second spike 46 are in fluid communication to the single internal compartment of the container 19. Preferentially, the first spike 45 is longer than the second spike 46. This configuration prevents that the fluid (for example air bubble) injected via the first spike is not (directly) drawn by the second spike 46. The arterial line 6 and the venous line 7 may be removably connected to the container 19 via connectors. The line 20 and the line 22 may be removably connected to the container 19 via connectors.

The first spike 45 and the second spike 46 may be a single piece with four external access intended to be connected to the blood circuit and two internal access intended to be inserted into the internal compartment of the container. As explained above, the shortest internal access is preferentially intended to be used as an inlet while the longest internal access is preferentially intended to be used as an outlet.

Focus on the FIGS. 62 to 68, the single container 19 comprises a single internal compartment intended to be in fluid communication with the arterial line 6, the venous line 7, the line 20 and the line 22, for example via dedicated connectors. The single container may comprise four access ports or less. A line may comprise a y-shape connector or similar device, thus, for example a first line connected to the container 19 may be connected to the arterial line 6 and the line 22 and/or a second line may be connected to the venous line 7 and the line 20.

The fluid system of the FIGS. 69 to 75 may comprise a single container comprising two distinct internal compartment or two distinct containers (each having one or more dedicated internal compartment). The container 19' may be a container distinct from the container 19 or may be a second internal compartment of the container 19. In both cases, the container 19 comprises a first internal compartment and the internal compartment of the element 19' is called second internal compartment.

The first internal compartment 19 may be in fluid communication with at least one of the arterial line 6, the venous line 7, the line 20 and the line 22. And the second internal compartment 19' may be in fluid communication with at least one of the arterial line 6 (through a line 24), the venous line 7, the line 20 and the line 22. More particularly, the arterial line 6 (resp. the venous line 7) may be connected to an access port of the second internal compartment 19' through the line 24 and at least one access port of the first internal compartment 19 may be connected to the venous line 7 through a line 26 (resp. the arterial line 6), the line 20 and the line 22. Preferentially, the second internal compartment is used/intended to receive the priming solution used to rinse the dialyzer. As the dialyzer may be primed from the venous line to the arterial line (preferentially with a reversed pumping mode), the access port of the second internal compartment 19' is preferentially connected to the arterial line 6 via the line 26 (for example via a removable connection). And as the first internal compartment 19 stores the solution used for priming the blood circuit and for moving the blood back to the patient, the at least one access port of the first internal compartment 19 is connected to the venous line 7 via the line 26, the line 20 and the line 22 (for example via a removably connection). The internal tube 26 extending into the first internal compartment 19 and connected to the venous line 7 may be short or long. But, preferentially, the internal tube extending into the first internal compartment 19 and connected to the line 20 is longer than the internal tube connected to the line 22.

Figure 69:
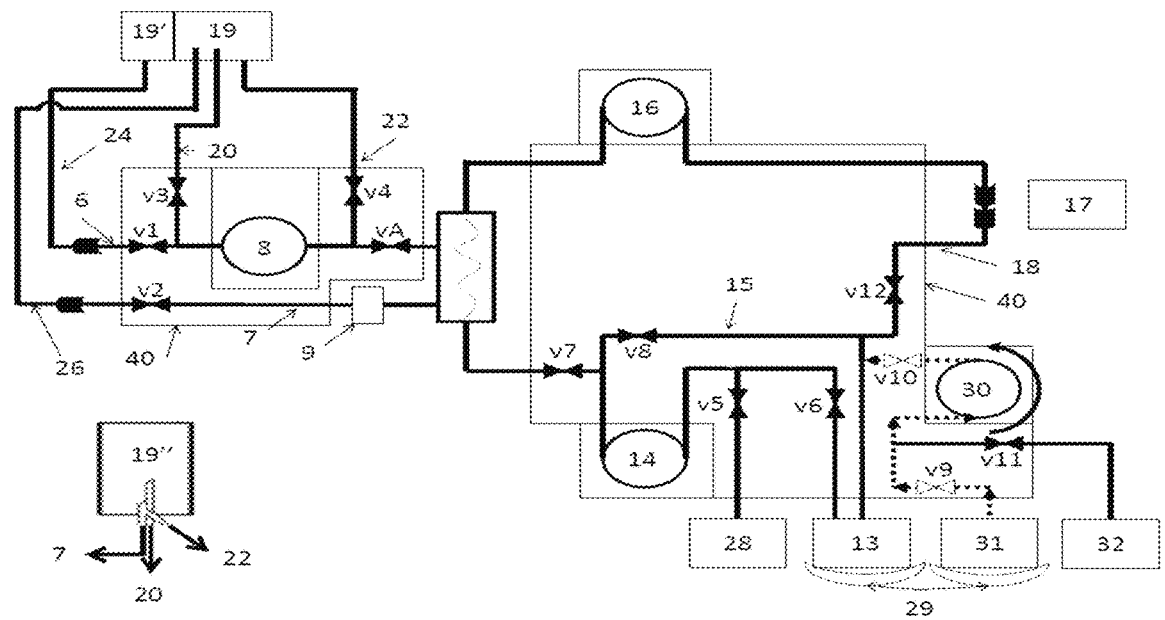

The FIG. 69 shows an alternative container 19" connected to the blood circuit via a first and second spike. The first spike may comprise a first internal access port which extends into the first internal compartment, a first external access port connected to the venous line 7 and a second external access port connected to the line 22. The second spike may comprise a second internal access port which extends into the first internal compartment and a third external port connected to the line 20. The second internal access port may be longer than the first internal access port.

Priming Sequences Shown by the FIGS. 56 to 61

Additive Line Priming

Figure 56:
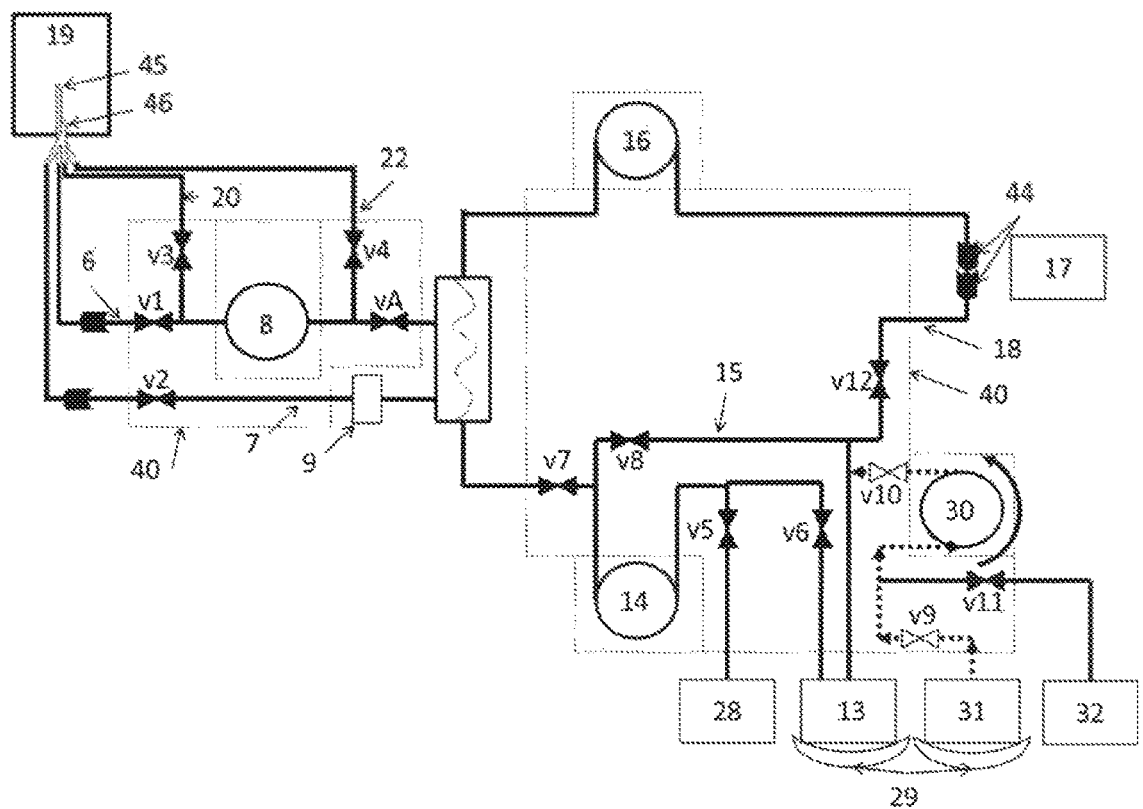

The FIG. 56 shows a priming step of the additive line which is substantially similar to the priming step described by the FIG. 49.

Priming of the Base of the Dialyzer

Figure 57:
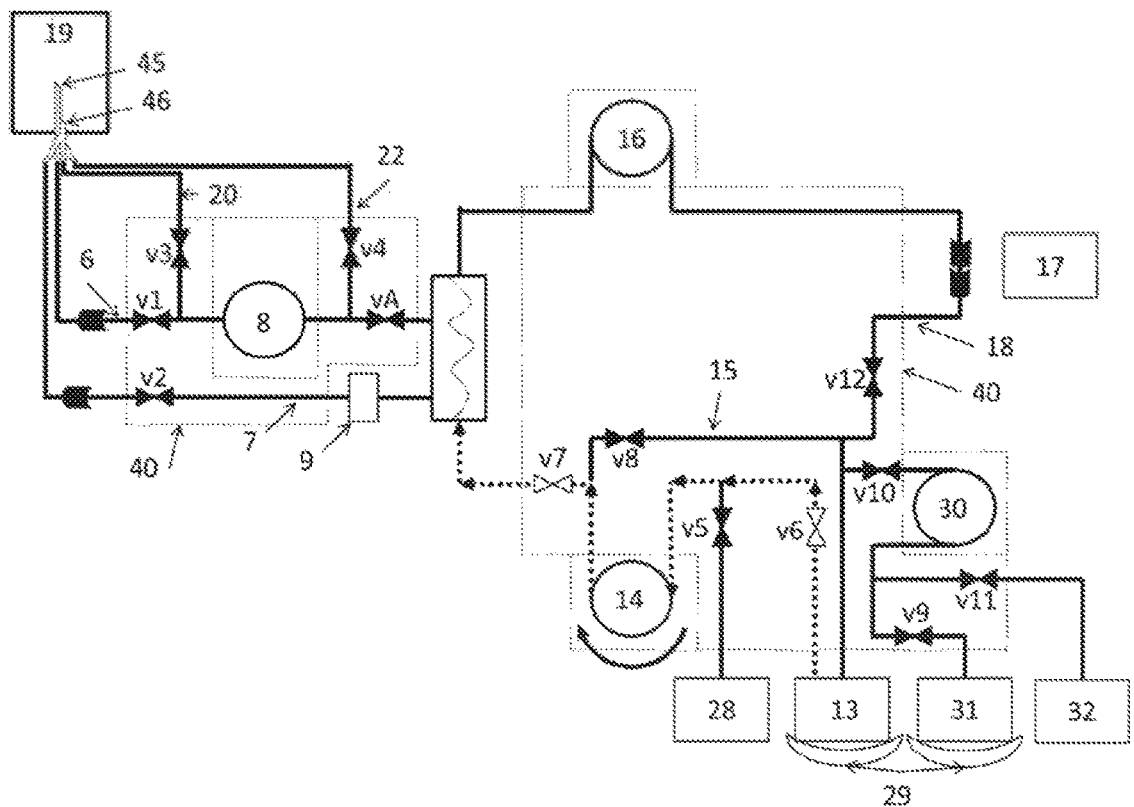

The FIG. 57 shows a priming step which is substantially similar to the priming step described by the FIG. 42.

Blood Circuit Priming

The processor may automatically trigger and perform this step for example without any user intervention. This step may be triggered after one of the previous described steps, preferentially after the previous step.

One of the goals of this step is to fill the venous line 7, the blood side of the dialyzer and the arterial line 6 with a priming solution. The air-trap (for example the drip chamber 9) may be also primed, for example up to a determined level such as the pipe on top of the air trap (if the air trap device has such pipe).

Figure 58:
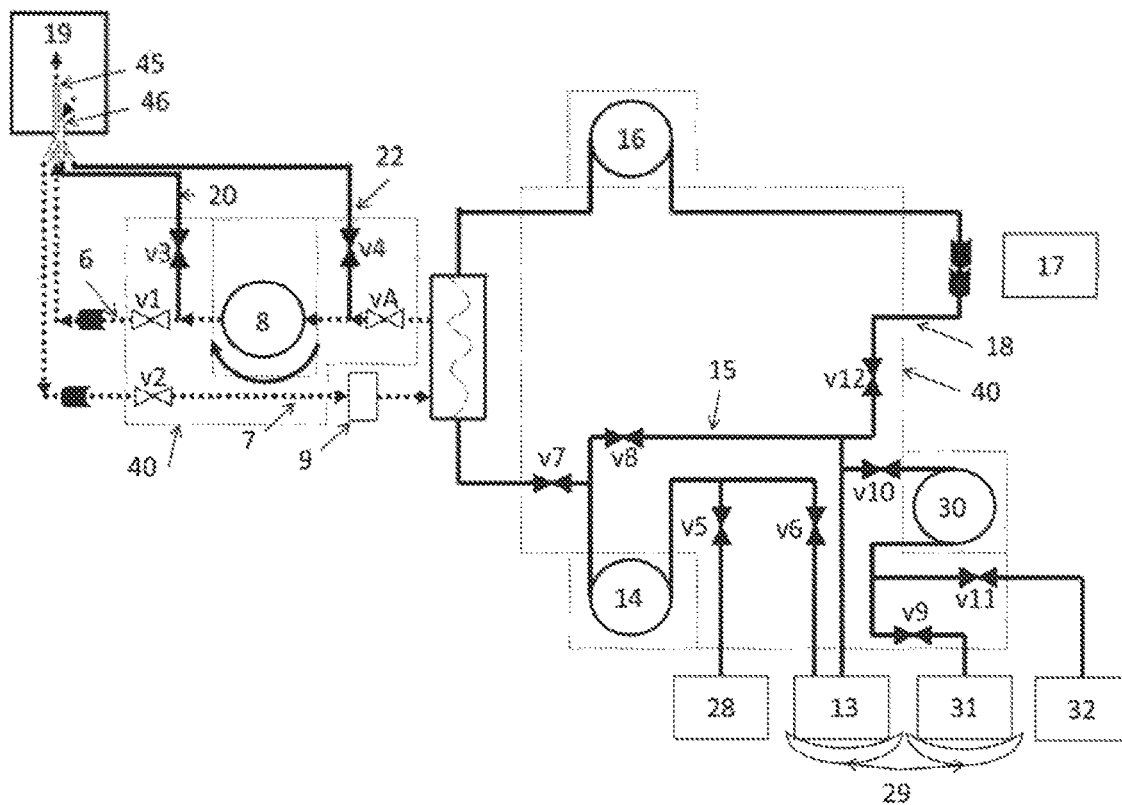

Focused on the FIG. 58, the fluid (for example air) initially present in the blood circuit is pushed to the container 19 by the priming solution initially stored in the container 19.

The valves V1, V2 and VA may be opened and the pump 8 is actuated by the processor in reversed pumping mode. The valves V3 and v4 are preferentially closed.

This priming step may be stopped when the arterial line 6, the venous line 7 and the blood side of the dialyzer 2 are substantially primed for example when a determined volume injected into the blood circuit is reached or when a determined period of time has been elapsed since the start of the priming or when the solution come back into the container 19. The end of this step may be triggered by the processor depending on the signal of a weight scale or a sensor (such as a pressure or optical sensor, . . . ) of the blood line or a timer or other (for example the number of rotation/revolution of the peristaltic pump).

The method of priming of the blood circuit may comprise at least one of the following steps of:

defining of a loop circuit of the blood circuit, wherein the loop circuit comprising at least one of the container 19, the pump 8, the arterial line 6, the venous line 7 and the blood side of the dialyzer 2, pumping a priming solution through the loop circuit of the blood circuit (for example having a portion in the blood cassette), for example from an internal compartment (for example of the container 19) to the same internal compartment, for example in a reversed pumping mode, sensing a fluid parameter (pressure and/or presence of air) inside the loop circuit and causing the pumping to stop when the solution has primed the lines of the blood circuit and the blood side of the dialyzer, sensing a weight of the container 19 and causing the pumping to stop when a determined volume of the solution is injected into the blood circuit or based on a measurement data of the container weight, monitoring the volume of fluid moved by the pump and causing the pumping to stop when a determined volume of the solution has been moved, counting the number of pump strokes and causing the pumping to stop when a determined number is reached, starting a timer and causing the pumping to stop when a determined time period is elapsed, priming at least a part of the drip chamber, or moving/pushing the fluid initially stored in the lines of the blood circuit and the blood side of the dialyzer into the container 19.

Priming of Lines Connected to the Container

The processor may automatically trigger and perform this step for example without any user intervention. This step may be triggered after one of the previous described steps.

Figure 59:
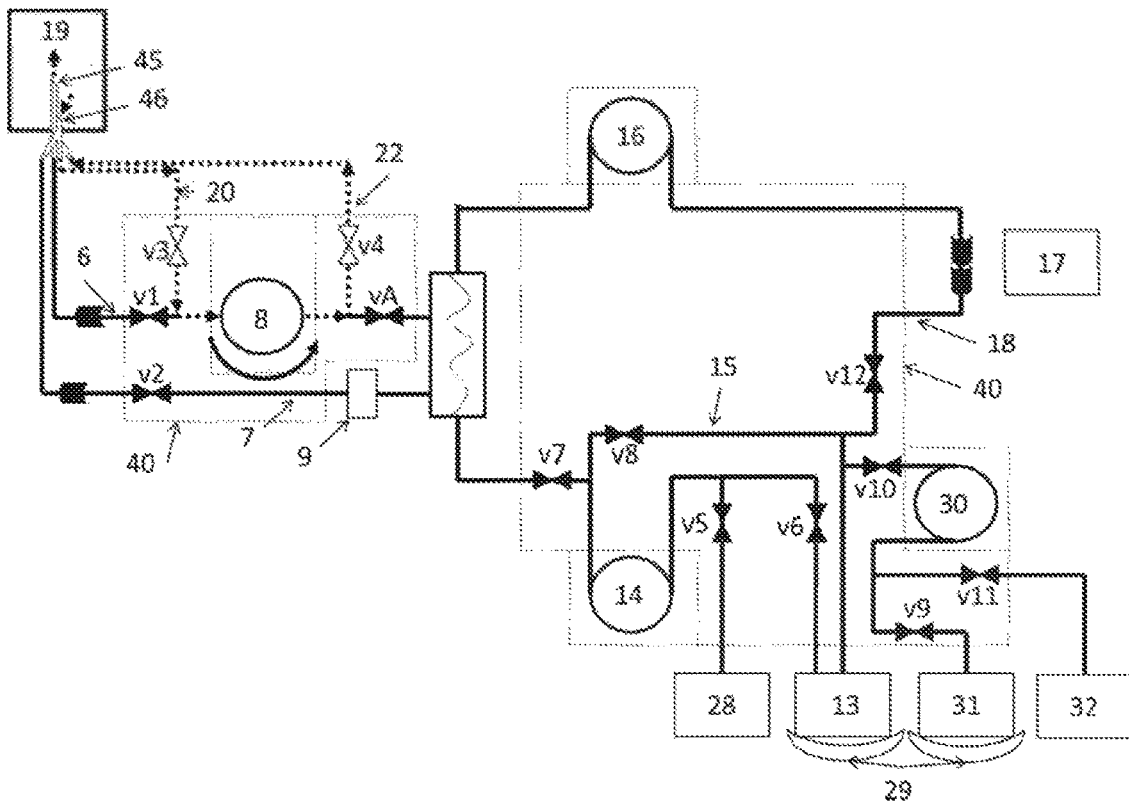

Focused on the FIG. 59, the fluid lines connected to (in fluid communication with) the container 19 may be purged during this priming step. The fluid (for example air) initially present in these lines may be pushed back to the container

19. The valves V3 and V4 are opened and the pump 8 is actuated by the processor (for example in normal pumping mode or in reversed pumping mode) during a period of time which depends on the length of the line and/or the flow rate of the pump 8. In this configuration, the system defines a closed loop where the fluid is moved from the container 19 to the container 19 (without passing through the dialyzer). An air sensor arranged into the line may be also used to detect air or liquid in order to stop this step.

The end of this step may be triggered by the processor depending on the signal of a sensor (such as a pressure or optical sensor, . . . ) of the purged line or a timer or other (for example the number of rotation/revolution of the peristaltic pump).

This step may be performed several times during the priming sequence of the system.

The method of purging the lines connected to the container 19 may comprise at least one of the following steps of:
- defining of a loop circuit comprising at least one of the pump 8, the container 19, the first fluid line and the second fluid line (and for example having a portion in the blood cassette),
- pumping the solution stored in the container 19, for example from the container 19 to the container 19, in a reversed pumping mode or in a normal pumping mode or in a first pumping mode followed by a second pumping mode,
- sensing a fluid parameter inside the fluid lines and causing the pumping to stop when there are no longer air in the fluid lines of the loop circuit or based on a measurement data of the fluid parameter,
- monitoring the volume of fluid moved by the pump and causing the pumping to stop when a determined volume of solution has been moved,
- counting the number of pump strokes and causing the pumping to stop when a determined number is reached,
- starting a timer and causing the pumping to stop when a determined time period is elapsed, or
- pushing the air to the container 19.

For example, the blood pump may be actuated in order to move the fluid at a flow rate comprised between 1 and 600 ml/min, preferentially between 100 and 500 ml/min, more preferentially between 200 and 400 ml/min.

This step may be stopped when the container weight is substantially stable. Otherwise, the number of pump stroke (such as pump rotation) of the blood pump may be monitored and when a threshold is reached the processor stops the blood pump.

This step may be stopped, after a time period of less than 1 min, preferentially less than 45 sec, more preferentially less than 30 sec.

At the end of this step, when the blood pump is stopped and the valves V3 and V4 may be maintained open, the processor may compare the fluid pressure upstream the blood pump to the fluid pressure downstream the blood pump via at least one pressure sensor. If both are substantially equal the goal is reached if not the blood pump may be re actuated.

Dialysate Circuit Priming

The processor may automatically trigger and perform this step for example without any user intervention (or launched by the user). This step may be triggered after one of the previous described steps, preferentially after the previous step.

Figure 60:
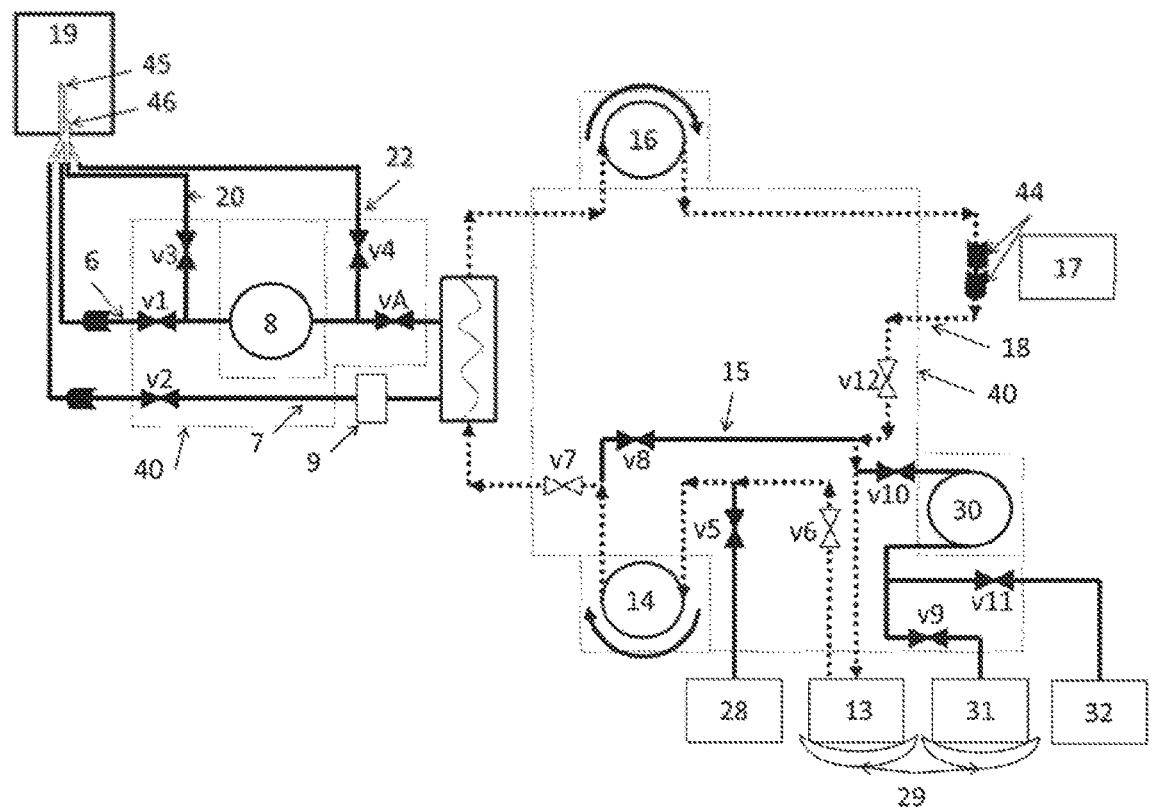

Referring to the FIG. 60, both dialysate pumps (14, 16) are actuated to move the solution, until the container 13; the sorbent connectors 44 are interconnected in order to provide a loop circuit without the sorbent cartridge 17. The pumps may be stopped as soon as the solution reaches the entrance of the container 13.

The valves V6, V7 and V12 may be open and the dialysate pumps are actuated in normal pumping mode.

The method may comprise at least one of the following steps of:
- defining a loop circuit of the dialysate circuit without any sorbent cartridge,
- actuating the dialysate pump(s), for example in a normal pumping mode,
- sensing a fluid parameter (for example the fluid pressure) inside the fluid line and causing the pumping to stop based on a measurement data of the fluid parameter,
- sensing a weight of the container 13 and causing the pumping to stop based on a measurement data of the container weight,
- monitoring the volume of fluid moved by the pump(s) and causing the pumping to stop when a determined volume of solution has been moved,
- counting the number of pump strokes and causing the pumping to stop when a determined number is reached,
- starting a timer and causing the pumping to stop when a determined time period is elapsed, or
- pushing the air to the container 13.

For example, the dialysate pumps may be actuated in order to move the fluid at a flow rate comprised between 1 and 400 ml/min, preferentially between 50 and 300 ml/min, more preferentially between 100 and 200 ml/min.

This step may be stopped when the remaining volume of the container 13 is substantially equal to the volume required to start the treatment, for example between 500 ml and 3500 ml, preferentially between 700 ml and 3000 ml, more preferentially 1000 ml and 2500 ml.

This step may be stopped, after a time period of less than 15 min, preferentially less than 10 min, more preferentially less than 7 min.

Figure 61:
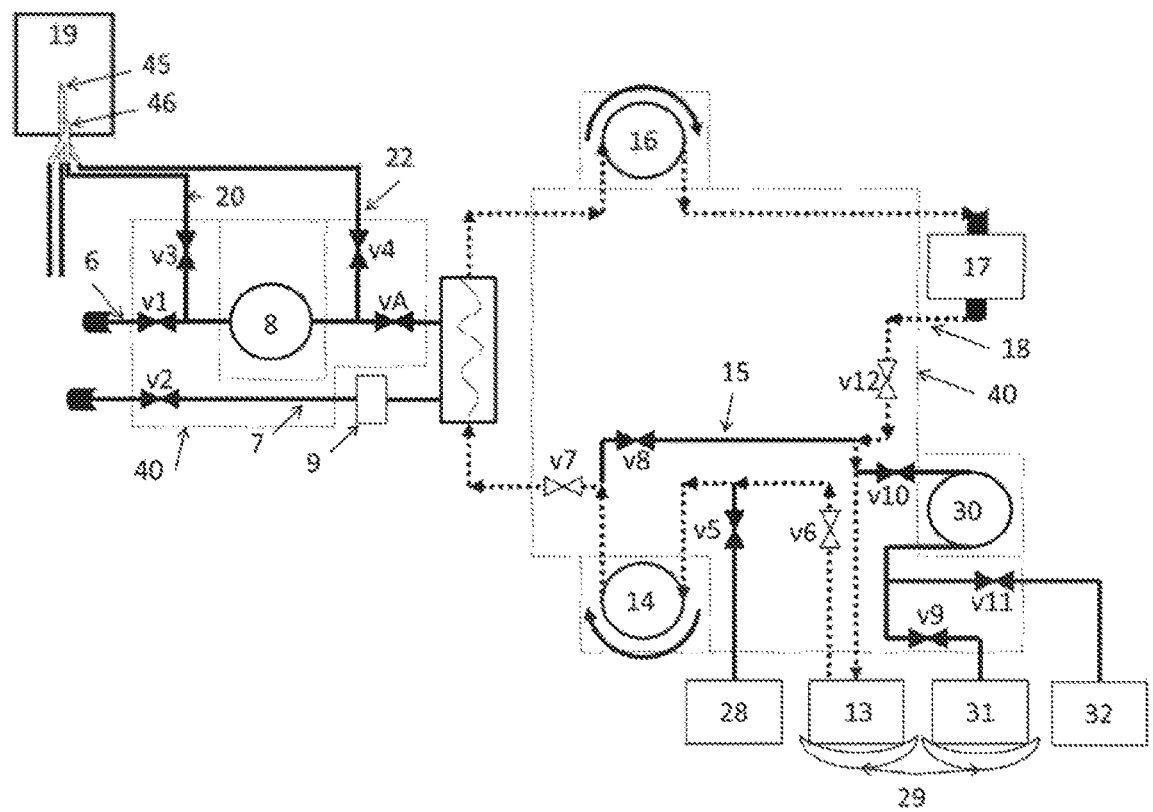

According to the FIG. 61, once the loop circuit of the dialysate circuit is substantially primed, the user connects the dedicated sorbent connectors 44 to the inlet and the outlet of the sorbent cartridge. The processor may actuate the pumps in order to prime the sorbent cartridge and the processor may actuate the additive pump (30) in order to add additive to the solution which has been passed through the sorbent cartridge.

If the blood circuit is substantially primed, the arterial line 6 and the venous line 7 may be disconnected from the container 19 and may be connected to the patient in order to start the treatment.

Priming Sequences Shown by the FIGS. 62 to 68

The FIGS. 62 to 68 show a priming sequence part wherein several priming steps are performed simultaneously in order to limit the time duration of the priming process.

Additive Line Priming

Figure 62:
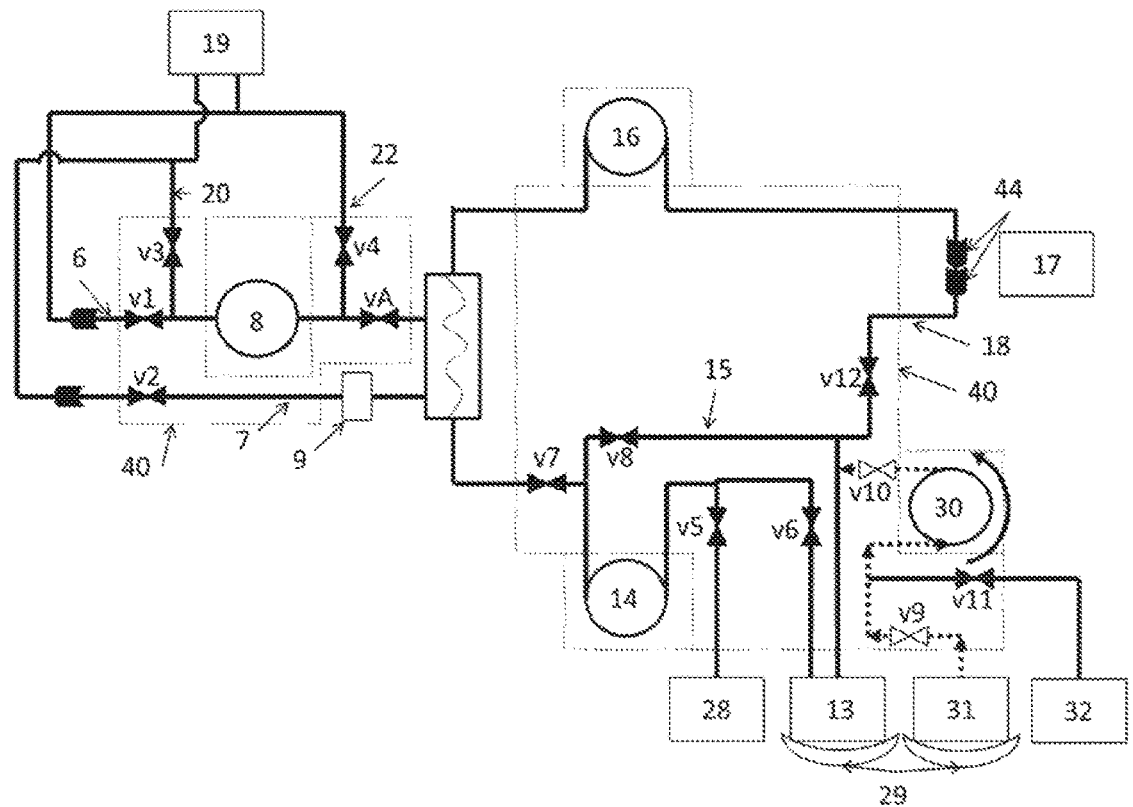

The FIG. 62 shows a priming step of the additive line which is substantially similar to the priming step described by the FIG. 49.

Priming of the Main Circuit

Figure 63:
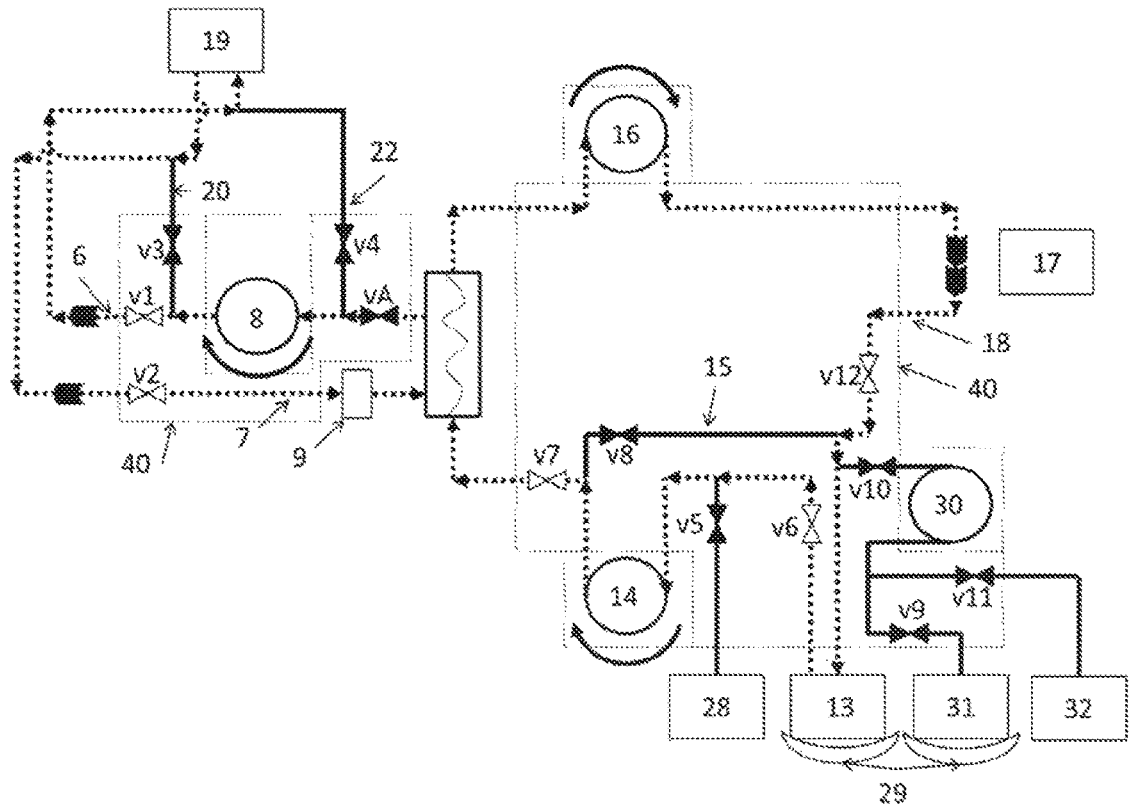

The FIG. 63 shows a simultaneous priming of the blood circuit and the dialysate circuit. Nevertheless, as the priming process previously described, the priming of both circuits may be performed by different steps.

The priming of the blood circuit may be substantially similar to the priming described by the FIG. 58. And the priming of the dialysate circuit may be substantially similar to the priming described by the FIG. 60.

Priming of Lines Connected to the Container

Figure 64:
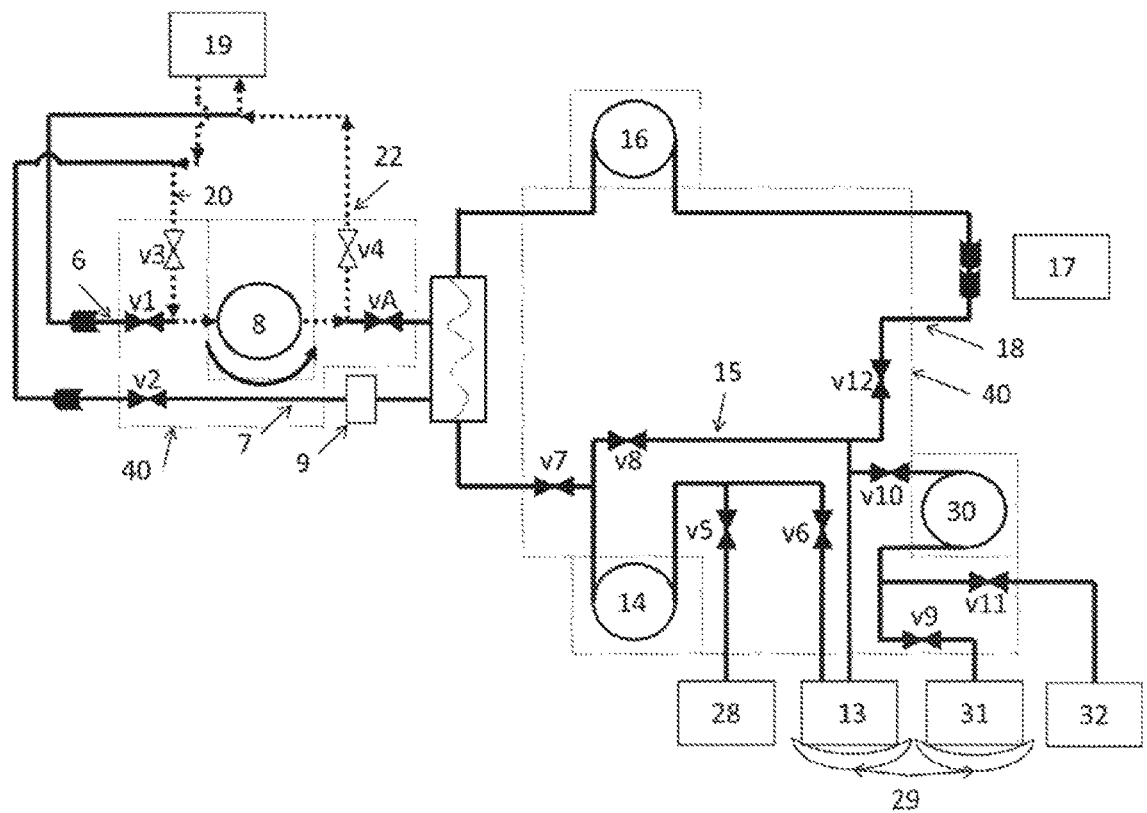

The FIG. 64 shows a priming step of the lines connected to the container 19 which is substantially similar to the priming step described by the FIG. 59.

Priming of the Drip Chamber

Figure 65:
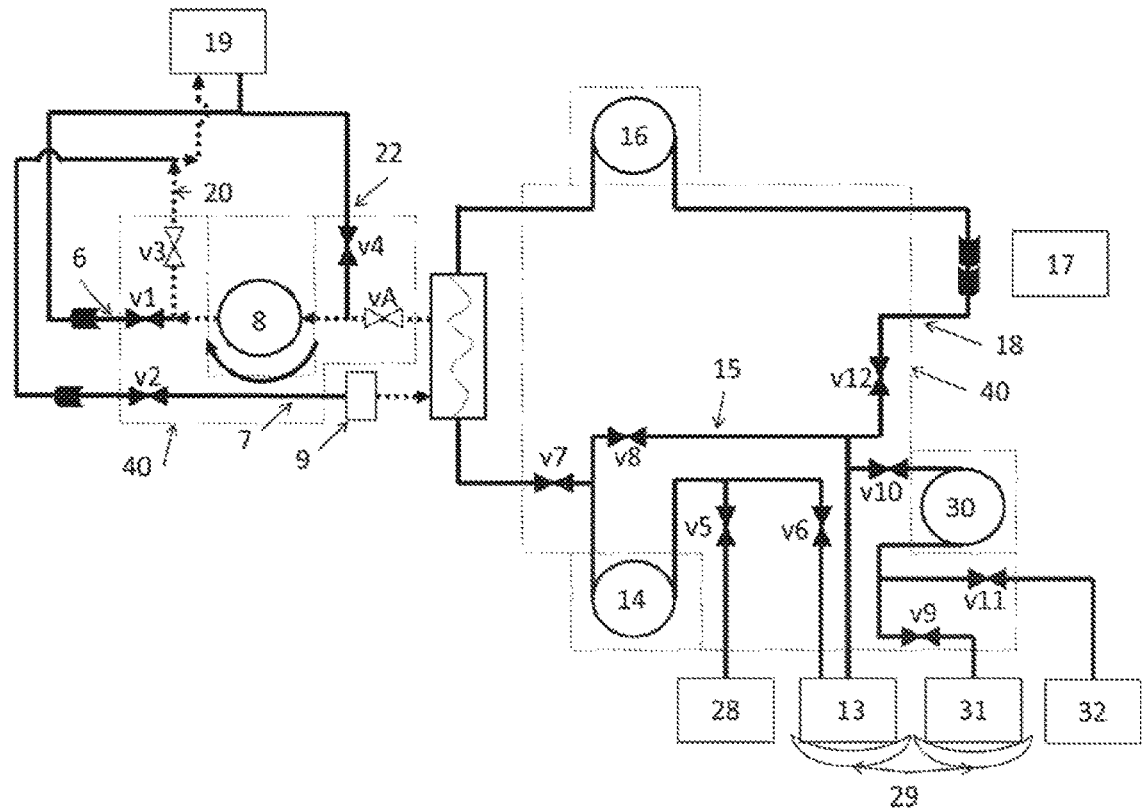
Figure 66:
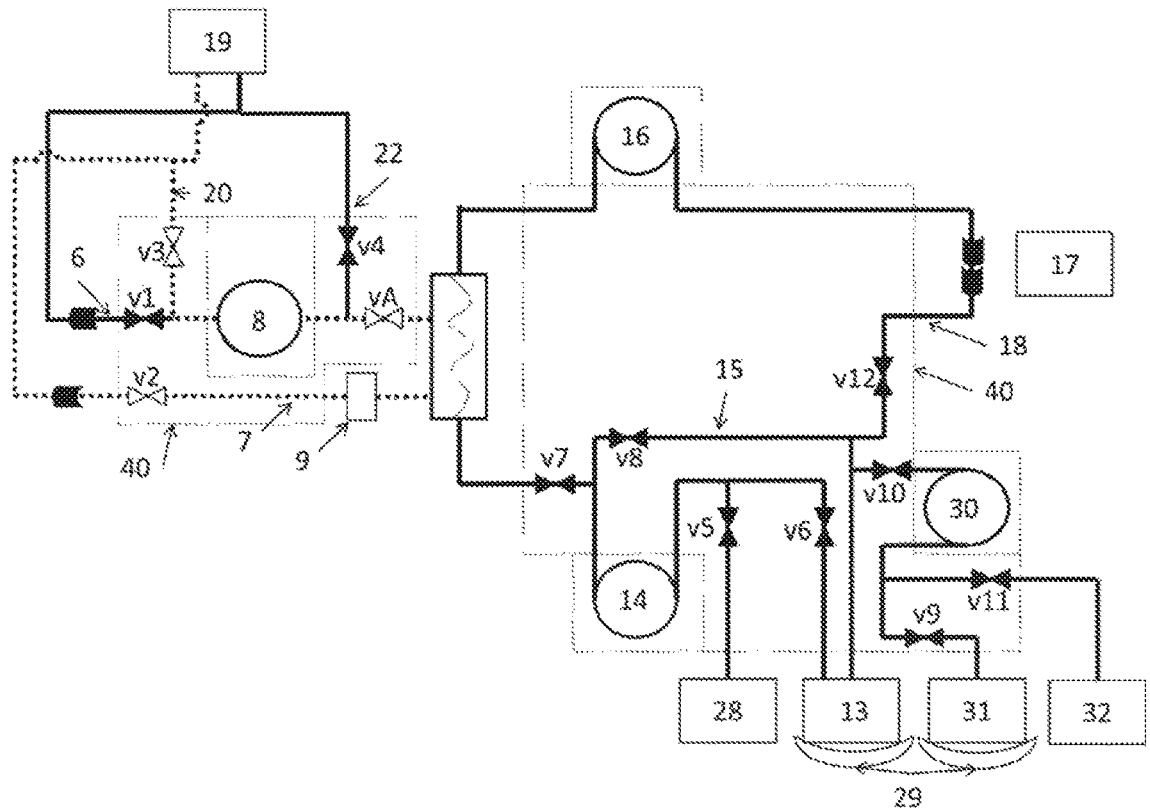

The FIGS. 65 and 66 show a priming step of the drip chamber 9 which may be carried out by the embodiments previously described. The concept may be to induce a negative pressure into the drip chamber by actuating a pump (such as the blood pump 8), maintaining the valve V2 closed and then (suddenly) opening the valve 2. This step may be performed several times until reaching a determined volume into the drip chamber 9.

The valve V1 and/or V3 (and the valve VA) may be open and the valve V4 is closed. The pump 8 may be actuated in reversed pumping mode.

When the valve V2 is open the pump 8 may be stopped. Optionally (simultaneously to the V2 opening) the valves V1, V3 and/or VA may be closed.

The method of priming the drip chamber may comprise at least one of the following steps of:
- defining of a circuit between the drip chamber 9 to the container 19 comprising at least one of the pump 8, the container 19, the drip chamber and lines in fluidic connection with the drip chamber (and for example having a portion in the blood cassette),
- pumping in a reversed pumping mode,
- maintaining closed or closing at least one valve (for example the valve V2 and/or the valve located downstream of the drip chamber according to the normal direction of the flow (i.e. the direction of the blood flow during the treatment)),
- maintaining opened or open at least one valve (for example the valve V3 or V1 and/or the valve located between the drip chamber and the pump and/or, the valve located upstream of the pump according to the normal direction of the flow in order to create a fluid path between the pump 8 and the container 19),
- sensing a fluid parameter inside the fluid lines and causing the pumping to stop when there are no longer air in a part of the drip chamber or based on a measurement data of the fluid parameter (for example fluid pressure),
- monitoring the volume of fluid moved by the pump and causing the pumping to stop when a determined volume of solution has been moved,
- monitoring the level of fluid in the drip chamber and causing the pumping to stop when a the level of fluid has reached a determined level,
- counting the number of pump strokes and causing the pumping to stop when a determined number is reached,
- starting a timer and causing the pumping to stop when a determined time period is elapsed,
- if the drip chamber comprise a valve with an external communication, this valve may be closed,
- opening the valve V2,
- stopping the pump when the valve V2 is opened,
- opening the valve V2 and closing at least one valve which has been previously opened (for example V1, V3 and/or VA), or
- opening and closing consecutively the valve V2 one or more times.

For example, the blood pump may be actuated in order to move the fluid at a flow rate comprised between 1 and 600 ml/min, preferentially between 100 and 500 ml/min, more preferentially between 200 and 400 ml/min.

This step may be stopped when the fluid pressure is substantially stable. The number of pump stroke (such as pump rotation) of the blood pump may be monitored and when a threshold is reached the processor stops the blood pump.

This step may be stopped, after a time period of less than 1 min, preferentially less than 45 sec, more preferentially less than 30 sec.

At the end of this step, when the blood pump is stopped, the processor may compare the fluid pressure upstream the blood pump to the fluid pressure downstream the blood pump via at least one pressure sensor. If both are substantially equal the goal is reached if not the blood pump may be re actuated.

End of Priming

Figure 67:
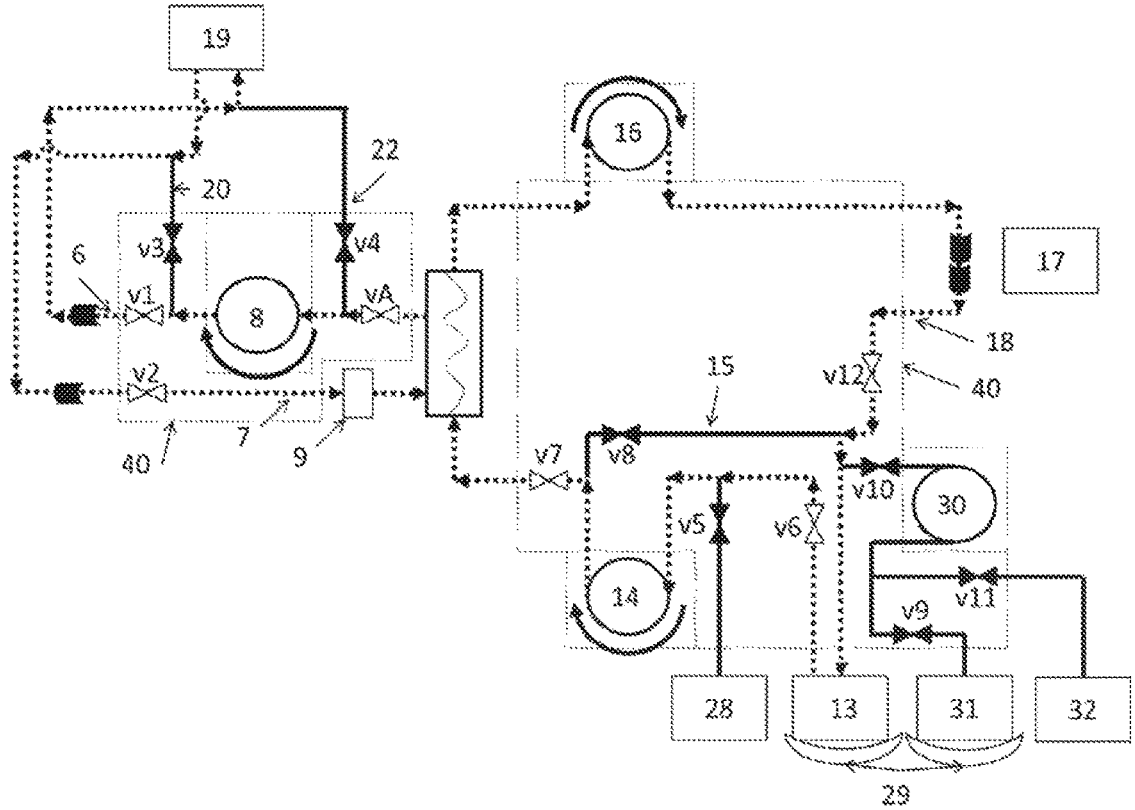
Figure 68:
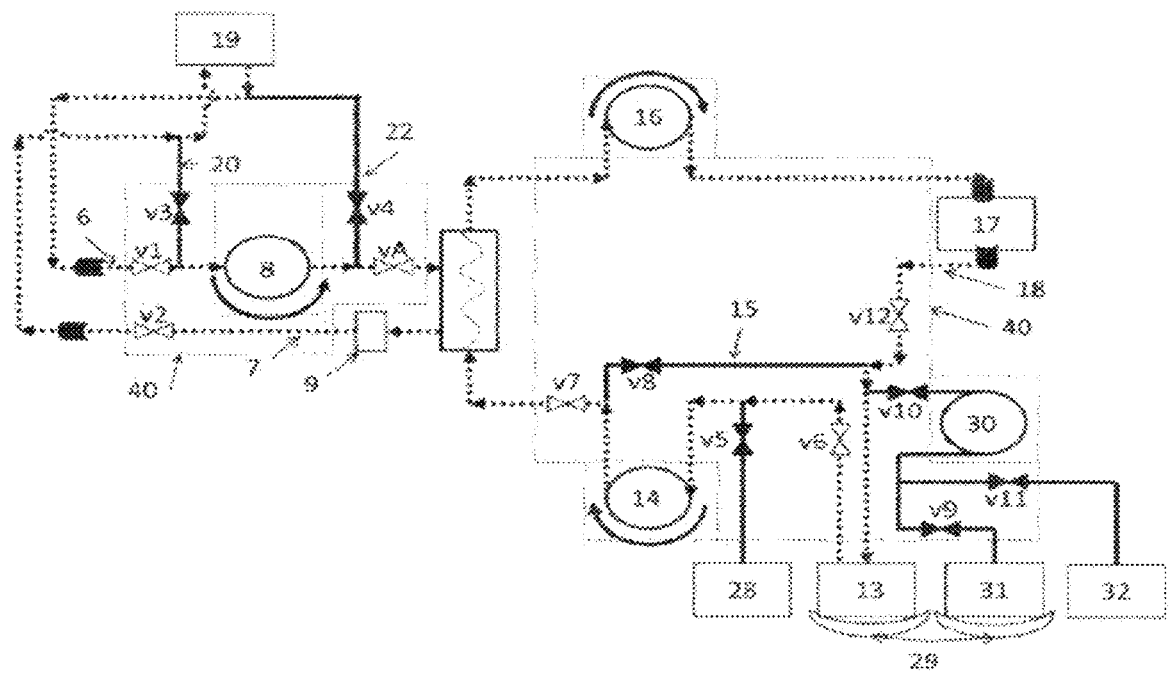

The FIGS. 67 and 68 show optional steps which may be performed after the (substantial) priming of the blood circuit and/or of the dialysate circuit.

The valve V1, V2, VA, V6, V7, V12 are open and the valve V3, V4 and other optional valves (V5, V8, . . . ) are closed. According to the FIG. 67, the blood pump 8 is actuated in a reversed pumping mode while the dialysate pumps (14, 16) are actuated in a normal pumping mode. According to the FIG. 68, the sorbent cartridge is connected to the dialysate circuit as shown by the FIG. 61 and the the blood pump 8 is actuated in a normal pumping mode.

Priming Sequences Shown by the FIGS. 69 to 75

The FIGS. 69 to 75 show a priming process part wherein several priming steps are performed simultaneously in order to limit the time duration of the priming process.

Additive Line Priming

The FIG. 69 shows a priming step of the additive line which is substantially similar to the priming step described by the FIG. 49.

Priming of the Main Circuit and Rinsing of the Dialyzer

The second internal compartment 19" may be intended to receive a fluid used for a rinse step. Thus if the dialyzer require a rinse step, for example of the blood compartment of the dialyzer, the second internal compartment may receive the rinsing fluid which has flowed through the dialyzer.

The volume used for the rinse step may be initially store in the first internal compartment of the container 19. As explained in this document, the fluid stored in the first internal compartment may be intended to flow through the blood circuit for at least one of the following action:
- Rinse of the blood circuit and/or the dialyzer,
- Priming of the blood circuit,
- Injection of a volume fraction to the patient in case of low blood pressure during the treatment (described in more detail below), or
- Pushing of the blood back to the patient at the end of the treatment.

Each action may require a determined volume of fluid. Thus the volume of the first internal compartment may be designed to store at least one fluid volume for at least one action. The second internal compartment is designed to at least receive a volume of the rinse fluid.

The rinse step may allow priming at least a part of the blood circuit.

Figure 70:
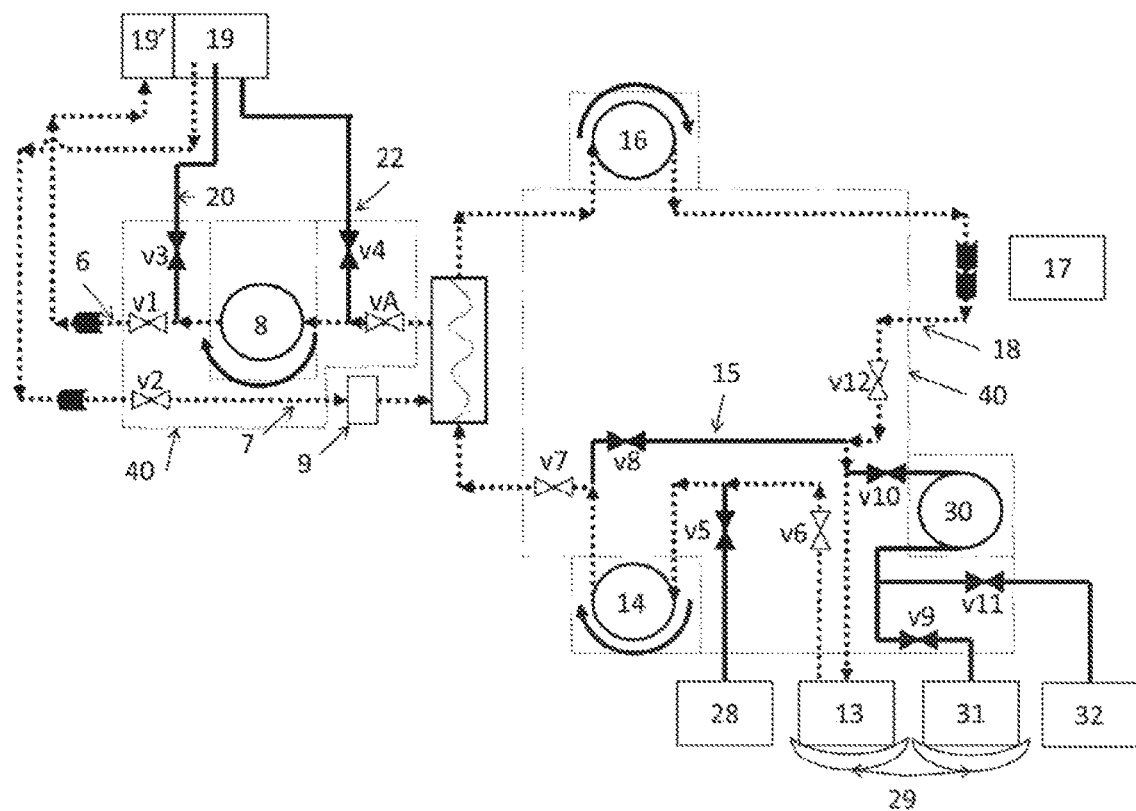

The FIG. 70 shows a priming step which is substantially similar to the priming step showed by the FIG. 63. The difference is that the first volume of fluid which flows through the dialyzer and/or a part of the blood circuit is moved into the second internal compartment 19'. At the end of the rinse step, the valve V1 may be closed, the valve V3 may be open and the pump 8 may be (continuously) actuated in reverse pumping mode in order to prime the line 20.

As explained for the FIG. 63, the priming of the blood circuit may be substantially similar to the priming described by the FIG. 58. Nevertheless, a rinse step is added in comparison with the priming described by the FIG. 58. And the priming of the dialysate circuit may be substantially similar to the priming described by the FIG. 60.

Priming of Lines Connected to the Container

The processor may automatically trigger and perform this step for example without any user intervention. This step may be triggered after one of the previous described steps.

Figure 71:
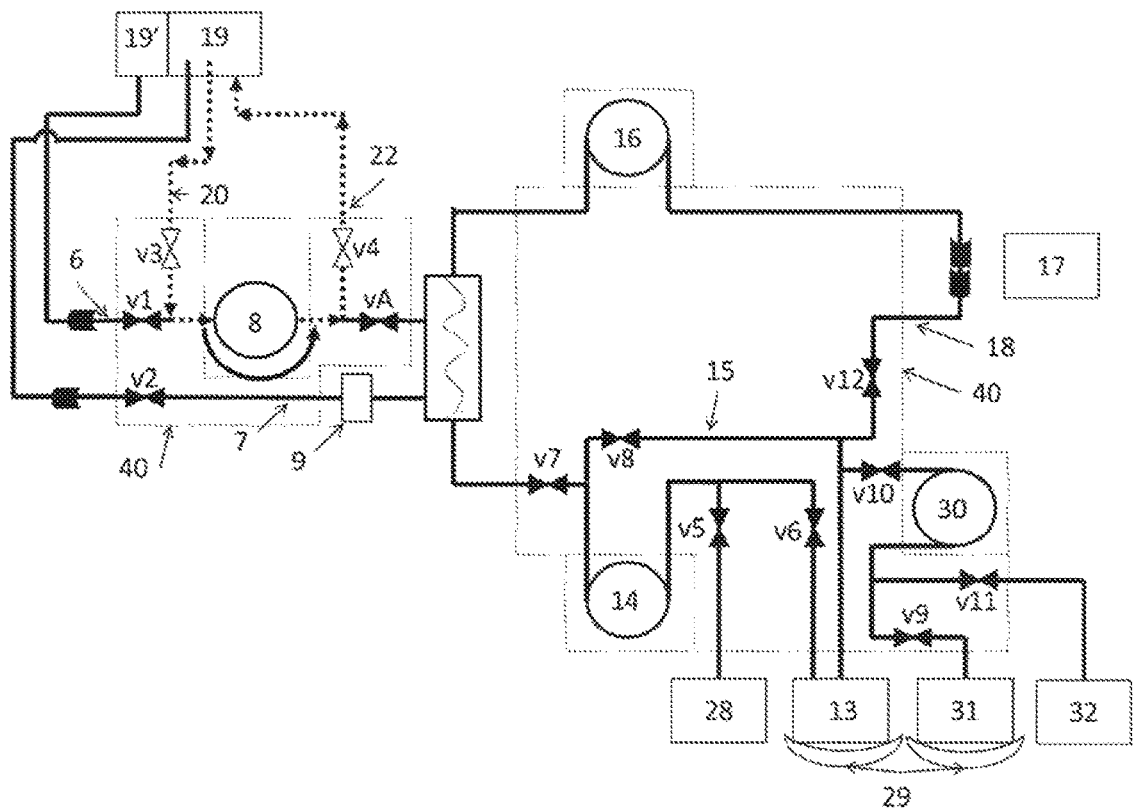

Focused on the FIG. 71, the fluid lines connected to (in fluid communication with) the container 19 may be purged during this priming step. The fluid (for example air) initially present in these lines may be pushed back to the container 19. The valves V3 and V4 are opened and the pump 8 is actuated by the processor (for example in normal pumping mode or in reversed pumping mode) during a period of time which depends on the length of the line and/or the flow rate of the pump 8. In this configuration, the system defines a closed loop where the fluid is moved from the container 19 to the container 19 (without passing through the dialyzer). An air sensor arranged into the line may be also used to detect air or liquid in order to stop this step.

The end of this step may be triggered by the processor depending on the signal of a sensor (such as a pressure or optical sensor, . . . ) of the purged line or a timer or other (for example the number of rotation/revolution of the peristaltic pump).

This step may be performed several times during the priming sequence of the system.

The method of purging the lines connected to the container 19 may comprise at least one of the following steps of:
  defining of a loop circuit comprising the pump 8, the container 19 and the first fluid line and the second fluid line (and for example having a portion in the blood cassette),
  pumping the solution stored in the container 19, for example from the container 19 to the container 19, in a reversed pumping mode or in a normal pumping mode or in a first pumping mode followed by a second pumping mode,
  sensing a fluid parameter inside the fluid lines and causing the pumping to stop when there are no longer air in the fluid lines of the loop circuit or based on a measurement data of the fluid parameter,
  monitoring the volume of fluid moved by the pump and causing the pumping to stop when a determined volume of solution has been moved,
  counting the number of pump strokes and causing the pumping to stop when a determined number is reached,
  starting a timer and causing the pumping to stop when a determined time period is elapsed, or
  pushing the air to the container 19.

For example, the blood pump may be actuated in order to move the fluid at a flow rate comprised between 1 and 600 ml/min, preferentially between 100 and 500 ml/min, more preferentially between 200 and 400 ml/min.

This step may be stopped when the container weight is substantially stable. Otherwise, the number of pump stroke (such as pump rotation) of the blood pump may be monitored and when a threshold is reached the processor stops the blood pump.

This step may be stopped, after a time period of less than 1 min, preferentially less than 45 sec, more preferentially less than 30 sec.

At the end of this step, when the blood pump is stopped, the processor may compare the fluid pressure upstream the blood pump to the fluid pressure downstream the blood pump via at least one pressure sensor. If both are substantially equal the goal is reached if not the blood pump may be re actuated.

Priming of the Drip Chamber

Figure 72:
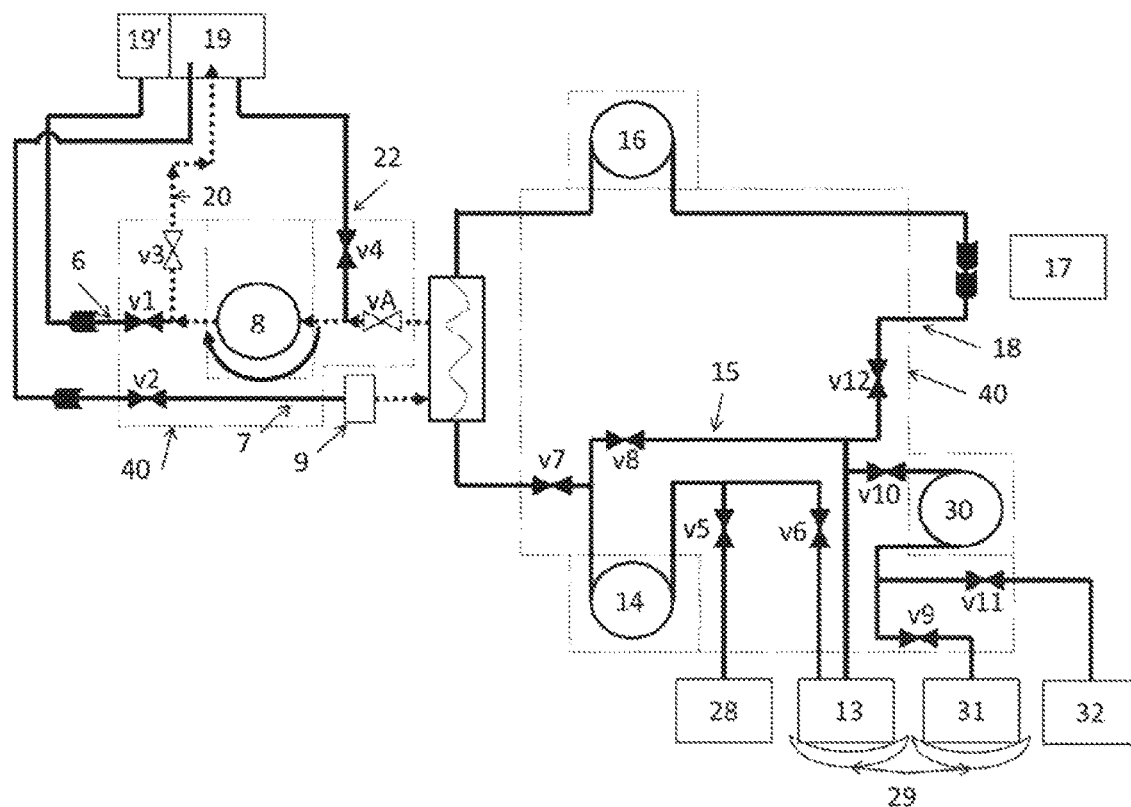
Figure 73:
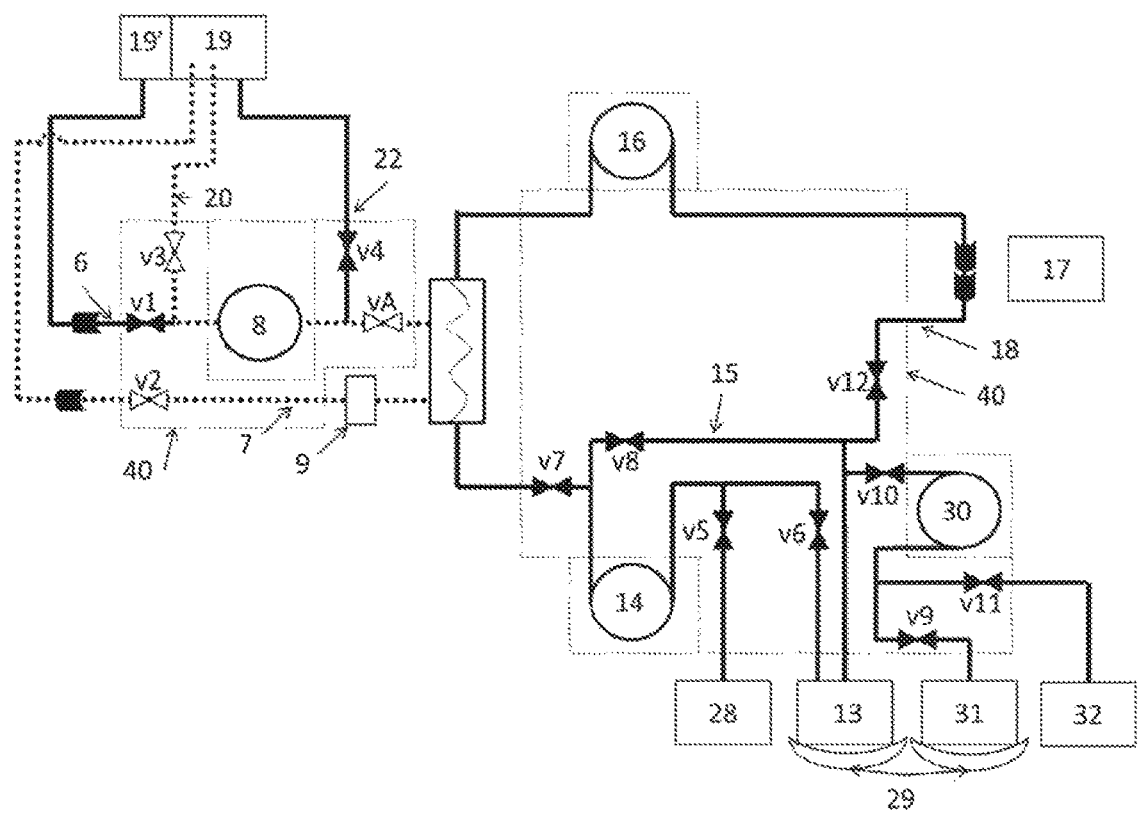

The FIGS. 72 and 73 show a priming step of the drip chamber 9 which may be substantially similar to the priming described by the FIGS. 65 and 66.

End of Priming

Figure 74:
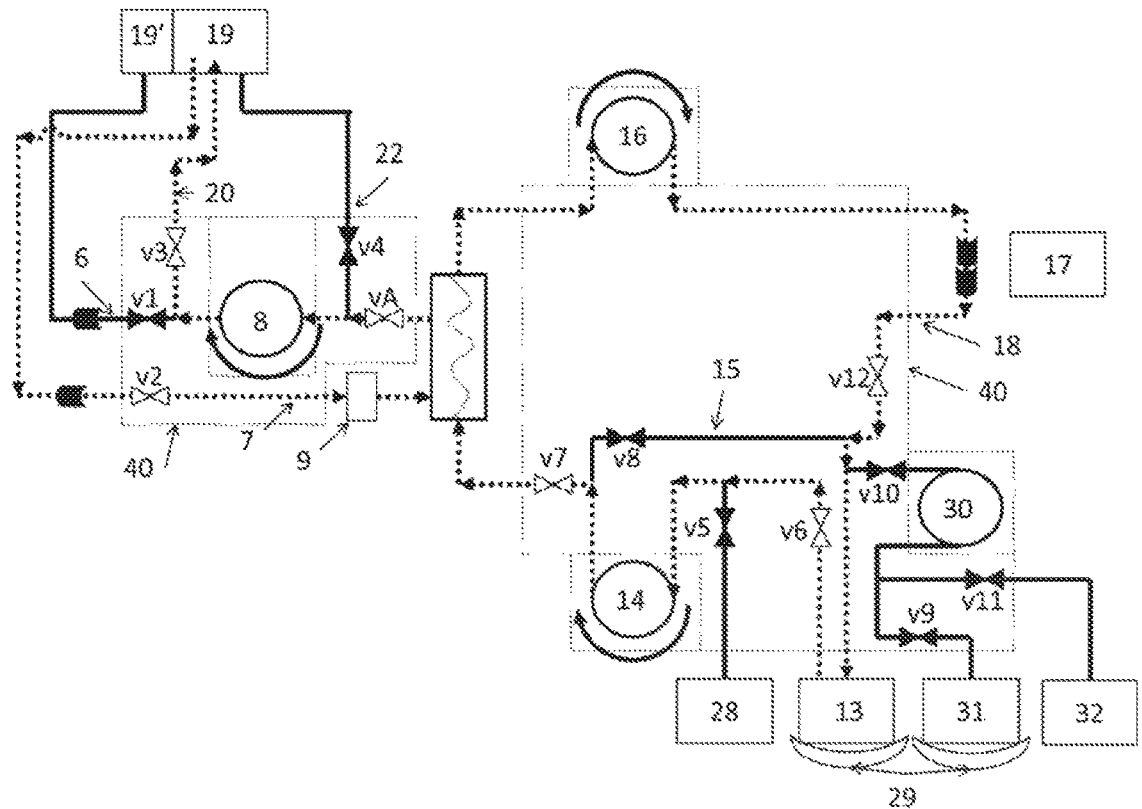
Figure 75:
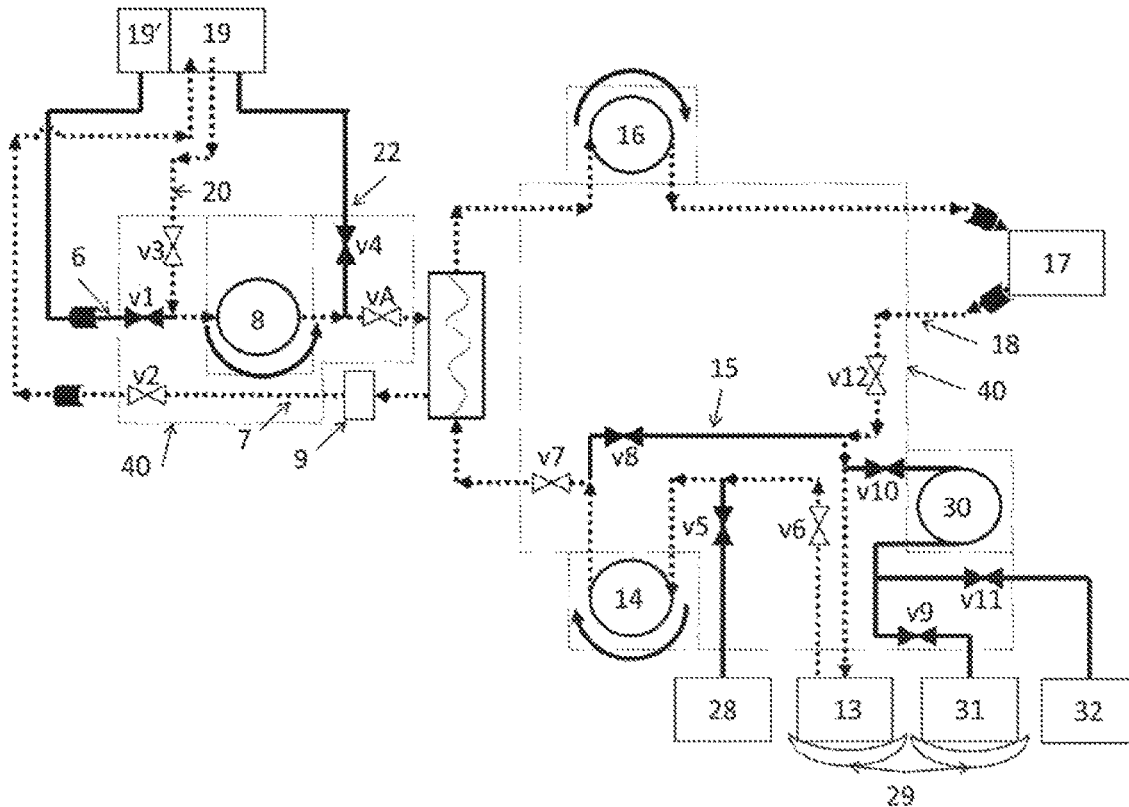

The FIGS. 74 and 75 show an end of the priming which may be substantially similar to the priming described by the FIGS. 67 and 68.

Blood Return Process

The processor may automatically trigger and perform this step for example without any user intervention, for example at the end of treatment.

FIGS. 54 and 55 illustrate the two steps of the blood-return phase. In the first step (FIG. 54), the blood pump pumps in reverse mode, with the valves V1 and V4 are opened. The solution contained in the blood return container 19 is used to push the patient blood of at least a part of the arterial line back to the patient. The valves V3 and VA and/or V2 are preferentially closed.

On the second step (FIG. 55), the blood pump pumps in forward mode and the valves V2 and V3 are opened. The solution stored in the blood return container is used to push the blood contained in the lines, the dialyzer, and the drip chamber, back to the patient.

The choice to execute these steps in this order is linked to the wish to let the blood stagnate for a duration as short as possible. Since the volume of blood in the arterial line between patient and pump is small, the remaining volume in the lines/dialyzer/drip chamber stagnates for a short time. Inversely, the larger volume contained in the lines/dialyzer/drip chamber takes more time to be brought back to the patient, resulting in longer stagnating time for the volume contained in the arterial line (between the patient and the pump).

This blood-return method offers two key advantages:
  First, the orientation of the dialyzer will be kept unchanged to return the blood to the patient with a circulation from top to bottom in the dialyzer. Thereby, all along the priming/treatment/blood-return, the patient does not need to change the orientation of the dialyzer;
  Second, there is no need to disconnect the arterial line from the patient to connect the bag with the return liquid.

As the volume of the lines/dialyzer/drip chamber is well known the stop of these steps may be determined depending on the solution volume injected into the blood circuit.

The method of rinsing blood back to the patient may comprise at least one of the following steps of:
  Moving a solution from a solution source (for example the blood return container) to the patient by actuating the blood pump in reverse mode in order to push a first volume of patient blood back to the patient,
  Moving the solution from the solution source (for example the blood return container) to the patient by actuating the blood pump in forward mode mode in order to push a second volume of patient blood back to the patient,
  Sensing a fluid parameter (such as the fluid level, the patient blood pressure, the fluid pressure) and causing the blood pump to stop when a determined fraction volume of solution is reached or based on a measurement data of the fluid parameter, monitoring the volume of solution moved by the pump and causing the blood pump to stop when a determined fraction volume of solution is reached, counting the number of pump strokes and causing the pumping to stop when a determined number is reached, or starting a timer and causing the blood pump to stop when a determined time period is elapsed.

Low Blood Pressure

The processor may automatically trigger a safety sequence and perform this safety sequence for example without any user intervention. The system may monitor the blood pressure of the patient during the treatment, in case of a decrease (if a threshold is reached for example), the system may be configured to inject a volume fraction of the solution contained in the blood return container into the blood circuit. Thus, the valve V3 or V4 may be opened and the valves V1 or V2 may be closed by the processor during this sequence.

This method may comprise at least one of the following steps of:

monitoring the patient blood pressure, under predetermined condition during the treatment, triggering a safety sequence by injecting at least a volume fraction of the solution stored in the blood return bag to the blood circuit, determining the fraction volume of solution, sensing a fluid parameter (such as the fluid level, the patient blood pressure, the fluid pressure) and causing this safety sequence to stop when the determined fraction volume is reached or based on a measurement data of the fluid parameter, monitoring the volume of fluid moved by the pump and causing this safety sequence to stop when the determined fraction volume is reached, counting the number of pump strokes and causing the pumping to stop when a determined number is reached, or starting a timer and causing this sequence to stop when a determined time period is elapsed.

Optionally, if the blood pressure drops under a threshold, the system may reduce or stop ultrafiltration flow rate.

The blood pump may not be stopped. The valve V3 is preferentially open and the valve V1 may be closed such that the injected volume is more controlled. The injected volume may be proportional to the decrease or predetermined. A table may be store in a memory device of the system used by the processor in order to determine the fraction volume to be injected.

After this safety sequence, the treatment may be continued. This safety sequence may be performed several times during the treatment.

Examples of General Methods and Embodiments

A dialysis system comprises at least one of:
a dialyzer having a blood compartment,
a blood circuit including at least one of:
  an arterial line having at least one of:
    a first arterial end including a first connector intended to be connected to a patient,
    a second arterial end connected to the blood compartment of the dialyzer, and
    an arterial valve,
  an venous line having at least one of:
    a first venous end including a second connector intended to be connected to the patient,
    a second venous end connected to the blood compartment of the dialyzer, and
    a venous valve, and
a blood pump configured to move a fluid through the blood circuit and to be actuated in at least one of a normal pump direction through the blood circuit and a reverse pump direction through the blood circuit, oppositely to the normal pump direction, and
a fluid system having at least one of:
  a first storing compartment intended to store at least one of a priming solution, a solution compatible with blood and a rinsing solution,
  a first line in fluid communication with the first storing compartment, having a first valve, and connected to the blood circuit for example between the arterial connector and the blood pump,
  a second line in fluid communication with the first storing compartment, having a second valve, and connected to the blood circuit for example between the venous connector and the blood pump, and
  an optional third line configured to be removably connected to at least one of the first connector and the second connector.

The fluid system may further comprise a second storing compartment in fluid communication with the blood circuit.

The third line may be in fluid communication with at least one of the first storing compartment and the second storing compartment.

The fluid system may further comprise a fourth line configured to be removably connected to at least one of the first connector and the second connector. The fourth line may be in fluid communication with at least one of the first storing compartment and the second storing compartment.

In one embodiment, the third line may be removably connected to the venous connector and the fourth line may be removably connected to the arterial connector.

In one embodiment, the third line may be removably connected to the arterial connector and the fourth line may be removably connected to the venous connector.

One or more storing compartment of the fluid system may be initially empty.

The dialysis system may further comprise a processor operatively connected to at least one of the arterial valve, the venous valve, the blood pump, the first valve of the first line and the second valve, wherein the processor is configured to carry out at least one operating sequence.

The at least one operating sequence may comprise:
a first operating sequence in which the blood pump is actuated in the reverse pump direction or in the normal pump direction, the first valve is in open state and the venous valve is in open state,
a second operating sequence (for example in case where the dialysis system comprises a drip chamber arrange in the blood circuit) in which the blood pump is actuated in the reverse pump direction, the first valve is in open state, the arterial valve and the second valve are in closed state and the venous valve is successively closed and opened at least one time,
a third operating sequence in which the blood pump is actuated in the reverse pump direction, the second valve is in open state and the arterial valve is in open state.

The dialyzer may further comprise a dialysate compartment in fluid communication with a dialysate circuit comprising a fluid source, wherein the fluid source may be moved by the blood pump to pass through the dialyzer so as to prime at least a part of the blood circuit.

A method of priming and rinsing back of a blood processing system including a blood circuit, a dialysate circuit and a dialyzer comprising a blood compartment in fluid communication with the blood circuit, a dialysate compartment in fluid communication with the dialysate circuit and a dialysis membrane separating the blood compartment and the dialysate compartment, wherein the blood processing system further comprises a source of priming fluid in fluid communication with the blood circuit and/or the dialysate circuit, wherein the blood circuit comprises a first bag and a blood pump, the method may comprise at least one of the steps of:

Moving the priming fluid from the source of priming fluid to the blood circuit;

Priming at least a part of the blood circuit with the priming fluid;

Filling the first bag with the priming fluid;

Priming at least a part of the blood circuit with patient blood; and

Moving the priming fluid from the first bag through the blood circuit.

The method may further comprise at least one of the following steps:

a step of injecting a volume fraction of priming fluid to the patient, a step of monitoring the patient blood pressure, wherein the step of injecting a volume fraction of priming fluid to the patient is launched depending on a data of the blood pressure, a step of passing the priming fluid from the dialysate circuit to the blood circuit, for example through the dialysate membrane, a step of actuating the blood pump in order to move a volume fraction of the priming fluid from the source of priming fluid to the first bag, The blood processing system may further include a dialysate pump and the method further comprises the step of actuating the dialysate pump during at least a part of the priming of the blood circuit. The first bag may comprise a first fluid pathway connected to the blood circuit upstream to the blood pump and a second fluid pathway connected to the blood circuit downstream to the blood pump, both are in fluid connection with the interior of the first bag and both comprise a dedicated valve.

A method of priming a blood processing system including a blood circuit, a dialysate circuit and a dialyzer comprising a blood compartment in fluid communication with the blood circuit, a dialysate compartment in fluid communication with the dialysate circuit and a dialysis membrane separating the blood compartment and the dialysate compartment, wherein the blood circuit further comprises an arterial line, a venous line and a first bag and the dialysate circuit comprises a dialysate pump and a source of priming fluid, the method may comprise at least one of the steps of:

Passing the priming fluid from the dialysate circuit to the blood circuit; and

Filling at least partially the first bag with the priming fluid by using the dialysate pump.

The arterial line may comprise a first end intended to be connected to a patient and the venous line may comprise a second end intended to be connected to the patient. Preferentially, during the step of filling the first bag, the first end and the second end are connected together or via an interconnection element. The the first bag may be connected to the arterial line.

The method may further comprise at least one of steps of:

passing the priming fluid through the venous line, the second end, the first end and then through a part of the arterial line in order to fill the first bag with the priming fluid, and at the end of the treatment, pushing back the blood stored in the blood circuit to the patient by using the fluid stored in the first bag A dialysis system may comprise at least one of:

a dialyzer having a blood chamber, a dialysate chamber and a membrane separating the blood chamber from the dialysate chamber;

a blood circuit including at least one of:

an arterial line having a first end with a connector intended to be connected to a patient and a second end connected to the blood chamber of the dialyzer;

an venous line having a first end with a connector intended to be connected to the patient and a second end connected to the blood chamber of the dialyzer;

a blood pump adapted to move the blood circuit;

a source of a priming fluid; and a first bag comprising a first port and a second port in fluid communication with blood circuit.

The first port of the first bag may be fluidly connected to the blood circuit upstream the blood pump and the second port of the first bag may be fluidly connected to the blood circuit downstream the blood pump. The bag may be initially empty.

A method of priming and rinsing back of a blood processing system which may include at least one of:

a blood circuit which may comprise a first bag and a blood pump, a dialysate circuit, a dialyzer which may comprise:

a blood compartment in fluid communication with the blood circuit, a dialysate compartment in fluid communication with the dialysate circuit and a dialysis membrane separating the blood compartment and the dialysate compartment, a source of priming fluid in fluid communication with at least one of the blood circuit and the dialysate circuit.

The method may comprise at least one of the steps of:

moving the priming fluid from the source of priming fluid to the blood circuit, priming at least a part of the blood circuit with the priming fluid, filling the first bag with the priming fluid, or priming at least a part of the blood circuit with patient blood;

The method may further comprise at least one of the steps of:

injecting a volume fraction of priming fluid to the patient, monitoring the patient blood pressure, wherein the step of injecting a volume fraction of priming fluid to the patient is launched depending on a data of the blood pressure, pushing the blood back to the patient with the priming fluid, or actuating the blood pump in order to move a volume fraction of the priming fluid from the source of priming fluid to the first bag The blood circuit may comprise an arterial blood connector intended to be connected to the patient in treatment condition and a venous blood connector intended to be connected to the patient in treatment condition. And the method may further comprise at least one of the steps of:

connecting the arterial blood connector to the venous blood connector, connecting the arterial blood connector and the venous blood connector to the priming fluid source, or passing the priming fluid from the dialysate circuit to the blood circuit, for example through the dialysate membrane.

The blood processing system may further include a dialysate pump and the method may comprise the step of actuating the dialysate pump during at least a part of the priming of the blood circuit. Preferentially, when the dialysate pump is actuated, the blood pump is not actuated and vice versa.

The first bag may comprise a first fluid pathway connected to the blood circuit upstream to the blood pump and a second fluid pathway connected to the blood circuit downstream to the blood pump, both may be in fluid connection with the interior of the first bag and both may comprise a dedicated valve. The method may further comprises at least one of the steps of closing the valve of the first fluid pathway,
opening the valve of the second fluid pathway,
actuating the blood pump in a reversed mode in order to push the blood back to the patient via the arterial line,
closing the valve of the second fluid pathway,
opening the valve of the first fluid pathway, or
actuating the blood pump in a normal mode in order to push the blood back to the patient via the venous line.

The first fluid pathway may be connected to the arterial line and the second fluid pathway is connected to the arterial line. The first fluid pathway may be connected to the arterial line and the second fluid pathway is connected to the venous line.

A method of priming a blood processing system which may include at least one of:

a blood circuit which may comprise an arterial line, a venous line and a first bag, a dialysate circuit which may comprise dialysate pump and a source of priming fluid and a dialyzer which may comprise a blood compartment in fluid communication with the blood circuit, a dialysate compartment in fluid communication with the dialysate circuit and a dialysis membrane separating the blood compartment and the dialysate compartment The method may comprise at least one of the steps of:
passing the priming fluid from the dialysate circuit to the blood circuit, or
filling at least partially the first bag with the priming fluid by using the dialysate pump The arterial line may comprise a first end intended to be connected to a patient and the venous line may comprise a second end intended to be connected to the patient, wherein during the step of filling the first bag, the first end and the second end may be connected together or via an interconnection element. The first bag may be connected to the arterial line and the method may further comprise the step of passing the priming fluid through the venous line, the second end, the first end and then through a part of the arterial line in order to fill the first bag with the priming fluid.

The first bag may comprise a first fluid pathway and a second fluid pathway, both are in fluid connection with the interior of the first bag and to the blood circuit. The blood circuit may further include a blood pump and wherein the first fluid pathway of the first bag may be connected to the blood circuit upstream to the blood pump and the second fluid pathway of the first bag may be connected to the blood circuit downstream to the blood pump, both may comprise a dedicated valve. The first fluid pathway may be connected to the arterial line and the second fluid pathway may be connected to the arterial line. The first fluid pathway may be connected to the arterial line and the second fluid pathway may be connected to the venous line.

During at least a part of the step of filing the first bag, the dialysate pump may be actuated and/or the blood pump may be not actuated.

During at least a part of the step of filing the first bag, the dedicated valve of the first fluid pathway may be open and the dedicated valve of the second fluid pathway may be closed or vice/versa.

The method may further comprise at least one of the steps of:

pushing the fluid initially stored in at least a part of the blood circuit into the first bag, or at the end of the treatment, pushing back the blood stored in the blood circuit to the patient by using the fluid stored in the first bag.

The source of priming fluid may comprises a priming fluid bag in which the fluid priming may be stored and the method may further comprise the step of monitoring the weight of the priming fluid bag.

During the step of passing the priming fluid from the dialysate circuit to the blood circuit, the priming fluid may be passed through the dialysate membrane. The priming fluid may be a dialysate solution.

A method of priming a blood processing system which may include at least one of:

a blood circuit which may comprise an arterial line, a venous line and a drip chamber connected to the venous line, a dialysate circuit which may comprise a dialysate pump and a source of priming fluid and a dialyzer comprising a blood compartment in fluid communication with the blood circuit, a dialysate compartment in fluid communication with the dialysate circuit and a dialysis membrane separating the blood compartment and the dialysate compartment.

The method may comprise at least one of the steps of:
transporting priming fluid from the dialysate circuit to the blood circuit, or
priming the drip chamber with the priming fluid by using the dialysate pump.

During the step of passing the priming fluid from the dialysate circuit to the blood circuit, the priming fluid may passed through the dialysate membrane.

The drip chamber may include a liquid level sensor and/or a vent. The priming solution may be stored in a bag. The system may further include a blood pump and a processor adapted to control at least one of the dialysate pump and the blood pump The method may further comprise at least one of the steps of:

monitoring the output of the liquid level sensor,
stopping the dialysate pump in order to stop the priming process of the drip chamber,
monitoring the weight of the bag storing the priming fluid, or
increasing the pressure of the priming fluid in the drip chamber by the dialysate pump in order to expel the air via the vent of the drip chamber During the priming of the drip chamber, the processor may be configured to actuate the dialysate pump and not to actuate the blood pump.

A dialysis system may include at least one of:
a dialyzer having a blood chamber, a dialysate chamber and a membrane separating the blood chamber from the dialysate chamber;
a blood circuit including:
   an arterial line having a first end with a connector intended to be connected to a patient and a second end connected to the blood chamber of the dialyzer;
   an venous line having a first end with a connector intended to be connected to the patient and a second end connected to the blood chamber of the dialyzer;
a blood pump adapted to move the blood circuit;
a source of a priming fluid; and
A first bag comprising a first port and a second port in fluid communication with blood circuit;
The first port of the first bag may be fluidly connected to the blood circuit upstream the blood pump and the second port of the first bag may be fluidly connected to the blood circuit downstream the blood pump.

Preferentially, the bag is initially empty.

The system may further comprise at least one of the:
a dialysate circuit including a dialysate pump and the source of the fluid priming;
a sorbent device adapted to clean the solution which has been passed through the dialysate chamber of the dialyzer;
a processor and a memory which stores a priming sequence in order to perform automatically the priming sequence in which the priming fluid is pumped in order to fill the first bag with a determined amount of the priming fluid. Preferentially, the determined amount of the priming fluid filled in the first bag is substantially equal to the amount of blood patient stored in the blood circuit in treatment condition;
a weight scale intended to monitor the amount of the priming fluid moved during at least a part of the priming sequence;
a processor and a memory which stores a blood return sequences in order to perform automatically the blood return sequence in which the priming fluid stored in the first bag at the end of the treatment is used to push the blood back to the patient.

The fluid priming may be at least one of a dialysate solution, a blood compatible solution, a saline solution and a pure water solution.

During a part of the priming sequence the dialysate pump may be configured to move the fluid priming through the membrane from the source of priming to the blood circuit.

During a part of the priming sequence the blood pump may be configured to move the fluid priming through the membrane from the source of priming to the blood circuit.

The first end of the arterial end and the first end of the venous line may comprise connector adapted to be connected there between or via an interconnector element in order to create a loop of the blood circuit.

The invention claimed is:
1. A dialysis system comprising:
a dialyzer having a blood compartment;
a blood circuit including:
   an arterial line having:
      a first arterial end including an arterial connector configured to connect to a patient during a treatment of the patient,
      a second arterial end connected to the blood compartment of the dialyzer, and
      an arterial valve,
   a venous line having:
      a first venous end including a venous connector configured to connect to the patient during the treatment of the patient,
      a second venous end connected to the blood compartment of the dialyzer, and
      a venous valve;
a blood pump having an inlet and an outlet in fluid communication with the arterial line and the venous line and configured to move a fluid through the blood circuit and to be actuated in at least one of a normal pump direction through the blood circuit and/or a reverse pump direction through the blood circuit, oppositely to the normal pump direction; and
a fluid system having:
   a first storing compartment configured to store at least one of a priming solution, a solution compatible with blood, and a rinsing solution,
   a first line having a first end connected to the first storing compartment and a second end connected to the venous line via the venous connector when the patient is not connected to the blood circuit,
   a second line having a third end connected to the first storing compartment and a fourth end connected to the arterial line, and
   a second storing compartment in fluid communication with the blood circuit via a third line when the patient is not connected to the blood circuit, the third line having a fifth end connected to the second storing compartment and a sixth end configured to be connected to the arterial connector to receive at least a part of at least one of the priming solution, the solution compatible with blood, and the rinsing solution initially stored in the first storing compartment before the treatment of the patient such that the second storing compartment is configured to receive the at least part of at least one of the priming solution, the solution compatible with blood, and the rinsing solution provided from the first storing compartment through the venous connector connected with the first storing compartment and at least one of the first line and the second line,
wherein the arterial connector and the venous connector are configured to be disconnected from the second end and the sixth end and to be connected to the patient during the treatment.

2. The system according to claim 1, wherein the second storing compartment of the fluid system is initially empty.

3. The system according to claim 1, further comprising:
a processor operatively connected to at least one of the arterial valve, the venous valve, and the blood pump,
wherein the processor is configured to carry out at least one operating sequence.

4. The system according to claim 3, wherein the at least one operating sequence comprises a first operating sequence in which the blood pump is actuated in the reverse pump direction or in the normal pump direction, and the venous valve is in an open state.

5. The system according to claim 3, further comprising a drip chamber arranged in the blood circuit, and
wherein the at least one operating sequence comprises a second operating sequence in which the blood pump is actuated in the reverse pump direction, and the arterial valve and the venous valve are successively closed and opened at least one time.

6. The system according to claim 3, wherein the at least one operating sequence comprises a third operating sequence in which the blood pump is actuated in the reverse pump direction, and the arterial valve is in an open state.

7. The system according to claim 1, wherein the dialyzer further comprises a semi-permeable membrane and a dialysate compartment in fluid communication with a comprising a fluid source,
   wherein the blood compartment and the dialysate compartment are separated by the semi-permeable membrane, and
   wherein the fluid source is moved by the blood pump to pass through the semi-permeable membrane of the dialyzer to prime at least a part of the blood circuit.

8. The system according to claim 1, wherein the second storing compartment is configured to receive the rinsing solution.

9. The system according to claim 1, wherein the solution stored in the first storing compartment is configured to prime and rinse the blood circuit before the treatment and to push back the patient blood at the end of the treatment.

10. The system according to claim 1, wherein the first line comprises a first valve.

11. The system according to claim 3, wherein the first valve is controlled by the processor.

12. An extracorporeal treatment system comprising:
   a dialyzer;
   a blood circuit comprising:
      an arterial line having:
         a first arterial end including an arterial connector configured to connect to a patient during a treatment of the patient, and
         a second arterial end connected to the dialyzer,
      a venous line having:
         a first venous end including a venous connector configured to connect to the patient during the treatment of the patient, and
         a second venous end connected to the dialyzer;
   a blood pump having an inlet and an outlet in fluid communication with the arterial line and the venous line and configured to move a fluid through the blood circuit;
   a first storing compartment configured to store a liquid solution and including a first line connected to the venous line via the venous connector when the patient is not connected to the blood circuit and a second line connected to the arterial line; and
   a second storing compartment configured to be connected to the arterial connector before the treatment of the patient to receive at least a part of the liquid solution initially stored in the first storing compartment before the treatment of the patient when the blood pump is actuated such that the second storing compartment is configured to receive the at least part of the liquid solution provided from the first storing compartment through the venous connector connected with the first storing compartment and at least one of the first line and the second line,
   wherein the arterial connector is configured to be disconnected from the second storing compartment and to be connected to the patient during the treatment while the venous connector is configured to be disconnected from the first storing compartment and to be connected to the patient during the treatment.

13. The system according to claim 12, wherein the first line includes a first valve and the arterial line includes an arterial valve.

14. The system according to claim 13, further including a processor configured to control the blood pump, the first valve, and the arterial valve.

15. An extracorporeal treatment system comprising:
   a dialyzer;
   a blood circuit including:
      an arterial line having:
         a first arterial end including an arterial connector configured to connect to a patient during a treatment of the patient, and
         a second arterial end connected to the dialyzer,
      a venous line having:
         a first venous end including a venous connector configured to connect to the patient during the treatment of the patient, and
         a second venous end connected to the dialyzer;
   a blood pump having an inlet and an outlet in fluid communication with the arterial line and the venous line and configured to move a fluid through the blood circuit;
   a first storing compartment configured to store a liquid solution and including a first line connected to the venous line via the venous connector when the patient is not connected to the blood circuit and a second line connected to the blood circuit; and
   a second storing compartment configured to receive a volume of the liquid solution and configured to be connected to the arterial connector to receive at least a part of the liquid solution initially stored in the first storing compartment before the treatment of the patient when the blood pump is actuated such that the second storing compartment is configured to receive the at least part of the liquid solution provided from the first storing compartment through the venous connector connected with the first storing compartment and at least one of the first line and the second line,
   wherein the arterial connector is configured to be disconnected from the second storing compartment and to be connected to the patient during the treatment while the venous connector is configured to be disconnected from the first storing compartment and to be connected to the patient during the treatment.

16. The system according to claim 15, wherein the first line includes a first valve and the arterial line includes an arterial valve.

17. The system according to claim 16 further including a processor configured to control the blood pump, the first valve, and the arterial valve.

18. The system according to claim 15, wherein the first line is connected to the arterial line between the arterial connector and the blood pump inlet.

19. The system according to claim 17, wherein the first line is connected to the arterial line between the arterial valve and the blood pump inlet.

20. The system according to claim 1, further comprising a container in which both the first storing compartment and the second storing compartment are disposed.

21. The system according to claim 1, further comprising a first container in which the first storing compartment is disposed and a second container in which the second storing compartment is disposed.

22. The system according to claim 1, wherein the second end is configured to be unplugged from the blood circuit once the priming sequence is complete.

23. The system according to claim 1, wherein the sixth end is configured to be unplugged from the blood circuit once the priming sequence is complete.

24. The system according to claim 1, further comprising at least one spike,
   wherein the first storing compartment comprises an access port configured to be connected to at least one of the first line and the second line via the at least one spike.

25. The system according to claim 1, wherein the second storing compartment comprises a fluid line and a removable connector configured to be connected to the arterial connector during the priming process.

26. The system according to claim 1, wherein the second storing compartment comprises a fluid line and a removable connector configured to be disconnected from the blood circuit once the priming process is complete.

27. The system according to claim 12, further comprising a container in which both the first storing compartment and the second storing compartment are disposed.

28. The system according to claim 12, further comprising a first container in which the first storing compartment is disposed and a second container in which the second storing compartment is disposed.

29. The system according to claim 12, wherein the second end is configured to be unplugged from the blood circuit once the priming sequence is complete.

30. The system according to claim 12, wherein an end of a third line connected to the second storing compartment is configured to be unplugged from the blood circuit once the priming sequence is complete.

31. The system according to claim 12, further comprising at least one spike,
   wherein the first storing compartment comprises an access port configured to be connected to at least one of the first line and the second line via at least one spike.

32. The system according to claim 12, wherein the second storing compartment comprises a fluid line and a removable connector configured to be connected to the arterial connector during the priming process.

33. The system according to claim 12, wherein the second storing compartment comprises a fluid line and a removable connector configured to be disconnected from the blood circuit once the priming process is complete.

34. The system according to claim 15, further comprising a container in which both the first storing compartment and the second storing compartment are disposed.

35. The system according to claim 15, further comprising a first container in which the first storing compartment is disposed and a second container in which the second storing compartment is disposed.

36. The system according to claim 15, wherein the second end is configured to be unplugged from the blood circuit once the priming sequence is complete.

37. The system according to claim 15, wherein an end of a third line connected to the second storing compartment is configured to be unplugged from the blood circuit once the priming sequence is complete.

38. The system according to claim 15, further comprising at least one spike,
   wherein the first storing compartment comprises an access port configured to be connected to at least one of the first line and the second line via the at least one spike.

39. The system according to claim 15, wherein the second storing compartment comprises a fluid line and a removable connector configured to be connected to the arterial connector during the priming process.

40. The system according to claim 15, wherein the second storing compartment comprises a fluid line and a removable connector configured to be disconnected from the blood circuit once the priming process is complete.

41. The system according to claim 1, wherein the first storing compartment and the second storing compartment of the fluid system are initially empty.

* * * * *